(12) United States Patent  (10) Patent No.: US 8,158,604 B2
Linden et al.  (45) Date of Patent: *Apr. 17, 2012

(54) 2-PROPYNYL ADENOSINE ANALOGS HAVING A2A AGONIST ACTIVITY AND COMPOSITIONS THEREOF

(75) Inventors: Joel M. Linden, Charlottesville, VA (US); Jayson M. Rieger, Charlottesville, VA (US); Timothy L. Macdonald, Charlottesville, VA (US); Gail W. Sullivan, Charlottesville, VA (US); Lauren J. Murphree, Rockville, MD (US); Robert Alan Figler, Earlysville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/712,022

(22) Filed: Feb. 24, 2010

(65) Prior Publication Data

US 2010/0152127 A1 Jun. 17, 2010

Related U.S. Application Data

(63) Continuation of application No. 11/691,374, filed on Mar. 26, 2007, now Pat. No. 7,737,127, which is a continuation of application No. 10/263,379, filed on Oct. 1, 2002, now Pat. No. 7,214,665.

(60) Provisional application No. 60/326,517, filed on Oct. 1, 2001, provisional application No. 60/383,200, filed on May 24, 2002.

(51) Int. Cl.
| | |
|---|---|
| C07D 473/34 | (2006.01) |
| A61K 31/52 | (2006.01) |
| A61K 31/7076 | (2006.01) |
| C07H 19/167 | (2006.01) |
| C07H 19/19 | (2006.01) |
| A61P 29/00 | (2006.01) |

(52) U.S. Cl. ..... 514/46; 514/263.4; 544/277; 536/27.22
(58) Field of Classification Search .................. 544/277; 536/27.22; 514/46, 263.4
See application file for complete search history.

(56) References Cited

U.S. PATENT DOCUMENTS

| | | | |
|---|---|---|---|
| 3,892,777 A | 7/1975 | Gruenman et al. |
| 4,012,495 A | 3/1977 | Schmeichen et al. |
| 4,193,926 A | 3/1980 | Schmiechen et al. |
| 4,242,345 A | 12/1980 | Brenner et al. |
| 4,448,721 A * | 5/1984 | DeLuca et al. ................. 540/50 |
| 4,559,157 A | 12/1985 | Smith et al. |
| 4,608,392 A | 8/1986 | Jacquet et al. |
| 4,665,074 A | 5/1987 | Amschler |
| 4,695,660 A | 9/1987 | Otte et al. |
| 4,820,508 A | 4/1989 | Wortzman |
| 4,824,660 A | 4/1989 | Angello et al. |
| 4,879,296 A | 11/1989 | Daluge et al. |
| 4,938,949 A | 7/1990 | Borch et al. |
| 4,956,345 A | 9/1990 | Miyasaka et al. |
| 4,965,271 A | 10/1990 | Mandell et al. |
| 4,968,697 A | 11/1990 | Hutchison |
| 4,992,478 A | 2/1991 | Geria |
| 5,070,877 A | 12/1991 | Mohiuddin et al. |
| 5,096,906 A | 3/1992 | Mandell et al. |
| 5,124,455 A | 6/1992 | Lombardo et al. |
| 5,140,015 A | 8/1992 | Olsson et al. |
| 5,189,027 A | 2/1993 | Miyashita et al. |
| 5,272,153 A | 12/1993 | Mandell et al. |
| 5,278,150 A | 1/1994 | Olsson et al. |
| 5,298,508 A | 3/1994 | Jacobson et al. |
| 5,364,862 A | 11/1994 | Spada et al. |
| 5,561,111 A | 10/1996 | Guerrant et al. |
| 5,561,134 A | 10/1996 | Spada et al. |
| 5,565,462 A | 10/1996 | Eitan et al. |
| 5,593,973 A | 1/1997 | Carter |
| 5,593,975 A | 1/1997 | Cristalli |
| 5,593,976 A | 1/1997 | Mongelli et al. |
| 5,665,754 A | 9/1997 | Feldman et al. |
| 5,668,139 A | 9/1997 | Belardinelli et al. |

(Continued)

FOREIGN PATENT DOCUMENTS

EP 0488331 A1 6/1992

(Continued)

OTHER PUBLICATIONS

Thomas Nogrady, Donald F. Weaver, Medicinal Chemistry: A Molecular and Biochemical Approach, 3rd edition (Oxford University Press 2005) p. 135.*
Silverman, R., The Organic Chemistry of Drug Design and Drug Action, (Academic Press 1992), pp. 16-17.*
Kerns, Edward et al, Drug-like Properties: Concepts, Structure Design and Methods: from ADME to Toxicity Optimization, (Elsevier, 2008) pp. 92, 96.*
Clerici, Digestive Diseases and Sciences, vol. 37, No. 5 (May 1992), pp. 791-798.*
Remuzon, J. Med. Chem. 1992,35, 2898-2909.*
Goodwin, J Med Chem 2001; 44:3721-3729.*
*The Merck Manual of Diagnosis and Therapy*, Beers, M.A., et al. (eds.), Merck and Company, (Jan. 1999), 924-925.

(Continued)

*Primary Examiner* — Mark Beach
(74) *Attorney, Agent, or Firm* — Schwegman, Lundberg & Woessner, P.A.

(57) ABSTRACT

The invention provides compounds having the following general formula (I):

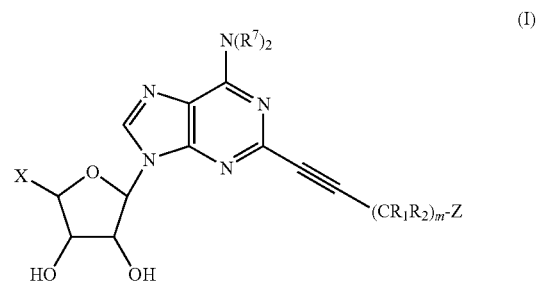

wherein X, $R^1$, $R^2$, $R^7$ and Z are as described here.

52 Claims, 17 Drawing Sheets

U.S. PATENT DOCUMENTS

| | | |
|---|---|---|
| 5,696,254 A | 12/1997 | Mansour et al. |
| 5,731,296 A | 3/1998 | Sollevi |
| 5,756,706 A | 5/1998 | Mansour et al. |
| 5,776,940 A | 7/1998 | Daluge et al. |
| 5,854,081 A | 12/1998 | Linden et al. |
| 5,877,180 A | 3/1999 | Linden et al. |
| 5,877,190 A | 3/1999 | Dhainaut et al. |
| 5,932,558 A | 8/1999 | Cronstein et al. |
| 5,998,386 A | 12/1999 | Feldman |
| 6,004,945 A | 12/1999 | Fukunaga |
| RE36,494 E | 1/2000 | Olsson et al. |
| 6,020,321 A | 2/2000 | Cronstein et al. |
| 6,020,339 A | 2/2000 | Perrier et al. |
| 6,034,089 A | 3/2000 | Han et al. |
| 6,060,481 A | 5/2000 | LaNoue et al. |
| 6,117,878 A | 9/2000 | Linden et al. |
| 6,232,297 B1 | 5/2001 | Linden et al. |
| 6,303,619 B1 | 10/2001 | Linden et al. |
| 6,322,771 B1 | 11/2001 | Linden et al. |
| 6,326,359 B1 | 12/2001 | Monaghan et al. |
| 6,332,771 B1 | 12/2001 | Adams et al. |
| 6,339,072 B2 | 1/2002 | Martin et al. |
| 6,350,735 B1 | 2/2002 | Monaghan |
| 6,387,889 B1 | 5/2002 | Endo et al. |
| 6,407,076 B1 | 6/2002 | Box et al. |
| 6,448,235 B1 | 9/2002 | Linden et al. |
| 6,455,510 B1 | 9/2002 | Charles et al. |
| 6,514,949 B1 | 2/2003 | Linden et al. |
| 6,525,032 B2 | 2/2003 | Mantrell et al. |
| 6,531,457 B2 | 3/2003 | Linden et al. |
| 6,545,002 B1 | 4/2003 | Linden et al. |
| 6,624,158 B2 | 9/2003 | Mantell et al. |
| 6,670,334 B2 | 12/2003 | Linden |
| 6,936,596 B2 | 8/2005 | Konno et al. |
| 7,160,890 B2 | 1/2007 | Castelhano et al. |
| 7,214,665 B2 | 5/2007 | Linden et al. |
| 7,217,702 B2 | 5/2007 | Beauglehole et al. |
| 7,226,913 B2 | 6/2007 | Linden et al. |
| 7,307,079 B2 | 12/2007 | Den Hartog et al. |
| 7,378,400 B2 * | 5/2008 | Rieger et al. ............... 514/46 |
| 7,396,825 B2 | 7/2008 | Okusa et al. |
| 7,427,606 B2 | 9/2008 | Linden et al. |
| 7,442,687 B2 | 10/2008 | Rieger et al. |
| 7,553,823 B2 * | 6/2009 | Zablocki et al. .............. 514/46 |
| 7,576,069 B2 | 8/2009 | Rieger et al. |
| 7,589,076 B2 | 9/2009 | Rieger et al. |
| 7,605,143 B2 | 10/2009 | Rieger et al. |
| 7,737,127 B2 | 6/2010 | Linden et al. |
| 7,875,595 B2 | 1/2011 | Rieger et al. |
| 7,888,329 B2 | 2/2011 | Rieger et al. |
| 7,989,431 B2 | 8/2011 | Rieger et al. |
| 8,058,259 B2 | 11/2011 | Thompson et al. |
| 2001/0027185 A1 | 10/2001 | Linden et al. |
| 2002/0032168 A1 | 3/2002 | Mantrell et al. |
| 2002/0058641 A1 | 5/2002 | Mantell et al. |
| 2002/0072597 A1 | 6/2002 | Mantell et al. |
| 2002/0111327 A1 | 8/2002 | Linden et al. |
| 2003/0013675 A1 | 1/2003 | Yeadon et al. |
| 2003/0162742 A1 | 8/2003 | Linden et al. |
| 2003/0186925 A1 | 10/2003 | Palmer et al. |
| 2003/0186926 A1 | 10/2003 | Linden et al. |
| 2004/0229246 A1 | 11/2004 | Fishman et al. |
| 2005/0004221 A1 | 1/2005 | Hildebrand et al. |
| 2005/0020532 A1 | 1/2005 | Elzein et al. |
| 2005/0065341 A1 | 3/2005 | Wang et al. |
| 2005/0182018 A1 | 8/2005 | Linden et al. |
| 2005/0261236 A1 | 11/2005 | Okusa et al. |
| 2005/0282831 A1 | 12/2005 | Beauglehole et al. |
| 2006/0030889 A1 | 2/2006 | Ben-Haim et al. |
| 2006/0040888 A1 | 2/2006 | Rieger et al. |
| 2006/0040889 A1 | 2/2006 | Rieger et al. |
| 2006/0052298 A1 | 3/2006 | Guerrant et al. |
| 2006/0100169 A1 | 5/2006 | Rieger et al. |
| 2006/0128652 A1 | 6/2006 | Jagtap et al. |
| 2006/0128708 A1 | 6/2006 | Diamond et al. |
| 2006/0217343 A1 | 9/2006 | Rieger et al. |
| 2007/0027073 A1 | 2/2007 | Rubinstein et al. |
| 2007/0032450 A1 | 2/2007 | Rieger |
| 2007/0072843 A1 | 3/2007 | Wang et al. |
| 2007/0232559 A1 | 10/2007 | Linden et al. |
| 2007/0265440 A1 | 11/2007 | Linden et al. |
| 2008/0009460 A1 | 1/2008 | Linden et al. |
| 2008/0027022 A1 * | 1/2008 | Linden et al. ............... 514/46 |
| 2008/0064653 A1 | 3/2008 | Li et al. |
| 2008/0214581 A1 * | 9/2008 | Allen et al. ................ 514/263.2 |
| 2008/0262001 A1 * | 10/2008 | Kranenburg et al. .... 514/263.22 |
| 2008/0312160 A1 * | 12/2008 | Guerrant et al. ................ 514/19 |
| 2009/0012035 A1 * | 1/2009 | Jacobson et al. ................ 514/46 |
| 2009/0081764 A1 * | 3/2009 | Pausch et al. ............. 435/254.2 |
| 2009/0118309 A1 | 5/2009 | Beauglehole et al. |
| 2009/0123510 A1 * | 5/2009 | Cronstein et al. ............ 424/422 |
| 2009/0162282 A1 | 6/2009 | Thompson et al. |
| 2009/0162292 A1 | 6/2009 | Thompson et al. |
| 2009/0170803 A1 | 7/2009 | Linden et al. |
| 2009/0181920 A1 * | 7/2009 | Watkins et al. ................ 514/45 |
| 2009/0253647 A1 | 10/2009 | Rieger et al. |
| 2009/0280059 A1 | 11/2009 | Rieger et al. |
| 2009/0298788 A1 | 12/2009 | Rieger et al. |
| 2009/0325967 A1 * | 12/2009 | Fairhurst et al. .............. 514/245 |
| 2010/0166698 A1 | 7/2010 | Rieger |
| 2011/0136755 A1 | 6/2011 | Rieger et al. |

FOREIGN PATENT DOCUMENTS

| | | |
|---|---|---|
| EP | 0488336 A1 | 6/1992 |
| EP | 0488336 B1 | 5/1995 |
| EP | 0700908 | 3/1996 |
| EP | 1110554 A1 | 6/2001 |
| EP | 1150991 | 11/2001 |
| EP | 1194440 A2 | 4/2002 |
| EP | 1194440 B1 | 2/2005 |
| HU | 174074 | 10/1979 |
| HU | 0200224 A | 6/2002 |
| IL | 144188 B | 12/2008 |
| JP | 6299330 A | 5/1987 |
| JP | 06299335 A | 5/1987 |
| JP | 03287537 A | 12/1991 |
| JP | 59197 A | 1/1993 |
| JP | 59198 A | 1/1993 |
| JP | 05025195 A | 2/1993 |
| JP | 05163294 A2 | 6/1993 |
| JP | 07508718 A | 9/1995 |
| JP | 11335302 A | 12/1999 |
| JP | 20007695 A | 1/2000 |
| JP | 2002536300 | 10/2002 |
| NZ | 530976 | 7/2005 |
| WO | WO-9005526 A1 | 5/1990 |
| WO | WO-9015812 A1 | 12/1990 |
| WO | WO-9109864 A1 | 7/1991 |
| WO | WO-93/22328 A1 | 11/1993 |
| WO | WO-95/11681 A1 | 5/1995 |
| WO | WO-96/02553 A2 | 2/1996 |
| WO | WO-96/04280 A1 | 2/1996 |
| WO | WO-98/47509 A1 | 10/1998 |
| WO | WO-9852611 | 11/1998 |
| WO | WO-98/57651 A1 | 12/1998 |
| WO | WO-98/57661 A1 | 12/1998 |
| WO | WO-99/34804 A1 | 7/1999 |
| WO | WO-99/38877 A2 | 8/1999 |
| WO | WO-99/41267 A1 | 8/1999 |
| WO | WO-99/62518 A1 | 12/1999 |
| WO | WO-99/63938 A | 12/1999 |
| WO | WO-99/67263 A1 | 12/1999 |
| WO | WO-99/67264 A1 | 12/1999 |
| WO | WO-99/67265 A1 | 12/1999 |
| WO | WO-99/67266 A1 | 12/1999 |
| WO | WO-0012098 A1 | 3/2000 |
| WO | WO-00/23457 A1 | 4/2000 |
| WO | WO-00/44763 A2 | 8/2000 |
| WO | WO-0044763 A3 | 8/2000 |
| WO | WO-00/72799 A2 | 12/2000 |
| WO | WO-00/78774 A2 | 12/2000 |
| WO | WO-00/78777 A1 | 12/2000 |
| WO | WO-00/78779 A2 | 12/2000 |
| WO | WO-0078774 A3 | 12/2000 |
| WO | WO-01/94368 A1 | 12/2001 |
| WO | WO-02/09701 A1 | 2/2002 |
| WO | WO-02/22630 A1 | 3/2002 |

| | | | |
|---|---|---|---|
| WO | WO-02/096462 A1 | 12/2002 |
| WO | WO-03/014137 A1 | 2/2003 |
| WO | WO-03/029264 A2 | 4/2003 |
| WO | WO-03029264 A2 | 4/2003 |
| WO | WO-03029264 A3 | 4/2003 |
| WO | WO-03/086408 A1 | 10/2003 |
| WO | WO-03086408 A1 | 10/2003 |
| WO | WO-03090733 A1 | 11/2003 |
| WO | WO-2005084653 A2 | 9/2005 |
| WO | WO-2005/097140 A2 | 10/2005 |
| WO | WO-2005/107463 A1 | 11/2005 |
| WO | WO-2006/015357 A2 | 2/2006 |
| WO | WO-2006015357 A3 | 2/2006 |
| WO | WO-2006/023272 A1 | 3/2006 |
| WO | WO-2006/028618 A1 | 3/2006 |
| WO | WO-2007/092936 A2 | 8/2007 |
| WO | WO-2007092936 A3 | 8/2007 |
| WO | WO-2007092936 C2 | 8/2007 |
| WO | WO-2007/120972 A2 | 10/2007 |
| WO | WO-2007120972 A3 | 12/2007 |
| WO | WO-2008124150 A1 | 10/2008 |

OTHER PUBLICATIONS

*Taber's Cyclopedic Medical Dictionary, 19th Edition*, Venes, et al. (eds.), F. A. Davis, Philadelphia, (2001), 960-961.

"STN Database Descriptions", *Chemical Abstracts Catalog*, (2006), p. 52.

"U.S. Appl. No. 10/263,379, Advisory Action mailed Mar. 1, 2006", 7 pgs.

"U.S. Appl. No. 10/263,379, Advisory Action mailed Apr. 11, 2006", 5 pgs.

"U.S. Appl. No. 10/263,379, Final Office Action mailed Nov. 1, 2006", 6 pgs.

"U.S. Appl. No. 10/263,379, Final Office Action mailed Nov. 9, 2005", 15 pgs.

"U.S. Appl. No. 10/263,379, Final Office Action mailed Nov. 23, 2004", 43 pgs.

"U.S. Appl. No. 10/263,379, Non-Final Office Action mailed Apr. 25, 2005", 13 pgs.

"U.S. Appl. No. 10/263,379, Non-Final Office Action mailed Jun. 14, 2006", 7 pgs.

"U.S. Appl. No. 10/263,379, Non-Final Office Action mailed Jun. 17, 2004", 35 pgs.

"U.S. Appl. No. 10/263,379, Notice of Allowance mailed Dec. 12, 2006", 4 pgs.

"U.S. Appl. No. 10/263,379, Response filed Feb. 8, 2006 to Final Office Action mailed Nov. 9, 2005", 19 pgs.

"U.S. Appl. No. 10/263,379, Response filed Feb. 23, 2005 to Final Office Action mailed Nov. 23, 2004", 20 pgs.

"U.S. Appl. No. 10/263,379, Response filed Apr. 4, 2006 to Final Office Action mailed Nov. 9, 2005 and Advisory Action mailed Mar. 1, 2006", 19 pgs.

"U.S. Appl. No. 10/263,379, Response filed May 2, 2006 to Final Office Action mailed Nov. 9, 2005 and Advisory Action mailed Apr. 11, 2006", 15 pgs.

"U.S. Appl. No. 10/263,379, Response filed Sep. 11, 2006 to Non Final Office Action mailed Jun. 14, 2006", 13 pgs.

"U.S. Appl. No. 10/263,379, Response filed Sep. 26, 2005 to Non Final Office Action mailed Apr. 25, 2005", 19 pgs.

"U.S. Appl. No. 10/263,379, Response filed Oct. 18, 2004 to Non Final Office Action mailed Jun. 17, 2004", 25 pgs.

"U.S. Appl. No. 10/263,379, Response filed Nov. 21, 2006 to Final Office Action mailed Nov. 11, 2006", 13 pgs.

"U.S. Appl. No. 10/412,726, Final Office Action mailed Jul. 19, 2007", 10 pgs.

"U.S. Appl. No. 10/412,726, Final Office Action mailed Jul. 23, 2008", 15 pgs.

"U.S. Appl. No. 10/412,726, Final Office Action mailed Oct. 8, 2004", 7 pgs.

"U.S. Appl. No. 10/412,726, Final Office Action mailed Dec. 5, 2005", 13 pgs.

"U.S. Appl. No. 10/412,726, Non Final Office Action mailed Mar. 16, 2005", 15 pgs.

"U.S. Appl. No. 10/412,726, Non Final Office Action mailed Apr. 7, 2004", 8 pgs.

"U.S. Appl. No. 10/412,726, Non Final Office Action mailed Oct. 30, 2006", 12 pgs.

"U.S. Appl. No. 10/412,726, Non-Final Office Action mailed Feb. 22, 2008", 10 pgs.

"U.S. Appl. No. 10/412,726, Notice of Allowance mailed Mar. 12, 2009", 10 pgs.

"U.S. Appl. No. 10/412,726, Response filed Jan. 22, 2009 to Final Office Action mailed Jul. 23, 2008", 23 pgs.

"U.S. Appl. No. 10/412,726, Response filed Feb. 8, 2005 to Final Office Action mailed Oct. 8, 2004", 22 pgs.

"U.S. Appl. No. 10/412,726, Response filed Apr. 10, 2008 to Non-Final Office Action mailed Feb. 22, 2008", 30 pgs.

"U.S. Appl. No. 10/412,726, Response filed Apr. 27, 2007 to Non Final Office Action mailed Oct. 30, 2006", 23 pgs.

"U.S. Appl. No. 10/412,726, Response filed May 5, 2006 to Final office action mailed Dec. 5, 2005", 23 pgs.

"U.S. Appl. No. 10/412,726, Response filed Jul. 9, 2004 to Non Final Office Action mailed Jul. 9, 2004", 20 pgs.

"U.S. Appl. No. 10/412,726, Response filed Sep. 16, 2005 to Non Final Office Action mailed Mar. 16, 2005", 25 pgs.

"U.S. Appl. No. 10/412,726, Response filed Oct. 31, 2007 to Final Office Action mailed Jul. 19, 2007", 28 pgs.

"U.S. Appl. No. 11/196,529, Final Office Action mailed Dec. 2, 2008", 13 pgs.

"U.S. Appl. No. 11/196,529, Non-Final Office Action mailed Jun. 23, 2008", 33 pgs.

"U.S. Appl. No. 11/196,529, Notice of Allowance mailed Feb. 24, 2009", 8 pgs.

"U.S. Appl. No. 11/196,529, Response filed Dec. 19, 2008 to Final Office Action mailed Dec, 2, 2008", 19 pgs.

"U.S. Appl. No. 11/196,529, Response filed Aug. 7, 2008 to Non Final Office Action mailed Jun. 23, 2008", 21 pgs.

"Application U.S. Appl. No. 11/196,798, Non-Final Office Action mailed Mar. 31, 2008", 30 pgs.

"U.S. Appl. No. 11/196,798, Non-Final Office Action mailed Sep. 17, 2008", 6 pgs.

"U.S. Appl. No. 11/196,798, Notice of Allowance mailed Feb. 24, 2009", 5 pgs.

"U.S. Appl. No. 11/196,798, Response filed May 21, 2008 to Non Final Office Action mailed Apr. 21, 2008", 18 pgs.

"U.S. Appl. No. 11/196,798, Response filed Dec. 17, 2008 to Non-Final Office Action mailed Sep. 17, 2008", 17 pgs.

"U.S. Appl. No. 11/196,802, Notice of Allowance mailed Mar. 28, 2008", 33 pgs.

"U.S. Appl. No. 11/672,868, Non-Final Office Action mailed Apr. 13, 2009", 21 pgs.

"U.S. Appl. No. 11/673,360, Final Office Action mailed Dec. 17, 2009", 27 pgs.

"U.S. Appl. No. 11/673,360, Non-Final Office Action mailed Apr. 22, 2009", 33 pgs.

"U.S. Appl. No. 11/673,360, Response filed Sep. 21, 2009 to Non Final Office Action mailed Apr. 22, 2009", 27 pgs.

"U.S. Appl. No. 11/739,680, Non-Final Office Action mailed Mar. 31, 2009", 59 pgs.

"U.S. Appl. No. 12/487,265, Non-Final Office Action mailed Dec. 18, 2009", 5 pgs.

"U.S. Appl. No. 12/487,235, Non-Final Office Action mailed Dec. 28, 2009", 7 pgs.

"Argentina Application Serial No. P000100433, Response filed to Office Action mailed Oct. 20, 2008", (w/ English Translation of Claims), 9 pgs.

"Australian Application Serial No. 2002362443, Examiner's First Report mailed May 29, 2007", 4 pgs.

"Australian Application Serial No. 2002362443, Response filed May 1, 2008 to Examiner's First Report mailed May 29, 2007", 46 pgs.

"Australian Patent Application No. 2005201255, Examiner's First Report mailed Apr. 13, 2007", 2 pgs.

"Australian Patent Application No. 2005201255, Response filed Oct. 2, 2007 to Examiner's Report mailed Apr. 13, 2007", 8 pgs.

"Australian Patent Application No. 27454/00, Examiner's Report mailed Feb. 20, 2003", 1 pg.

"Australian Patent Application No. 27454/00, Response filed Oct. 19, 2004 to Examiner's Report mailed Feb. 20, 2003", 14 pgs.

"Canadian Application Serial No. 2,460,911, Office Action mailed Jun. 12, 2009", 7 pgs.
"Canadian Patent Application No. 2,361,614, Office Action mailed Jul. 20, 2007", 2 pgs.
"Canadian Patent Application No. 2,361,614, Response filed Nov. 7, 2007 to Office Action mailed Jul. 20, 2007", 9 pgs.
"European Application Serial No. 02800432.3, Communication mailed Jan. 13, 2005", 3 pgs.
"European Application Serial No. 02800432.3, Communication mailed Aug. 30, 2005", 2 pgs.
"European Application Serial No. 02800432.3, Communication mailed Sep. 20, 2004", 6 pgs.
"European Application Serial No. 02800432.3, Communication mailed Oct. 16, 2006", 5 pgs.
"European Application Serial No. 02800432.3, Response filed Feb. 21, 2007 to Communication mailed Oct. 16, 2006", 19 pgs.
"European Application Serial No. 02800432.3, Response filed Nov. 1, 2005 to Communication mailed Aug. 30, 2005", 19 pgs.
"European Patent Application No. 00905833.0, Response filed May 14, 2003 to Communication mailed Nov. 13, 2002", 12 pgs.
"European Patent Application No. 00905833.0, Communication mailed Nov. 13, 2002", 3 pgs.
"Indian Application Serial No. 00383/KOLNP/2004, Examination Report mailed Jun. 8, 2007", 1 pg.
"Indian Application Serial No. 00383/KOLNP/2004, First Examination Report mailed Aug. 28, 2006", 2 pgs.
"Indian Application Serial No. 00383/KOLNP/2004, Response filed Mar. 6, 2007 to First Examination Report mailed Aug. 28, 2006", 33 pgs.
"Indian Application Serial No. 00383/KOLNP/2004, Response filed Aug. 2, 2007 to Examination Report mailed Jun. 8, 2007", 19 pgs.
"Indian Application Serial No. 00383/KOLNP/2004, Voluntary Amendment filed Apr. 26, 2007", 4 pgs.
"Indian Patent Application No. IN/PCT/2001/00763, First Examination Report mailed Aug. 31, 2007", 12 pgs.
"Indian Patent Application No. IN/PCT/2001/00763, Response filed Apr. 4, 2008 to First Examination Report mailed Aug. 31, 2007", 55 pgs.
"International Search Report for corresponding PCT Application No. PCT/US02/31383 mailed May 2, 2003", 8 pgs.
"International Search Report for corresponding PCT Application No. PCT/US2005/027474", (Jan. 25, 2006), 5 pgs.
"International Search Report for corresponding PCT Application No. PCT/US2005/027479", (Sep. 6, 2006), 6 pgs.
"Israeli Application Serial No. 144188, Response filed Feb. 24, 2005 to Notification of Defects dated Aug. 30, 2004", (w/ English Translation), 11 pgs.
"Japanese Application serial No. 2003-532511, Office Action mailed Oct. 13, 2009", 2 pgs.
"Japanese Application Serial No. 2003-583427, Office Action Mailed Aug. 25, 2009", 1 pg.
"Malaysian Patent Application No. PI200000343, Response filed Mar. 7, 2005 to Substantive Examination Adverse Report mailed Dec. 7, 2004", 14 pgs.
"Malaysian Patent Application No. PI20000343, Substantive Examination Examiner's Report to the Registrar mailed Dec. 7, 2004", 2 pgs.
"New Zealand Application Serial No. 532062, First Examination Report mailed May 14, 2004", 1 pg.
"New Zealand Application Serial No. 532062, Response filed Feb. 9, 2006 to Second Examination Report mailed Dec. 13, 2005", 8 pgs.
"New Zealand Application Serial No. 532062, Response filed Jul. 6, 2005 to First Examination Report mailed May 14, 2004", 6 pgs.
"New Zealand Application Serial No. 532062, Second Examination Report mailed Dec. 13, 2005", 2 pgs.
"New Zealand Application Serial No. 532062, Examination Report mailed May 11, 2006", 1 pg.
"New Zealand Application Serial No. 532062, Response filed May 24, 2006 to Examination Report mailed May 11, 2006", 16 pgs.
"New Zealand Application Serial No. 545787, First Examination Report mailed Mar. 14, 2006", 2 pgs.
"New Zealand Application Serial No. 545787, Fourth Examination Report mailed Oct. 11, 2007", 2 pgs.
"New Zealand Application Serial No. 545787, Reponse filed Nov. 12, 2007 to Examination Report mailed Oct. 11, 2007", 5 pgs.
"New Zealand Application Serial No. 545787, Response filed Jul. 5, 2007 to Examination Report mailed Jan. 11, 2007", 5 pgs.
"New Zealand Application Serial No. 545787, Response filed Aug. 14, 2007 to Examination Report mailed Jul. 11, 2007", 11 pgs.
"New Zealand Application Serial No. 545787, Response filed Dec. 13, 2006 to Examination Report mailed Mar. 14, 2006", 21 pgs.
"New Zealand Application Serial No. 545787, Second Examination Report mailed Jan. 11, 2007", 4 pgs.
"New Zealand Application Serial No. 545787, Third Examination Report mailed Jul. 11, 2007", 2 pgs.
"New Zealand Application Serial No. 556354, Examination Report mailed Jul. 11, 2007", 21 pgs.
"New Zealand Application Serial No. 556354, Response filed Jul. 4, 2008 to Examination Report mailed Jul. 11, 2007", 22 pgs.
"New Zealand Application Serial No. 556354, First Examination Report mailed Jul. 11, 2007", 21 pgs.
"New Zealand Application Serial No. 556354, Response filed Sep. 10, 2008 to Examination Report mailed Jul. 17, 2008", 12 pgs.
"New Zealand Application Serial No. 556354, Second Examination Report mailed Jul. 17, 2008", 1 pg.
"Norweigan Application Serial No. 20013507, Office Action mailed Oct. 24, 2005", (w/ English Translation), 10 pgs.
"Norweigan Application Serial No. 20013507, Response filed Feb. 6, 2006 to Office Action mailed Oct. 24, 2005", 94 pgs.
"Norweigan Application Serial No. 20013507, Response filed Apr. 26, 2005 to Office Action mailed Nov. 2, 2004", 16 pgs.
"Norweigan Application Serial No. 20013507, Response filed Oct. 17, 2005 to Office Action mailed Jun. 1, 2005", 23 pgs.
"Norweigan Patent Application No. 20013507, Office Action mailed Jun. 1, 2005", 3 pgs.
"Norweigan Patent Application No. 20013507, Office Action mailed Nov. 2, 2004", 5 pgs.
"PCT Application No. PCT/US00/02324, Written Opinion mailed Dec. 1, 2000", 6 pgs.
"PCT Application No. PCT/US00/02324. International Search Report mailed Oct. 20, 2000", 8 pgs.
"PCT Application No. PCT/US07/61919 International Search Report mailed Nov. 7, 2007", 3 pgs.
"PCT Application No. PCT/US07/61919, Written Opinion mailed Nov. 7, 2007", 8 pgs.
"Russian Application Serial No. 2001124348, Official Action mailed Sep. 29, 2003", (w/ English Translation), 9 pgs.
"Russian Application Serial No. 2001124348, Response filed—Jan. 30, 2004 to Official Action mailed Sep. 29, 2003", (w/ English Translation of Claims), 48 pgs.
"Singapore Application Serial No. 200401458-5, Invitation to Respond to Written Opinion mailed Nov. 17, 2006", 12 pgs.
"Singapore Application Serial No. 200401458-5, Response filed Apr. 16, 2007 to Invitation to Respond to Written Opinion mailed Nov. 17, 2006", 30 pgs.
Abiru, T., et al., "Nucleosides and nucleotides. 107. 2-(cycloakylalkynyl)adenosines: adenosine $A_2$ receptor agonists with potent antihypertensive effects", *Journal of Medicial Chemistry*, 35(12), (Jun. 12, 1992), 2253-2260.
Adah, S. A., "Synthesis of Complex Ethynyladenosines Using Organic Triflic Enolates in Palladium-Catalyzed Reactions: Potential Agonists for the Adenosine $A_2$ Receptor", *Tetrahedron*, 53, (1997), 6747-6754.
Adah, S. A, et al., "Synthesis of complex ethynyladenosines using organic triflic enolates in palladium-catalyzed reactions: Potential agonists for the adenosine $A_2$ receptor", *Tetrahedron*, 53(20), (May 19, 1997), 6747-6754.
Ali, H., et al., "Methylxanthines Block Antigen-induced Responses in RBL-2H3 Cells Independently of Adenosine Receptors or Cyclic AMP: Evidence for Inhibition of Antigen Binding to IgE", *Journal of Pharmacology and Experimental Therapeutics*, 258, (1991), 954-962.
Andersson, P., et al., "Anti-anaphylactic and anti-inflammatory effects of xanthines in the lung", *Curr. Clin. Pract. Ser.*, (1985), 187-192.

Andrews, F. J., et al., "Effect of Nonsteroidal Anti-Inflammatory Drugs on LFA-1 and ICAM-1 Expression in Gastric Mucosa", *American Journal of Physiology—Gastrointestinal and Liver Physiology*, 266, (1994), G657-G664.

Appleyard, C. B., et al., "Tumor Necrosis Factor Mediation of NSAID-Induced Gastric Damage: Role of Leukocyte Adherence", *American Journal of Physiology—Gastrointestinal and LIve Physiology*, 33, (1996), G42-G48.

Auchampach, et al., "A3 adenosine receptor agonist IB-MECA reduces myocardial ischemiaa-reperfusion injury in dogs", *Am J Physiol Heart Circ Physiol* vol. 285, (2003), pp. H607-H613.

Ballas, S. K, "Sickle Cell Anaemia: Progress in Pathogenesis and Treatment", *Drugs* vol. 62 No. (8), (2002), 1143-1172.

Baraldi, Pier G., et al., "Synthesis and Biological Activity of a New Series of $N^6$-Arylcarboamoyl, 2-(Ar)alkynyl-$N^6$-arylcarbomoyl, and $N^6$-Carboxamido derivatives of adenosine-5'-N-ethyluronamide and $A_1$ and $A_3$ Adenosine receptor agonists", *Journal of Medicainal Chemistry*, 41(17), (Aug. 13, 1998), 3174-3185.

Barold, S. S., et al., "Significance of Transient Electrocardiographic Q Waves in Coronary Artery Diseasse", *Cardiology Clinics*, 5(3), (Aug. 1987), 367-380.

Beck, P. L., et al., "Mechanisms of NSAID-Induced Gastrointestinal Injury Defined Using Mutant Mice", *Gastroenterology*, 119(3), (2000), 699-705.

Beers, M. H, et al., "The Merck Manual of Diagnosis and Therapy", *Merck Research Laboratories*, (1999), 245-256.

Belcher, J. D., et al., "Transgenic Sickle Mice Have Vascular Inflammation", *Blood*, 101(10), (2003), 3953-3959.

Berkich, D. A., et al., "Evidence of Regulated Coupling of A1 Adenosine Receptors by Phosphorylation in Zucker Rats.", *American Journal of Physiology*, 268 (4), (Apr. 1995).

Bhattacharya, S., et al., "Effects of Long-term Treatment With the Allosteric Enhancer, PD81,723, on Chinese Hamster Ovary Cells Expressing Recombitant Human A1 Adenosine Receptors", *Molecular Pharmacology*, 50 (1), (Jul. 1996), 104-111.

Bhattacharya, S., et al., "The Allosteric Enhancer, PD 81,723, Stabilizes Human A1 Adenosine Receptor Coupling to G Proteins", *Biochimica et Biophysica Acta*, 1265 (1), (Feb. 1995), 15-21.

Bradford, M. M., "A Rapid and Sensitive Method for the Quantities of Quantitation of Microgram Quantities of Protein Utilizing the Principle of Protein-Dye Binding", *Analytical Biochemistry*, 72, (1976), 248-254.

Bridges, A. J., et al., "$N^6$-[2-(3,5-Dimethoxyphenyl)-2-(2-Methylphenyl)-Ethyl]Adenosine and Its Uronamide Derivatives. Novel Adenosine Agonists With Both High Affinity and High Selectivity for the Adenosine $A_2$ Receptor", *Jouranl of Medicinal Chemistry*, 31(7), (Jul. 1988), 1282-1285.

Brodie, D. A., et al., "A Study of the Factors Involved in the Production of Gastric Ulcers by the Restraint Technique", *Gastroenterology*, 38(3), (1960), 353-360.

Bruns, R. F., "Adenosine Receptors—Roles and Pharmacology", *Biological Actions of Extracellular ATP*, 603, Annals of The New York Academy of Sciences, (1990), 211-226.

Bruns, R. F., et al., "Characterization of the $A_2$ Adenosine Receptor Labeled by [$^3$H]NECA in Rat Striatal Membranes", *Molecular Pharmacology*, 29, (1986), 331-346.

Buchanan, G. R., et al., "Sickle Cell Disease", *Hematology 2004*, (2004), 35-47.

Buster, B., et al., "The Effect of Adenosine Receptor Agonists on Neutrophil Pleoctosis and Blood-Brain Barrier Pathophysiology in Experimental Bacterial Meningitis", *Abstract of the Interscience Conference on Antimicrobial Agent and Chemotherapy*, 27, Abstract No. B-72, (1997), p. 39.

Camaioni, E, et al., "Adenosine receptor agonists: synthesis and bilogical evaluation of the diastereoisomers of 2-(3-Hydroxy-3-phenyl-1-propyn-1-yl)NECA", *Bioorganic & Medicinal Chemistry* 5(12), (Dec. 1997), 2267-2275.

Cargnoni, et al., "Role of $A_{2A}$ Receptors in the Modulation of Myocardial Reperfusion damage", *Journal of Cardiovascular Pharmacology* vol. 33 No. (6), (1999), 883-893.

Carruthers, A. M., et al., "Hypotensive Responses to the Putative Adenosine $A_3$ REceptor Agonist $N^6$-2-(4-Aminophenyl)-Ethyladenosine in the Rat", *Drug Development Research*, 30, (1993), 147-152.

Cassada, D C, et al., "Adenosine $A^{2A}$ agonist reduces paralysis after spinal cord ischemia: correlation with $A_{2A}$ receptor expression on motor neurons", *Annals of Thoracic Surgery*, 74(3), (Sep. 2002), 846-849; discussion 849-50.

Cassada, D C, et al., "Adenosine A2A analogue ATL-146e reduces systemic turor necrosing factor-alpha and spinal cord capillary platelet-endothelial cell adhesion molecule-1 expression after spinal cord ischemia", *Jouranl of Vascular Surgery*, 35(5), (May 2002), 994-98.

Cassada, D C, et al., "Adenosine A2A analogue improves neurologic outcome after spinal cord trauma in the rabbit.", *Journal of Trauma-Injury Infection & Critical Care*, 53(2), (Aug. 2002), 225-9.

Cassada, D C, et al., "Adenosine Analogue Reduces Spinal Cord Reperfusion Injury in a Time-Dependent Fashion", *Surgery*, 130(2), (Aug. 2001), 230-35.

Cassada, D C, et al., "An adenosine A2A agonist, ATL-146e, reduces paralysis and apoptosis during rabbit spinal cord reperfusion.", *Journal of Vascular Surgery*, 34(3), (Sep. 2001), 482-88.

Cassada, D C, et al., "Systemic A2A agonist ameliorates ischemic reperfusion injury in the rabbit spinal cord", *Annals of Thoracic Surgery*, 72(4), (Oct. 2001), 1245-50.

Cembrzynska-Nowak, M, et al., "Elevated Release of Tumor Necrosis Factor-alpha and Interferon-gamma by Bronchoalveolar Leukocytes From Patients With Bronchial Asthma.", *American Review of Respiratory Disease*, 147(2), (1993), 291-295.

Charache, S., et al., "Effect of Hydroxyurea on the Frequency of Painful Crisis in Sickle Cell Anemia", *The New England Journal of Medicine*, 332(20), (1995), 1317-1322.

Chies, J. A. B., et al., "Sickle Cell Disease: A Chronic Inflammatory Condition", *Medical Hypotheses*, 57(1), (2001), 46-50.

Cohen, S. B, et al., "Adenosine-2 alpha analogue augments the treatment in experimental infectious arthritis", *Poster presented at the 48th Annual Meeting of the Orthopaedic Research Society*, Dallas, USA, (Feb. 10-13, 2002, Poster No. 0689.

Cothran, D. L., et al., "Ontogeny of Rat Myocardial A1 Adenosine Receptors", *Biol Neonate*, 68 (2), , (1995), pp. 111-118.

Cristalli, G, et al., "2-Alkynyl Derivatives of Adenosine-5'-N-ethyluronamide: Selective A2 Adenosine Receptor Agonists with Potent Inhibitory Activity on Platelet Aggregation", *Journal of Medicinal Chemistry*, (1994), 1720-1726.

Cristalli, G., "2-Alkynyl Derivatives of Adenosine and Adenosine-5'-N-ethyluronamide as Selective Agonists at A2 Adenosine Receptors", *Journal of Medicinal Chemistry*, 35 (13), (1992), 2363-2368.

Cristalli, G., et al., "2-Alkynyl derivatives of adenosine-5'-N-ethyluronamide: selective A2 adenosine receptor agonists with potent inhibitory activity on platelet aggregation.", *J Med Chem.*, 37 (11), (May 27, 1994), 1720-6.

Cristalli, G., et al., "2-Aralkynyl and 2-Heteroalkynyl Derivatives of Adenosine-5'-N-ethyluronamide as Selective A2a Adenosine Receptor Agonists", *J. Med. Chem.*, 38 (9), (1995), 1462-1472.

Cristalli, G., et al., "2-Aralkynyl and 2-heteroalkynyl derivatives of adenosine-5'-N-ethyluronamide as selective A2a adenosine receptor agonists.", *J Med Chem.*, 38(9), (Apr. 28, 1995), 1462-72.

Cristalli, G., et al., "Characterization of Potent Ligands at Human Recombinant Adenosine Receptors", *Drug Development Research*, 45, Research Overview, (1998), 176-181.

Cronstein, B N., et al., "Neutrophil Adherence to Endothelium is Enhanced Via Adenosine A1 Receptors and Inhibited Via Adenosine A2 Receptors", *The Journal of Immunology*, 148(7), (1992), pp. 2201-2206.

Cronstein, B. N., "Adenosine Modulates the Generation of Superoxide Anion by Stimulated Human Neutrophils Via Interaction With a Specific Cell Surface Receptor", *Annals New York Academy of Science*, 451, (1985), 291-314.

Cronstein, B. N., "Adenosine, an Endogenous Anti-Inflammatory Agent", *Journal of Applied Physiology*, 76(1), (1994), 5-13.

Cronstein, B. N., "Adenosine; A Physiologic Modulator of Superoxide Anion Generated by Human Neutrophils. Adenosine Acts Via an A2 Receptor on Human Neutrophils", *Journal of Immunology*, 135 (2), (1985), pp. 1366-1371.

Cronstein, B. N., "Engagement of Adenosine Receptors Inhibits Hydrogen Peroxide (H2O2) Release by Activated Human Neutrophils", *Clinical Immunology and Immunopathology*, 42(1), (1987), 76-85.

Cronstein, B. N., "Methotrexate Inhibits Leukocyte Influx Into Inflammatory Sites Via the Adenosine (A2) Receptor", *Clinical Research*, 41 (2), (1993), p. 244A.

Cronstein, B. N., et al., "Occupancy of Adenosine Receptors Raises Cyclic AMP Alone and in Synergy With Occupancy of Chemoattractant Receptors and Inhibits Membrane Depolarization", *Biochemical Journal*, 252 (3), (1988), 709-715.

Cronstein, B. N., "The Adenosine/Neutrophil Paradox Resolved: Human Neutrophils Possess Both A1 and A2 Receptors That Promote Chemotaxis and Inhibits O2 Generation, Respectively", *Journal of Clinical Investigation*, 85 (4), (1990), pp. 1150-1157.

Day, Y., et al., "A2A adenosine receptors on bone marrow-derived cells protect liver from ischemia-reperfusion injury", *The Journal of Immunology*, 174(8), (Apr. 15, 2005), 5040-6.

Day, Y. J., et al., "Renal Protection from Ischemia Mediated by A2A Adenosine Receptors on Bone Marrow-Derived Cells.", *Journal of Clinical Investigation*, 112(6), (2003), 883-891.

Day, Y.-J., et al., "Protection From Ischemic Liver Injury by Activation of A2A Adenosine Receptors During Reperfusion: Inhibition of Chemokine Induction",*American Journal of Physiology Gastrointestinal and Liver Physiology*, 286, (2004), G285-293.

De La Harpe, J., "Adenosine Regulates the Respiratory Burst of Cytokine—Triggered Neutrophils Adherent to Biological Surfaces", *Journal of Immunology*, 143(2), (1989), 596-602.

De Moraes, V. L., et al., "Effect of Cyclo-Oxygenase Inhibitors and Modulators of Cyclic AMP Formation on Lipopolysaccharide-Induced Neutrophil Infiltration in Mouse Lung", *British Journal of Pharmacology*, 117, (1996), 1792-1796.

De Sarro, G., et al., "Effects of adenosine Receptor Agonists and Antagonists on Audiogenic Seizure-sensible DBA / 2 mice", *European Journal of Pharmacology*, 371,(1999), 137-145.

De Zwart, M, et al., "5-N-Substituted Carboxamidoadenosines as Agonists for Adenosine Receptors",*Journal of Medicinal Chemistry*, (Apr. 22, 1999), 1384-1392.

Dechatelet, L R., et al., "Mechanism of the Luminol-Dependent Chemiluminescence of Human Neutrophils", *The Journal of Immunology*, 129 (4), (1982), 1589-1593.

Dinarello, C. A., "Interleukin-1 and Tumor Necrosis Factor: Effector Cytokines in Autoimmune Diseases", *Seminars in Immunology*, 4, (1992), 133-145.

Doyle, M. P., et al., "Nucleoside-induced Arteriolar Constriction: a Mast Cell-dependent Response.", *American Journal of Physiology*, 266(5), (May 1994), H2042-H2050.

Elzein, E., et al., "Design, Synthesis and Biological Evaluation of 2-(4-Substituted-N-Pyrazolyl)-Adenosine Derivatives As Novel Short Acting Adenosine A2A Receptor Agonists", *Drug Development Research*, 50 (1), Abstracts From Purines 2000: Biochemical, Pharmacological, and Clinical Perspective: Abstract No. 061, (May 2000), p. 64.

Entman, M. L., et al., "Inflammation in the course of early myocardial ischemia", *FASEB Journal*, vol. 5, (1991), 2529-2537.

Fabry, M. E., et al., "High Expression of Human $\beta^S$—and $\alpha$-globins in Transgenic Mice: Hemoglobin Composition and Hematological Consequences", *Proc. Natl. Acad. Sci. USA*, 89, (1992), 12150-12154.

Fabry, M. E., et al., "High Expression of Human $\alpha^S$—and $\alpha$-globins in Transgenic Mice: Erythrocyte Abnormalities, Organ Damage, and the Effect of Hypoxia", *Proc. Natl. Acad. Sci. USA*, 89, (1992), 12155-12159.

Fang, G. D, et al., "ATL 146e (ATL), a Selective A[2A] Adenosine Receptor Agonist, Combined with Ceftriaxone, Markedly Improves Survival in a Mouse Model of *E. coli* 026:B6 Sepsis", *Meeting Abstract B-1110, Presented at the 41st Interscience Conference on Antimicrobial Agents and Chemotherapy*, Chicago, USA, (Dec. 16-19, 2001).

Fang, G. D., et al., "DWH146e (DWH), A New Selective Adenosine A2a Receptor Agonist, Improves Survival in *E. coli* O26:B6 Lipopolysaccharide (LPS)-Induced Experimental Murine Endotoxemia", *Journal of Investigative Medicine*, Abstract No. 797, (2000), p. 148A.

Fenster, M. S., et al., "Activation of adenosine A2 alpha receptors inhibits mast cell degranulation and mast cell-dependent vasoconstriction", *Microcirculation*, 7(2), (Apr. 2000), 129-135.

Feoktistov, I., et al., "Adenosine A2B receptors", *The American Society for Pharmacological and Experimental Therapeutics*, 49(4), (1997), 381-402.

Feoktistov, I., et al., "Role of Adenosine in Asthma", *Drug Development Research*, 39,(1996), 333-336.

Ferrante, A., "Optimal Conditions for Simultaneous Purification of Mononuclear and Polymorphonuclear Leucocytes From Human Blood by the Hypaque-Ficoll Method", *Journal of Immunological Methods*, 36(2), (1980), 109-117.

Figler, R. A., et al., "Reconstitution Bovine A1 Adenosine Receptors and G Proteins in Phospholipid Vesicles: .Beta..Gamma.-Subunit Composition Influences Guanine Nucleotide Exchange and Agonist Binding", *Biochemistry*, 36 (51), (1997), pp. 16288-16299.

Figler, R. A., et al., "Reconstitution of Recombinant Bovine A1 Adenosine Receptors in Sf9 Cell Membranes with Recombinant G Proteins of Defined Composition.", *Molecular Pharmcology*, 50(6), (Dec. 1996), 1587-1595.

Firestein, G. S., "Adenosine Regulating Agents: A Novel Approach to Inflammation and Inflammatory Arthritis", *Clinical Research*, 41(2), (1993), 170A.

Fiser, S M, et al., "Adenosine A2A receptor activation decreases reperfusion injury associated with high-flow reperfusion.", *Journal of Thoracic & Cardiovascular Surgery*, 124(5), (Nov. 2002), 973-8.

Fozard, J. R., et al., "Adenosine A3 Receptors Mediate Hypotension in the Angiotensin II-supported Circulation of the Pithed Rat", *British Journal of Pharmacology*, 109(1), (1993), 3-5.

Francis, J. E., "Highly Selective Adenosine A2 Receptor Agonists in a Series of N-Alkylated 2-Aminoadenosines", *Journal of Medicinal Chemistry*, 34 (8), (1991), 2570-2579.

Frangogiannis, N. G, et al., "The Role of the Neutrophil in Myocardial Ischemia and Reperfusion", *Myocardial Iscehmia: Mechanisms, Reperfusion, Protection*, M. Karmazyn, Editor, Birkhauser Verlag Basel, (1996), 236-284.

Frenette, P. S., "Sickle Cell Vasoocclusion: Heterotypic, Multicellular Aggregations Driven by Leukocyte Adhesion", *Microcirculation*, 11, (2004), 167-177.

Gao, Z, et al., "Purification of A1 Adenosine Receptor-G-protein Complexes: Effects of Receptor Down-regulation and Phosphorylation on Coupling", *Biochemical Journal*, 338 (Pt3), (1999), 729-736.

Gao, Z., et al., "A2B Adenosine and P2Y2 Receptors Stimulate Mitogen-activated Protein Kinase in Human Embryonic Kidney-293 Cells. Cross-talk Between Cyclic AMP and Protein Kinase c Pathways", *Journal of Biological Chemistry*, 274(9), (Feb. 26, 1999), 5972-5980.

Gilchrist, A., et al., "Antagonists of the Receptor-G Protein Interface Block Gi-coupled Signal Transduction", *Journal of Biological Chemistry*, 273 (24), (Jun. 12, 1998), 14912-14919.

Girardi, N, et al., "Inflammatory Aneurysm of the Ascending Aorta and Aortic Arch", *Ann. Thor. Surg.*, 64, (1997), 251-253.

Glover, D K, et al., "Pharmacological stress myocardial perfusion imaging with the potent and selective A(2A) adenosine receptor agonists ATL193 and ATL146e administered by either intravenous infusion or bolus injection", *Circulation*, 104(10),(Sep. 4, 2001), 1181-1187.

Glover, D. K., et al., "Bolus Injection of DWE-146E, A Novel Adenosine A2A Receptor Agonist for Use in Vasodilator Stress Imaging", *Journal of Nuclear Cardiology*, 7 (4), Abstract No. 44.20, (Sep. 23, 2000), 1 p.

Glover, D. K., et al., "Characterization of a New, Highly Selective Adenosine A2A Receptor Agonist with Potential Use in Pharmacologic Stress Perfusion Imaging", *Circulation*, 100, Abstract, (1999), 1 p.

Glover, D. K., et al., "Pharmacological stress thallium scintigraphy with 2-cyclohexylmethylidenehydrazinoadenosine (WRC-0470). A novel, short-acting adenosine A2A receptor agonist.", *Circulation*, 94(7), (Oct. 1, 1996), 1726-1732.

Glover, D. K., et al., "Vasodilator Stress Imaging Using New Adenosine A2A Receptor Agonists Administered by Bolus Injection", *J. Am. Coll. Cardiol.*, 35, Abstract, (2000), 1 pg.

Griswold, D. E., et al., "Effect of Selective Phosphodieasterase Type IV Inhibitor, Rolipram, on Fluid and Cellular Phases of Inflammatory Respons", *Inflammation*, 17 (3), (1993), 333-334.

Hall, J., et al., "Abnormal Hypothalamic-Pituitary-Adrenal Axis Function in Rheumatoid Arthritis", *Arthritis & Rheumatism*, 37(8), (1994), 1132-1137.

Hamaguchi, M., et al., "Mechanisms and Roles of Neutrophil Infiltration in Stress-Induced Gastric Injury in Rats", *Digestive Diseases and Sciences*, 46(12), (2001), 2708-2715.

Hamajima, E., et al., "Effects of FK506, An Immunosuppressive Agent, on Genesis of Water-Immersion Stress-Induced Gastric Lesions in Rats", *Digestive Diseases and Sciences*, 39(4), (1994), 713-720.

Hanlon, W. A., "rTNF alpha Facilitate Human Polymorphonuclear Leukocyte Adherence to Fibrinogen Matrices With Mobilization of Specific and Tertiary But Not Azurophilic Granule Markers", *Journal of Leukocyte Biology*, 50 (1), (1991), pp. 43-48.

Harada, N., et al., "Adenosine and Selective A2a Receptor Agonist Reduce Ischemia/Reperfusion Injury of Rat Liver Mainly by Inhibiting Leukocyte Activation", *The Journal of Pharmacology and Experimental Therapeutics*, 294(3), (2000), 1034-1042.

Hartung, H. P., "Immune-Mediated Demyelination", *Annals of Neurology*, 33 (6), (Jun. 1993), pp. 563-567.

Hasko, G., et al., "Adenosine Inhibits IL-12 and TNF-alpha Production via Adenosine A2a Receptor-Dependent and Independent Mechanisms", *The FASEB Journal*, 14 (2000), 2065-2074.

Hatley, M. E., et al., "Increased Production of 12/15 Lipoxygenase Eicosanoids Accelerations Monocytes/Endothelial Interactions in Diabetic db/db Mice", *The Journal of Biological Chemistry*, 278(28), (2003), 25369-25375.

Hebbel, R. P., "Special Issue of Microcirculation: Examination of the Vascular Pathobiology of Sickle Cell Anemia", *Microcirculation*, 11, (2004), 99-100.

Hebbel, R. P., et al., "The Endothelial Biology of Sickle Cell Disease: Inflammation and a Chronic Vasculopathy", *Microcirculation*, 11, (2004), 129-151.

Heller, L. J., et al., "Effect of Adenosine on Histamine Release and Atrioventricular Conduction During Guinea Pig Cardiac Anaphylaxis", *Circulation Research*, 62(6), (Jun. 1988), 1147-1158.

Hogan, C. J., et al., "Inhibiting the inflammatory response in joint sepsis", *Arthroscopy*, 17(3), (Mar. 2001), 311-315.

Holmes, D, R., et al., "Restenosis After Percutaneous Transluminal Coronary Angioplasty (PTCA): A Report From the PTCA Registry of the National Heart, Lung, and Blood Institute", *American Journal of Cardiology*, 53, (1984), 77C-81C.

Homma, H, et al., "Nucleosides and nucleotides. 112. 2-(1-Hexyn-1-yl)adenosine-5'-uronamides: a new entry of selective A2 adenosine receptor agonists with potent antihypertensive activity.", *Journal of Medicinal Chemistry*, 35(15), (Jul. 1992), 2881-90.

Hussain, T., et al., "125I-APE Binding to Adenosine Receptors in Coronary Artery: Photoaffinity Labeling With 125I-azidoAPE", *The Journal of Pharmacology and Experimental Therapeutics*, 276(1), , (Jan. 1996), pp. 284-288.

Hutchison, A. J., "2-(Arylalkylamino)Adenosine-5'-Uronamides: A New Class of Highly Selective Adenosine A2 Receptor Ligands", *Journal of Medicinal Chemistry*, 33 (7), (1990), pp. 1919-1924.

Hutchison, A. J., "CGS 21680C, an A2 Selective Adenosine Receptor Agonist With Preferential Hypotensive Activity", *The Journal of Pharmacology and Experimental Therapeutics*, 251 (1), (1989), pp. 47-55.

Iannone, M. A., "Effects of Adenosine on Human Neutrophil Function and Cyclic AMP Content", *In: Topics and Perspectives in Adenosine Research*, Eds. E. Gerlach et al., Springer-Verlag, Berlin, Germany, (1986), pp. 286-298.

Imagawa, D. K., et al., "The Role of Tumor Necrosis Factor in Allograft Rejection", *Transplantation*, 51, (Jan. 1991), 57-62.

Ishiwata, K., et al., "Further Characterization of a CNS Adenosine A2a Receptor Ligand [11C]KF18446 with in vitro Autoradiography and in vivo Tissue Uptake", *Annals of Nuclear Medicine*, 14 (2), Abstract Only, Obtained from Chemicals Abstracts, 133, Abstract No. 346544, HCAPlus Accession No. 480897 (2000), 81-89.

Ito, B. R., et al., "Role of Cardiac Mast Cells in Complement C5a-induced Myocardial Ischemia", *American Journal of Physiology—Heart and Circulatory Physiology*, 264(5), (May 1993), H1346-H1354.

Jarvis, M. F., "[3H]CGS 21680, A Selective A2 Adenosine Receptor Agonist Directly Labels A2 Receptors in Rat Brain.", *Journal of Pharmacology and Experimental Therapeutics*, 251(3), (Dec. 1989), 888-893.

Jolly, S. R., "Effects of Lodoxamide on Ischemic Reperfused Myocardium", *Journal of Cardiovascular Pharmacology*, 4(3), (1982), 441-448.

Jordan, J. E., et al., "Adenosine A2 Receptor Activation Attenuates Reperfusion Injury by Inhibiting Neutrophil Accumulation, Superoxide Generation and Coronary Endothelial Adherence", *The Journal of Pharmacology and Experimental Therapeutics*, 280(1), (1997), 301-309.

Kahky, M. P., et al., "Portal Infusion of Tumor Necrosis Factor Increases Mortality in Rats", *Journal of Surgical Research*, 49(2), (1990), 138-145.

Kaminuma, O., et al., "Effect of T-440, a Novel Type IV Phosphodiesterase Inhibitor, on Allergen-Induced Immediate and Late Asthmatic Reaction and Leukocyte Infiltration into the Airways of Guinea Pigs", *International Archives of Allergy & Immunology*, 112(4), (1997), 406-411.

Kanko, et al., "Protective Effects of Clopidogrel on Oxidant Damage in a Rat Model of Acute Ischemia", *Tohoku J. Exp. Med.* vol. 205, (2005), pp. 133-139.

Kaul, D. K., et al., "Anti-Inflammatory Therapy Ameliorates Leukocyte Adhesion and Microvascular Flow Abnormalities in Transgenic Sickle Mice", *American Journal of Physiology—Heart and Circulatory Physiology*, 287, (2004), H293-H301.

Kaul, D. K., et al., "Hypoxia/Reoxygenation Causes Inflammatory Response in Transgenic Sickle Mice but Not in Normal Mice", *The Journal of Clinical Investigation*, 106(3), (2000), 411-420 .

Keller, A. M., "Acute Reoxygeneration Injury in the Isolated Rat Heart: Role of Resident Cardiac Mast Cells", *Circulation Research*, 63(6), (Dec. 1988), 1044-1052.

Kennedy, A. P., et al., "Covalent Modification of Transmembrane Span III of the A1 Adenosine Receptor With an antagonist Photoaffinity Probe.", *Molecular Pharmacology*, 50, , (Oct. 1996), pp. 789-798.

Klotz, Karl-Norbert, et al., "2-Substituted N-ethylcarboxamidoadenosine as high-affinity agonists at human A3 adenosine receptors",*Naunyn-Schmiedebergs Archives of Pharmacology*, 360(2), (Aug. 1999), 103-108.

Knapp, C. M., et al., "The Type IV Phosphodiester Inhibitors, Ro 20-1724 and Rolipram,Block the Initiation of Cocaine Self Administration", *Pharmocology, Biochemistry and Behavior*,62(1), (Jan. 1999), 151-158.

Kokura, S., et al., "T-Lymphocyte-Derived Tumor Necrosis Factor Exacerbates Anoxia-Reoxygenation-Induced Neutrophil-Endothelia Cell Adhesion", *Circulation Research*, 86, (2000), 205-213.

Kollias-Baker, C., et al., "Allosteric Enhancer PD 81,723 Acts by Novel Mechanism to Potentiate Cardiac Actions of Adenosine", *Circulation Research*, 75(6), (Dec. 1994), 961-971.

Koshiba, M, et al., "Patterns of A2A Extracellular Adenosine Receptor Expression in Different Functional Subsets of Human Peripheral T Cells. Flow cytometry Studies With Anti-A2A Receptors Monoclonal Antibodies.", *Molecular Pharmacology*, 55 (3), , (Mar. 1999), pp. 614-624.

Koshiba, M., "Patterns of A2A Extracellular Adenosine Receptor Expression in Different Functional Subsets of Human Peripheral T Cells", *The FASEB Journal*, Abstract No. 703.38, (1999), p. A944.

Krawisz, J. E., et al., "Quantitative Assay for Acute Intestinal Inflammation Based on Myeloperoxidase Activity", *Gastroenterology*, 87(6), (1984), 1344-1350.

Lappas, C. M, et al., "A2A adenosine receptor induction inhibits IFN-gamma production in murine CD4+ T cells", *Journal of Immunology*, 174(2), (Jan. 15, 2005), 1073-1080.

Lard, L. R., "Neutrophil Activation in Sickle Cell Disease", *Journal of Leukocyte Biology*,66, (1999), 411-415.

LeClerc, G., et al., "Percutaneous Arterial Gene Transfer in a Rabbit Model", *Journal of Clinical Investigation*, 90 (3), (1992), 936-944.

LeGrand-Poels, S., et al., "Activation of Human Immunodeficiency Virus Type 1 by Oxidative Stress", *AIDS Research and Human Retroviruses*, 6(12), (1990), 1389-1397.

Lette, J., et al., "Safety of Dipyridamole Testing in 73,806 Patients: The Multicenter Dipyridamole Safety Study", *Journal of Nuclear Cardiology*, 2 (1), (1995), pp. 3-17.

Linden, J, "Cloned Adenosine A3 Receptors: Phamacological Properties, Species Differences and Receptors Functions.", *Trends in Pharmacological Sciences*, 15 (8), , (Aug. 1994), pp. 298-306.

Linden, J, et al., "The Structure and Function of A1 and A2B Adenosine Receptors", *Life Science*, 62 (17/18) (1998), pp. 1519-1524.

Linden, J., et al., "(125I)Aminobenzyladenosine, a New Radioligand with Improved Specific Binding to Adenosine Receptors in Heart", *Circulation Research*, 56 (2), (Feb. 1985), 279-284.

Linden, J., "Allosteric Enhancement of Adenosine Receptors", *In: Purinergic Approaches in Experimental Therapeutics*, Chapter 5, Edition by K.A. Jacobson et al., and Published by Wiley-Liss, Inc., (1997), pp. 85-97.

Linden, J., "Calculating the Dissociation Constant of an Unlabeled Compound from the Concentration Required to Displace Radiolabel Binding by 50%", *Journal of Cyclic Nucleotide Research*, 8 (3), (1982), pp. 163-172.

Linden, J., et al., "Chapter 2—Adenosine Receptors", *In: Handbook of Receptors and Channels—G Protein Coupled Receptors*, Peroutka, S. J., Editor, CRC Press, Boca Raton, FL. (1994), 29-44.

Linden, J., "Chapter 2—Recombinant Techniques as Applied to the Study of A1 Adenosine Receptors", *In: Adenosine and Adenine Nucleotides: From the Molecular Biology to Integrative Physiology*, Belardinelli, L., Editor, Kluwer Academic Publishers, Boston, (1995), 15-19.

Linden, J., "Molecular Approach to Adenosine Receptors: Receptor-Mediated Mechanisms of Tissue Protection", *Annual Review of Pharmacology and Toxicology*, 41 (2001), 775-787.

Linden, J., et al., "Molecular Cloning and Functional Expression of Sheep A3 Adenosine Receptor with Widespread Tissue Distribution", *Molecular Pharmacology*, 44(3), (1993), 524-532.

Link, A. A., et al., "Ligand-Activation of the Adenosine A2a Receptors Inhibits IL-12 Production by Human Monocytes", *The Journal of Immunology*, 164, (2000), 436-442.

Lum, A. F. H., et al., "Inflammatory Potential of Neutrophils Detected in Sickle Cell Disease", *American Journal of Hematology*, 76, (2004), 126-133.

Luthin, D. R., et al., "Adenosine Receptors", *Biomembranes*, 2B, (1996), pp. 321-347.

Luthin, D. R., "Characterization of Two Affinity States of Adenosine A2a Receptor With a New Radioligand, 2-[2-(4-amino-3-[125I]iodophenyl) Ethylamino]Adenosine.", *Molecular Pharmacology*, 47 (2), (Feb. 1995), pp. 307-313.

Luthin, D. R., et al., "Comparison of A4 and A2a Binding Sites in Striatum and COS Cells Transfected With Adenosine A2a Receptors. ", *The Journal of Phamacology and Experimental Therapeutics*, 272, , (Feb. 1995), pp. 511-518.

Luthin, D. R., et al., "Photoaffinity Labeling With 2(−)[2-(4-azido-3(−)[125I]-iodophenyl)ethylamino]Adenosine and Autoradiography With 2(−)[2-(4-amino-3(−)[125I]iodophenyl)ethylamino]Adenosine of A2a Adenosine Receptor in Rat Brain.", *Journal of Neurochemistry*, 65 (5), (Nov. 1995), pp. 2072-2079.

Mager, Paul P., "Neural network approaches applied to selective A2a adenosine receptor agonists", *Med. Chem. Res.*, vol. 8, No. 6, (1998), pp. 277-290.

Mahan, L. C., et al., "Cloning and Expression of an A1 Adenosine Receptor from Rat Brain", *Molecular Pharmacology*, 40 (1), (Jul. 1991), pp. 1-7.

Mannel, D. N., "Tumor Necrosis Factor: A Cytokine Involved in Toxic Effects of Endotoxin", *Reviews of Infectious Diseases*, 9, (1987), S602-S606.

March, Jerry, *Advanced Organic Chemistry: Reactions, Mechanisms, and Structure*, Fourth Edition, John Wiley & Sons, (1992), p. 400.

Martin, P. L., et al., "Characterization of 8-(N-Methylisopropyl)Amino-N6-(5'-Endohydroxy-endonorbornyl)-9-methyladenine (WRC-0571), a Highly Potent and Selective, Nonxanthine Antagonist of A1 Adenosine Receptors.", *The Journal of Pharmacology and Experimental Therapeutics*, 276-(2), (Feb. 1996), 490-499.

Martin, P. L., et al., "Pharmacology of 2-cyclohexylmethylidenehydrazinoadenosine (WRC-0470), a Novel, Short-acting Adenosine A2A Receptor Agonist That Produces Selective Coronary Vasodilation.", *Drug Development Research*, 40 (4), , (1997), pp. 313-324.

Matherne, G. P., et al., "Transgenic A1 Adenosine Receptor Overexpression Increases Myocardial Resistance ot Ischemia", *Proceedings of the National Academy of Science*, 94, (Jun. 1997), pp. 6541-6546.

Matsuyama, T., "Cytokines and HIV Infection: is AIDS a Tumor Necrosis Factor Disease?", *AIDS*, 5(12), (1991), 1405-1417.

McGarrity, S. T., "Inhibition of Neutrophil Superoxide Anion Generation by Platelet Products: Role of Adenine Nucleotides", *Journal of Leukocyte Biology*, 44(5), (1988), 411-421.

McGarrity, S. T., "Regulation of Human Neutrophil Function by Adenine Nucleotides", *Journal of Immunology*, 142(6), (1989), 1986-1994.

McLaughlin, D. P., et al., "Hemodynamic and Metabolic Correlates of Dipyridamole-induced Myocardial Thallium-201 Perfusion Abnormalities in Multivessel Coronary Artery Disease.", *American Journal of Cardiology*, 73 (16) (Jun. 1994), pp. 1159-1164.

McPherson, J A, "Adenosine A(2A) receptor stimulation reduces inflamation and neointimal growth in a murine carotid ligation model", *Arteriosclerosis, Thrombosis & Vascular Biology*, 21(5), (May 2001), 791-6.

McPherson, J. A, et al., "Effect of Prolonged Adenosine A2A Receptor Activation on Neointimal Formation in the Injured and Mouse Carotid Artery", *The FASEB Journal*, Abstract No. 299.2, (1999), A367.

McPherson, J. A., et al., "Prolonged Adenosine A2a Receptor Stimulation Reduces Inflammation and Neointima Formation in a Murine Carotid Ligation Model", *Supplement to Circulation*, 100(18), Abstract No. 3652, (Nov. 2, 1999), 1 p.

Miyamoto, F, et al., "Retinal Cytokine Response in Mouse Alkali-Burned Eye", *Othalmic Research*, 30(1997), 168-171.

Mizumura, T., et al., "PD 81,723, an Allosteric Enhancer of the A1 Adenosine Receptor, Lowers the Threshold for Ischemic Preconditioning in Dogs.", *Circulation Research*, 79 (3), (Sep. 1996), pp. 415-423.

Molnar-Kimber, K. L., et al., "Modulation of TNF alpha and IL-1 beta From Endotoxin-Stimulated Monocytes by Selective PDE Isozyme Inhibitors", *Agents & Actions*, 39, , (1993), C77-C79.

Moore, C. C., et al., "A2A Adenosine Receptor Agonists Modify Inflammatory Responses in an *E. voli* Peritonitis Murine Septic Shock Model", *Proceedings of the 43rd Annual Meeting of the Infectious Dises Society of America*, Abstract No. 52, San Francisco, (Oct. 6-9, 2005), p. 43.

Morabito, L., et al., "Methotrexate and Sulfasalazine Promote Adenosine Release by a Mechanism that Requires Ecto-5'-Nucleotidase-mediated Conversion of Adenine Nucleotides", *Journal of Clinical Investigation*, 101(2), (1998), 295-300.

Mumby, S. M., et al., "G-protein alpha-subunit expression, myristoylation, and membrane association in COS cells", *Proceedings of the National Academy of Sciences*, 87 (2), , (Jan. 1990), pp. 728-732.

Murphree, L. J., et al., "Human A2a Adenosine Receptors: High-Affinity Agonist Binding to Receptor-G Protein Complexes Containing GBeta4", *Molecular Pharmacology*, 61(2), (2002), 455-462.

Nabel, Elizabeth G., "Site-Specific Gene Expression in Vivo by Direct Gene Transfer into the Arterial Wall", *Science*, 249, (1990), 1285-1288.

Nagel, R. L., et al., "Review—The Panoply of Animal Models for Sickle Cell Anaemia", *British Journal of Haematology*, 112, (2001), 19-25.

Needleman, J. P., et al., "Breathing Patterns During Vaso-occlusive Crisis of Sickle Cell Disease", *Chest*, 122(1), (2002), 43-46.

Newman, K. D., "Adenovirus-mediated Gene Transfer into Normal Rabbit Arteries Results in Prolonged Vascular Cell Activation, Inflammation and Neointimal Hyperplasia", *Journal of Clinical Investigation*, 96 (6), (1995), pp. 2955-2965.

Nielson, C. P., "Effects of Adenosine on Polymorphonuclear Leucocyte Function, Cyclic 3': 5'-adenosine Amonophosphate, and Intracellular Calcium", *British Journal of Pharmacology*, 97(3), (1989), 882-888.

Niiya, K., "2-(N'-Alkylidenehydrazino)Adenosines: Potent and Selective Coronary Vasodilators", *Journal of Medicinal Chemistry*, 35 24 , (1992), 4557-4561.

Nolte, D., et al., "Reduction of Postischemic Leukocyte-Endothelium Interaction by Adenosine Via A2 Receptor", *Naunyn-Schmiedeberg's Archives of Pharmacology*, 346(2), (1992), 234-237.

Odashima, M., et al., "Attenuation of Gastric Mucosal Inflammation Induced by Aspirin Through the Activation of A2a Adenosine Receptor in Rats", *World Journal of Gastroenterology*, 12(4), (2006), 6 pgs.

Odashima, M., et al., "Selective Adenosine A2 Receptor Agonist, ATL-146e, Attenuates Stress-Induced Gastric Lesions in Rats", *Journal of Gastroenterology and Hepatology*, 20(2), (2005), 275-280.

Okusa, M D, et al., "A(2A) Adenosine Receptor-Mediated Inhibition of Renal Injury and Neutrophil Adhesion", *American Journal of Physiology—Renal Fluid & Electrolyte Physiology*, 279(5), (2000), F809-F818.

Okusa, M D, et al., "Enhanced Protection from Renal Ischemia: Reperfuison Injury With A2A-Adenosine Receptor Activation and PDE 4 Inhibition", *Kidney International*, 59(6), (2001), 2114-2125.

Okusa, M. D., et al., "Selective A2A adenosine receptor activation reduces ischemia-reperfusion injury in rat kidney", *Am. J. Physiol.*, vol. 277 (3, Pt 2), (1999), F404-F412.

Olah, M. E., et al., "Adenosine Receptor Subtypes: Characterization and Therapeutic Regulation", *Annual Review of Pharmacology and Toxicology*, 35, (1995), 581-606.

Olsson, R. A., et al., "N6 Substituted N-Alkyladenosine-5'-Uronamides: Bifunctional Ligands Having Recognition Groups for A1 and A2 Adenosine Receptors", *Journal of Medicinal Chemistry*, 29 (9), (1986), 1683-1689.

O'Regan, M. H., et al., "Adenosine Receptor Agonists Inhibit the Release of y-Aminobutyric Acid (GABA) From the Ischemic Rat Cerebral Cortex", *Brain Research*, 582(1), (1992), 22-26.

Orringer, E. P., et al., "Purified Poloxamer 188 for Treatment of Acute Vaso-occlusive Crisis of Sickle Cell Disease", *JAMA*, 286(17), (2001), 2099-2106.

Osuka, M. D, et al., "Enhanced protection from renal ischemia-reperfusion [correction of ischemia:reperfusion] injury with A(2A)-adenosine receptor activation and PDE 4 inhibition", *Kidney Int.*, 59(6), (Jun. 2001), 2114-25.

Pathare, A., et al., "Hemoglobinopathy—Cytokines in Sickle Cell Disease", *Hematology*, 8(5), (2003), 329-337.

Peart, J, et al., "Adenosine-mediated cardioprotection in ischemic-reperfused mouse heart.", *Journal of Cardiovascular Pharmacology*, 39(1), (Jan. 2002), 117-129.

Peet, N. P., et al., "Conformationally Restrained, Chiral (Phenylisopropyl)Amino-Substituted Pyrazolo[3,4-d]Pyrimidines and Purines With Selectivity for Adenosine A1 and A2 Receptors", *Journal of Medicinal Chemistry*, 35 (17), (1992), 3263-3269.

Peirce, S M, "Selective A(2A) adenosine receptor activation reduces skin pressure ulcer formation and inflammation", *American Journal of Physiology—Heart & Circulatory Physiology*, 281(1), (Jul. 2001), H67-74.

Peirce, S. M., et al., "Attenuation of I/R Injury in Skin Using a Selective A2A Adenosine Receptor Agonist", *FASEB Journal*, 14 (4), Abstract No. 333.1, (Mar. 15, 2000), p. A466.

Pennell, R L, et al., "Inflammatory abdominal aortic aneurysms: A thirty-year review", *Journal of Vascular Surgery*, 2, (1985), 859-869.

Pfister, J. R., et al., "Synthesis and Biological Evaluation of the Enantiomers of the Potent and Selective A1- adenosine Antagonist 1,3-dipropyl-8-[2-(5,6-epoxynorbonyl)]-xanthine", *Journal of Medicinal Chemistry*, 40 (12), (1997), 1773-1778.

Platt, O. S., et al., "Pain in Sickle Cell Disease—Rates and Risk Factors", *The New England Journal of Medicine*, 325(1), (1991), 11-15.

Platt, O. S., "Sickle Cell Anemia as an Inflammatory Disease", *The Journal of Clinical Investigation*, 106(3), (2000), 337-338.

Pulle, V., et al., "Design, Synthesis and Pharmacological Evaluation of 2(1-Alkyl-Pyrazol-4-YL) Adenosine Derivatives as Short Acting Adenosine A2A Receptor Agonists", *Drug Development Research*, 40 (1), Abstract From Purines 2000: Biochemical, Pharmacolgical and Clinical Perspectives: Abstract No. 062, (May 2000), p. 64.

Raitt, M. H., et al., "Abnormal Q Waves are Common Early in AMI and Do Not Predict Decreased Myocardial Salvage WIth Thrombolytic Therapy", *Special Issue Journal of American College of Cardiology*, Abstract No. 895-77, (Feb. 1994), p. 195A.

Ranhosky, A., et al., "The Safety of Intravenous Dipyridamole Thallium Myocardial Perfusion Imaging", *Circulation*, 81(4), (Apr. 1990), pp. 1205-1209.

Rashad, S., et al., "Effect of Non-Steroidal Anti-Inflammatory Drugs on the Course of Osteoarthritis", *The Lancet*, 2(8662), (Sep. 2, 1989), 519-522.

Rieger, G. M, et al., "Synthesis and Evaluation of Novel A2A Adenosine Receptor Agonist", *Journal of Medicinal Chemistry*, 44(4), (Feb. 15, 2001), 531-539.

Rieger, J. M., et al., "Design, Synthesis, and Evaluation of Novel A2A Adenosine Receptor Agonists", *Journal of Medicinal Chemistry*, 44(4), (2001), 531-539.

Rieger, J. M., "Design, Synthesis, and Evaluation of Novel A2A Adenosine Receptor Agonists", *J. Med. Chem.*, 44, (2001), 531-539.

Rieger, J. M, et al., "Design, synthesis, and evaluation of novel A2A adenosine receptor agonists.", *J Med Chem.*, 44(4), (Feb. 15, 2001), 531-9.

Riou, L M, et al., "Influence of propranolol, enalaprilat, verapamil, and caffeine on adenosine A(2A)-receptor-mediated coronary vasodilation",*Journal of the American College of Cardiology*, 40(9), (Nov. 6, 2002), 1687-1694.

Roberts, P. A., et al., "Inhibition by Adenosine of Reactive Oxygen Metabolite Production by Human Polymorphonuclear Leucocytes", *Biochemical Journal*, 227(2), (1985), 669-674.

Robeva, A. S., et al., "Double Tagging Recombinant A1- and A2A-Adenosine Receptors With Hexahistidine and the FLAG Epitope. Development of an Efficient Generic Protein Purification Procedure. ",*Biochemical Pharmacology*, 51(4), (Feb. 1996), 545-555.

Robeva, A. S., et al., "Molecular Characterization of Recombinant Human Adenosine Receptors", *Drug Development Research*, 39, (1996), pp. 243-252.

Rosin, D. L., et al., "Immunohistochemical Localization of Adenosine $A_{2A}$ Receptors in the Rat Central Nervous System", *The Journal of Comparative Neurology*, 401, (1998), 163-186.

Ross, R., "The Pathogenesis of Atherosclerosis: A Perspective for the 1990s", *Nature*, 362, (Apr. 29, 1993), 801-809.

Ross, S D, et al., "Selective Adenosine-A2A Activation Reduces Lung Reperfusion Injury Following Transplantation", *Journal of Heart & Lung Transplantation*, 18(10), (1999), 994-1002.

Ross, S. D, et al., "Selective Adenosine-A2A Activation Reduces Lung Reperfusion Injury Following Transplantation", *Journal of Heart and lung transplantation*, 18 (1), Abstract Only, Proceedings of the Nineteenth Annual Meeting and Scientific Sessions of the International Society for Heart and Lung Transplantation, San Francisco, CA, (Jan. 1999), p. 72.

Rothe, G. A., et al., "Flow Cytometric Measurement of the Respiratory Burst Activity of Phagocytes Using Dhydrorhodamine 123", *Journal of Immunological Methods*, 138(1), (1991), 133-135.

Santucci, L., et al., "Pentoxifylline Prevents Indomethacin Indcued Acute Gastric Mucosal Damage in Rats: Role of Tumour Necrosis Factor Alpha", *Gut*, 35, (1994), 909-915.

Saunthararajah, Y., et al., "Effects of 5-aza-2'-deoxycytidine on Fetal Hemoglobin Levels, Red Cell Adhesion, and Hematopoietic Differentiation in Patients With Sickle Cell Disease", *Blood*, 102(12), (2003), 3865-3870.

Sawmiller, D. R., et al., "Effects of Xanthine Amine Congener on Hypoxic Resistence and Venous and Epicardial Adenosine Concentrations.", *Cardiovascular Research*, 28 (5), (May 1994), pp. 604-609.

Schiffmann, S. N., et al., "Distribution of adenosine A2 receptor mRNA in the human brain", *Neuroscience Letters*, 130, (1991), pp. 177-181.

Schlack, W., et al., "Adenosine A2-Receptor Activation at Reperfusion reduces Infarct Size and Improves Myocardial Wall Function in Dog Heart", *Journal of Cardiovascular Pharmacology*, 22, (1993), 89-96.

Schrier, D. J., et al., "The Effects of Adenosine Agonists on Human Neutrophil Function", *Journal of Immunology*, 137 (10), (1986), 3284-3289.

Seekamp, A., "Ischemia—Reperfusion Injury", *Agents and Actions Supplements*, 41, (1993), 137-152.

Shapiro, B. S., "The Management of Pain in Sickle Cell Disease", *Pediatric Clinics of North America*, 36(4), (1989), 1029-1041.

Sharief, M. K., et al., "Elevated Serum Levels of Tumor Necrosis Factor-alpha in Guillain-Barre Syndrome", *Annals of Neurology*, 33, (Jun. 1993), 591-596.

Sharma, H S, et al., "Role of cytokines in myocardial ischemia and reperfusion", *Med. of Inflamm*, 6, (1987), 175-183.

Shay, H., et al., "A Simple Method for the Uniform Production of Gastric Ulceration in the Rat", *Gastroenterology*, 5(1), (1945), 43-61.

Sheardown, M. J, "Unexpected Neuroprotection Observed with the Adenosine A2A Receptor Agonist CGS 21680", *Drug Development Research*, 39, (1996), 108-114.

Shepherd, R. K., et al., "Adenosine-induced Cell Vasoconstriction in Vivo. role of the Mast Cell and A3 Adenosine Receptor.", *Circulation Research*, 78(4), , (Apr. 1996), pp. 627-634.

Shi, W., et al., "Endothelial Responses to Oxidized Lipoproteins Determine Genetic Susceptibility to Atherosclerosis in Mice", *Circulation*, 102, (2000), 75-81.

Silverman, R., "Chapter 2, Drug Discovery, Design and Chemistry of Drug Design and Drug Action", *The Organic Chemistry of Drug Design and Drug Action*, San Diego : Academic Press, (1992), 4-47.

Sipka, S., "Adenosine Induced Delay of Expression of AIDs Virus, HIV, in H9T Cells", *Acta. Biochimica et Biophysica Hungarica*, 23(1), (1988), 75-82.

Siragy, H. M., et al., "Sodium Intake Markedly Alters Renal Interstitial Fluid Adenosine", *Hypertension*, 27 (3 Pt 1), (Mar. 1996), 404-407.

Smits, P., et al., "Cardiovascular effects of two xanthines and the relation to adenosine antagonism", *Clinical Pharmacology and Therapeutics*, 45 (6), (1989), 593-599.

Solovey, A., "Circulating Activated Endothelial Cells in Sickle Cell Anemia", *The New England Journal of Medicine*, 337(22), (1997), 1584-1590.

Solovey, A., et al., "Tissue Factor Expression by Endothelial Cells in Sickle Cell Anemia", *Journal of Clinical Investigation*, 101(91, (1998), 1899-1904.

Steinberg, M. H., et al., "Effect of Hydroxyurea on Mortality and Morbidity in Adult Sickle Cell Anemia", *JAMA*, 289(13), Correction, published in JAMA, 290(6) (2003) at p. 756, (2003), 1645-1651.

Stuart, M. J., et al., "Sickle-Cell Disease", *The Lancet*, 364, (2004), 1343-1360.

Sullivan, G W., et al., "Interactions of Human Neutrophils with Leukotoxic *Streptococci*", *Infection and Immunity*, 30 (1), (1980), pp. 272-280.

Sullivan, G. W., "A2A Adenosine Receptor Activation Improves Survival in Mouse Models of Endotoxemia and Sepsis", *Journal of Infectious Diseases*, 189(10), (May 15, 2004), 1897-1904.

Sullivan, G. W., "Adenosine (ADO) Modulates Endotoxin and TNF-Induced PMN Activation", *Clinical Research*, 41(2), (1993), 172A.

Sullivan, G. W., et al., "Adenosine and Related Compounds Counteract Tumor Necrosis Factor ~a Inhibition of Neutrophil Migration: Implication of a Novel Cyclic AMP-Independent Action on the Cell Surface", *The Journal of Immunology*, 145(5), (1990), 1537-1544.

Sullivan, G. W., et al., "Neutrophil A2A Adenosine Receptor Inhibits Inflammation in a Rat Model of Meningitis: Synergy with the Type IV Phosphodiesterase Inhibitor, Rolipram", *The Journal of Infectious Diseases*, 180, No. 5, , (1999), pp. 1550-1560.

Sullivan, G. W, et al., "Neutrophil A2A adenosine receptor inhibits inflammation in a rat model of meningitis: synergy with the type IV phosphodiesterase inhibitor, rolipram", *J Infect Dis.*, 180(5), (Nov. 1999), 1550-60.

Sullivan, G. W, et al., "Neutrophil A2A adenosine receptor inhibits inflammation in a rat model of meningitis: synergy with the type IV phosphodiesterase inhibitor, rolopram.", *The Journal of Infectious Diseases*, 180(5), (Nov. 1999), 1550-1560.

Sullivan, G. W., et al., "Role of A2A Adenosine Receptors in Inflammation", *Drug Development Research*,.45 (3/4), (1998), 103-112.

Sullivan, G. W., et al., "The role of inflammation in vascular diseases", *Journal of Leukocyte Bilogy*, 67, (May 2000), pp. 591-602.

Sullivan, G. W., et al., "The Specific Type IV Phosphodiesterase Inhibitor Rolipram Combined with Adenosine Reduces Tumor Necrosis Factor-a-Primed Neutrophil Oxidative Activity", *International Journal of Immunonopharmacology*, 17(10), (1995), 793-803.

Sullivan, G. W., "Two Methylxanthines, Pentoxifylline (PTX) and Caffeine (CAF) Have Divergent Effects on Tumor Necrosis Factor (TNF)-Primed Human Neutrophil (PMN) Activation", *Clinical Research*, 41(2), (1993), p. 172A.

Sullivan, Gail W., et al., "Cyclic AMP-Dependent Inhibition of Human Neutrophil Oxidative Activity by Substitued 2-Propynylcyclohexyl Adenosine A2A Receptor Agonists", *British Journal of Pharmacology*, 132(5), (2001), 1017-1026.

Takeuchi, K., et al., "Oxygen Free Radicals and Lipid Peroxidation in the Pathogenesis of Gastric Mucosal Lesions Induced by Indomethacin in Rats", *Digestion*, 49(3), (1991), 175-184.

Takiguchi, Y., et al., "Early administration of YT-146, an adenosine A2 receptor agonist, inhibits neointimal thickening after rat femoral artery endothelium injury", *European Journal of Pharmacology 281* (1995), 205-207.

Terrosu, P., et al., "Angiographic Correlate of Post-Reperfusion Abnormal Q Waves", *Japanese Heart Journal*, 29(2), (Mar. 1988), 179-187.

Tomer, A., "Platelet Activation as a Marker for in vivo Prothrombotic Activity: Detection by Flow Cytometry", *Journal of Biological Regulators and Homeostatic Agents*, 18, (2004), 172-177.

Topol, E. J., et al., "Randomised Trial of Coronary Intervention With Antibody Against Platelet IIb/IIIa integrin for Reduction of Clinical Restenosis: Results at Six Months", *The Lancet*, 343(8902), (1994), 881-886.

Tracey, K. J., "Cachectin/Tumor Necrosis Factor Induces Cachexia, Anemia, and Inflammation", *Journal of Experimental Medicine*, 167, (Mar. 1988), 1211-1227.

Tucker, A. L., et al., "A1 adenosine receptors. Two amino acids are responsible for species differences in ligand recognition", *Journal of Biological Chemistry*, 268(45), (Nov. 11, 1994), 27900-27906.

Turhan, A., et al., "Primary Role for Adherent Leukocytes in Sickle Cell Vascular Occlusion: A New Paradigm", *Proc. Natl. Acad. Sci. USA*, 99(5), (2002), 3047-3051.

Ueeda, M., et al., "2-Alkoxyadenosines: Potent and Selective Agonists at the Coronary Artery A2 Adenosine Receptor", *Journal of Medicinal Chemistry*, 34(4), (1991), pp. 1334-1339.

Ukena, D., et al., "Species Differences in Structure-Activity Relationships of Adenosine Agoisnt and Xanthine Antagonists at Brain A1 Adenosine Receptors", *FEBS Letters*, 209(1), , (Dec. 1986), pp. 122-128.

Underwood, D. C., et al., "Inhibition of Antigen-Induced Bronchoconstriction and Eosinophil Infiltration in the Guinea by the Cyclic AMP-Specific Phosphodiesterase Inhibitor, Rolipram", *The Journal of Pharmacology and Experminetal Therapeutics*, 266(1), (1993), 306-313.

Van Calker, D., et al., "Adenosine Regulates via Two Different Types of Receptors, the Accumulation of Cyclic Amp in Cultured Brian Cells", *Journal of Neurochemistry*, 33, , (1979), pp. 999-1005.

Van Calker, D., et al., "Carbamazepine Distinguishes Between Adenosine Receptors The Mediate Different Second Messenger Responses", *European Journal of Pharmacology*, 206(4), (1991), 285-290.

Venes, et al., "Taber's Cyclopedic Dictionary", *Taber's Cyclopedic Medical Dictionary*, 19, 960-961, 2001

Vittori, S, et al., "2-alkenyl and 2-alkyl derivatives of adenosine and adenosine-5'-N-ethyluronamide: different affinity and selectivity of E- and Z-diastereomers at A2A adenosine receptors.", *Journal of Medicinal Chemistry*, 39(21), (Oct. 1996), 4211-7.

Volpini, R., et al., "Synthesis Di- and Tri-Substituted Adenosine Derivatives and Their Affinities at Human Adenosine Receptor Subtypes", *Nucleosides & Nucleotides*, 18(11,12), (1999), 2511-2520.

Wagner, M. C., "Sickle Cell Adhesion Depends on Hemodynamics and Endothelial Activation", *J. Lab. Clin. Med.*, 144, (2004), 260-267.

Walker, Blair A., et al., "Adenosine A2a Receptor Activation Delays Apoptosis in Human Neutrophils", *The American Association of Immunologists*, , (1997), pp. 2926-2931.

Walker, D I, et al., "Inflammatory Aneurysms of the Abdominal Aorta", *Brit. J. Surg.*, 59, (1972), 609-614.

Wallace, J. L., et al., "Gastric Ulceration Induced by Nonsteroidal Anti-Inflammatory Drugs is a Neutorphil-Dependent Process", *American Journal of Physiology Gastrointestinal and Liver Physiology*, 259, (1990), G462-G467.

Wan, A. A., et al., "Binding of the Adenosine A2 Receptor Human (3H)CGS 21680 to Human and Rat Brain: Evidence for Multiple Affinity Sites", *Journal of Neurochemistry*, , (1990), pp. 1763-1771.

Webster, M., "Merriam-Webster's Collegiate Dictionary", *Tenth Edition*, (1998), 924 and 935.

Weiner, D. L., "Preliminary Assessment of Inhaled Nitric Oxide for Acute Vaso-occulsive Crisis Pediatric Paties With Sickle Cell Disease", *JAMA*, 289(9), Correction, published in JAMA, 292(8), (2004) at p. 925, (2003), 1136-1142.

Wolff, A. A., et al., "Ventricular Arrhythmias Parallel Cardiac Histamine Efflux After Coronary Artery Occlusion in the Dog", *Agents and Actions*, 25 (3/4), (1988), pp. 296-306.

Wood, K C., et al., "Endothelial Cell P-Selectin Mediates a Proinflammatory and Prothrombogenic Phenotype in Cerebral Venules of Sickle Cell Transgenic Mice", *American Journal of Physiology—Heart and Circulatory Physiology*, 286, (2004), H1608-H1614.

Wun, T., et al., "Platelet-Erythrocyte Adhesion in Sickle Cell Disease", *Journal of Investigative Medicine*, 47(3), (1999), 121-126

Yale, S. H., et al., "Approach to the Vaso-Occlusive Crisis in Adults With Sickle Cell Disease", *American Family Physician*, 61(5), Correction, published in American Family Physician, 64(2) (2001), p. 220, (2000), 1349-1356, 1363-1364.

Yoneyama, F., "Vasodepressor Mechanisms of 2-(1-octynyl)-Adenosine (YT-146), a Selective Adenosine A2 Receptor Agonist, Involve the Opening of Glibenclamide-sensitive K+ Channels", *European Journal of Pharmacology*, 213 (1), (1992), 199-204.

Yoshida, N., et al., "Role of Neutrophil-Mediated Inflammation in Aspirin-Induced Gastric Mucosal Injury", *Digestive Diseases and Sciences*, 40(11), (1995), 2300-2304.

Yoshikawa, T., et al., "Augmentative Effects of Tumor Necrosis Factor-Alpha (Human, Natural Type) on Polymorphonuclear Leukocyte-Derived Superoxide Generation Induced by Various Stimulants", *International Journal of Immunopharmacology*, 14(8), (1992), 1391-1398.

Yoshikawa, T., et al., "Role of Active Oxygen, Lipid Peroxidation, and Antioxidants in the Pathogenesis of Gastric Mucosal Injury Induced by Indomethacin in Rats", *Gut*,34(6), (1992), 732-737.

Zablocki, J., et al., "Novel Short Acting Coronary Vasodilators The Are Functionally Selective For The A2A Receptor Based On 2-Heterocyclic Substituted Adenosine Derivatives", *Drug Development Research*, 50 (1), Abstracts From Purines 2000: Biochemical, Pharmacological and Clinical Perspectives: Abstract No. 059, (May 2000), p. 63.

Zhang, X., et al., "Cellular Accumulation and Retention of the Technetium-99m-Labelled Hypoxia Markers BRU59-21 and Butylene Amine Oxime", *Nuclear Medicine and Biology*, 28, (2001), 949-957.

Zipursky, A., et al., "Oxygen Therapy in Sickle Cell Disease", *The American Journal of Pediatric Hematology/Oncology*, 14(3), (1992), 222-228.

"U.S. Appl. No. 08/272,821, Non Final Office Action mailed Mar. 9, 1998", 6 pgs.

"U.S. Appl. No. 08/272,821, Notice of Allowance mailed Aug. 5, 1998", 4 pgs.

"U.S. Appl. No. 08/272,821, Preliminary Amendment filed Jun. 20, 1997", 5 pgs.

"U.S. Appl. No. 08/272,821, Response filed Jun. 9, 2008 to Non Final Office Action mailed May 9, 2008", 8 pgs.

"U.S. Appl. No. 08/272,821, Response filed Nov. 3, 1997 to Restriction Requirement mailed Oct. 2, 1997", 5 pgs.

"U.S. Appl. No. 08/272,821, Restriction Requirement mailed Oct. 2, 1997", 5 pgs.

"U.S. Appl. No. 09/003,930, Final Office Action mailed Aug. 6, 1999", 6 pgs.

"U.S. Appl. No. 09/003,930, Non-Final Office Action mailed Nov. 4, 1998", 7 pgs.

"U.S. Appl. No. 09/003,930, Preliminary Amendment filed Feb. 8, 1999", 5 pgs.

"U.S. Appl. No. 09/003,930, Response filed May 4, 1999 to Non-Final Office Action mailed Nov. 4, 1998", 12 pgs.

"U.S. Appl. No. 09/003,930, Response filed Nov. 4, 1999 to Final Office Action mailed Aug. 6, 1999", 10 pgs.

"U.S. Appl. No. 09/320,769, Non Final office action mailed Jul. 18, 2000", 5 pgs.

"U.S. Appl. No. 09/333,387, Non-Final Office Action mailed Jul. 13, 2000", 5 pgs.

"U.S. Appl. No. 09/333,387, Notice of Allowance mailed Aug. 25, 2000", 2 pgs.

"U.S. Appl. No. 09/333,387, Response filed Aug. 28, 2000 to Non-Final Office Action mailed Jul. 13, 2000", 2 pgs.

"U.S. Appl. No. 09/333,387, Supplemental Amendment filed Aug. 28, 2000", 2 pgs.

"U.S. Appl. No. 09/333,387, Supplemental Notice of Allowability mailed Mar. 31, 2001", 4 pgs.

"U.S. Appl. No. 09/336,198, Non Final Office Action mailed Mar. 8, 2001", 7 pgs.

"U.S. Appl. No. 09/336,198, Notice of allowance mailed Jun. 25, 2001", 4 pgs.

"U.S. Appl. No. 09/336,198, Response filed Jun. 8, 2001 to Non Final office action mailed Mar. 8, 2001", 4 pgs.

"U.S. Appl. No. 09/543,385, Notice of Allowance mailed Mar. 25, 2002", 5 pgs.

"U.S. Appl. No. 09/543,385, Notice of Allowance mailed Sep. 24, 2001", 5 pgs.

"U.S. Appl. No. 09/543,385, Preliminary Amendment filed Apr. 4, 2000", 2 pgs.

"U.S. Appl. No. 09/543,385, Response filed Jun, 29, 2001 to Restriction Requirement mailed May 29, 2001", 2 pgs.

"U.S. Appl. No. 09/543,385, Restriction Requirement mailed May 29, 2001", 3 pgs.

"U.S. Appl. No. 09/543,385, Supplemental Preliminary Amendment filed Aug. 31, 2000", 6 pgs.

"U.S. Appl. No. 09/634,407, Non Final office action mailed Sep. 25, 2001", 21 pgs.

"U.S. Appl. No. 09/634,407, Notice of allowance mailed Sep. 4, 2002", 10 pgs.

"U.S. Appl. No. 09/634,407, Response filed Feb. 26, 2002 to Non Final office action mailed Sep. 25, 2001", 8 pgs.

"U.S. Appl. No. 09/827,083, 312 Amendment filed Dec. 10, 2002", 2 pgs.

"U.S. Appl. No. 09/827,083, Notice of Allowance mailed Sep. 10, 2002", 6 pgs.

"U.S. Appl. No. 09/827,083, Preliminary Amendment mailed Apr. 5, 2001", 5 pgs.

"U.S. Appl. No. 10/041,776, Non final office action mailed Dec. 31, 2002", 14 pgs.

"U.S. Appl. No. 10/041,776, Notice of allowance mailed Jul. 15, 2003", 14 pgs.

"U.S. Appl. No. 10/041,776, Response filed Apr. 30, 2003 to Non final office action mailed Dec. 31, 2002", 11 pgs.

"U.S. Appl. No. 10/263,379, Response filed Apr. 23, 2004 to Restriction Requirement mailed Mar. 24, 2004", 2 pgs.

"U.S. Appl. No. 10/263,379, Restriction Requirement mailed Mar. 24, 2004", 4 pgs.

"U.S. Appl. No. 10/379,154, 312 Amendment filed Apr. 4, 2007", 3 pgs.

"U.S. Appl. No. 10/379,154, Final Office Action mailed Feb. 17, 2004", 4 pgs.

"U.S. Appl. No. 10/379,154, Final Office Action mailed Mar. 30, 2006", 5 pgs.

"U.S. Appl. No. 10/379,154, Non-Final Office Action mailed Jun. 17, 2004", 4 pgs.

"U.S. Appl. No. 10/379,154, Non-Final Office Action mailed Aug. 1, 2005", 5 pgs.
"U.S. Appl. No. 10/379,154, Non-Final Office Action mailed Aug. 8, 2003", 4 pgs.
"U.S. Appl. No. 10/379,154, Non-Final Office Action mailed Dec. 15, 2004", 5 pgs.
"U.S. Appl. No. 10/379,154, Notice of Allowance mailed Jan. 4, 2007", 5 pgs.
"U.S. Appl. No. 10/379,154, Response filed May 16, 2005 to Non-Final Office Action mailed Dec. 15, 2004", 7 pgs.
"U.S. Appl. No. 10/379,154, Response filed May 17, 2004 to Final Office Action mailed Feb. 17, 2004", 6 pgs.
"U.S. Appl. No. 10/379,154, Response filed May 31, 2006 to Final Office Action mailed Mar. 30, 3006", 7 pgs.
"U.S. Appl. No. 10/379,154, Response filed Sep. 17, 2004 to Non-Final Office Action Jun. 17, 2004", 6 pgs.
"U.S. Appl. No. 10/379,154, Response filed Nov. 5, 2003 to Non-Final Office Action mailed Aug. 8, 2003", 8 pgs.
"U.S. Appl. No. 10/379,154, Response filed Dec. 1, 2005 to Non-Final Office Action mailed Aug. 1, 2005", 7 pgs.
"U.S. Appl. No. 10/412,726, Examiner Interview Summary mailed Mar. 21, 2007", 3 pgs.
"U.S. Appl. No. 10/412,726, Examiner Interview Summary mailed Apr. 23, 2007", 4 pgs.
"U.S. Appl. No. 10/412,726, Examiner Interview Summary mailed Apr. 26, 2007", 4 pgs.
"U.S. Appl. No. 10/412,726, Examiner Interview Summary mailed Jul. 11, 2006", 5 pgs.
"U.S. Appl. No. 10/412,726, Non-Final Office Action mailed Apr. 16, 2010", 5 pgs.
"U.S. Appl. No. 11/002,008, Final office action mailed Apr. 2, 2007", 25 pgs.
"U.S. Appl. No. 11/002,008, Non Final office action mailed Jul. 13, 2006", 11 pgs.
"U.S. Appl. No. 11/002,008, Response filed Dec. 18, 2008 to Non Final office action mailed Jul. 13, 2006", 31 pgs.
"U.S. Appl. No. 11/002,008, Notice of Allowance mailed Dec. 12, 2007", 8 pgs.
"U.S. Appl. No. 11/002,008, Response filed Sep. 17, 2007 to Final Office Action mailed Apr. 2, 2007.", 26 pgs.
"U.S. Appl. No. 11/121,169, Non-Final Office Action Mailed Aug. 21, 2007", 8 pgs.
"U.S. Appl. No. 11/121,169, Notice of Allowance mailed Feb. 29, 2008", 6 pgs.
"U.S. Appl. No. 11/121,169, Response to Non-Final Office Action filed Dec, 20, 2007", 16 pgs.
"U.S. Appl. No. 11/196,529, Preliminary Amendment filed Nov. 7, 2005", 20 pgs.
"U.S. Appl. No. 11/196,798, Response filed Feb. 8, 2008 to Restriction Requirement mailed Jan. 9, 2008", 18 pgs.
"U.S. Appl. No. 11/196,798, Restriction Requirement mailed Jan. 9, 2008", 6 pgs.
"U.S. Appl. No. 11/196,802, Preliminary Amendment filed Nov. 10, 2005", 16 pgs.
"U.S. Appl. No. 11/196,802, Response filed Feb. 8, 2008 to Restriction Requirement mailed Jan. 9, 2008", 16 pgs.
"U.S. Appl. No. 11/196,802, Restriction Requirement mailed Jan. 9, 2008", 6 pgs.
"U.S. Appl. No. 11/222,664, Non final office action mailed Mar. 16, 2007", 10 pgs.
"U.S. Appl. No. 11/222,664, Non final office action mailed Jul. 14, 2006", 28 pgs.
"U.S. Appl. No. 11/222,664, Preliminary Amendment mailed Jun. 17, 2006", 4 pgs.
"U.S. Appl. No. 11/222,664, Response filed Sep. 17, 2007 to Non-Final Office Action mailed Mar. 16, 2007.", 25 pgs.
"U.S. Appl. No. 11/222,664, Response filed Dec. 14, 2006 to Non final office action mailed Jul. 14, 2006", 28 pgs.
"U.S. Appl. No. 11/222,664, Notice of Allowance Mailed Dec. 12, 2007", 11 pgs.
"U.S. Appl. No. 11/497,280, Non-Final Office Action mailed Jun. 3, 2009", 14 pgs.
"U.S. Appl. No. 11/672,868, Examiner Interview Summary mailed Nov. 5, 2009", 2 pgs.
"U.S. Appl. No. 11/672,868, Preliminary Amendment mailed Feb. 12, 2008", 15 pgs.
"U.S. Appl. No. 11/673,360, Response filed Jun. 17, 2010 to Final Office Action mailed Dec. 17, 2009", 25 pgs.
"U.S. Appl. No. 11/691,374, Final Office Action mailed Jun. 17, 2009", 14 pgs.
"U.S. Appl. No. 11/691,374, Non Final Office Action mailed Sep. 29, 2009", 6 pgs.
"U.S. Appl. No. 11/691,374, Non-Final Office Action mailed Jan. 12, 2009", 40 pgs.
"U.S. Appl. No. 11/691,374, Notice of Allowance mailed Feb. 1, 2010", 7 pgs.
"U.S. Appl. No. 11/691,374, Preliminary Amendment filed Mar. 26, 2007", 3 pgs.
"U.S. Appl. No. 11/691,374, Preliminary Amendment filed Jun. 12, 2007", 21 pgs.
"U.S. Appl. No. 11/691,374, Response filed Apr. 13, 2009 to Non Final Office Action mailed Jan. 12, 2009", 23 pgs.
"U.S. Appl. No. 11/691,374, Response filed Aug. 17, 2009 to Final Office Action mailed Jun. 17, 2009", 14 pgs.
"U.S. Appl. No. 11/691,374, Response filed Dec. 3, 2009 to Non Final Office Action mailed Sep. 29, 2009", 16 pgs.
"U.S. Appl. No. 11/739,680, Preliminary Amendment filed Apr. 24, 2007", 3 pgs.
"U.S. Appl. No. 11/739,680, Supplemental Preliminary Amendment filed Jul. 18, 2007", 6 pgs.
"U.S. Appl. No. 11/765,320, Non-Final Office Action mailed Aug. 20, 2010", 24 pgs.
"U.S. Appl. No. 11/765,320, Response filed Jun. 2, 2010 to Restriction Requirement mailed Apr. 2, 2010", 20 pgs.
"U.S. Appl. No. 11/765,320, Restriction Requirement mailed Apr. 2, 2010", 5 pgs.
"U.S. Appl. No. 12/338,599, Preliminary Amendment filed Feb. 20, 2009", 7 pgs.
"U.S. Appl. No. 12/487,235 Final Office Action mailed Sep. 20, 2010", 15 pgs.
"U.S. Appl. No. 12/487,235, Response filed Jun. 28, 2010 to Non Final Office Action mailed Dec. 28, 2009", 12 pgs.
"U.S. Appl. No. 12/487,265, Notice of Allowance mailed Apr. 6, 2010", 4 pgs.
"U.S. Appl. No. 12/487,265, Notice of Allowance mailed Sep. 7, 2010", 6 pgs.
"U.S. Appl. No. 12/487,265, Response filed Jan. 21, 2010 to Non Final Office Action mailed Dec. 18, 2009", 7 pgs.
"U.S. Appl. No. 12/630,231, Non Final Office Action mailed Jun. 28, 2010", 14 pgs.
"Australian Application Serial No. 2005201255, Response filed Feb. 7, 2008 to Examiner's Report dated Oct. 31, 2007", 6 pgs.
"Australian Application Serial No. 21082/99, Examiner's First Report dated Jun. 29, 2001", 3 pgs.
"Canadian Application Serial No. 2,361,614, Notice of Allowance mailed Mar. 26, 2008", 1 pg.
"Canadian Application Serial No. 2,375,374, Office Action Mailed Jan. 14, 2009", 11 pgs.
"Canadian Application Serial No. 2,375,374, Response filed Mar. 16, 2009 to Office Action Mailed Jan. 14, 2009", 7 pgs.
"Canadian Application Serial No. 2,460,911, Office Action mailed Apr. 16, 2010", 2 pgs.
"Canadian Application Serial No. 2,460,911, Response filed Dec. 14, 2009 to Non Final Office Action mailed Jun. 12, 2009", 35 pgs.
"Canadian Application Serial No. 2375374, Notice of Allowance mailed Jul. 23, 2009", 1 pg.
"Chemical Abstracts Registry No. 152918-18-8", (Feb. 10, 1994), 1 pg.
"Chemical Abstracts Registry No. 250386-15-3", (Dec. 9, 1999), 1 pg.
"Chemical Abstracts Registry No. 287179-78-6", (Aug. 24, 2000), 1 pg.
"Chemical Abstracts Registry No. 313348-27-5", (Jan. 10, 2001), 1 pg.

"European Application Serial No. 00941335.Feb. 2110, Communication mailed Aug. 26, 2002", 4 pgs.
"European Application Serial No. 00941335.2-2110, Response filed Dec. 20, 2002 to Communication mailed Aug. 26, 2002", 10 pgs.
"European Application Serial No. 02800432.3, Office Action mailed Apr. 22, 2010", 3 Pgs.
"European Application Serial No. 02800432.3, Office Action Response Filed Jun. 23, 2010", 2 pgs.
"European Application Serial No. 03728372.8, Office Action mailed Apr. 11, 2005", 4 pgs.
"European Application Serial No. 03728372.8, Office Action mailed Nov. 24, 2005", 3 pgs.
"European Application Serial No. 03728372.8, Response filed Feb. 22, 2006 to Office Action mailed Nov. 24, 2005", 10 pgs.
"European Application Serial No. 03728372.8, Response filed Oct. 21, 2005 to Office Action mailed Apr. 11, 2005", 14 pgs.
"European Application Serial No. 05756108.6, Office Action mailed Aug. 6, 2010", 9 pgs.
"European Application Serial No. 05803845.6, Communication mailed Jul. 26, 2007", 3 pgs.
"European Application Serial No. 05803845.6, Response filed Dec, 16, 2007 to Communication mailed Jul. 26, 2007", 28 pgs.
"European Application Serial No. 99901368.3, Communication dated Aug. 16, 2000", 2 pgs.
"International Application Serial No. PCT/US00/02324, International Preliminary Examination Report completed Apr. 5, 2001", 14 pgs.
"International Application Serial No. PCT/US00/02324, International Search Report mailed Oct. 20, 2000", 8 pgs.
"International Application Serial No. PCT/US00/02324, Response filed Mar. 1, 2001 to Written Opinion mailed Dec. 1, 2000", 13 pgs.
"International Application Serial No. PCT/US00/02324, Written Opinion mailed Dec. 1, 2000", 6 pgs.
"International Application Serial No. PCT/US00/14548, International Search Report mailed Feb. 1, 2001", 4 pgs.
"International Application Serial No. PCT/US00/14548, Response filed May 20, 2001 to Written Opinion mailed Feb. 27, 2001", 13 pgs.
"International Application Serial No. PCT/US00/14548, Written Opinion mailed Feb. 27, 2001", 7 pgs.
"International Application Serial No. PCT/US00/14548, Written Opinion mailed Jun. 25, 2001", 4 pgs.
"International Application Serial No. PCT/US00/16029, Amendment and Response filed Jun. 26, 2001 to Written Opinion mailed Apr. 26, 2001", 12 pgs.
"International Application Serial No. PCT/US00/16029, International Preliminary Examination Report completed Jul. 24, 2001", 14 pgs.
"International Application Serial No. PCT/US00/16029, International Search Report mailed Feb. 8, 2001", 6 pgs.
"International Application Serial No. PCT/US00/16029, Written Opinion mailed Apr. 26, 2001", 6 pgs.
"International Application Serial No. PCT/US05/15241, International Search Report mailed Aug. 19, 2005", 3 pgs.
"International Application Serial No. PCT/US07/61919, International Search Report mailed Nov. 7, 2007", 3 pgs.
"International Application Serial No. PCT/US07/61919, Written Opinion mailed Nov. 7, 2007", 8 pgs.
"International Application Serial No. PCT/US2005/015241, International Preliminary Examination Report mailed Nov. 16, 2006", 6 pgs.
"International Application Serial No. PCT/US2005/015241, International Search Report and Written Opinion mailed Sep. 14, 2005", 10 pgs.
"International Application Serial No. PCT/US2005/027474, International Preliminary Examination Report mailed Feb. 15, 2007", 10 pgs.
"International Application Serial No. PCT/US2005/027474, International Search Report and Written Opinion mailed Jan. 25, 2006", 16 pgs.
"International Application Serial No. PCT/US2005/027475, International Preliminary Examination Report mailed Feb. 15, 2007", 7 pgs.
"International Application Serial No. PCT/US2005/027475, International Search Report mailed Jan. 23, 2006", 6 pgs.
"International Application Serial No. PCT/US2005/027475, Written Opinion mailed Jan. 23, 2006", 8 pgs.
"International Application Serial No. PCT/US2005/027479, International Preliminary Examination Report mailed Feb. 15, 2007", 12 pgs.
"International Application Serial No. PCT/US2005/027479, International Search Report mailed Sep. 6, 2006", 6 pgs.
"International Application Serial No. PCT/US2005/027479, Written Opinion mailed Sep. 6, 2006", 10 pgs.
"International Application Serial No. PCT/US2007/061867, International Preliminary Examination Report mailed Aug. 21, 2008", 8 pgs.
"International Application Serial No. PCT/US2007/061867, International Search Report mailed Nov. 26, 2007", 3 pgs.
"International Application Serial No. PCT/US2007/061867, Written Opinion mailed Nov. 26, 2007", 8 pgs.
"International Application Serial No. PCT/US2007/061919, International Preliminary Examination Report mailed Aug. 21, 2008", 8 pgs.
"International Application Serial No. PCT/US2008/004553, International Preliminary Examination Report mailed Oct. 22, 2009", 8 pgs.
"International Application Serial No. PCT/US2008/004553, International Search Report mailed Jul. 30, 2008", 2 pgs.
"International Application Serial No. PCT/US2008/004553, Written Opinion mailed Jul. 30, 2008", 7 pgs.
"International Application Serial No. PCT/US99/00366, International Preliminary Examination Report completed Mar. 20, 2000", 9 pgs.
"International Application Serial No. PCT/US99/00366, International Search Report mailed Mar. 20, 2000", 7 pgs.
"International Application Serial No. PCT/US99/00366, Remarks and Response filed Jan. 5, 2000 to Written Opinion mailed Oct. 29, 1999", 2 pgs.
"International Application Serial No. PCT/US99/00366, Written Opinion mailed Oct. 29, 1999", 8 pgs.
"International International Application U.S. Appl. No. PCT/US00/14548, Response filed Jul. 23, 2001 to Written Opinion mailed Jun. 25, 2001", 2 pgs.
Abiru, T., et al., "Differential vasodilatory action of 2-octynyladenosine (YT-146), an adenosine A2 receptor agonist, in the isolated rat femoral artery and vein.", Eur J Pharmacol., 281(1), (Jul. 25, 1995), 9-15.
Brito, G. A. C., et al., "*Clostridium difficile* Toxin a Induces Intestinal Epithelial Cell Apoptosis and Damage: Role of Gln and Ala-Gln in Toxin a Effects", Digestive Diseases and Sciences, 50(7), (2005), 1271-1278.
Cavalcante, I. C, et al., "Effect of Novel A2A Adenosine Receptor Agonist ATL 313 on *Clostridium difficile* Toxin A-Induced Murine Ileal Enteritis", Infection and Immunity, vol. 74, No. 5, (May 2006), 2606-2612.
Chou, T. C., et al., "Quantitative analysis of dose-effect relationships: the combined effects of multiple drugs or enzyme inhibitors", Advances in Enzyme Regulation, 22, (1984), 27-55.
Chow, F., et al., "Macrophages in mouse type 2 diabetic nephropathy: correlation with diabetic state and progressive renal injury", Kidney Int., 65(1), XP002593910, ISSN: 0085-2538, (Jan., 2004), 116-28.
Cristalli, G, et al., "Platelet aggregation inhibitory activity of selective A2 Adenosine Receptor Agonists", Nucleosides & Nucleotides, vol. 14 No. 3-5, (1995), 449-453.
Harada, N., et al., "Adenosine reduces ischemia/reperfusion injury of rat liver by inhibiting leukocyte activation: Involvement of adenosine A2a receptor", Jpn. J. Pharmacol., 79(Suppl), Abstract No. O-214, (1999), 89P.
Li, Y., et al., "Mouse Spinal Cord Compression Injury is Reduced by Either Activation of the Adenosine A2A Receptor on Bone Marrow-Derived Cells or Deletion of the A2A Receptor on Non-Bone Marrow-Derived Cells", Neuroscience, 141, (2006), 2029-2039.
Okusa, M. D, "A(2A) adenosine receptor: a novel therapeutic target in renal disease", Am J Physiol Renal Physiol., 282(1), XP002593908; ISSN : 0002-9513, (Jan. 2002), F10-8.
Okusa, Mark D, "Attenuation of renal inflammation by adenosine 2A receptor (A2A-AR) activation in ischemia-reperfusion injury (I/R) Regulation adhesion molecule and cytokine expression", 33RD Annual Meeting of the American Society of Nephrology vol. 11, No. Program and A, XP008124542; ISSN : 1046-6673, (Sep. 1, 2000), 132A.

Pflueger, A. C, et al., "Adenosine-Induced Renal Vasoconstriction in Diabetes Mellitus Rats: Role of Nitric Oxide", Am. J. Physiol. Renal Physiol., 276, (1999), F340-F346.

Takahashi, T., et al., "Increased spontaneous adherence of neutrophils from type 2 diabetic patients with overt proteinuria: possible role of the progression of diabetic nephropathy.", Diabetes Care, 23(3), XP002593909; ISSN: 0149-5992, (Mar. 2000), 417-8.

Vu, C. B., et al., "Piperazine Derivatives of [1,2,4] Triazolo [1,5-a][1,3,5]triazine as Potent and Selective Adenosine a (sub 2a) Receptor Antagonists", J. Med. Chem., 47, (2004), 4291-4299.

"U.S. Appl. No. 10/412,726, Examiner Interview Summary mailed Nov. 30, 2010", 2 pgs.

"U.S. Appl. No. 11/497,280, Examiner Interview Summary mailed Dec. 16, 2009", 2 pgs.

"U.S. Appl. No. 11/673,360, Non Final Office Action mailed Nov. 26, 2010", 26 pgs.

"U.S. Appl. No. 11/765,320, Response filed Jan. 20, 2011 to Non Final Office Action mailed Aug. 20, 2010", 22 pgs.

"U.S. Appl. No. 12/338,599, Supplemental Preliminary Amendment filed Oct. 15, 2010", 3 pgs.

"U.S. Appl. No. 12/487,235, Examiner Interview Summary Dec. 7, 2010", 3 pgs.

"Australian Application Serial No. 2005267706, Examiner Report mailed on Sep. 16, 2010", 2 Pgs.

"Canadian Application Serial No. 2,460,911, Office Action Response Filed Oct. 14, 2010", 4 pgs.

"European Application Serial No. 02800432.3 , Office Action mailed Dec. 29, 2010", 3 pgs.

"European Application Serial No. 05803845.6, Communication mailed Oct. 18, 2010", 4 pages.

"European Application Serial No. 10181920.9 , Extended European Search Report mailed Nov. 30, 2010", 11 pgs.

"International Application Serial No. PCT/US09/30565, International Search Report and Written Opinion mailed Apr. 6, 2009", 7 pgs.

"Japanese Application Serial No. 2000-596019, Office Action Response Filed Nov. 15, 2010", 23 pgs.

"Singapore Application Serial No. 200706337-3, Response to Written Opinion Filed: Dec. 13, 2010", 15 pgs.

"Canadian Application Serial No. 2460911, Notice of Allowance mailed Dec. 21, 2010", 1 pg.

"European Application Serial No. 05756108.6, Office Action mailed Feb. 3, 2011", 7 pgs.

"European Application Serial No. 05803845.6, Response filed Feb. 9, 2011 to Non Final Office Action mailed Oct. 18, 2010", 3 pgs.

"Japanese Application Serial No. 2001-504969, Response filed Jan. 7, 2011 to Office Action mailed Jul. 1, 2010", 3 pgs.

"Japanese Application Serial No. 2007-511486, Office Action mailed Feb. 8, 2011".

"Journal of Clinical and Experimental Medicine", 209(1), (2004), 54-59.

Okusa, M. D., et al., "Enhanced protection from renal ischemia-reperfusion injury with A(2A)-adenosine receptor activation and PDE 4 inhibition.", Kidney Int., 59(6), (Jun. 2001), 2114-25.

Okusa, M. D, et al., "Selective A2A adenosine receptor activation reduces ischemia-reperfusion injury in rat kidney", Am J Physiol., 277(3 Pt 2), (Sep. 1999), F404-12.

"U.S. Appl. No. 11/673,360, Final Office Action mailed May 3, 2011", 18 pgs.

"U.S. Appl. No. 11/673,360, Response filed Mar. 25, 2011 to Non Final Office Action mailed Nov. 26, 2010", 27 pgs.

"U.S. Appl. No. 11/765,320, Non Final Office Action mailed Apr. 15, 2011", 7 pgs.

"U.S. Appl. No. 12/487,235, Notice of Allowance mailed Mar. 25, 2011", 7 pgs.

"U.S. Appl. No. 12/487,235, Response filed Feb. 28, 2011 to Final Office Action mailed Sep. 20, 2010", 11 pgs.

"U.S. Appl. No. 13/027,901, Non Final Office Action mailed Mar. 31, 2011", 15 pgs.

"European Application Serial No. 02800432.3, Response filed Mar. 17, 2011 to Non Final Office Action mailed Dec. 29, 2010", 40 pgs.

"Singapore Application Serial No. 200706337-3, Office Action mailed May 3, 2011", 10 pgs.

"U.S. Appl. No. 11/673,360, Response filed Oct. 7, 2011 to Final Office Action mailed May 3, 2011", 19 pgs.

"U.S. Appl. No. 11/765,320, Response filed Oct. 27, 2011 to Non Final Office Action mailed Apr. 14, 2011", 21 pgs.

"U.S. Appl. No. 12/338,599, Notice of Allowance mailed Jun. 28, 2011", 9 pgs.

"U.S. Appl. No. 13/027,901, Non Final Office Action mailed Jul. 6. 2011", 8 pgs.

"Brazil Application Serial No. PI 0007864-6,Office Action mailed May 18, 2011", 5 pgs.

"Brazil Application Serial No. PI0011725-0, Office Action mailed Jun. 9, 2011", 4 pgs.

"Canadian Application Serial No. 2,576,826, Office Action mailed Sep. 22, 2011", 4 pgs.

"European Application Serial No. 05756108.6, Response filed Jul. 20, 2011 to Non Final Office Action dated Feb. 3, 2011", 22 pgs.

"European Application Serial No. 10181920.9, Office Action mailed Jul. 21, 2011", 4 pgs.

"European Divisional Application Serial No. 10181920.9, Response filed Jun. 29, 2011 to EP Search Report dated Nov. 30, 2010", 53 pgs.

"Japanese Application Serial No. 2001-504939, Final Office Action mailed Jul. 28, 2011", 6 pgs.

"Japanese Application Serial No. 2007-524924, Office Action mailed Sep. 16, 2011", 3 pgs.

"New Zealand Application Serial No. 585697, Non Final Office Action dated Aug. 29, 2011", 2 pgs.

"New Zealand Application Serial No. 585697, Response filed Aug. 11, 2011 to Examination Report dated Jun. 3, 2010", 3 pgs.

"New Zealand Application Serial No. 585697, Response filed Sep. 28, 2011 to Office Action mailed Aug. 31, 2011", 13 pgs.

"Pakistan Application Serial No. 7812000, Response filed Oct. 15, 2011 to Non Final Office Action dated May 14, 2010", 1.

"Singapore Application Serial No. 200706337-3, Response to Written Opinion filed Oct. 3, 2011", 13 pgs.

\* cited by examiner

2-PROPYNYL ADENOSINE ANALOGS HAVING A2A AGONIST ACTIVITY AND COMPOSITIONS THEREOF

CROSS-REFERENCE TO RELATED APPLICATIONS

This application is a continuation of U.S. patent application Ser. No. 11/691,374, filed Mar. 26, 2007 now U.S. Pat. No. 7,737,127, and published as US2007/0232559, which is a continuation of U.S. patent application Ser. No. 10/263,379, filed Oct. 1, 2002, now U.S. Pat. No. 7,214,665, which claims priority of U.S. provisional patent application Ser. No. 60/326,517, filed Oct. 1, 2001, and U.S. provisional patent application Ser. No. 60/383,200, filed May 24, 2002, all of which are incorporated by reference herein.

GOVERNMENT FUNDING

This invention was made with government support under Grant Number RO1-HL37942 awarded by the National Institutes of Health. The government has certain rights in the invention.

BACKGROUND OF THE INVENTION

The inflammatory response serves the purpose of eliminating harmful agents from the body. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma. Inflammation normally is a very localized action which serves in expulsion, attenuation by dilution, and isolation of the damaging agent and injured tissue. The body's response becomes an agent of disease when it results in inappropriate injury to host tissues in the process of eliminating the targeted agent, or responding to a traumatic insult.

As examples, inflammation is a component of pathogenesis in several vascular diseases or injuries. Examples include: ischemia/reperfusion injury (N. G. Frangogiannis et al., in *Myocardial Ischemia: Mechanisms, Reperfusion, Protection*, M. Karmazyn, ed., Birkhuser Verlag (1996) at 236-284; H. S. Sharma et al., *Med. of Inflamm.,* 6, 175 (1987)), atherosclerosis (R. Ross, *Nature,* 362, 801 (1993)), inflammatory aortic aneurysms (N. Girardi et al., *Ann. Thor. Surg.,* 64, 251 (1997); D. I. Walker et al., *Brit. J. Surg.,* 59, 609 (1972); R. L. Pennell et al., *J. Vasc. Surg.,* 2, 859 (1985)), and restenosis following balloon angioplasty (see, R. Ross cited above). The cells involved with inflammation include leukocytes (i.e., the immune system cells—neutrophils, eosinophils, lymphocytes, monocytes, basophils, macrophages, dendritic cells, and mast cells), the vascular endothelium, vascular smooth muscle cells, fibroblasts, and myocytes.

The release of inflammatory cytokines such as tumor necrosis factor-alpha (TNFα) by leukocytes is a means by which the immune system combats pathogenic invasions, including infections. TNFα stimulates the expression and activation of adherence factors on leukocytes and endothelial cells, primes neutrophils for an enhanced inflammatory response to secondary stimuli and enhances adherent neutrophil oxidative activity. See, Sharma et al., cited above. In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and nonoxidative (e.g., myeloperoxidase and other enzymes) inflammatory activity. Inappropriate and over-release of cytokines can produce counterproductive exaggerated pathogenic effects through the release of tissue-damaging oxidative and nonoxidative products (K. G. Tracey et al., *J. Exp. Med.,* 167, 1211 (1988); and D. N. Männel et al., *Rev. Infect. Dis.,* 9 (suppl. 5), S602-S606 (1987)). For example, TNFα can induce neutrophils to adhere to the blood vessel wall and then to migrate through the vessel to the site of injury and release their oxidative and non-oxidative inflammatory products.

Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including TNFα), complement, lipids, reactive oxygen species, proteases and growth factors that remodel tissue and regulate surrounding tissue functions.

For example, inflammatory cytokines have been shown to be pathogenic in: arthritis (C. A. Dinarello, *Semin. Immunol.,* 4, 133 (1992)); ischemia (A. Seekamp et al., *Agents-Actions-Supp.,* 41, 137 (1993)); septic shock (D. N. Männel et al., *Rev. Infect. Dis.,* 9 (suppl. 5), S602-S606 (1987)); asthma (N. M. Cembrzynska et al., *Am. Rev. Respir. Dis.,* 147, 291 (1993)); organ transplant rejection (D. K. Imagawa et al., *Transplantation,* 51, 57 (1991); multiple sclerosis (H. P. Hartung, *Ann. Neurol.,* 33, 591 (1993)); AIDS (T. Matsuyama et al., *AIDS,* 5, 1405 (1991)); and in alkali-burned eyes (F. Miyamoto et al., *Opthalmic Res.,* 30, 168 (1997)). In addition, superoxide formation in leukocytes has been implicated in promoting replication of the human immunodeficiency virus (HIV) (S. Legrand-Poels et al., *AIDS Res. Hum. Retroviruses,* 6, 1389 (1990)).

It is well known that adenosine and some analogs of adenosine that nonselectively activate adenosine receptor subtypes decrease neutrophil production of inflammatory oxidative products (B. N. Cronstein et al., *Ann. N.Y. Acad. Sci.,* 451, 291 (1985); P. A. Roberts et al., *Biochem. J.,* 227, 669 (1985); D. J. Schrier et al., *J. Immunol.,* 137, 3284 (1986); B. N. Cronstein et al., *Clinical Immunol. and Immunopath.,* 42, 76 (1987); M. A. Iannone et al., in *Topics and Perspective in Adenosine Research*, E. Gerlach et al., eds., Springer-Verlag, Berlin, p. 286 (1987); S. T. McGarrity et al., *J. Leukocyte Biol.,* 44, 411-421 (1988); J. De La Harpe et al., *J. Immunol.,* 143, 596 (1989); S. T. McGarrity et al., *J. Immunol.,* 142, 1986 (1989); and C. P. Nielson et al., *Br. J. Pharmacol.,* 97, 882 (1989)). For example, adenosine has been shown to inhibit superoxide release from neutrophils stimulated by chemoattractants such as the synthetic mimic of bacterial peptides, f-met-leu-phe (fMLP), and the complement component $C_5a$ (B. N. Cronstein et al., *J. Immunol.,* 135, 1366 (1985)). Adenosine can decrease the greatly enhanced oxidative burst of PMN (neutrophil) first primed with TNF-α and then stimulated by a second stimulus such as f-met-leu-phe (G. W. Sullivan et al., *Clin. Res.,* 41, 172A (1993)). Additionally, it has been reported that adenosine can decrease the rate of HIV replication in a T-cell line (S. Sipka et al., *Acta. Biochim. Biopys. Hung.,* 23, 75 (1988)). However, there is no evidence that in vivo adenosine has anti-inflammatory activity (G. S. Firestein et al., *Clin. Res.,* 41, 170A (1993); and B. N. Cronstein et al., *Clin. Res.,* 41, 244A (1993)).

It has been suggested that there is more than one subtype of adenosine receptor on neutrophils that can have opposite effects on superoxide release (B. N. Cronstein et al., *J. Clin. Invest.,* 85, 1150 (1990)). The existence of $A_{2A}$ receptor on neutrophils was originally demonstrated by Van Calker et al. (D. Van Calker et al., *Eur. J. Pharmacology*, 206, 285 (1991)).

There has been progressive development of compounds that are more and more potent and/or selective as agonists of $A_{2A}$ adenosine receptors (AR) based on radioligand binding assays and physiological responses. Initially, compounds with little or no selectivity for $A_{2A}$ receptors were developed, such as adenosine itself or 5N-carboxamides of adenosine, such as 5N—N-ethylcarboxamidoadeno sine (NECA) (B. N. Cronstein et al., *J. Immunol.*, 135, 1366 (1985)). Later, it was shown that addition of 2-alkylamino substituents increased potency and selectivity, e.g., CV1808 and CGS21680 (M. F. Jarvis et al., *J. Pharmacol. Exp. Ther.*, 251, 888 (1989)). 2-Alkoxy-substituted adenosine derivatives such as WRC-0090 are even more potent and selective as agonists at the coronary artery $A_{2A}$ receptor (M. Ueeda et al., *J. Med. Chem.*, 34, 1334 (1991)). The 2-alklylhydrazino adenosine derivatives, e.g., SHA 211 (also called WRC-0474) have also been evaluated as agonists at the coronary artery $A_{2A}$ receptor (K. Niiya et al., *J. Med. Chem.*, 35, 4557 (1992)).

There is one report of the combination of relatively nonspecific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (M. A. Iannone et al., *Topics and Perspectives in Adenosine Research*, E. Garlach et al., eds., Springer-Verlag, Berlin, pp. 286-298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block."

R. A. Olsson et al. (U.S. Pat. No. 5,278,150) disclose selective adenosine $A_2$ receptor agonists of the formula:

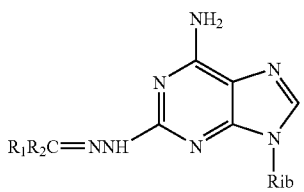

wherein Rib is ribosyl, $R_1$ can be H and $R_2$ can be cycloalkyl. The compounds are disclosed to be useful for treating hypertension, atherosclerosis and as vasodilators.

Olsson et al. (U.S. Pat. No. 5,140,015) disclose certain adenosine $A_2$ receptor agonists of formula:

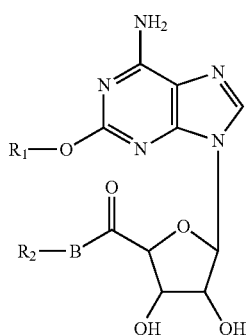

wherein $C(X)BR_2$ can be $CH_2OH$ and $R_1$ can be alkyl- or alkoxyalkyl. The compounds are disclosed to be useful as vasodilators or an antihypertensives.

Linden et al. (U.S. Pat. No. 5,877,180) is based on the discovery that certain inflammatory diseases, such as arthritis and asthma, may be effectively treated by the administration of compounds which are selective agonists of $A_{2A}$ adenosine receptors, preferably in combination with a Type IV phosphodiesterase inhibitor. An embodiment of the Linden et al. invention provides a method for treating inflammatory diseases by administering an effective amount of an $A_{2A}$ adenosine receptor of the following formula:

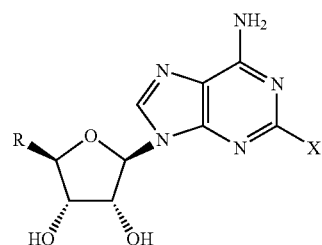

wherein R and X are as described in the patent.

In one embodiment, the Linden et al. invention involves the administration of a Type IV phosphodiesterase (PDE) inhibitor in combination with the $A_{2A}$ adenosine receptor agonist. The Type IV phosphodiesterase (PDE) inhibitor includes racemic and optically active 4-(polyalkoxyphenyl)-2-pyrrolidones of the following formula:

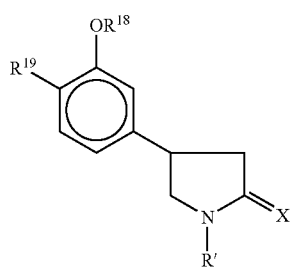

wherein RN, $R^{18}$, $R^{19}$ and X are as disclosed and described in U.S. Pat. No. 4,193,926. Rolipram is an example of a suitable Type IV PDE inhibitor included within the above formula.

G. Cristalli (U.S. Pat. No. 5,593,975) discloses 2-arylethynyl, 2-cycloalkylethynyl or 2-hydroxyalkylethynyl derivatives, wherein the riboside residue is substituted by carboxy amino, or substituted carboxy amino ($R_3HNC(O)$—). 2-Alkynylpurine derivatives have been disclosed in Miyasaka et al. (U.S. Pat. No. 4,956,345), wherein the 2-alkynyl group is substituted with ($C_3$-$C_{16}$)alkyl. The '975 compounds are disclosed to be vasodilators and to inhibit platelet aggregation, and thus to be useful as anti-ischemic, anti-atherosclerosis and anti-hypertensive agents.

Recently, U.S. Pat. No. 6,232,297 to Linden, et al. disclosed compounds having the general formula:

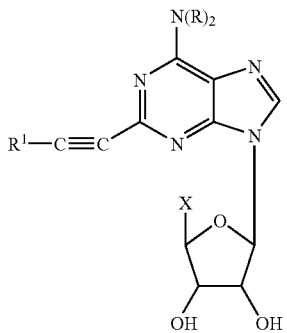

wherein each R is H, X is ethylaminocarbonyl and $R^1$ is 4-carboxycyclo-hexylmethyl (DWH-146a), $R^1$ is 4-methoxycarbonylcyclohexylmethyl (DWH-146e) or $R^1$ is 4-acetoxymethyl-cyclohexylmethyl (JMR-193). These compounds are reported to be $A_{2A}$ agonists.

However, a continuing need exists for selective $A_2$ adenosine receptor agonists useful for therapeutic applications, that have reduced side effects.

SUMMARY OF THE INVENTION

The present invention comprises compounds and methods of their use for the treatment of inflammatory activity in mammalian tissue. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. The present compounds comprise a novel class of 2-alkynyladenosine derivatives, substituted at the ethyn-2-yl position by substituted cycloalkyl and heterocycle (heterocyclic) moieties. Preferably, the riboside residue is substituted at the 5N-position by an N-alkyl-(or cycloalkyl)carboxyamino ("aminocarbonyl") moiety ("X"). Thus, the present invention provides a method for inhibiting the inflammatory response in a mammal, such as a human subject, and protecting the tissue subject to the response, by administering an effective amount of one or more compounds of the invention.

The compounds of the invention have general formula (I):

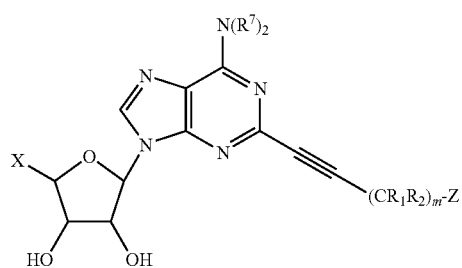

wherein
Z is $CR^3R^4R^5$ or $NR^4R^5$;
each $R^1$ is independently hydrogen, halo, $-OR^a$, $-SR^a$, $(C_1-C_8)$alkyl, cyano, nitro, trifluoromethyl, trifluoromethoxy, $C_{3-8}$cycloalkyl, heterocycle, hetrocycle$(C_1-C_8)$alkylene-, aryl, aryl$(C_1-C_8)$alkylene-, heteroaryl, heteroaryl$(C_1-C_8)$ alkylene-, $-CO_2R^a$, $R^aC(=O)O-$, $R^aC(=O)-$, $-OCO_2R^a$, $R^aR^bNC(=O)O-$, $R^bOC(=O)N(R^a)-$, $R^aR^bN-$, $R^aR^bNC(=O)-$, $R^aC(=O)N(R^b)-$, $R^aR^bNC(=O)N(R^b)-$, $R^aR^bNC(=S)N(R^b)-$, $-OPO_3R^a$, $R^aOC(=S)-$, $R^aC(=S)-$, $-SSR^a$, $R^aS(=O)-$, $R^aS(=O)_2-$, $-N=NR^a$, or $-OPO_2R^a$;

each $R^2$ is independently hydrogen, halo, $(C_1-C_8)$alkyl, $(C_3-C_8)$cycloalkyl, heterocycle, heterocycle$(C_1-C_8)$alkylene-, aryl, aryl$(C_1-C_8)$alkylene-, heteroaryl, or heteroaryl $(C_1-C_8)$alkylene-; or $R^1$ and $R^2$ and the atom to which they are attached is $C=O$, $C=S$ or $C=NR^c$.

$R^4$ and $R^5$ together with the atoms to which they are attached form a saturated or partially unsaturated, mono-, bicyclic- or aromatic ring having 3, 4, 5, 6, 7, 8, 9 or 10 ring atoms optionally comprising 1, 2, 3, or 4 heteroatoms selected from non-peroxide oxy ($-O-$), thio ($-S-$), sulfinyl ($-SO-$), sulfonyl ($-S(O)_2-$) or amine ($-NR^a-$) in the ring;

wherein any ring comprising $R^4$ and $R^5$ is substituted with from 1 to 14 $R^6$ groups; wherein each $R^6$ is independently halo, $-OR^a$, $-SR^a$, $(C_1-C_8)$alkyl, cyano, nitro, trifluoromethyl, trifluoromethoxy, $(C_1-C_8)$cycloalkyl, $(C_6-C_{12})$bicycloalkyl, heterocycle or hetrocycle $(C_1-C_8)$alkylene-, aryl, aryl $(C_1-C_8)$alkylene-, heteroaryl, heteroaryl$(C_1-C_8)$alkylene-, $-CO_2R^a$, $R^aC(=O)O-$, $R^aC(=O)-$, $-OCO_2R^a$, $R^aR^bNC(=O)O-$, $R^bOC(=O)N(R^a)-$, $R^aR^bN-$, $R^aR^bNC(=O)-$, $R^aC(=O)N(R^b)-$, $R^aR^bNC(=O)N(R^b)-$, $R^aR^bNC(=S)N(R^b)-$, $-OPO_3R^a$, $R^aOC(=S)-$, $R^aC(=S)-$, $-SSR^a$, $R^aS(=O)-$, $-NNR^a$, $-OPO_2R^a$, or two $R^6$ groups and the atom to which they are attached is $C=O$, $C=S$ or; two $R^6$ groups together with the atom or atoms to which they are attached can form a carbocyclic or heterocyclic ring.

$R^3$ is hydrogen, halo, $-OR^a$, $-SR^a$, $(C_1-C_8)$alkyl, cyano, nitro, trifluoromethyl, trifluoromethoxy, $(C_3-C_8)$cycloalkyl, heterocycle, heterocycle$(C_1-C_8)$alkylene-, aryl, aryl$(C_1-C_8)$ alkylene-, heteroaryl, heteroaryl$(C_1-C_8)$alkylene-, $-CO_2R^a$, $R^aC(=O)O-$, $R^aC(=O)-$, $-OCO_2R^a$, $R^aR^bNC(=O)O-$, $R^bOC(=O)N(R^a)-$, $R^aR^bN-$, $R^aR^bNC(=O)-$, $R^aC(=O)N(R^b)-$, $R^aR^bNC(=O)N(R^b)-$, $R^aR^bNC(=S)N(R^b)-$, $-OPO_3R^a$, $R^aOC(=S)-$, $R^aC(=S)-$, $-SSR^a$, $R^aS(=O)-$, $R^aS(=O)_2-$, $-NNR^a$, $-OPO_2R^a$; or if the ring formed from $CR^4R^5$ is aryl or hetreroaryl or partially unsaturated then $R^3$ can be absent;

each $R^7$ is independently hydrogen, $(C_1-C_8)$alkyl, $(C_3-C_8)$ cycloalkyl, aryl or aryl$(C_1-C_8)$alkylene, heteroaryl, heteroaryl$(C_1-C_8)$alkylene-;

X is $-CH_2OR^a$, $-CO_2R^a$, $-OC(O)R^a$, $-CH_2OC(O)R^a$, $-C(O)NR^aR^b$, $-CH_2SR^a$, $-C(S)OR^a$, $-OC(S)R^a$, $-CH_2OC(S)R^a$ or $C(S)NR^aR^b$ or $-CH_2N(R^a)(R^b)$;

wherein any of the alkyl, cycloalkyl, heterocycle, aryl, or heteroaryl, groups of $R^1$, $R^2$, $R^3$, $R^6$ and $R^7$ is optionally substituted on carbon with one or more (e.g. 1, 2, 3, or 4) substituents selected from the group consisting of halo, $-OR^a$, $-SR^a$, $(C_1-C_8)$alkyl, cyano, nitro, trifluoromethyl, trifluoromethoxy, $(C_3-C_8)$cycloalkyl, $(C_6-C_{12})$bicycloalkyl, heterocycle or hetrocycle$(C_1-C_8)$alkylene-, aryl, aryloxy, aryl $(C_1-C_8)$alkylene-, heteroaryl, heteroaryl$(C_1-C_8)$ alkylene-, $-CO_2R^a$, $R^aC(=O)O-$, $R^aC(=O)-$, $-OCO_2R^a$, $R^aR^bNC(=O)O-$, $R^bOC(=O)N(R^a)-$, $R^aR^bN-$, $R^aR^bNC(=O)-$, $R^aC(=O)N(R^b)-$, $R^aR^bNC(=O)N(R^b)-$, $R^aR^bNC(=S)N(R^b)-$, $-OPO_3R^a$, $R^aOC(=S)-$, $R^aC(=S)-$, $-SSR^a$, $R^aS(=O)_p-$, $R^aR^bNS(O)_p-$, $-N=NR^a$, and $-OPO_2R^a$;

wherein any $(C_1-C_8)$alkyl, $(C_3-C_8)$cycloalkyl, $(C_6-C_{12})$bicycloalkyl, $(C_1-C_8)$alkoxy, $(C_1-C_8)$alkanoyl, $(C_1-C_8)$alkylene, or heterocycle, is optionally partially unsaturated;

$R^a$ and $R^b$ are each independently hydrogen, $(C_1-C_8)$alkyl, or $(C_1-C_8)$alkyl substituted with 1-3 $(C_1-C_8)$alkoxy, $(C_3-C_8)$ cycloalkyl, $(C_1-C_8)$alkylthio, amino acid, aryl, aryl$(C_1-C_8)$ alkylene, heteroaryl, or heteroaryl$(C_1-C_8)$alkylene; or $R^a$ and $R^b$, together with the nitrogen to which they are attached, form a pyrrolidino, piperidino, morpholino, or thiomorpholino ring; and $R^c$ is hydrogen or $(C_1-C_6)$alkyl;

m is 0 to about 8 and p is 0 to 2;

provided that when $CR^4R^5$ is a carbocyclic ring then at least one of $R^1$, $R^2$, or $R^3$ is a group other than hydrogen or at least one $R^6$ group is a group other than —$CH_2OH$, —$CO_2R^a$, $R^aC(=O)O$—, $R^aC(=O)OCH_2$— or $R^aR^bNC(=O)$—;

provided that m is at least 1 when Z is $NR^4R^5$;

or a pharmaceutically acceptable salt thereof.

The invention provides a compound of formula I for use in medical therapy, preferably for use in treating inflammation or protecting mammalian tissue from inflammation such as an inflammatory response, e.g., resulting from allergy, trauma or ischemia/reperfusion injury, as well as the use of a compound of formula I for the manufacture of a medicament for the treatment of an inflammatory response due to a pathological condition or symptom in a mammal, such as a human, which is associated with inflammation.

Although certain $A_{2A}$ adenosine receptor agonists have been reported to be vasodilators, and thus to be useful to directly treat hypertension, thrombus, atherosclerosis and the like, the tissue-protective anti-inflammatory activity of the compounds of formula (I) is not suggested by the prior art.

The invention also includes the use of a combination of these compounds with type IV phosphodiesterase inhibitors to preferably cause synergistic decreases in the inflammatory response mediated by leukocytes.

The invention also provides a pharmaceutical composition comprising an effective amount of the compound of formula I, or a pharmaceutically acceptable salt thereof, in combination with a pharmaceutically acceptable diluent or carrier, and optionally, in combination with a Type IV phosphodiesterase (PDE) inhibitor. Preferably, the composition is presented as a unit dosage form.

Additionally, the invention provides a therapeutic method for preventing or treating a pathological condition or symptom in a mammal, such as a human, wherein the activity of $A_{2A}$ adenosine receptors is implicated and agonism of said receptors is desired, comprising administering to a mammal in need of such therapy, an effective amount of a compound of formula I, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

Among the inflammatory responses that can be treated (including treated prophylactically) with a compound of formula I, optionally with a Type IV PDE inhibitor, are inflammation due to:

(a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis;

(b) allergic diseases such as asthma, hay fever, rhinitis, poison ivy, vernal conjunctivitis and other eosinophil-mediated conditions;

(c) skin diseases such as psoriasis, contact dermatitis, eczema, infectious skin ulcers, open wounds, cellulitis;

(d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), lyme disease, HIV infection, (TNFα-enhanced HIV replication, TNFα inhibition of reverse transcriptase inhibitor activity);

(e) wasting diseases: cachexia secondary to cancer and HIV;

(f) organ, tissue or cell transplantation (e.g., bone marrow, cornea, kidney, lung, liver, heart, skin, pancreatic islets) including transplant rejection, and graft versus host disease;

(g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression;

(h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes;

(i) dialysis, including pericarditis, due to peritoneal dialysis;

(j) gout; and (k) chemical or thermal trauma due to burns, acid, alkali and the like.

Of particular interest and efficacy is the use of the present compounds to limit inflammatory responses where the ischemia/reperfusion injury is caused by angioplasty or throbolysis. Also of particular interest and efficacy is the use of the present compounds to limit inflammatory responses due to organ, tissue or cell transplantation, i.e., the transplantation of allogeneic or xenogeneic tissue into a mammalian recipient, autoimmune diseases and inflammatory conditions due to circulatory pathologies and the treatment thereof, including angioplasty, stent placement, shunt placement or grafting. Unexpectedly, it was found that administration of one or more compounds of formula (I) was effective after the onset of the inflammatory response, e.g., after the subject was afflicted with the pathology or trauma that initiates the inflammatory response.

Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extent of displacement of the ligand and/or binding of the agent, or the cellular response to said agent (e.g., cAMP accumulation).

DETAILED DESCRIPTION OF THE INVENTION

Figure 1:
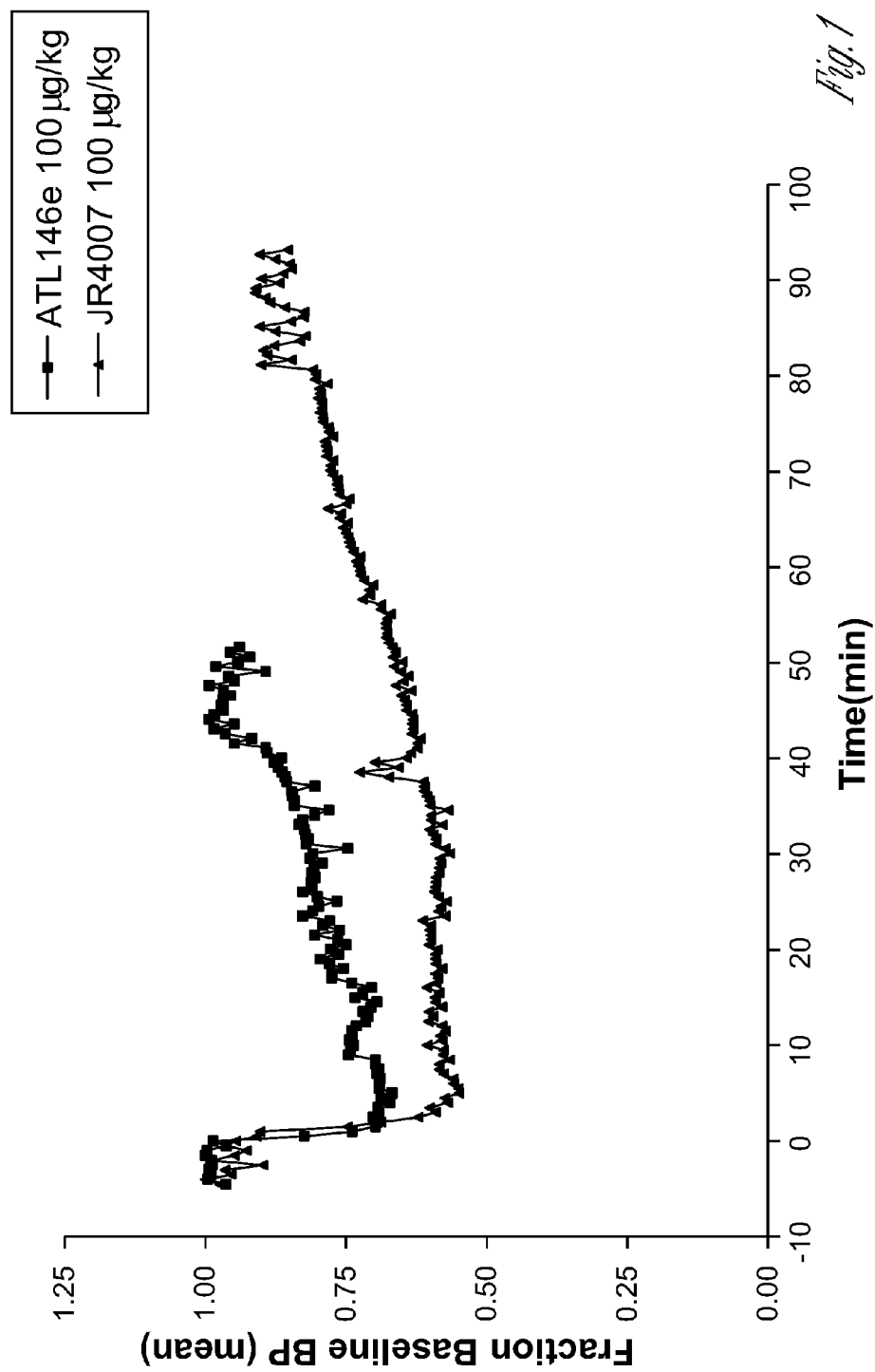
FIG. 1 illustrates the results of a comparison of the depression of blood pressure in rats using the compound ATL-146e and JR4007 at 100 ug/kg.
Figure 2:
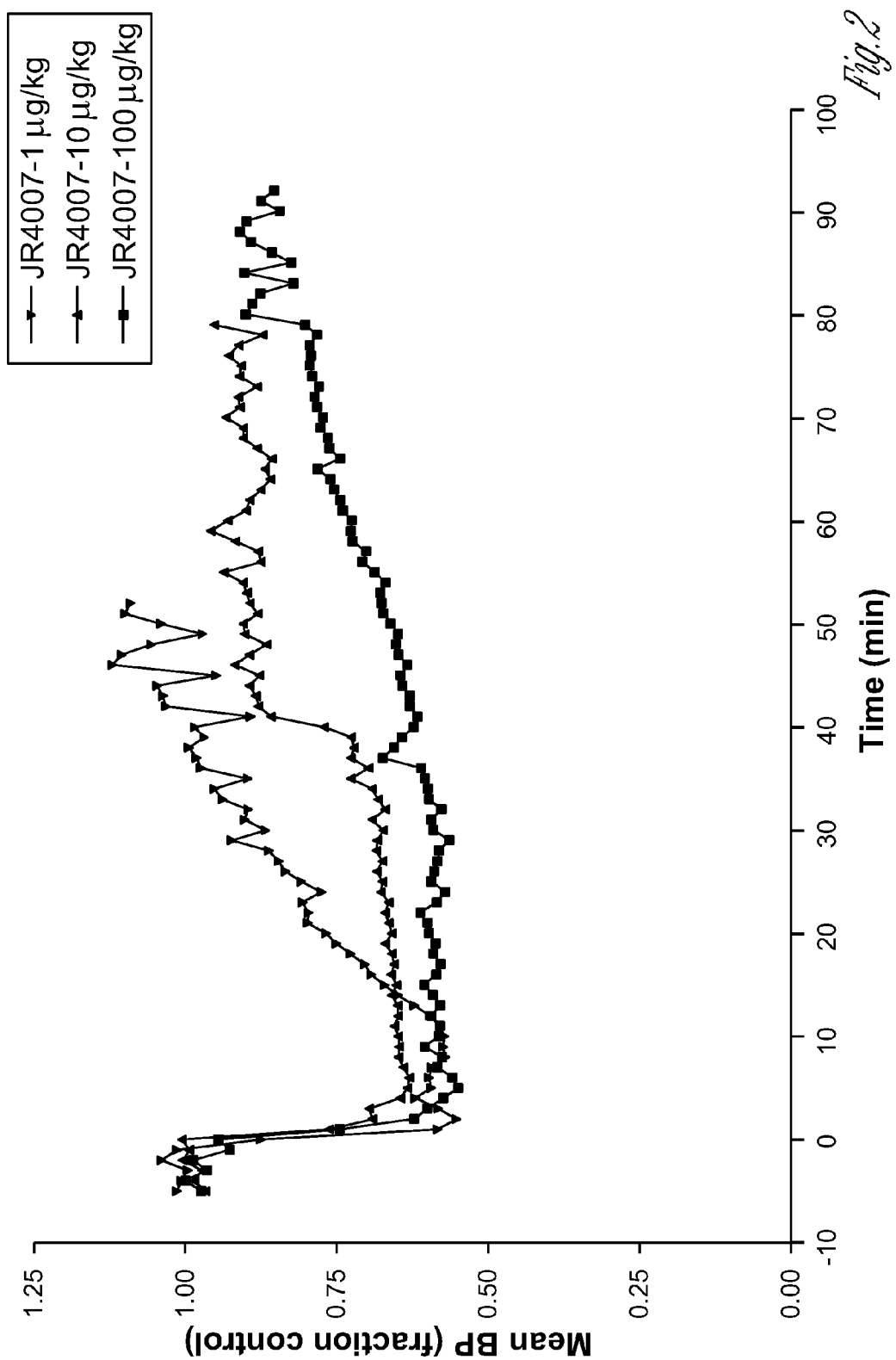
FIG. 2 illustrates the results of a dose-response experiment for the depression of blood pressure in rats using the compound JR4007 at concentrations of 1, 10, and 100 ug/kg.
Figure 3:
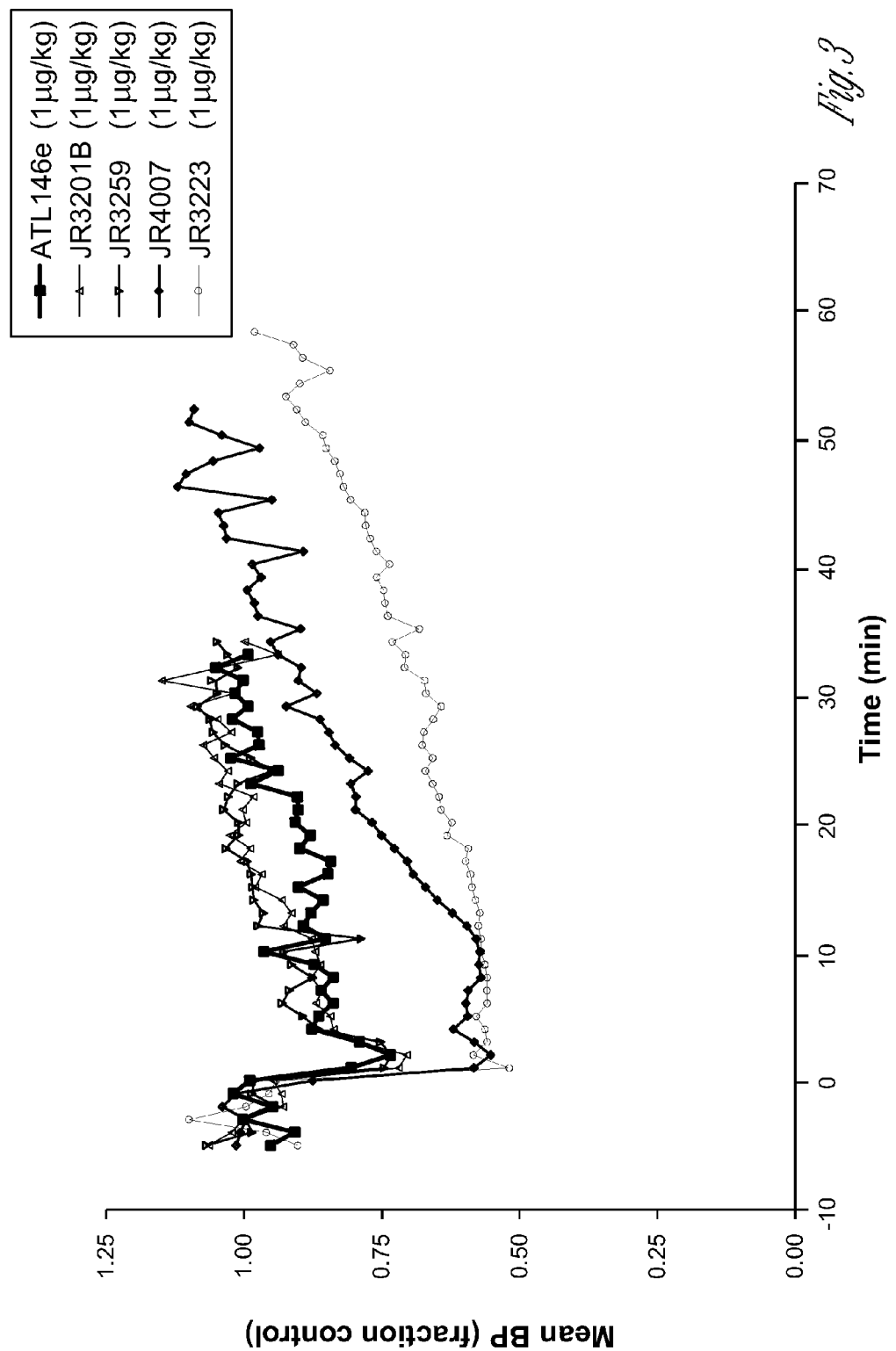
FIG. 3 illustrates the results of a comparison of the depression of blood pressure in rats using test compounds at 1 ug/kg.
Figure 4:
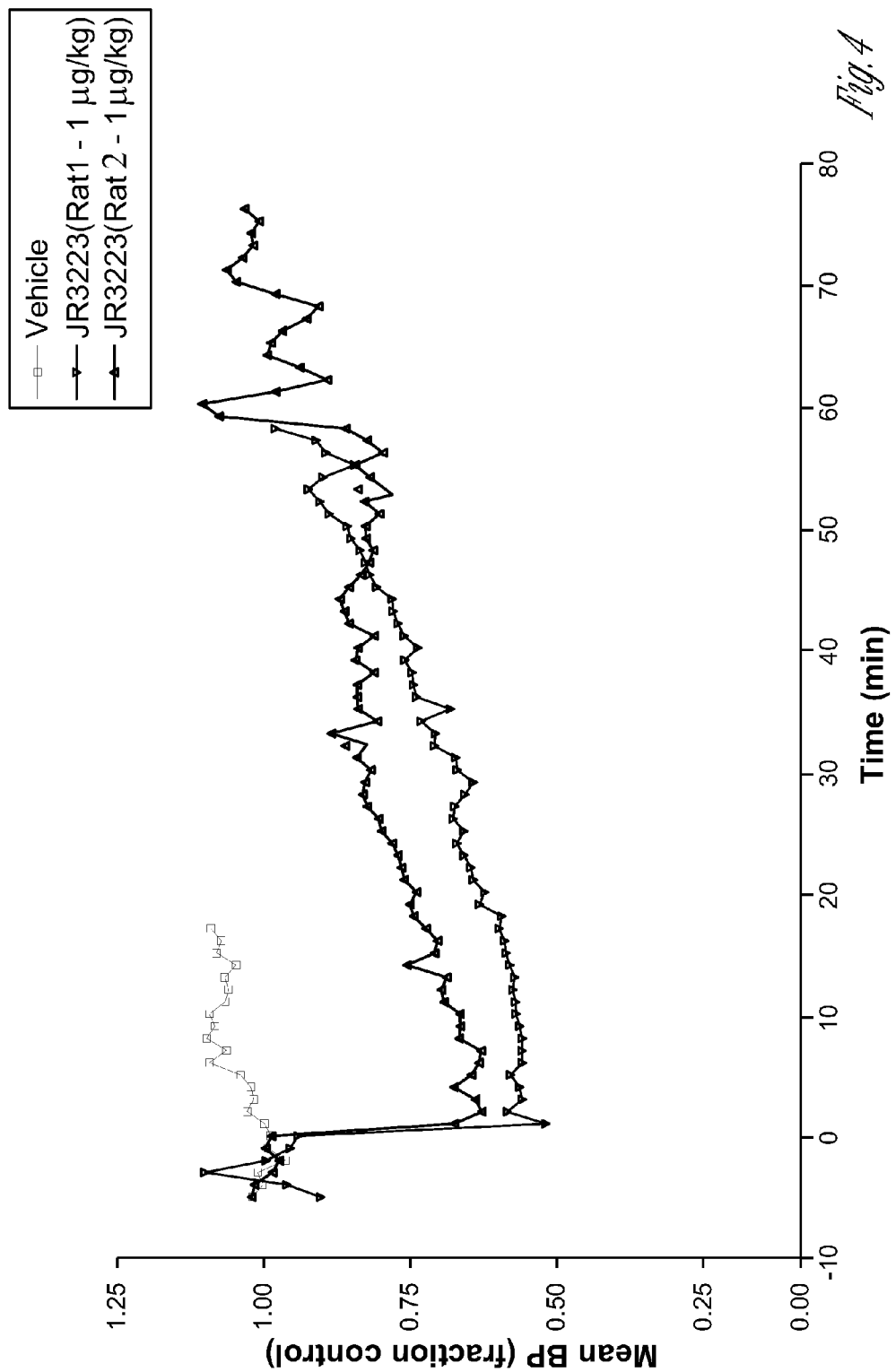
FIG. 4 illustrates the results of a comparison of the depression of blood pressure in rats using test compound JR 3223 in two animals.
Figure 5:
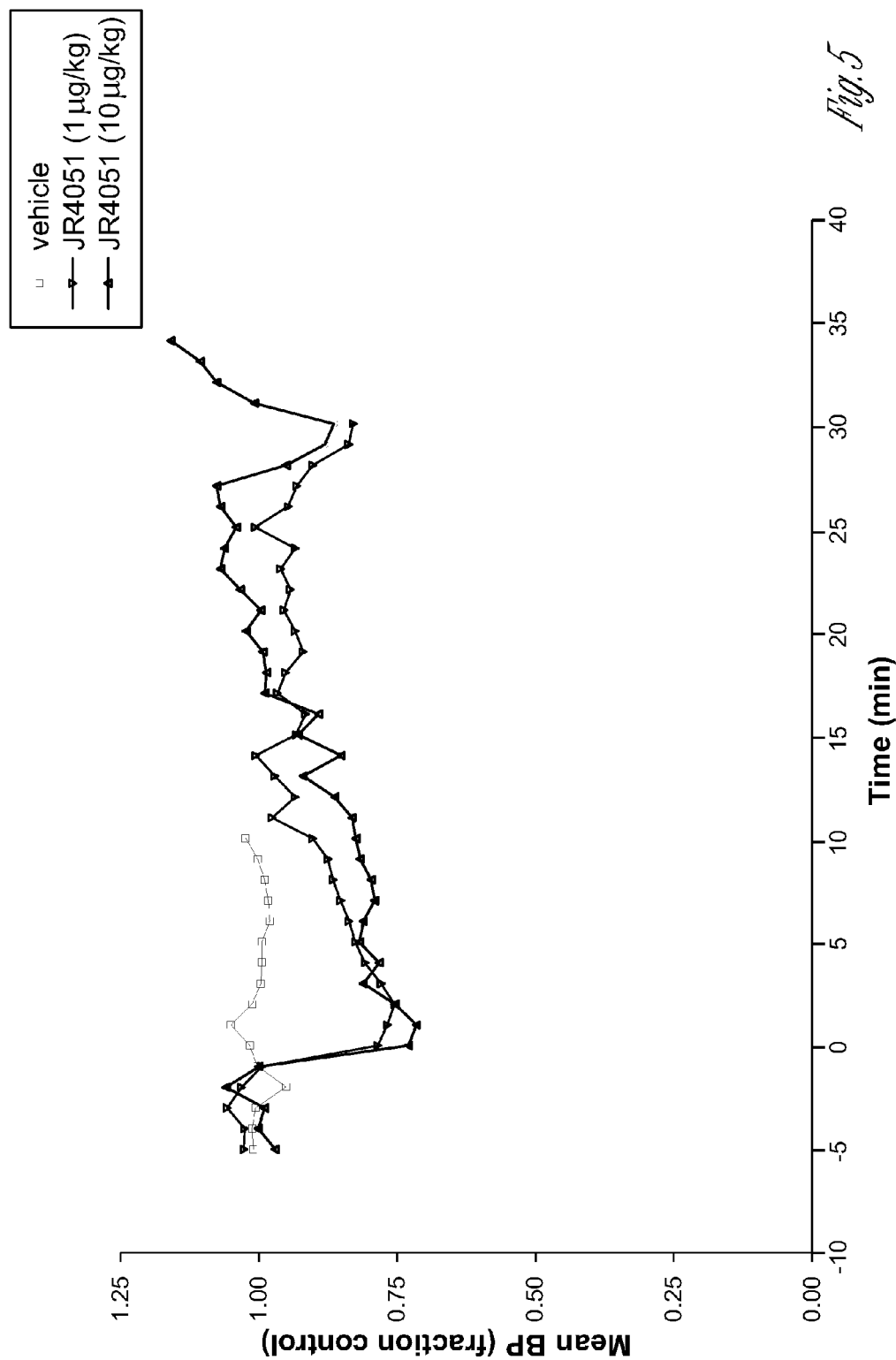
FIG. 5 illustrates the results of a of a dose-response experiment for the depression of blood pressure in rats using for JR4051 at concentrations of 1 and 10 ug/kg.
Figure 6:
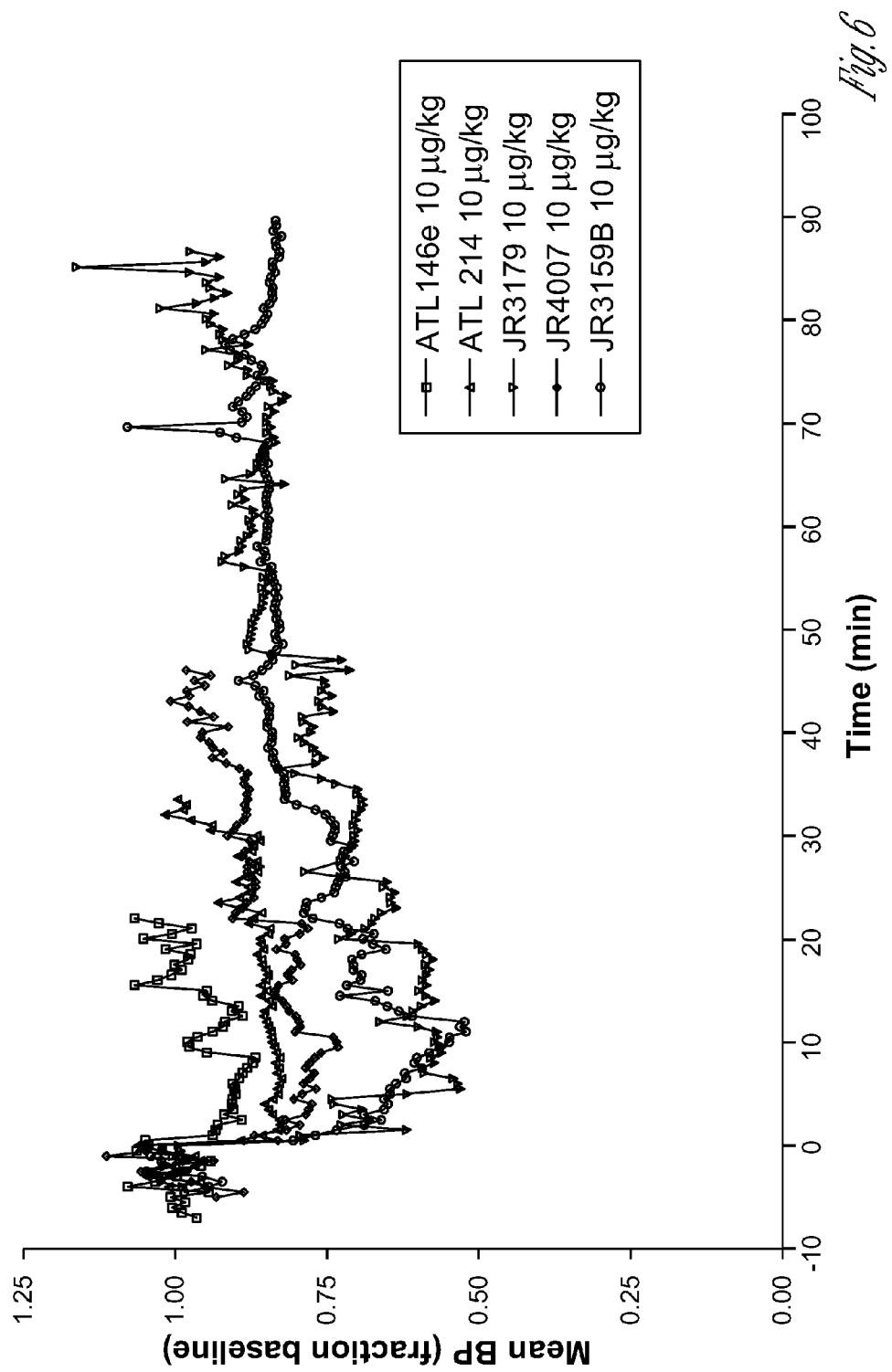
FIG. 6 illustrates the results of a comparison of the depression of blood pressure in rats using the compounds of the invention.
Figure 7:
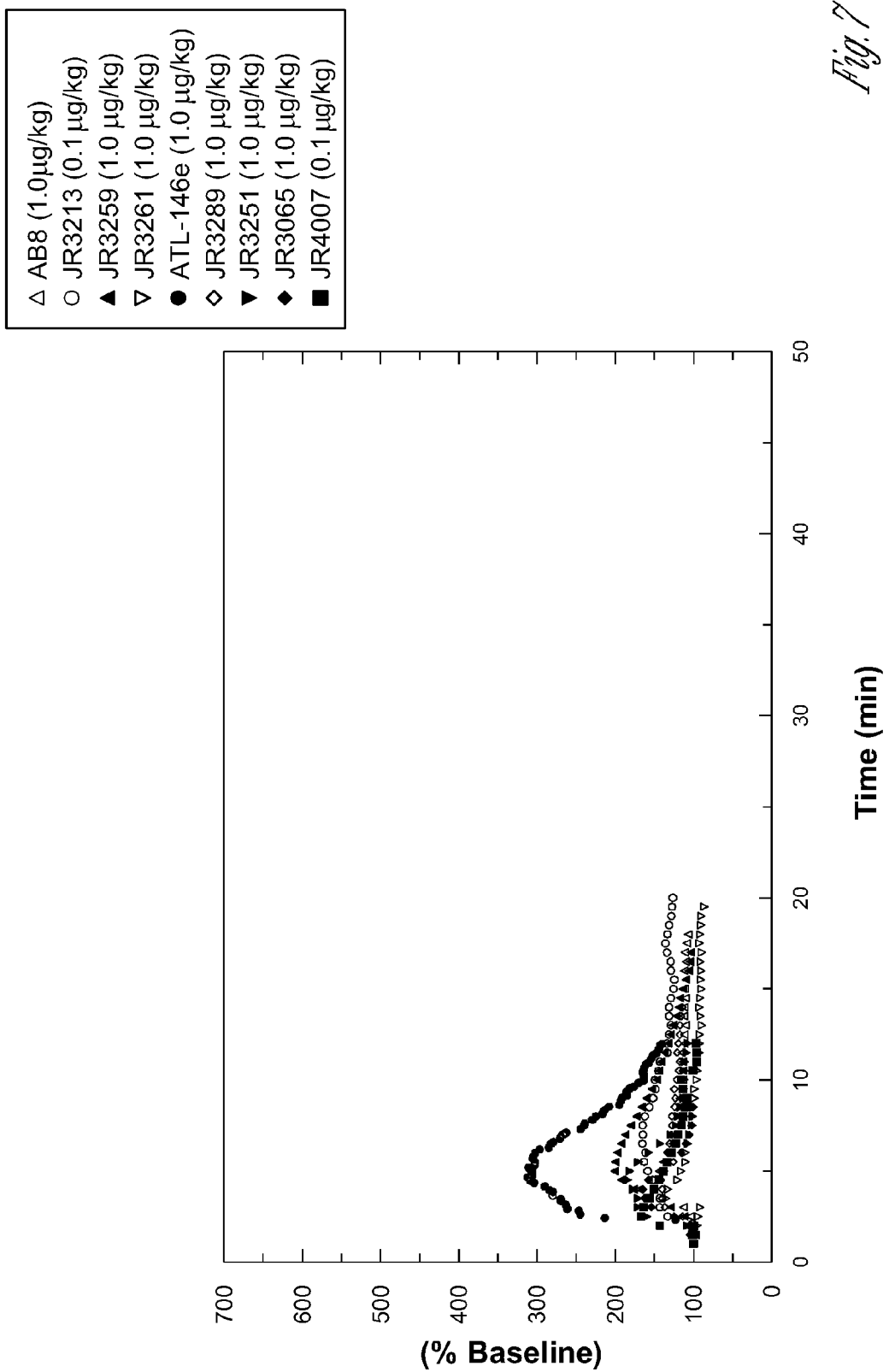
FIGS. 7-16 illustrate the results of the coronary blood flow for test compounds in dogs.
Figure 8:
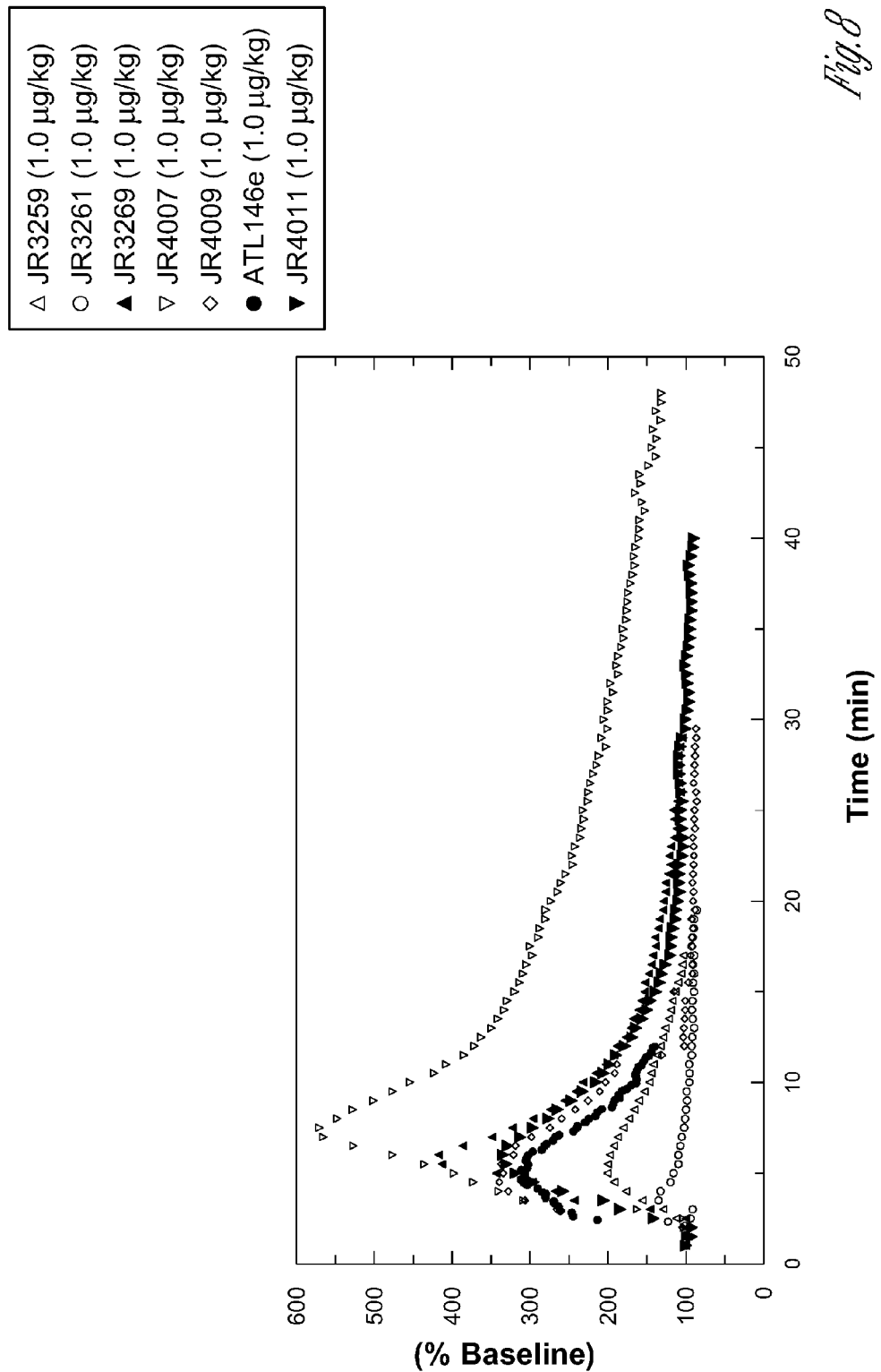
Figure 9:
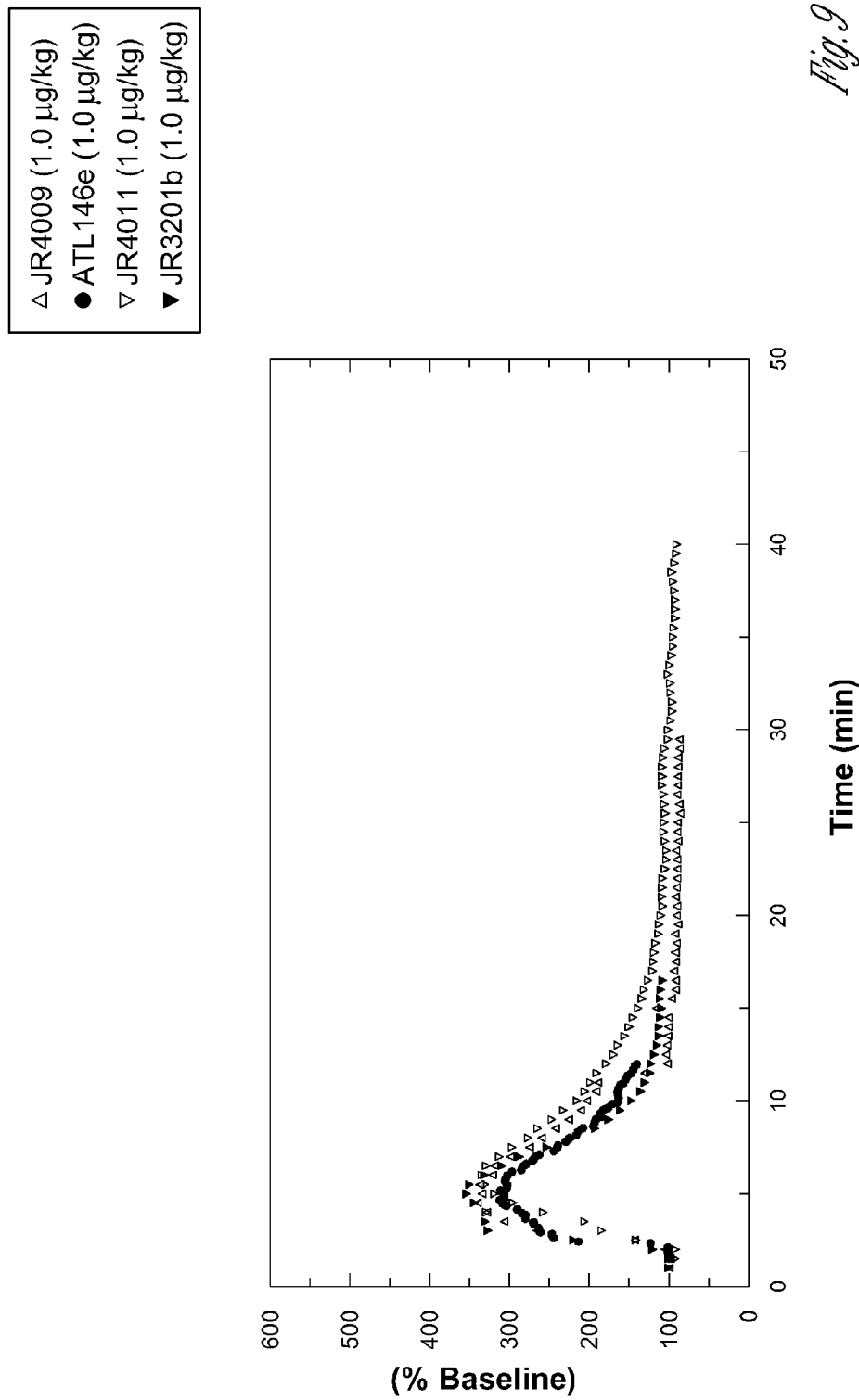
Figure 10:
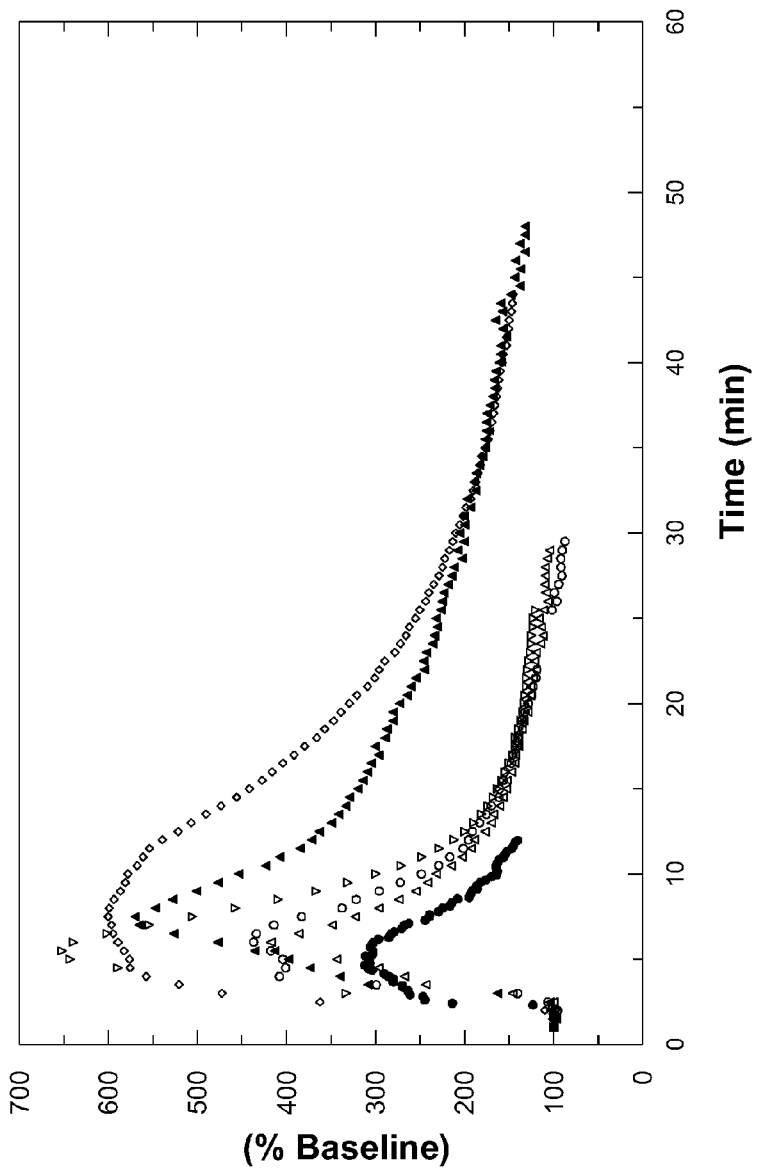
Figure 11:
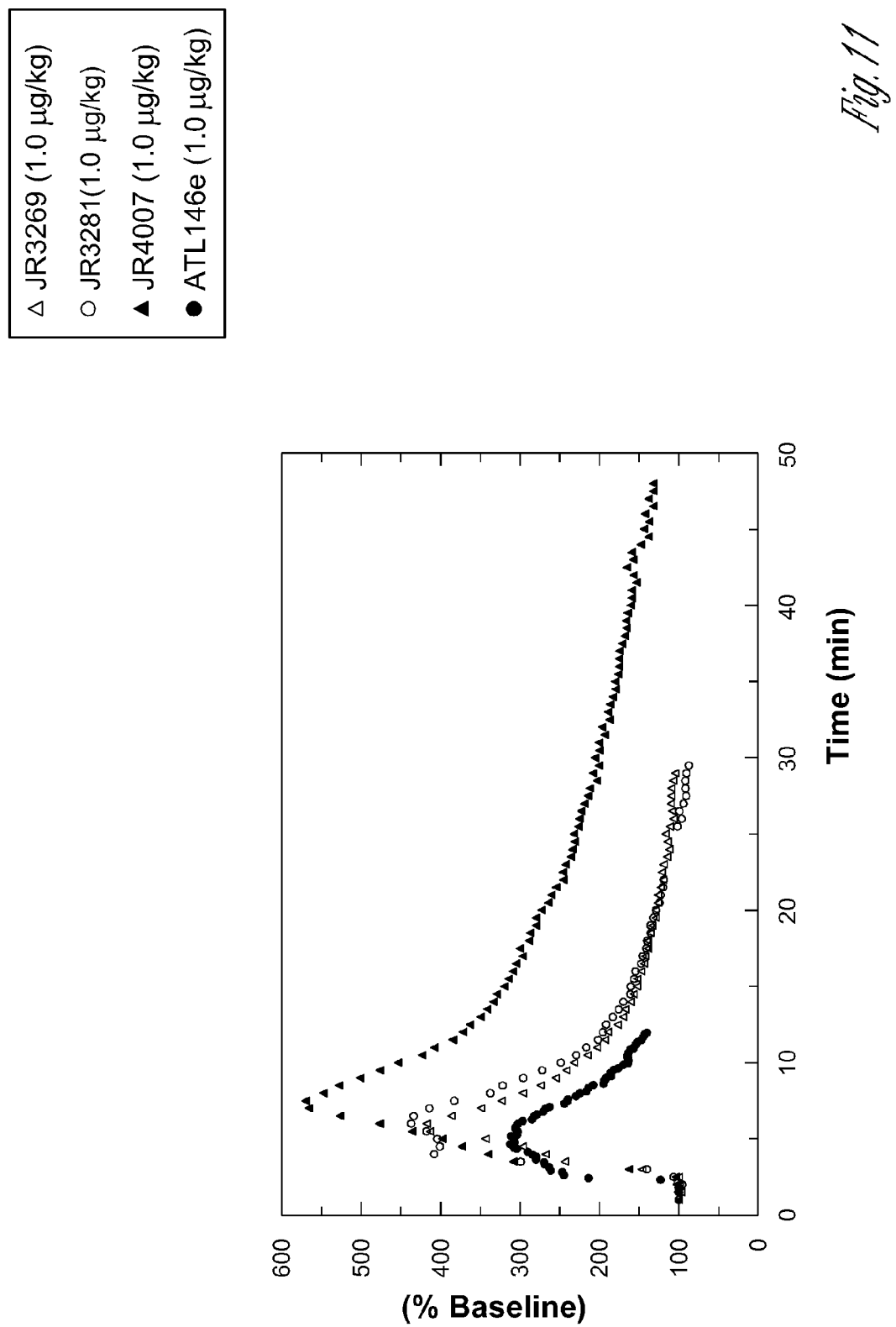
Figure 12:
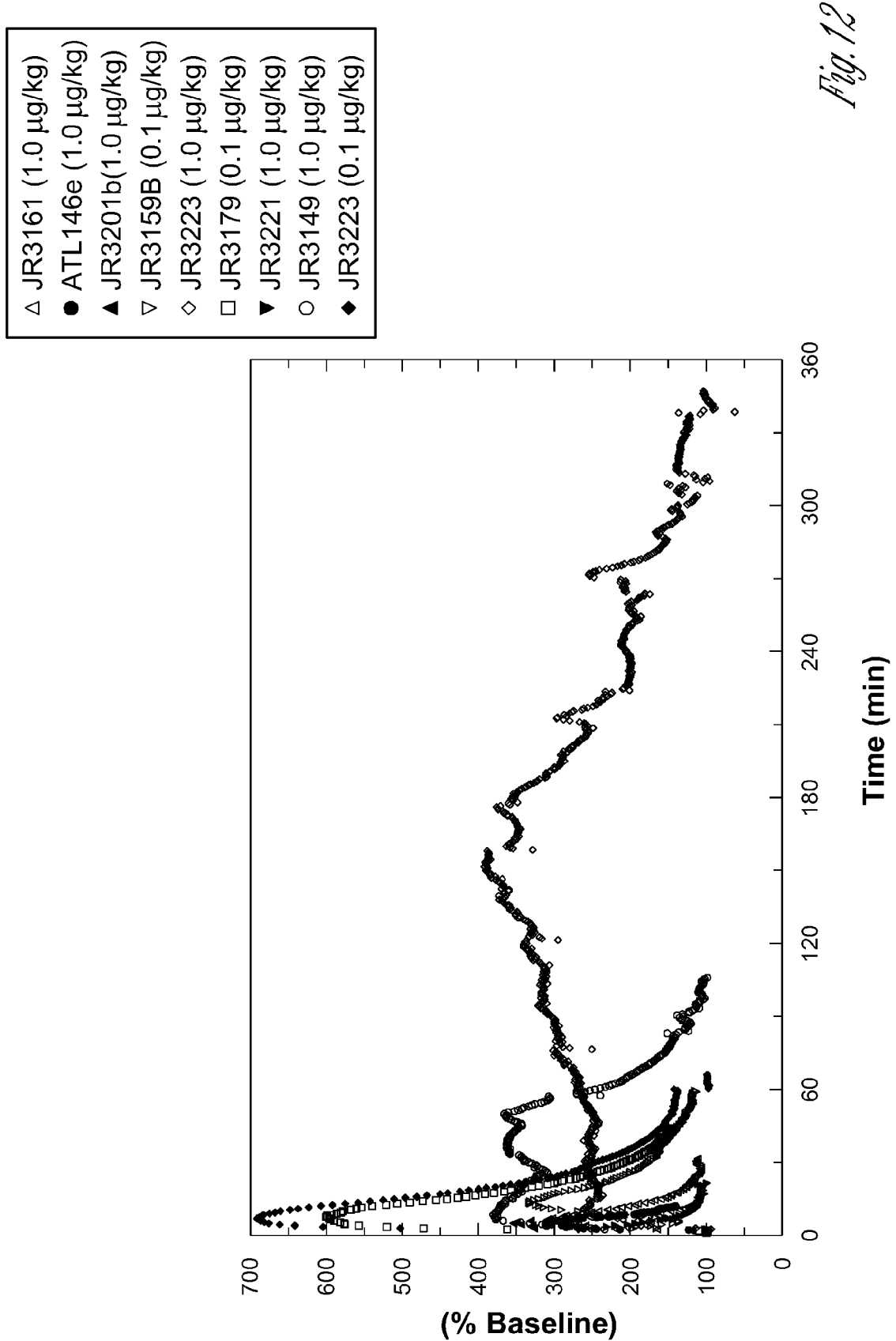
Figure 13:
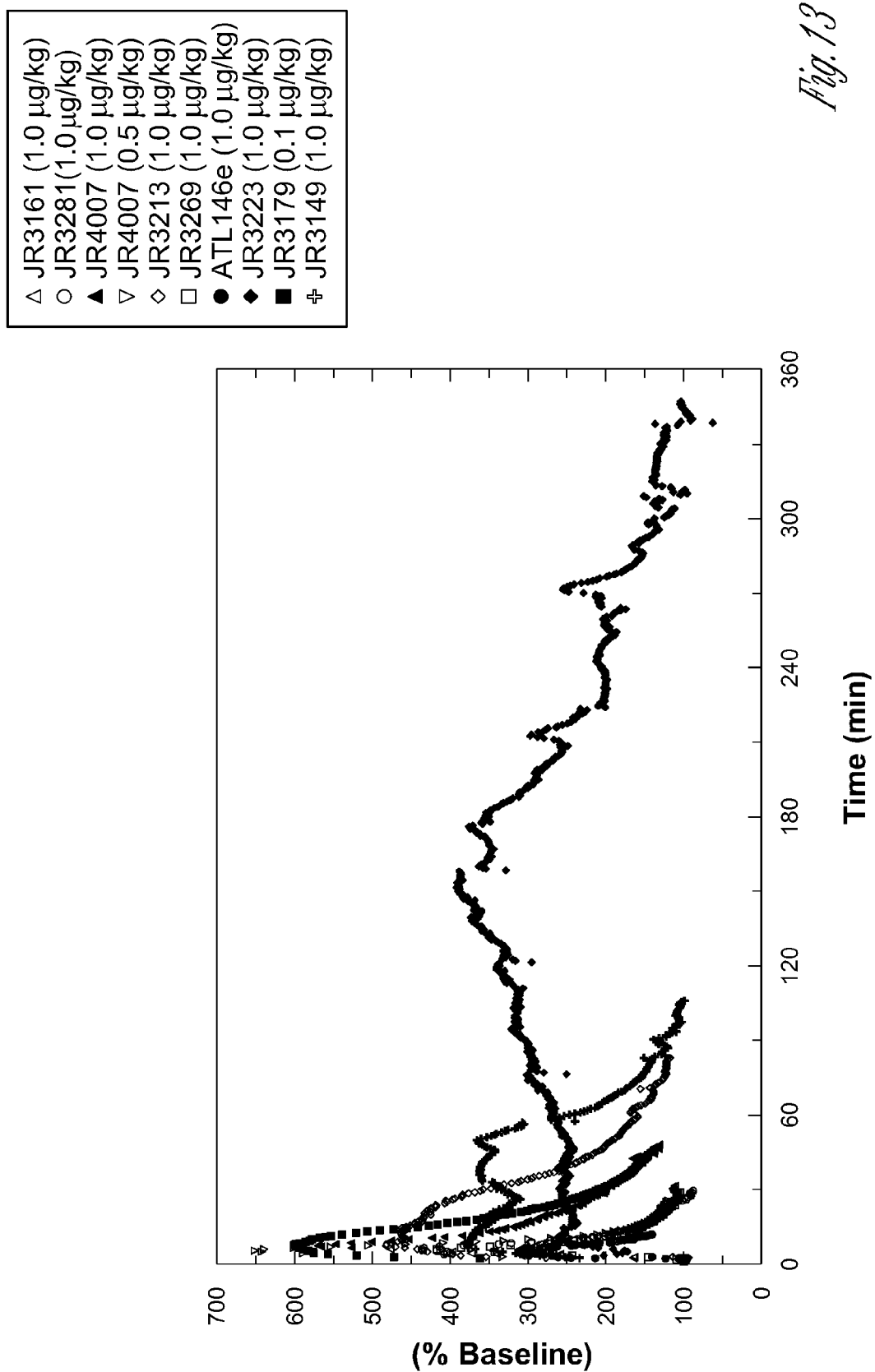
Figure 14:
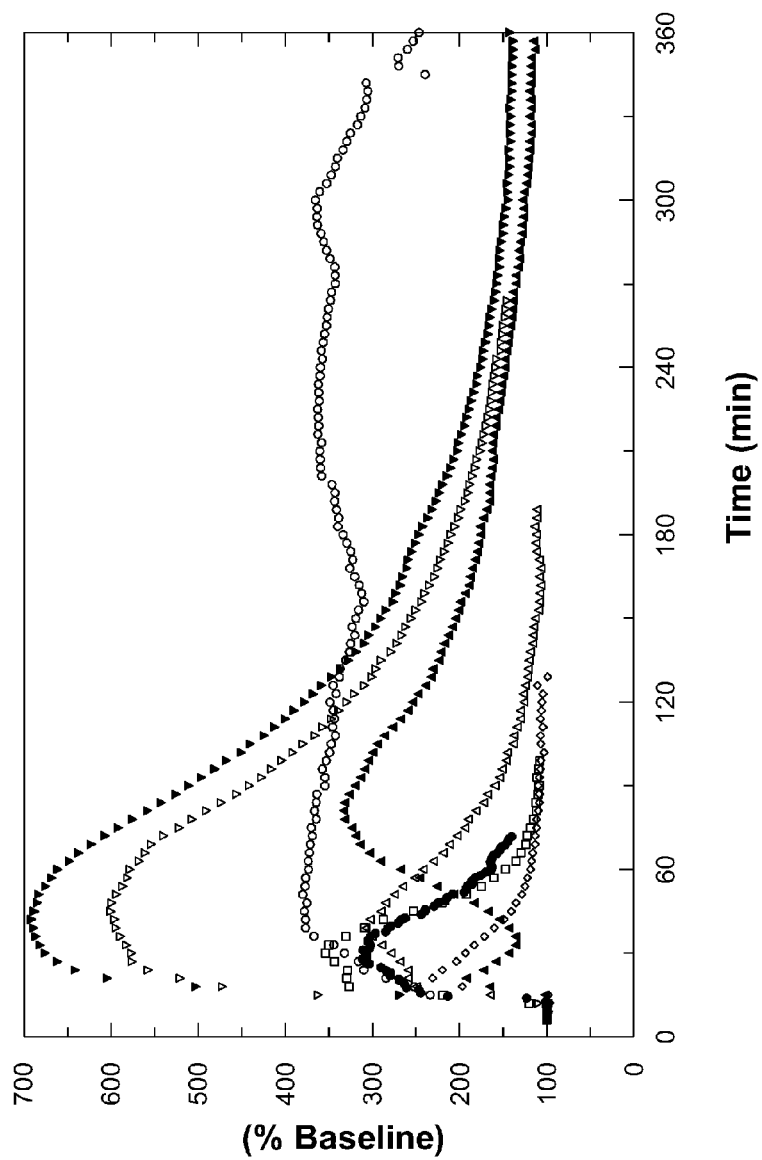
Figure 15:
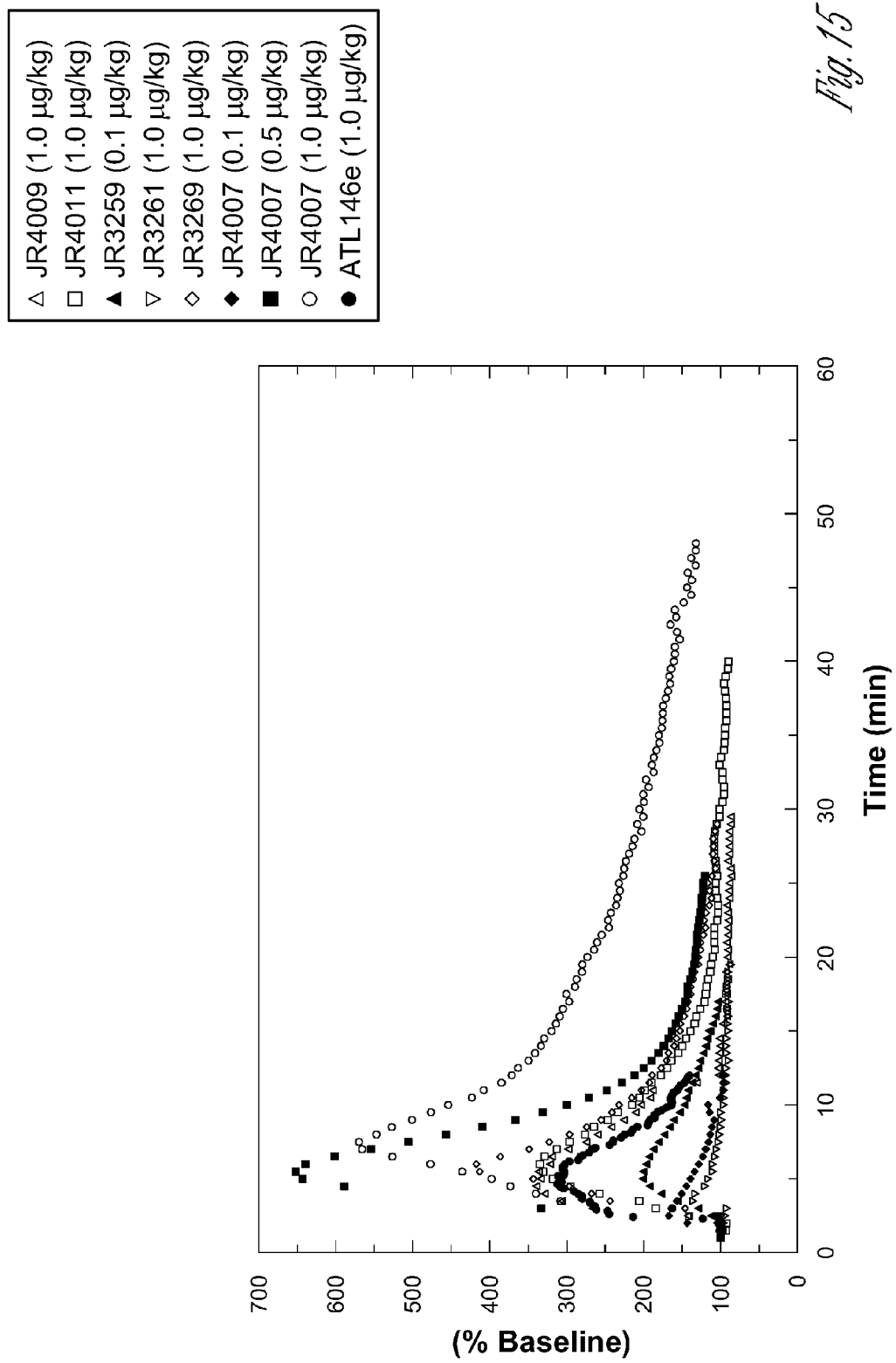
Figure 16:
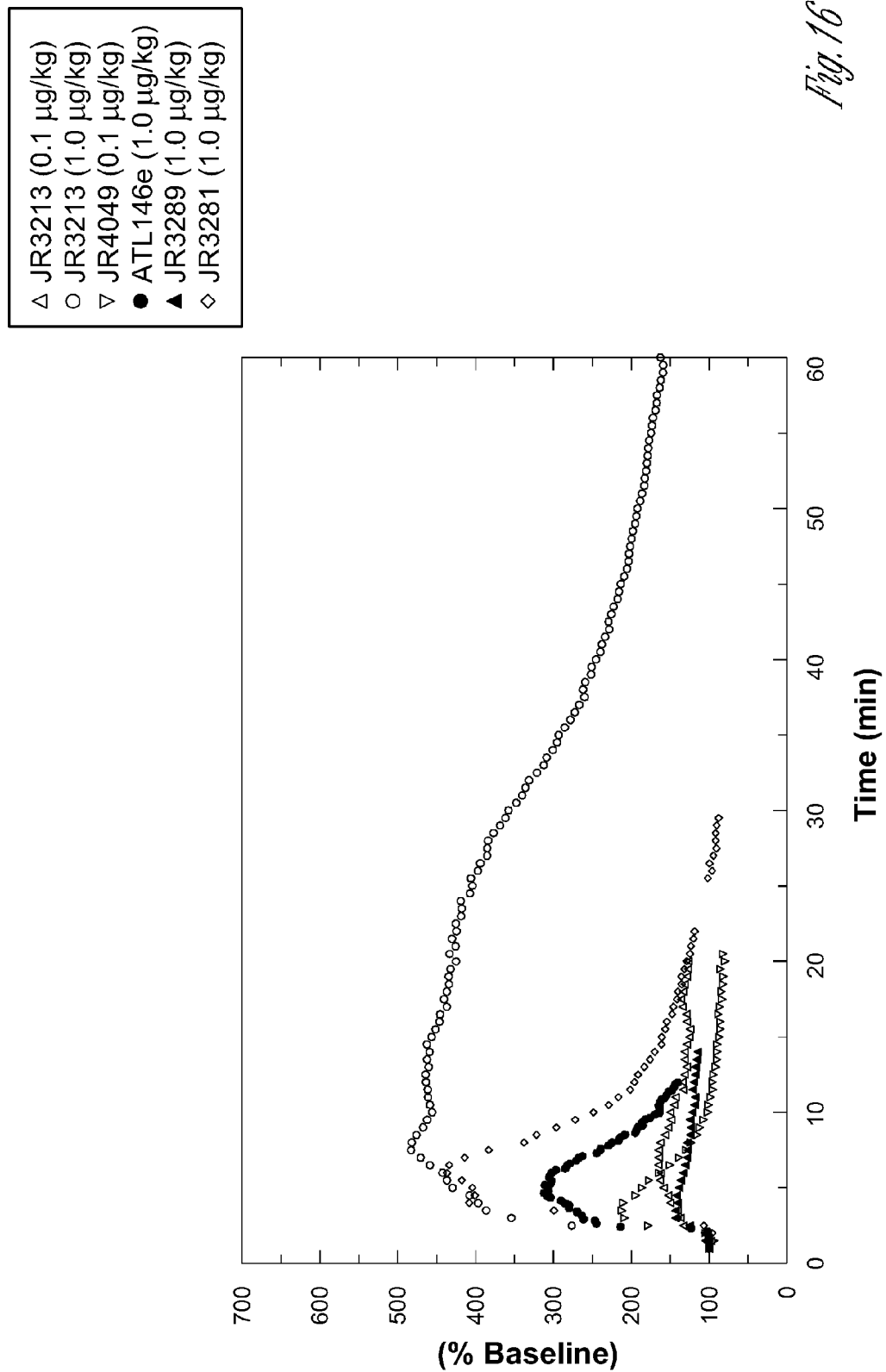

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formula (I) have more than one chiral center and may be isolated in optically active and racemic forms. Preferably, the riboside moiety of formula (I) is derived from D-ribose, i.e., the 3N,4N-hydroxyl groups are alpha to the sugar ring and the 2N and 5N groups is beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$-$C_8$)alkyl can be methyl, ethyl, propyl, isopropyl, butyl, iso-butyl, sec-butyl, pentyl, 3-pentyl, hexyl, heptyl or octyl. As used herein, the term "cycloalkyl" encompasses bicycloalkyl (norbornyl, 2,2,2-bicyclooctyl, etc.) and tricycloalkyl (adamantyl, etc.), optionally comprising 1-2 N, O or S. Cycloalkyl also encompasses (cycloalkyl)alkyl. Thus, ($C_3$-$C_6$)cycloalkyl can be cyclopropyl, cyclobutyl, cyclopentyl, cyclohexyl and the like.

($C_1$-$C_8$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo ($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl ($CO_2R^2$) can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio, ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazoyl, isothiazoyl, pyraxolyl, pyrrolyl, pyrazinyl, tetrazolyl, puridyl (or its N-oxide), thientyl, pyrimidinyl (or its N-oxide), indolyl, isoquinolyl (or its N-oxide) or quinolyl (or its N-oxide).

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, ($C_1$-$C_8$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Nonlimiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "alkylene" refers to a divalent straight or branched hydrocarbon chain (e.g. ethylene —$CH_2CH_2$—).

The term "aryl($C_1$-$C_8$)alkylene" for example includes benzyl, phenethyl, naphthylmethyl and the like.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, ($C_1$-$C_8$)alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, ($C_1$-$C_8$)alkyl can be methyl, ethyl, propyl, isopropyl, butyl, iso-butyl, sec-butyl, pentyl, 3-pentyl, hexyl, or heptyl; ($C_1$-$C_8$)alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is
hydrogen, —OH, —$CH_2OH$, —OMe, —OAc, —$NH_2$, —NHMe, —$NMe_2$ or —NHAc.

Another specific value for $R^1$ is
hydrogen, —OH, —OMe, —OAc, —$NH_2$, —NHMe, —$NMe_2$ or —NHAc.

Another specific value for $R^1$ is hydrogen, —OH, —OMe, or —$NH_2$.

Another specific value for $R^1$ is hydrogen, —OH, or —$NH_2$.

A more specific value for $R^1$ is hydrogen or —OH.

A specific value for $R^1$, $R^2$ and the carbon atom to which they are attached is carbonyl (C=O).

A specific value for $R^2$ is hydrogen or ($C_1$-$C_8$)alkyl, cyclopropyl, cyclohexyl or benzyl.

Another specific value for $R^2$ is hydrogen, methyl, ethyl or propyl.

Another specific value for $R^2$ is hydrogen or methyl.

A more specific value for $R^2$ is hydrogen

A specific value for $R^3$ is hydrogen, OH, OMe, OAc, $NH_2$, NHMe, $NMe_2$ or NHAc.

Another specific value for $R^3$ is hydrogen, OH, OMe, or $NH_2$.

Another specific value for $R^3$ is hydrogen, OH, or $NH_2$.

A more specific value for $R^3$ is hydrogen or OH.

A specific value for the ring comprising $R^4$, $R^5$ and the atom to which they are connected is cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and. pyrazolidine.

A more specific value for the ring comprising $R^4$ and $R^5$ and the atom to which they are connected is, cyclohexane, piperidine or piperazine.

A specific value for $R^6$ is ($C_1$-$C_8$)alkyl, or substituted ($C_1$-$C_8$)alkyl, —$OR^a$, —$CO_2R^a$, $R^aC$(=O)—, $R^aC$(=O)O—, $R^aR^bN$—, $R^aR^bNC$(=O)—, or aryl.

Another specific value for $R^6$ is ($C_1$-$C_8$)alkyl, —$OR^a$, —$CO_2R^a$, $R^aC$(=O)—, $R^aC$(=O)O—, $R^aR^bN$—, $R^aR^bNC$(=O)—, or aryl.

Another specific value for $R^6$ is methyl, ethyl, butyl, OH, $OR^a$, —$CO_2R^a$, $R^aC$(=O)—, OC(=O)$CH_2CH_3$, —$CONR^aR^b$, —$NR^aR^b$ or phenyl.

Another specific value for $R^6$ is OH, OMe, methyl, ethyl, t-butyl, —$CO_2R^a$, —C(=O)$NR^aR^b$, —OAc, —$NH_2$, —NHMe, —$NMe_2$, —NHEt or —$N(Et)_2$.

Another specific value for $R^6$ is —$(CH_2)_{1-2}OR^a$, —$(CH_2)_{1-2}C$(=O)$OR^a$, —$(CH_2)_{1-2}OC$(=O)$R^a$, —$(CH_2)_{1-2}C$(=O)$R^a$, —$(CH_2)_{1-2}OCO_2R^a$, —$(CH_2)_{1-2}NHR^a$, —$(CH_2)_{1-2}NR^aR^b$, —$(CH_2)_{1-2}OC$(=O)$NHR^a$, or —$(CH_2)_{1-2}C$(=O)$NR^aR^b$.

Another specific value for $R^6$ is —$CH_2OH$, —$CH_2OAc$, —$CH_2OCH_3$, —$CH_2C$(=O)$OCH_3$, —$CH_2C$(=O)$CH_3$, —$CH_2C$(=O)$CH_3$, —$CH_2OCO_2CH_3$, —$CH_2NH(CH_3)$, or —$(CH_2)_{1-2}N(CH_3)_2$.

Another specific value for $R^6$ is methyl, ethyl, t-butyl, phenyl, —$CO_2R^a$, —$CONR^aR^b$, or $R^aC$(=O)—.

Another specific value for $R^6$ is —$CH_2OH$, —$CH_2OAc$, —C(=O)$OCH_3$, —C(=O)$CH_3$, $OCO_2CH_3$—$OCO_2CH_3$, —$CH_2NH(CH_3)$, or —$(CH_2)_{1-2}N(CH_3)_2$.

A more specific value for $R^6$ is methyl, ethyl, —$CO_2R^a$— $CONR^aR^b$, or $R^aC$(=O)—.

A specific number of $R^6$ groups substituted on the $R^4R^5$ ring is from 1 to about 4.

A specific value for $R^a$ and $R^b$ is independently hydrogen, ($C_1$-$C_4$)alkyl, aryl or aryl($C_1$-$C_8$)alkylene.

A specific value for $R^a$ and $R^b$ is independently hydrogen, methyl, ethyl, phenyl or benzyl.

A more specific value for $R^a$ is ($C_1$-$C_8$)alkyl.

Another specific value for $R^a$ is methyl, ethyl, propyl or butyl.

A more specific value for $R^a$ is methyl, ethyl, i-propyl, i-butyl or tert-butyl.

Another specific value for $R^a$ and $R^b$ is a ring

A specific value for $R^7$ is hydrogen, alkyl, aryl or aryl($C_1$-$C_8$)alkylene.

Another specific value for $R^7$ is hydrogen, methyl or ethyl, phenyl or benzyl.

A more specific value for $R^7$ is H, or methyl.

A specific value for —$N(R^7)_2$ is amino, methylamino, dimethylamino, ethylamino, pentylamino, diphenylethylamino, pyridylmethylamino, diethylamino or benzylamino.

A specific value for —$N(R^7)_2$ is amino, methylamino, dimethylamino, ethylamino, diethylamino diphenylethylamino, pentylamino or benzylamino.

A specific value for $N(R^7)_2$ is amino, or methylamino.

A specific value for X
is —$CH_2OR^a$, —$CO_2R^a$, —$OC(O)R^a$, —$CH_2OC(O)R^a$, —$C(O)NR^aR^b$.

Another specific value for X is —$CH_2OR^a$ or —$C(O)NR^aR^b$.

A more specific value for X is —$CH_2OH$ or —$C(O)NHCH_2CH_3$.

A specific value for m is 0, 1, or 2.

A more specific value for m is 0, or 1.

Specific examples of rings comprising $R^4$, $R^5$ and the atom to which they are connected include:

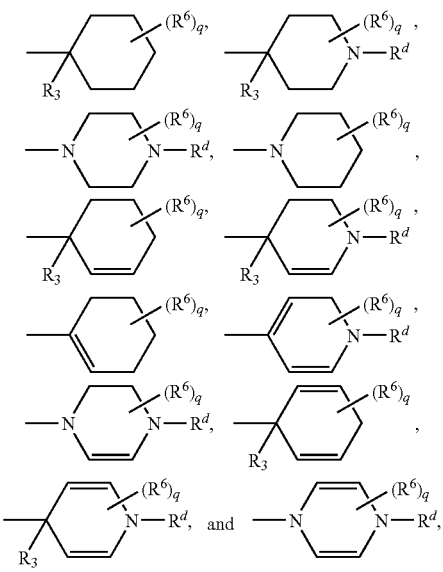

where q is from 0 to 14 and $R^d$ is hydrogen, provided that when q is zero then $R^d$ is not hydrogen.

More specific examples of rings comprising $R^4$, $R^5$ and the atom to which they are connected include:

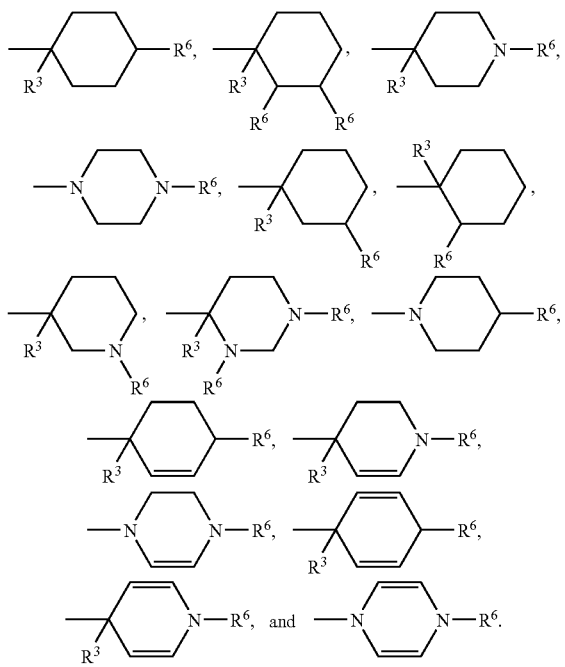

A specific value for the ring comprising —C($R^3$)$R^4R^5$ is 2-methyl cyclohexane, 2,2-dimethylcyclohexane, 2-phenylcyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane. 4-cyclohexanecarboxyic acid, 4-cyclohexanecarboxyic acid esters, or 4-methyloxyalkanoyl-cyclohexane.

A specific value for the ring comprising —C($R^3$)$R^4R^5$ is 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 1-piperidine, 1-piperidine-4-carboxylic acid methyl ester, 1-piperidine-4-carboxylic acid ethyl ester, 1-piperidine-4-carboxylic acid propyl ester, 1-piperidine-4-carboxylic acid tert-butyl ester, 1-piperidine-4-carboxylic acid methyl ester, 3-piperidine, 3-piperidene-1-carboxylic acid, 3-piperidine-1-carboxylic acid methyl ester, 3-piperidine-1-carboxylic acid tert-butyl ester, 1,4-piperazine, 4-piperazine-1-carboxylic acid, 4-piperazine-1-carboxylic acid methyl ester, 4-piperazine-1-carboxylic acid ethyl ester, 4-piperazine-1-carboxylic acid propyl ester, 4-piperazine-1-carboxylic acid tert-butylester, 1,3-piperazine, 3-piperazine-1-carboxylic acid, 3-piperazine-1-carboxylic acid methyl ester, 3-piperazine-1-carboxylic acid ethyl ester, 3-piperazine-1-carboxylic acid propyl ester, 3-piperidine-1-carboxylic acid tert-butylester, 1-piperidine-3-carboxylic acid methyl ester, 1-piperidine-3-carboxylic acid ethyl ester, 1-piperidine-3-carboxylic acid propyl ester or 1-piperidine-3-carboxylic acid tert-butyl ester.

A specific value for the ring comprising $R^4$ and $R^5$ is 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, 1-piperidine-3-carboxylic acid tert-butyl ester In another embodiment the invention includes a compound having the general formula (I):

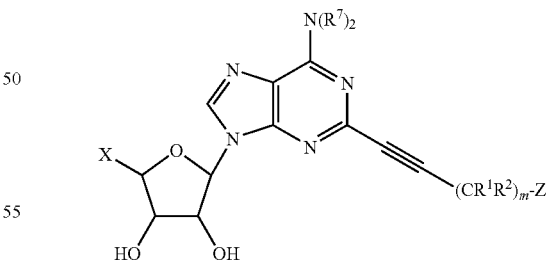

(I) wherein
Z is $CR^3R^4R^5$ or $NR^4R^5$;
each $R^1$ is independently hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, heterocycle, hetrocycle($C_1$-$C_8$)alkylene-, aryl, aryl($C_1$-$C_8$)alkylene-, heteroaryl, heteroaryl($C_1$-$C_8$) alkylene-, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC$ (=O)N(R$^b$)—, R$^a$R$^b$NC(=S)N(R$^b$)—, —OPO$_3$R$^a$, R$^a$OC(=S)—, R$^a$C(=S)—, —SSR$^a$, R$^a$S(=O)—, —N=NR$^a$, or —OPO$_2$R$^a$;

each R$^2$ independently hydrogen, (C$_1$-C$_8$)alkyl, (C$_3$-C$_8$)cycloalkyl, heterocycle, heterocycle(C$_1$-C$_8$)alkylene-, aryl, aryl(C$_1$-C$_8$)alkylene-, heteroaryl, or heteroaryl(C$_1$-C$_8$)alkylene-; or R$^1$ and R$^2$ and the atom to which they are attached can be C=O or C=NR$^c$.

R$^4$ and R$^5$ together with the atoms to which they are attached can form a saturated or unsaturated, mono-, bicyclic- or aromatic ring having 3, 4, 5, 6, 7 or 8 ring atoms optionally comprising 1, 2, 3, or 4 heteroatoms selected from oxy (—O—), thio (—S—), sulfinyl (—SO—), sulfonyl (—S(O)$_2$—) or amine (—NR$^a$—) in the ring;

wherein any ring comprising R$^4$ and R$^5$ is substituted with from 1 to 14 R$^6$ groups; wherein each R$^6$ is independently halo, —OR$^a$, —SR$^a$, (C$_1$-C$_8$)alkyl, cyano, nitro, trifluoromethyl, trifluoromethoxy, (C$_3$-C$_8$)cycloalkyl, (C$_3$-C$_8$)bicycloalkyl, heterocycle or hetrocycle(C$_1$-C$_8$)alkylene-, aryl, aryl(C$_1$-C$_8$)alylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, —OPO$_3$R$^a$, R$^a$OC(=S—, R$^a$C(=S)—, —SSR$^a$, R$^a$S(=O)—, —NNR$^a$ or —OPO$_2$R$^a$;

R$^3$ is hydrogen, halo, —OR$^a$, —SR$^a$, C$_{1-8}$alkyl, cyano, nitro, trifluoromethyl, trifluoromethoxy, (C$_3$-C$_8$)cycloalkyl, heterocycle or hetrocycle(C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, —OPO$_3$R$^a$, R$^a$OC(=S)—, R$^a$C(=S)—, —SSR$^a$, R$^a$S(=O)—, —N=NR$^a$, —OPO$_2$R$^a$; or if the ring formed from CR$^4$R$^5$ is aryl or hereroaryl or partially unsaturated then R$^3$ can be absent;

each R$^7$ is independently hydrogen, (C$_1$-C$_8$)alkyl, (C$_3$-C$_8$)cycloalkyl, aryl or aryl(C$_1$-C$_8$)alkylene;

X is —CH$_2$OR$^a$, —CO$_2$R$^a$, —OC(O)R$^a$, —CH$_2$OC(O)R$^a$, —C(O)NR$^a$R$^b$, —CH$_2$SR$^a$, —C(S)OR$^a$, —OC(S)R$^a$, —CH$_2$OC(S)R$^a$ or C(S)NR$^a$R$^b$ or —CH$_2$N(R$^a$)(R$^b$);

wherein any of R$^1$, R$^2$, R$^3$ and R$^6$ is optionally substituted with (C$_1$-C$_8$)alkyl, aryl, heteroaryl, heterocycle, aryloxy, (C$_3$-C$_8$)cycloalkyl, hydroxy, nitro, halo, cyano, (C$_1$-C$_8$)alkoxy, (C$_1$-C$_8$)alkanoyl, (C$_1$-C$_8$)alkoxycarbonyl, (C$_1$-C$_8$)alkanoyloxy, R$^a$S(O)$_p$, R$^a$R$^b$NS(O)—, R$^a$R$^b$NS(O)$_2$—, R$^a$R$^b$N—, or R$^a$R$^b$NC(=O)—;

wherein any (C$_1$-C$_8$)alkyl, (C$_3$-C$_8$)cyclo alkyl, (C$_3$-C$_8$)bicycloalkyl, (C$_1$-C$_8$)alkoxy, (C$_1$-C$_8$)alkanoyl, (C$_1$-C$_8$)alkylene, or heterocycle, is optionally partially unsaturated;

R$^a$ and R$^b$ are each independently hydrogen, (C$_1$-C$_8$)alkyl, or (C$_1$-C$_8$)alkyl substituted with 1-3 (C$_1$-C$_8$)alkoxy, (C$_3$-C$_8$)cycloalkyl, (C$_1$-C$_8$)alkylthio, amino acid, aryl, aryl(C$_1$-C$_8$)alkylene, heteroaryl, or heteroaryl(C$_1$-C$_8$)alkylene; or R$^a$ and R$^b$, together with the nitrogen to which they are attached, form a pyrrolidino, piperidino, morpholino, or thiomorpholino ring; and R$^c$ is hydrogen or C$_{1-6}$ alkyl;

m is 0 to about 8 and p is 0 to 2; provided that when m is 0 or all R$^1$ and R$^2$ groups present are hydrogen then R$^3$ is not hydrogen; provided that m is at least 1 when Z is NR$^4$R$^5$; or a pharmaceutically acceptable salt thereof.

Specific compounds of formula (I) are those wherein each R$^7$ is H, X is ethylaminocarbonyl and R$^1$ is hydroxy, R$^2$ is hydrogen, and Z is 4-carboxycyclohexyl, wherein R$^a$ is hydrogen, 4; Z is 4-methoxycarbonylcyclohexylmethyl, R$^a$ is methyl, 5; R$^1$ and R$^2$ together are oxo, Z is a 4-carbonylcyclohexyl group, wherein R$^a$ is methyl, methoxy, ethyl, ethoxy, propyl, isopropoxy, -isobutyl, tert-butyl, amine, methylamine or dimethylamine, 6.

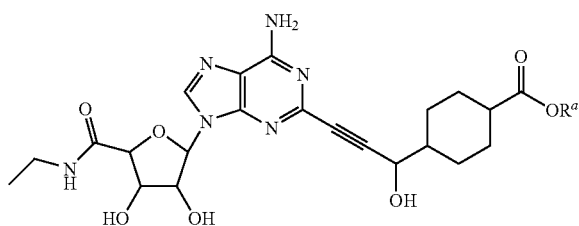

4, R$^a$ is H
5, R$^a$ is CH$_3$

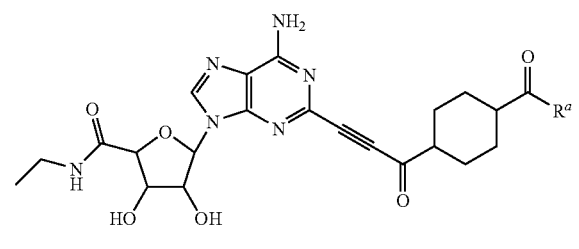

6

Another group of specific compounds of formula (I) are those wherein each R$^7$ is H, X is ethylaminocarbonyl, R$^1$ is hydroxy, R$^2$ is hydrogen, and Z is a substituted 4-(methyleneoxy-carbonyl)cyclohexyl group, wherein R$^a$ is methyl, ethyl, propyl, tert-butyl, methoxy, ethoxy, methylamine or dimethylamine, 7; or R$^1$ and R$^2$ together are oxo, and Z is a substituted -(methyleneoxycarbonyl)cyclohexyl group, wherein R$^a$ is methyl, ethyl, propyl, tert-butyl, methoxy, ethoxy, methylamine or dimethylamine, 8.

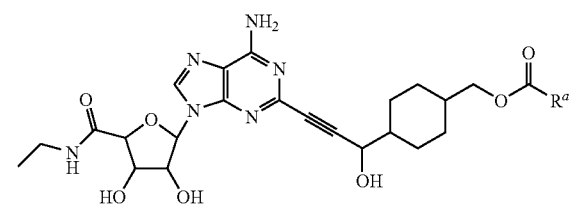

7

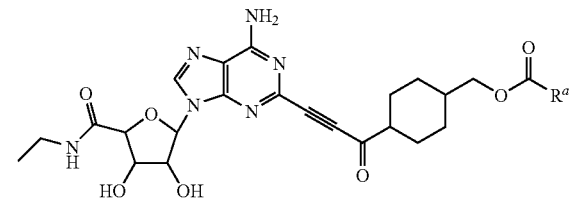

8

Another group of specific compounds of formula (I) are those wherein each $R^7$ is H, X is ethylaminocarbonyl, and $R^1$ and $R^2$ are each hydrogen, and Z is a 1-piperidyl-4-carboxylic acid or ester group, wherein $R^a$ is hydrogen, methyl, ethyl, propyl, isopropyl, or t-butyl, 9; $R^1$ and $R^2$ together are oxo, and Z is a 1-piperidyl-4-carboxylic acid or ester group, wherein $R^a$ is hydrogen, methyl, ethyl, propyl, isopropyl, or t-butyl, 10; $R^1$ and $R^2$ are each hydrogen and Z is a 4-(methyleneoxy-carbonyl)piperidin-4-yl group wherein $R^a$ is methyl, ethyl, propyl or t-butyl, amine, methylamine, dimethylamine, 11; or $R^1$ and $R^2$ together are oxo, and Z is a 4-(methyleneoxy-carbonyl)piperidin-4-yl wherein $R^a$ is methyl, ethyl, propyl or t-butyl, amine, methylamine, dimethylamine, 12; $R^1$ and $R^2$ are each hydrogen and Z is a 4-(methyleneoxycarbonyl)piperidin-4-yl-oxy wherein $R^a$ is hydrogen, methyl, ethyl, propyl isopropyl, isobutyl, or t-butyl, 13 or $R^1$ and $R^2$ together are oxo, Z is a 4-(methyleneoxycarbonyl)piperidin-4-yl-oxy wherein $R^a$ is hydrogen, methyl, ethyl, propyl, isopropyl, isobutyl, or t-butyl, 14.

9

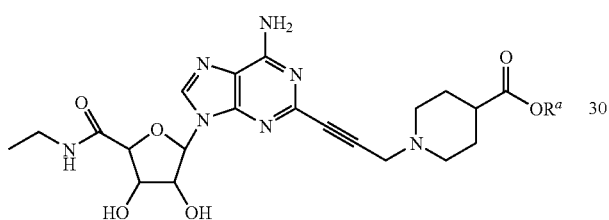

10

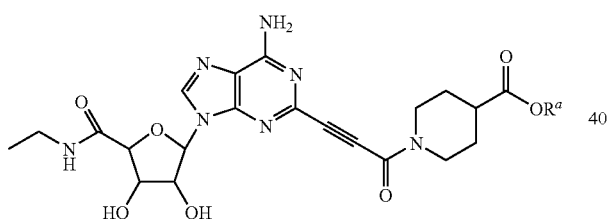

11

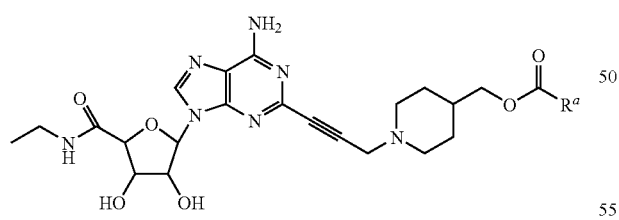

12

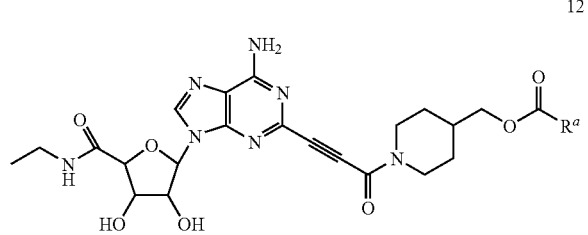

13

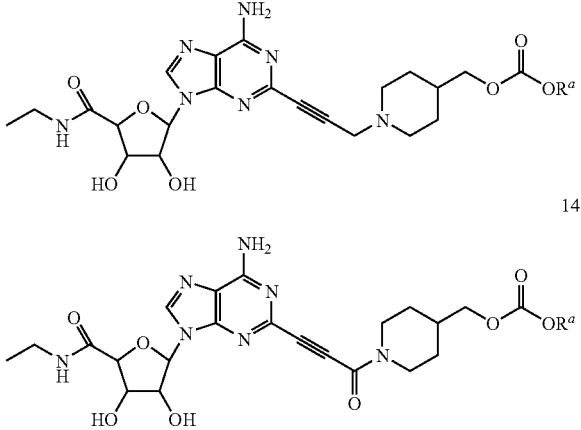

14

Another group of specific compounds of formula (I) are those wherein each $R^7$ is H, X is ethylaminocarbonyl, $R^1$ and $R^2$ are each hydrogen, and Z is a 4-piperidyl-1-carboxylic acid or ester group, wherein $R^a$ is methyl, ethyl, propyl, isopropyl, isobutyl, or t-butyl, 15, $R^1$ is hydroxy, $R^2$ is hydrogen, and Z is a 4-piperidyl-1-carboxylic acid or ester group, wherein $R^a$ is methyl, ethyl, propyl, isopropyl, isobutyl, or t-butyl, 16; or $R^1$ and $R^2$ together are oxo, and Z is a 4-piperidyl-1-carboxylic acid or ester group, wherein $R^a$ is methyl, ethyl, propyl, isopropyl, isobutyl, or t-butyl, 17.

15

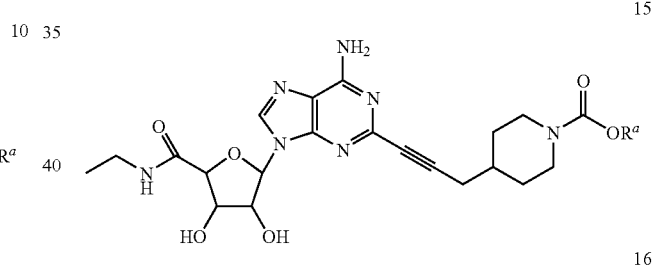

16

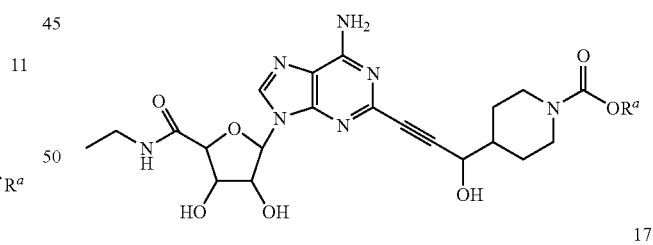

17

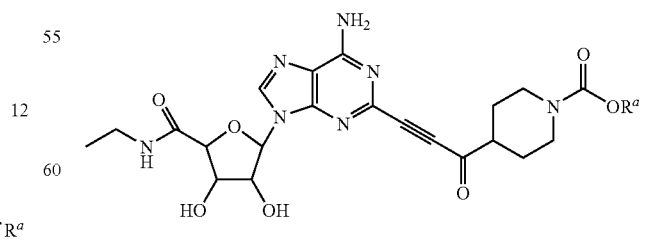

Another group of specific compounds of formula (I) are those wherein each $R^7$ is H, X is ethylaminocarbonyl, $R^1$ and $R^2$ are each hydrogen, Z is a 4-piperazine-1-carboxylic acid or ester group wherein $R^a$ is methyl, ethyl, isopropyl, isobutyl, or t-butyl, 18; or $R^1$ and $R^2$ together are oxo, Z is a 4-piperazine-1-carboxylic acid or ester group wherein $R^a$ is methyl, ethyl, isopropyl, isobutyl, or t-butyl, 19.

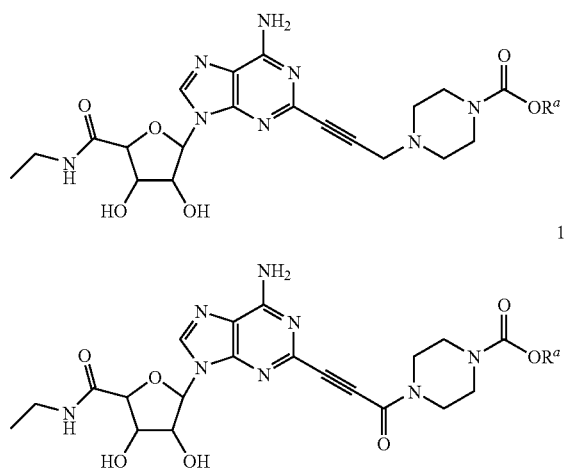

Additional compounds of the invention are depicted in tables 1, 2, 3, 4, 5, 6 and 7 below:

TABLE 1

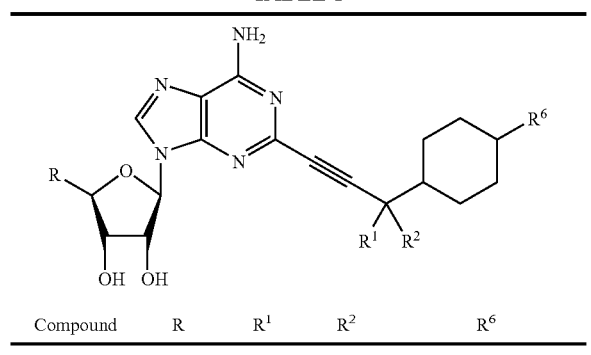

| Compound | R | $R^1$ | $R^2$ | $R^6$ |
|---|---|---|---|---|
| ATL2037 | NECA | H | H | CH₂OH |
| MP9056 | NECA | OH | H | CH₂OH |
| ATL146a | NECA | H | H | CO₂H |
| MP9057 | NECA | OH | H | CO₂H |
| ATL146e | NECA | H | H | CO₂Me |
| MP9058 | NECA | OH | H | CO₂Me |
| JR2145 | CH₂OH | H | H | CO₂Me |
| MP9059 | CH₂OH | OH | H | CO₂Me |
| ATL193 | NECA | H | H | CH₂OAc |
| MP9060 | NECA | OH | H | CH₂Oac |
| JR2147 | CH₂OH | H | H | CH₂Oac |
| MP9061 | CH₂OH | OH | H | CH₂Oac |
| JR3023 | NECA | H | H | CH₂N(CH₃)₂ |
| MP9062 | NECA | OH | H | CH₂N(CH₃)₂ |
| JR3021 | NECA | H | H | COOCH₂CH₂NHBoc |
| MP9063 | NECA | OH | H | COOCH₂CH₂NHBoc |
| JR3033 | NECA | H | H | COOCH₂CH₂NH₂ |
| MP9064 | NECA | OH | H | COOCH₂CH₂NH₂ |
| JR3037 | NECA | H | H | CONHCH₂CH₃ |
| MP9065 | NECA | OH | H | CONHCH₂CH₃ |
| JR3055 | NECA | H | H | CONH₂ |
| MP9072 | NECA | OH | H | CONH₂ |
| JR3065 | NECA | H | H | CONHMe |
| MP9066 | NECA | OH | H | CONHMe |
| JR3067B | NECA | H | H | Me, cis CO₂Me |
| MP9067 | NECA | OH | H | Me, cis CO₂Me |
| JR3067A | NECA | H | H | Me, trans CO₂Me |
| MP9068 | NECA | OH | H | Me, trans CO₂Me |

TABLE 1-continued

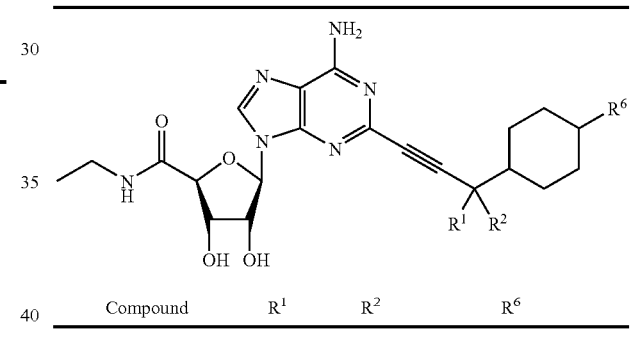

| Compound | R | $R^1$ | $R^2$ | $R^6$ |
|---|---|---|---|---|
| JR3087 | NECA | H | H | CH₂CH₃ |
| MP9069 | NECA | OH | H | CH₂CH₃ |
| JR3159A | NECA | OH | H | H |
| JR3159B | NECA | OH | H | H |
| JR3119 | NECA | H | H | COCH₃ |
| MP9070 | NECA | OH | H | COCH₃ |
| JR3121 | NECA | H | H | CHCH₃(OH) |
| MP9071 | NECA | OH | H | CHCH₃(OH) |
| JR3139 | NECA | OH | C₆H₁₁ | H |

NECA = CH₃CH₂N(H)C(O)—

TABLE 2

| Compound | $R^1$ | $R^2$ | $R^6$ |
|---|---|---|---|
| JR3261 | H | H | H |
| JR3259 | H | H | CO₂tBu |
| JR3269 | H | H | CO₂Et |
| JR4011 | H | H | CO₂iBu |
| JR4009 | H | H | CO₂iPr |
| JR4007 | H | H | COMe |
| JR4051 | H | H | COC(CH₃)₃ |
| JR4047 | H | H | COCH₂(CH₃)₃ |
| MP9047 | H | H | COCH₃ |
| MP9048 | H | H | C(O)N(CH₃)₂ |
| MP9049 | H | H | C(O)N(CH₃)Et |
| MP9050 | H | H | C(O)N(CH₃)iPr |
| MP9051 | H | H | C(O)N(CH₃)iBu |
| MP9052 | H | H | C(O)NH(CH₃) |
| MP9053 | H | H | C(O)NH(Et) |
| MP9054 | H | H | C(O)NH(iPr) |
| MP9055 | H | H | C(O)NH(iBu) |
| TX3261 | OH | H | H |
| TX3259 | OH | H | CO₂tBu |
| TX3269 | OH | H | CO₂Et |
| TX4011 | OH | H | CO₂iBu |
| TX4009 | OH | H | CO₂iPr |
| TX4007 | OH | H | COMe |
| TX4051 | OH | H | COC(CH₃)₃ |
| TX4047 | OH | H | COCH₂(CH₃)₃ |
| TX9047 | OH | H | COCH₃ |
| TX9048 | OH | H | C(O)N(CH₃)₂ |
| TX9049 | OH | H | C(O)N(CH₃)Et |
| TX9050 | OH | H | C(O)N(CH₃)iPr |
| TX9051 | OH | H | C(O)N(CH₃)iBu |
| TX9052 | OH | H | C(O)NH(CH₃) |
| TX9053 | OH | H | C(O)NH(Et) |

TABLE 2-continued

| Compound | R¹ | R² | R⁶ |
|---|---|---|---|
| TX9054 | OH | H | C(O)NH(iPr) |
| TX9055 | OH | H | C(O)NH(iBu) |

TABLE 3

| Compound | n | R³ | R⁶ |
|---|---|---|---|
| JR3135 | 1 | OH | H |
| JR3089 | 2 | OH | H |
| JR3205 | 2 | NH₂ | H |
| JR3177A | 2 | OH | 2-CH₃ |
| JR3177B | 2 | OH | 2-CH₃ |
| JR3181A | 2 | OH | 2-CH₃ |
| JR3181B | 2 | OH | 2-CH₃ |
| JR3227 | 2 | OH | 2-C(CH₃)₃ |
| JR9876 | 2 | OH | 2-C₆H₅ |
| JR3179 | 2 | OH | 3-CH₃ |
| JR3221 | 2 | OH (R) | 3-CH₃ (R) |
| JR3223 | 2 | OH (S) | 3-CH₃ (R) |
| MP9041 | 2 | OH (R) | 3-CH₃ (S) |
| MR9042 | 2 | OH (S) | 3-CH₃ (S) |
| JR3201B | 2 | OH | 3-(CH₃)₂ |
| MP9043 | 2 | OH (R) | 3-CH₂CH₃ (R) |
| MP9044 | 2 | OH (S) | 3-CH₂CH₃ (R) |
| MP9045 | 2 | OH (R) | 3-CH₂CH₃ (S) |
| MP9046 | 2 | OH (S) | 3-CH₂CH₃ (S) |
| JR3163 | 2 | OH | 3-(CH₃)₂, 5-(CH₃)₂ |
| JR9875 | 2 | OH | 4-CH₃ |
| JR3149 | 2 | OH | 4-C₂H₅ |
| JR3203 | 2 | OH | 4-C(CH₃)₃ |
| JR3161 | 2 | OH | 4-C₆H₅ |

TABLE 4

| Compound | R¹ | R² | R⁶ |
|---|---|---|---|
| JR3213 | H | H | CO₂Et |
| JR3281 | H | H | CO₂tBu |
| JR3289 | H | H | H |
| JR4025 | H | H | cyclohexyl |
| JR4053 | H | H | COMe |
| JR4049 | H | H | CO2iBu |
| JR3283 | H | H | 2-Pyrimidinyl |
| MP9029 | H | H | COMe |
| MP9030 | H | H | COC(CH₃)₃ |
| MP9031 | H | H | COCH₂(CH₃)₃ |
| MP9032 | H | H | COCH₃ |
| MP9033 | H | H | C(O)N(CH₃)₂ |
| MP9034 | H | H | C(O)N(CH₃)Et |
| MP9035 | H | H | C(O)N(CH₃)iPr |
| MP9036 | H | H | C(O)N(CH₃)iBu |
| MP9037 | H | H | C(O)NH(CH₃) |
| MP9038 | H | H | C(O)NH(Et) |
| MP9039 | H | H | C(O)NH(iPr) |
| MP9040 | H | H | C(O)NH(iBu) |

TABLE 5

| Compound | R | R¹ | R² | R⁶ |
|---|---|---|---|---|
| MP9021 | NECA | H | H | CH₂OH |
| MP9022 | NECA | H | H | CO₂H |
| JR3251 | NECA | H | H | CO₂Me |
| JR3279 | NECA | H | H | CO₂Et |
| MP9027 | CH₂OH | H | H | CO₂Me |
| MP9028 | NECA | H | H | CO₂MeCH₂OAc |
| MP9015 | CH₂OH | H | H | CH₂OAc |
| MP9016 | NECA | H | H | CH₂N(CH₃)₂ |
| MP9017 | NECA | H | H | COOCH₂CH₂NHBoc |
| MP9018 | NECA | H | H | COOCH₂CH₂NH₂ |
| MP9019 | NECA | H | H | CONHCH₂CH₃ |
| MP9020 | NECA | H | H | CONH₂ |
| MP9023 | NECA | H | H | CONHMe |
| MP9024 | NECA | H | H | CH₂CH₃ |
| MP9025 | NECA | H | H | COCH₃ |
| MP9026 | NECA | H | H | CHCH₃(OH) |

NECA = CH₃CH₂N(H)C(O)—

TABLE 6

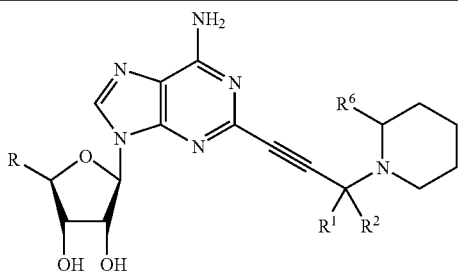

| Compound | R | R¹ | R² | R⁶ |
|---|---|---|---|---|
| MP9001 | NECA | H | H | $CH_2OH$ |
| MP9002 | NECA | H | H | $CO_2H$ |
| JR3253 | NECA | H | H | $CO_2Me$ |
| MP9003 | $CH_2OH$ | H | H | $CO_2Me$ |
| MP9004 | NECA | H | H | $CH_2OAc$ |
| MP9005 | $CH_2OH$ | H | H | $CH_2OAc$ |
| MP9006 | NECA | H | H | $CH_2N(CH_3)_2$ |
| MP9007 | NECA | H | H | $COOCH_2CH_2NHBoc$ |
| MP9008 | NECA | H | H | $COOCH_2CH_2NH_2$ |
| MP9009 | NECA | H | H | $CONHCH_2CH_3$ |
| MP9010 | NECA | H | H | $CONH_2$ |
| MP9011 | NECA | H | H | $CONHMe$ |
| MP9012 | NECA | H | H | $CH_2CH_3$ |
| MP9013 | NECA | H | H | $COCH_3$ |
| MP9014 | NECA | H | H | $CHCH_3(OH)$ |

NECA = $CH_3CH_2N(H)C(O)$—

TABLE 7

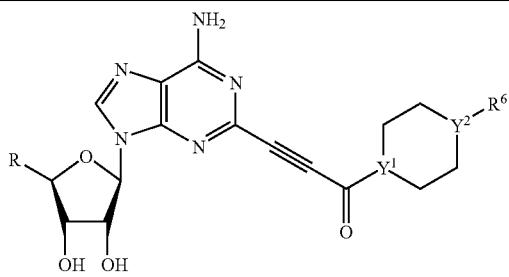

| Compound | R | Y | Y' | R6 |
|---|---|---|---|---|
| RJ1111 | NECA | CH | CH | $CO_2Me$ |
| RJ1112 | NECA | CH | N | $CO_2Me$ |
| RJ1113 | NECA | N | CH | $CO_2Me$ |
| RJ1114 | NECA | N | N | $CO_2Me$ |
| RJ1115 | NECA | CH | CH | $CH_2OH$ |
| RJ1116 | NECA | CH | N | $CH_2OH$ |
| RJ1117 | NECA | N | CH | $CH_2OH$ |
| RJ1118 | NECA | N | N | $CH_2OH$ |
| RJ1119 | NECA | CH | CH | $CO_2H$ |
| RJ1120 | NECA | CH | N | $CO_2H$ |
| RJ1121 | NECA | N | CH | $CO_2H$ |
| RJ1122 | NECA | N | N | $CO_2H$ |
| RJ1123 | NECA | CH | CH | $CH_2OAc$ |
| RJ1124 | NECA | CH | N | $CH_2OAc$ |
| RJ1125 | NECA | N | CH | $CH_2OAc$ |
| RJ1126 | NECA | N | N | $CH_2OAc$ |
| RJ1127 | NECA | CH | CH | $CONH_2$ |
| RJ1128 | NECA | CH | N | $CONH_2$ |
| RJ1129 | NECA | N | CH | $CONH_2$ |
| RJ1130 | NECA | N | N | $CONH_2$ |
| RJ1131 | NECA | CH | CH | $CONHMe$ |
| RJ1132 | NECA | CH | N | $CONHMe$ |
| RJ1133 | NECA | N | CH | $CONHMe$ |
| RJ1134 | NECA | N | N | $CONHMe$ |
| RJ1135 | NECA | CH | CH | $CO_2tBu$ |
| RJ1136 | NECA | CH | N | $CO_2tBu$ |
| RJ1137 | NECA | N | CH | $CO_2tBu$ |

TABLE 7-continued

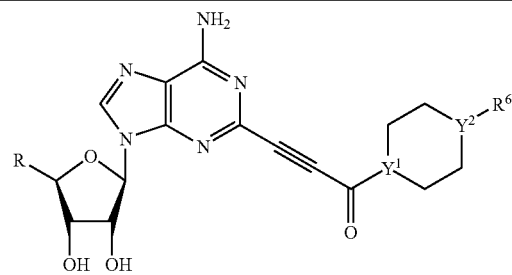

| Compound | R | Y | Y' | R6 |
|---|---|---|---|---|
| RJ1138 | NECA | N | N | $CO_2tBu$ |
| RJ1139 | NECA | CH | CH | $CO_2Et$ |
| RJ1140 | NECA | CH | N | $CO_2Et$ |
| RJ1141 | NECA | N | CH | $CO_2Et$ |
| RJ1142 | NECA | N | N | $CO_2Et$ |
| RJ1143 | NECA | CH | CH | $CO_2iBu$ |
| RJ1144 | NECA | CH | N | $CO_2iBu$ |
| RJ1145 | NECA | N | CH | $CO_2iBu$ |
| RJ1146 | NECA | N | N | $CO_2iBu$ |
| RJ1147 | NECA | CH | CH | $CO_2iPr$ |
| RJ1148 | NECA | CH | N | $CO_2iPr$ |
| RJ1149 | NECA | N | CH | $CO_2iPr$ |
| RJ1150 | NECA | N | N | $CO_2iPr$ |
| RJ1151 | NECA | CH | CH | $COMe$ |
| RJ1152 | NECA | CH | N | $COMe$ |
| RJ1153 | NECA | N | CH | $COMe$ |
| RJ1154 | NECA | N | N | $COMe$ |
| RJ1155 | NECA | CH | CH | $COC(CH_3)_3$ |
| RJ1156 | NECA | CH | N | $COC(CH_3)_3$ |
| RJ1157 | NECA | N | CH | $COC(CH_3)_3$ |
| RJ1158 | NECA | N | N | $COC(CH_3)_3$ |
| RJ1159 | NECA | CH | CH | $COCH_2(CH_3)_3$ |
| RJ1160 | NECA | CH | N | $COCH_2(CH_3)_3$ |
| RJ1161 | NECA | N | CH | $COCH_2(CH_3)_3$ |
| RJ1162 | NECA | N | N | $COCH_2(CH_3)_3$ |
| RJ1163 | NECA | CH | CH | $C(O)N(CH_3)_2$ |
| RJ1164 | NECA | CH | N | $C(O)N(CH_3)_2$ |
| RJ1165 | NECA | N | CH | $C(O)N(CH_3)_2$ |
| RJ1166 | NECA | N | N | $C(O)N(CH_3)_2$ |
| RJ1167 | NECA | CH | CH | $C(O)N(CH_3)Et$ |
| RJ1168 | NECA | CH | N | $C(O)N(CH_3)Et$ |
| RJ1169 | NECA | N | CH | $C(O)N(CH_3)Et$ |
| RJ1170 | NECA | N | N | $C(O)N(CH_3)Et$ |
| RJ1171 | NECA | CH | CH | $C(O)N(CH_3)iPr$ |
| RJ1172 | NECA | CH | N | $C(O)N(CH_3)iPr$ |
| RJ1173 | NECA | N | CH | $C(O)N(CH_3)iPr$ |
| RJ1174 | NECA | N | N | $C(O)N(CH_3)iPr$ |
| RJ1175 | NECA | CH | CH | $C(O)N(CH_3)iBu$ |
| RJ1176 | NECA | CH | N | $C(O)N(CH_3)iBu$ |
| RJ1177 | NECA | N | CH | $C(O)N(CH_3)iBu$ |
| RJ1178 | NECA | N | N | $C(O)N(CH_3)iBu$ |
| RJ1179 | NECA | CH | CH | $C(O)NH(Et)$ |
| RJ1180 | NECA | CH | N | $C(O)NH(Et)$ |
| RJ1181 | NECA | N | CH | $C(O)NH(Et)$ |
| RJ1182 | NECA | N | N | $C(O)NH(Et)$ |
| RJ1183 | NECA | CH | CH | $C(O)NH(iPr)$ |
| RJ1184 | NECA | CH | N | $C(O)NH(iPr)$ |
| RJ1185 | NECA | N | CH | $C(O)NH(iPr)$ |
| RJ1186 | NECA | N | N | $C(O)NH(iPr)$ |
| RJ1187 | NECA | CH | CH | $C(O)NH(iBu)$ |
| RJ1188 | NECA | CH | N | $C(O)NH(iBu)$ |
| RJ1189 | NECA | N | CH | $C(O)NH(iBu)$ |
| RJ1190 | NECA | N | N | $C(O)NH(iBu)$ |
| RJ1191 | NECA | CH | CH | $CH_2OCOCH_3$ |
| RJ1192 | NECA | N | CH | $CH_2OCOCH_3$ |
| RJ1193 | NECA | CH | CH | $CH_2OCOEt$ |
| RJ1194 | NECA | N | CH | $CH_2OCOEt$ |
| RJ1195 | NECA | CH | CH | $CH_2OCOiPr$ |
| RJ1196 | NECA | N | CH | $CH_2OCOiPr$ |
| RJ1197 | NECA | CH | CH | $CH_2OCOiBu$ |
| RJ1198 | NECA | N | CH | $CH_2OCOiBu$ |

NECA = $CH_3CH_2N(H)C(O)$—

The following abbreviations have been used herein:

| | |
|---|---|
| 2-Aas | 2-alkynyladenosines; |
| $^{125}$I-ABA | $N^6$-(4-amino-3-[125]iodo-benzyl)adenosine |
| APCI | Atmospheric pressure chemical ionization |
| ATL146e | 4-{3-[6-Amino-9-(5-ethylcarbamoyl-3,4-dihydroxy-tetrahydro-furan-2-yl)-9H-purin-2-yl]-prop-2-ynyl}cyclo-hexanecarboxylic acid methyl ester; |
| CCPA | 2-chloro-$N^6$-cyclopentyladenosine; |
| CGS21680 | 2-[4-(2-caboxyethyl)phenethylamino]-5'-N-ethyl-carboxamidoadenosine; |
| Cl-IB-MECA | $N^6$-3-iodo-2-chlorobenzyladenosine-5'-N-methyluronamide; |
| CPA | $N^6$-cyclopentyladenosine |
| DMF | dimethylformamide |
| DMSO | dimethylsulfoxide |
| DMSO-$d_6$ | deuterated dimethylsulfoxide |
| EtOAc | ethyl acetate |
| eq | equivalent |
| GPCR | G protein coupled receptor; h$A_{2A}$AR, Recombinant human $A_{2A}$ adenosine receptor; |
| IADO | 2-Iodoadenosine |
| $^{125}$I-APE, | 2-[2-(4-amino-3-[$^{125}$I]iodophenyl)ethylamino]adenosine; NECA, 5'-N-ethylcarboxamidoadenosine; |
| IB-MECA | $N^6$-3-iodobenzyladenosine-5'-N-methyluronamide; |
| 2-Iodoadenosine | 5-(6-amino-2-iodo-purin-9-yl)-3,4-dihydroxytetra-hydro-furan-2carboxylic acid ethylamide |
| HPLC | high-performance liquid chromatography |
| HRMS | high-resolution mass spectrometry |
| [125]I-ZM241385, | [125]I-4-(2-[7-amino-2-[2-furyl][1,2,4]triazolo[2,3-a][1,3,5]-triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220, | N-(9-chloro-2-furan-2-yl-[1,2,4]triazolo[1,5-c]-quinazolin-5-yl)-2-phenylacetamide; |
| MS | mass spectrometry |
| NECA | N-ethylcarboxamidoadenosine |
| NMR | nuclear magnetic resonance |
| RP-HPLC | reversephase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |
| THF | tetrahydrofuan |
| TLC | thin layer chromatography |
| p-TSOH | para-toluenesulfonic acid |
| XAC | 8-(4-((2-a-minoethyl)aminocarbonyl-methyloxy)-phenyl)-1-3-dipropylxanthine; |

Compounds of the invention can generally be prepared as illustrated in Schemes 1A and 1B below. Starting materials can be prepared by procedures described in these schemes, procedures described in the General methods below or by procedures that would be well known to one of ordinary skill in organic chemistry. The variables used in Schemes 1A and Scheme 1B are as defined herein or as in the claims.

The preparation of alkynyl cycloalkanols is illustrated in Scheme 1A. A solution of an appropriate cycloalkanone (where j is from 0-5) is prepared in a solvent such as THF. A solution of a suitable ethynylmagnesium halide compound in a solvent is added to the cycloalkanone. After addition, the solution is allowed to stir at about 20° C. for about 20 hours. The reaction is monitored via TLC until the starting material is consumed. The reaction is quenched with water, filtered over a plug of sand and silica, washed with a solvent, such as EtOAc, and evaporated to provide the product. Typically, two products are formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

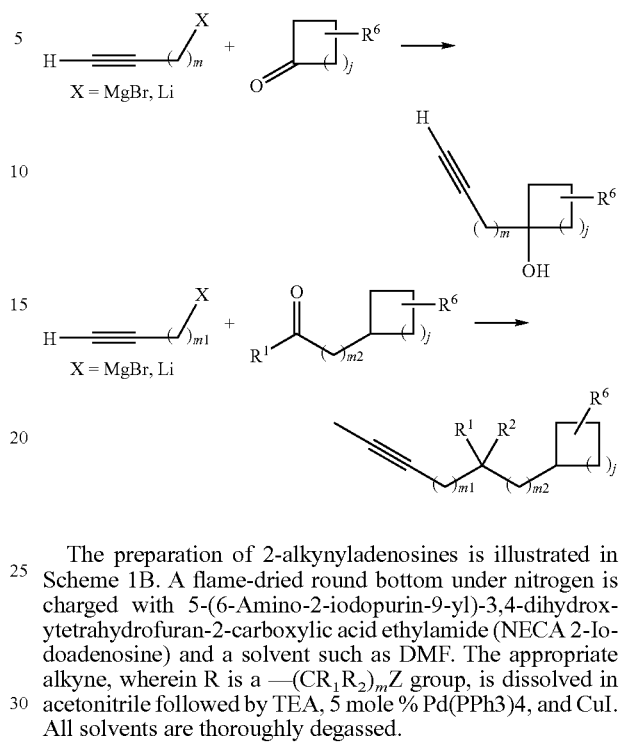

Scheme 1A
General Route to Synthesis of Alkyne Precursors

The preparation of 2-alkynyladenosines is illustrated in Scheme 1B. A flame-dried round bottom under nitrogen is charged with 5-(6-Amino-2-iodopurin-9-yl)-3,4-dihydroxytetrahydrofuran-2-carboxylic acid ethylamide (NECA 2-Iodoadenosine) and a solvent such as DMF. The appropriate alkyne, wherein R is a —$(CR_1R_2)_mZ$ group, is dissolved in acetonitrile followed by TEA, 5 mole % Pd(PPh3)4, and CuI. All solvents are thoroughly degassed.

The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

Scheme 1B
General Coupling Scheme for the Synthesis of 2-alkynyl-adenosine.

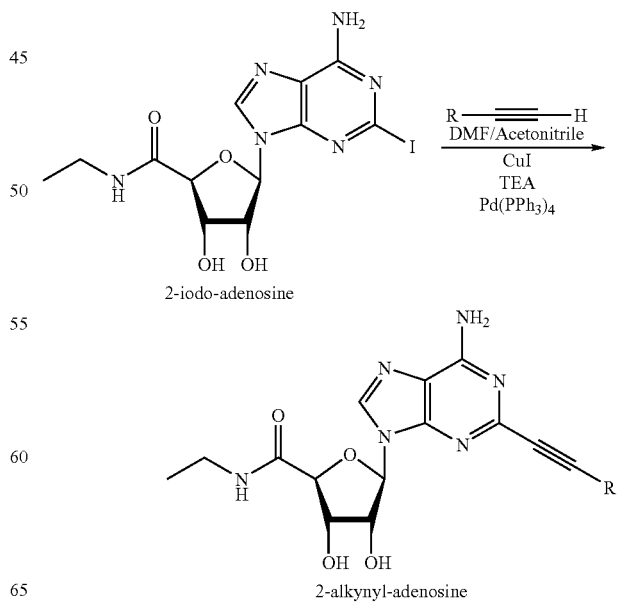

Examples of pharmaceutically acceptable salts are organic acid addition salts formed with acids which form a physiological acceptable anion, for example, tosylate, methanesulfonate, malate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid, a liquid or in a dermatological patch.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Useful dosages of Type IV PDE inhibitors are known to the art. For example, see, U.S. Pat. No. 5,877,180, Col. 12.

Generally, the concentration of the compound(s) of formula (I) in a liquid composition, such as a lotion, will be from about 0.1-25% wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 μg/kg, e.g., from about 10 to about 75 μg/kg of body weight per day, such as 3 to about 50 μg per kilogram body weight of the recipient per day, preferably in the range of 6 to 90 μg/kg/day, most preferably in the range of 15 to 60 μg/kg/day.

The compound is conveniently administered in unit dosage form; for example, containing 5 to 1000 μg, conveniently 10 to 750 μg, most conveniently, 50 to 500 μg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 5% solution of the active ingredient, optionally in saline, or orally administered as a bolus containing about 1-100 μg of the active ingredient. Desirable blood levels may be maintained by continuous infusion to provide about 0.01-5.0 μg/kg/hr or by intermittent infusions containing about 0.4-15 μg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. For example, it is desirable to administer the present compositions intravenously over an extended period of time following the insult that gives rise to inflammation.

The ability of a given compound of the invention to act as an $A_{2A}$ adenosine receptor agonist (or antagonist) may be determined using pharmacological models which are well known to the art, or using tests described below.

The invention will be further described by reference to the following detailed examples, which are given for illustration of the invention, and are not intended to be limiting thereof.

DESCRIPTION OF PREFERRED EMBODIMENTS

All melting points were determined with a Thomas Hoover capillary melting point apparatus and are uncorrected. Nuclear magnetic resonance spectra for proton ($^1$H NMR) were recorded on a 300 MHz GE spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LcQ Classic. High resolution mass spectrometry (HRMS) data was provided by the Nebraska Center for Mass Spectrometry. Analytical HPLC was done on a Waters 2690 Separation Module with a Waters Symmetry C8 (2.1×150 mm) column operated at room temperature. Compounds were eluted at 200 μL/min with 70:30 acetonitrile:water, containing 0.5% acetic acid, with UV detection at 214 nm using a Waters 486 Tunable Detector. Preparative HPLC was performed on a Shimadzu Discovery HPLC with a Shim-pack VP-ODS $C_{18}$ (20×100 mm) column operated at room temperature. Compounds were eluted at 30 mL/min with a gradient 20-80% of water (containing 0.1% TFA) to methanol over 15 minutes with UV detection at 214 nm using a SPD10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester N.H. Analytical thin-layer chromatography was done on Merck Kieselgel 60 F254 aluminum sheets. Preparative thin-layer chromatography was done using 1000 micron Analtech Uniplate with silica gel. All reactions were done under a nitrogen atmosphere in flame-dried glassware unless otherwise stated.

General Method 1: Preparation of Alkynyl Cyclohexanols

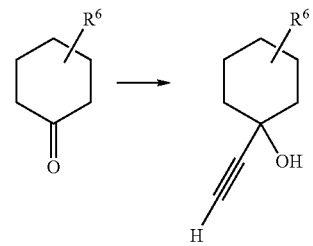

To a solution of about 10 mmol of the appropriate cyclohexanone in about 50 mL of THF is added to about 60 mL (30 mmol) of 0.5 M ethynylmagnesium bromide in THF. The solution is allowed to stir at about 20° C. for about 20 hours. After the starting material had been consumed, monitored by TLC, the reaction is quenched with about 5 mL of water, filtered over a plug of sand and silica, washed with EtOAc, and evaporated to yield a yellow oil. Usually the oil contained two spots on TLC with 20% EtOAc/Hexanes, which are visualized with Vanillin Usually these two products are the different isomers formed by the axial/equatorial addition of the alkyne to the ketone. The compounds are purified via flash chromatography using 10% EtOAc/Hexanes to provide clear oils or white solids in a yield of about 50-80%.

General Method 2: Preparation of Propargyl Piperadines/Piperazines

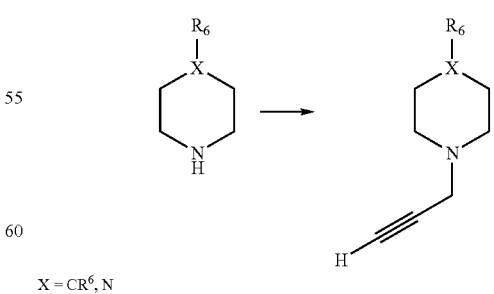

To a solution of the appropriate piperazine/piperadine (about 10.0 mmol), in about 20 mL acetonitrile, is added about 12.0 mmol of propargyl bromide (80% stabilized in toluene) and about 50.0 mmol of anhydrous potassium carbonate. The reaction mixture is filtered, and evaporated to dryness. The residue is taken up in about 50 mL of dichloromethane/water and the organic layers removed. The aqueous layer is washed with an additional 3×25 mL dichloromethane. The organic layer is dried using anhydrous sodium sulfate, filtered, and concentrated to provide the crude product, which is purified using column chromatography.

General Method 3: Preparation of Modified Piperadines/Piperazines

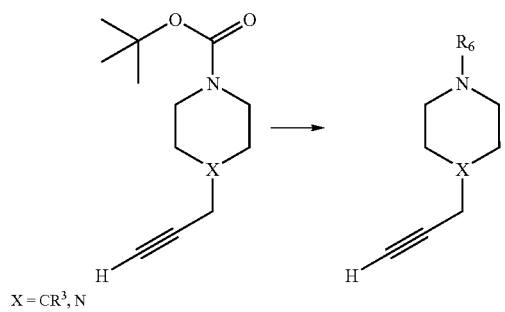

To about 100 mg of the appropriate Boc-protected piperazine/piperadine is added 2-4 mL of neat TFA. The solution is allowed to stir for 6 hours. The TFA is removed under reduced pressure to yield a yellow oil. This oil is taken up in about 10 mL of dichloromethane to which is added 10-fold excess of TEA and 3 equivalents of the appropriate acyl chloride. The yellow solution is allowed to stir at room temperature for about 12 hours, after which time the solvents are removed and the product purified using a 1.1×30 cm 14 g column from Robert Thompson Scientific with a 5%-30% gradient of ethyl acetate/hexanes.

General Method 4: Preparation of 2-AAs (2-Alkynyladenosines)

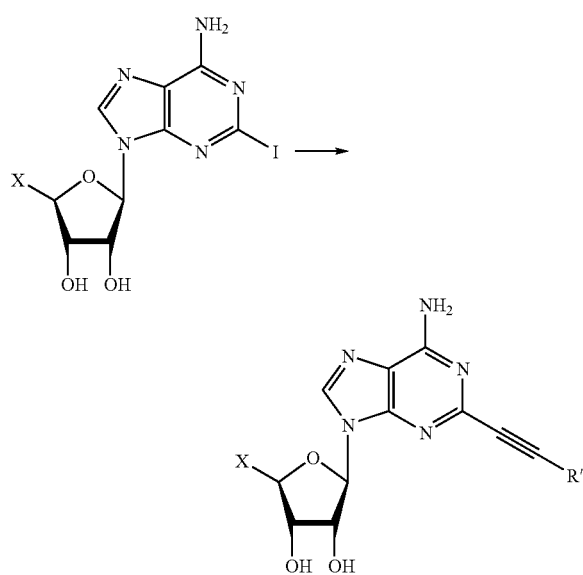

A flame-dried 25 mL round bottom under nitrogen is charged with 5-(6-amino-2-iodo-purin-9-yl)-3,4-dihydroxytetrahydrofuran-2-carboxylic acid ethylamide (2-Iodoadenosine) (about 40 mg) (X=CH$_3$CH$_2$NHC(O)—) and dissolved in about 2 mL of DMF. The appropriate alkyne (approx 0.1 mL) is then added followed by about 4 mL of acetonitrile and about 0.1 mL of TEA. All three solvents had been degassed with nitrogen for at least 24 hours. To this solution is added 5 mole percent Pd(PPh$_3$)$_4$ and 6 mole % copper iodide. The yellowish solution is allowed to stir for 24 hours at room temperature, or until complete by HPLC. If the reaction is not complete at this time, additional catalyst, CuI, and TEA are added. After the reaction is complete, the solvents are removed under high-vacuum and the red/black residue taken back up in a small amount of DMF. This solution is added to a preparative silica TLC plate (Analtech 1000 microns, 20 cm×20 cm) and eluted first with 120 mL of 40% Hexanes/CH$_2$Cl$_2$, and then again after addition of 40 mL of MeOH. The UV active band (usually yellow in color) in the middle of the plate is collected, slowly washed with 4×25 mL 20% MeOH/CH$_2$Cl$_2$, and concentrated. This product is then purified by RP-HPLC.

Preparation 1: [(2R,3R,4R,5R)-3,4-diacetyloxy-5-(2-amino-6-oxohyropurin-9-yl)oxolan-2-yl]methyl acetate (6.2)

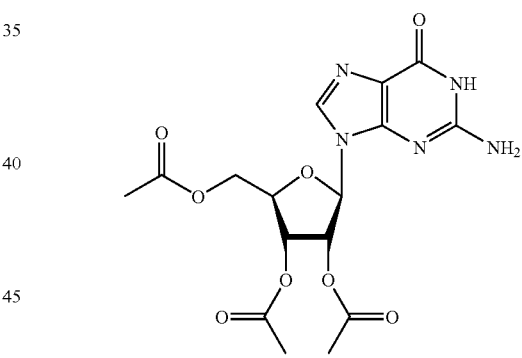

A suspension of 113 g (0.4 mol) of dry guanosine (6.1), acetic anhydride (240 mL, 2.5 mol), dry pyridine (120 mL) and dry DMF (320 mL) was heated for 3.75 hours at 75° C. without allowing the temperature to exceed 80° C. The clear solution was then transferred to a 3 L Erlenmyer flask and filled with 2-propanol. Upon cooling the solution to room temperature crystallization was initiated and allowed to proceed at 4° C. overnight. The white solid filtrate was filtered, washed with 2-propanol and recrystallized from 2-propanol to provide 6.2 (96%). $^1$H NMR (300 Mhz, CDCl$_3$) 8.20 (s, 1H, H-8), 6.17 (d, J=5.41 Hz, 1H, H-1) 5.75 (t, J=5.39 Hz, 1H, H-2), 5.56 (t, J=5.0, H-3), 4.41 (m, 3H, H-4,5), 2.14 (s, 3H, Ac), 2.11 (s, 3H, Ac), 2.10 (s, 3H, Ac). $^{13}$C NMR (300 MHz, CD$_3$OD) 171.0, 170.3, 1702, 157.7, 154.8, 152.4, 136.7, 117.7, 85.5, 80.4, 73.0, 71.3, 64.0, 31.3, 21.2, 21.0.

Preparation 2: [(2R,3R,4R,5R)-3,4-diacetyloxy-5-(2-amino-6-chloropurin-9-yl)oxolan-2-yl]methyl acetate (6.3)

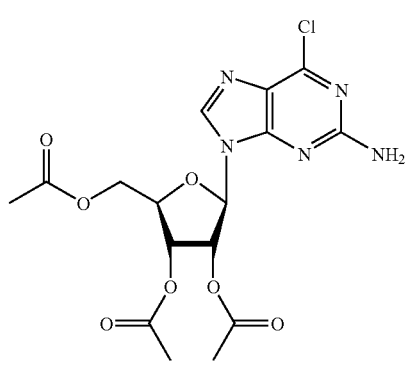

To a 1 L flask was added 80 g (0.195 mol) [(2R,3R,4R,5R)-3-4-diacetyloxy-5-(2-amino-6-oxohyropurin-9-yl)oxolan-2-yl]meth yl acetate (6.2), tetramethylammonium chloride (44 g, 0.4 mol), anhydrous acetonitrile (400 mL) and N,N-dimethlaniline (25 mL). The flask was placed in an ice salt bath and cooled to 2° C. To this solution was added dropwise POCl$_3$ (107 mL 1.15 mol) at a rate that maintained the temperature below 5° C. (45 minutes). The flask was then removed from the ice bath, outfitted with a condenser, placed in an oil bath and allowed to reflux for 10 minutes. The solution changed to a red/brown color. The solvent was removed under reduced pressure to yield an oily residue which was transferred to a beaker containing 1000 g of ice and 400 mL of CHCl$_3$ and allowed to stir for 1.5 hours to decompose any remaining POCl$_3$. The organic phase was removed and the aqueous phase extracted with 3×50 mL of CHCl$_3$ and pooled with the organic phase. The pooled organic layers were back extracted with 50 mL of water followed by stirring with 200 mL of saturated NaHCO$_3$. The organic layer was further extracted with NaHCO$_3$ until the aqueous extract was neutral (2×). The organic layer was finally extracted with brine and dried over MgSO$_4$ for 16 hours. To the solution was added 800 mL of 2-propanol after which the solution was concentrated under reduced pressure. To the oily solid was added 200 mL of 2-propanol and the solution was refrigerated overnight. The crystalline product was filtered, washed, and allowed to dry overnight to give 6.3 (77%). $^1$H NMR (300 MHz, CD$_3$OD) 8.31 (s, 1H, H-8), 7.00 (s, 2H, NH$_2$) 6.06 (d, J=5.8 Hz, 1H, H-1), 5.83 (t, J=6.16 Hz, 1H, H-2), 5.67 (m, 1H, H-3), 4.29 (m, 3H, H-4,5), 2.07 (s, 3H, Ac), 1.99 (s, 3H, Ac), 1.98 (s, 3H, Ac). $^{13}$C NMR (300 MHz, CD$_3$OD) 171.0, 170.4, 170.2, 160.8, 154.6, 150.8, 142.2, 124.5, 85.8, 80.6, 72.8, 71.2, 63.9, 21.4, 21.3, 21.1.

Preparation 3: [(2R,3R,4R,5R)-3,4-diacetyloxy-5-(6-chloro-2-iodopurin-9-yl)oxolan-2-yl]methyl acetate (6.4)

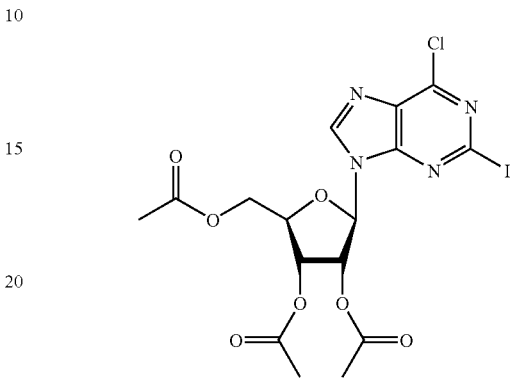

Isoamyl nitrite (5 mL, 37 mmol) was added to a mixture of 5.12 g (12 mmol) [(2R,3R,4R,5R)-3-,4-diacetyloxy-5-(2-amino-6-chloropurin-9-yl)oxolan-2-yl]methy l acetate (6.3), I$_2$ (3.04 g, 12 mmol), CH$_2$I$_2$ (10 mL, 124 mmol), and CuI (2.4 g, 12.6 mmol) in THF (60 mL). The mixture was heated under reflux for 45 minutes and then allowed to cool to room temperature. To this solution was added 100 ml of saturated Na$_2$S$_2$O$_3$. This step removed the reddish color. The aqueous layer was extracted 3× with chloroform, which was pooled, dried over MgSO$_4$, and concentrated under reduced pressure. The product was then purified over a silica gel column using CHCl$_3$-MeOH (98:2) to collect [(2R,3R,4R,5R)-3,4-diacetyloxy-5-(6-chloro-2-iodopurin-9-yl)oxolan-2-yl]methyl acetate (6.4) (80% crystallized from EtOH). $^1$H NMR (300 MHz, CDCl$_3$) 8.20 (s, 1H, H-8), 6.17 (d, J=5.41 Hz, 1H, H-1), 5.75 (t, J=5.39 Hz, 1H, H-2), 5.56 (t, J=5.40 Hz, 1H, H-3), 4.38 (m, 3H, H-4,5), 2.14 (s, 1H, Ac), 2.11 (s, 1H, Ac), 2.10 (s, 1H, Ac).

Preparation 4: (4S,2R,3R,5R)-2-(6-amino-2-iodopurin-9-yl)-5-(hydroxy-methyl)oxolane-3,4-diol (6.5)

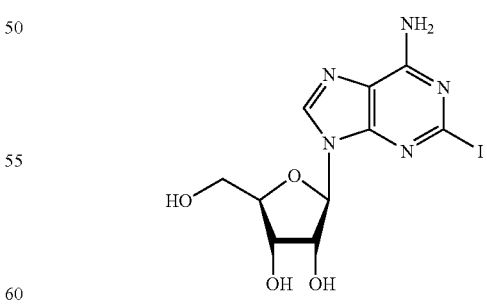

To a flask containing 6.0 g (11.1 mmol) [(2R,3R,4R,5R)-3,4-diacetyloxy-5-(6-chloro-2-iodopurin-9-yl)oxolan-2-yl] methyl acetate (6.4) was added 100 ml of liquid NH$_3$ at −78° C. and the solution was allowed to stir for 6 hours. After which time it was allowed to come to room temperature overnight with concurrent evaporation of the NH$_3$ to yield a brown oil.

The product was crystallized from hot isopropanol to provide 6.5 (80%), m.p. 143-145° C., r.f.=0.6 in 20% MeOH/CHCl₃. ¹H NMR (300 MHz, DMSO-d₆) 8.24 (s, 1H), 7.68 (s, 2H), 5.75 (d, J=6.16, 1H), 5.42 (d, J=5.40 Hz, 1H), 5.16 (d, J=4.62 Hz, 1H), 4.99 (t, J=5.39 Hz, 1H), 4.67 (d, J=4.81 Hz, 1H), 4.06 (d, J=3.37 Hz, 1H), 3.89 (m, 1H), 3.54 (m, 2H).

Preparation 5: [(1R,2R,4R,5R)-4-(6-amino-2-iodopurin-9-yl)-7-7-dimethyl-3,6,8-trioxabicyclo[3.3.0]oct-2-yl]methan-1-ol (6.6)

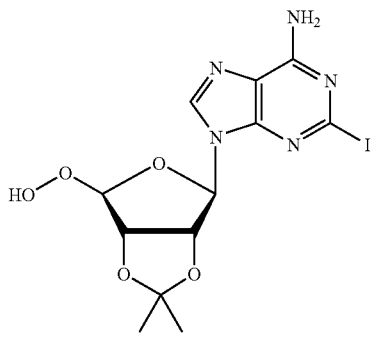

To a solution of 2.0 g (5.08 mmol) (4S,2R,3R,5R)-2-(6-amino-2-iodopurin-9-yl)-5(hydroxymethyl)oxolane-3,4-diol (6.6) in 100 mL acetone was added 9.6 g of p-toluenesulfonic acid and 5 ml of dimethoxypropane. The reaction was stirred at room temperature for 1 hour. Solid NaHCO₃, 15 g, was added to the solution. The slurry was stirred for an additional 3 hours. The residue was filtered and washed 2× with EtOAc. The filtrate was then concentrated under reduced pressure. The residue was chromatographed on a silica gel column with MeOH—CHCl₃ (1:99) to give 6.6 (72%) as a solid, m.p. 185-187° C. ¹H NMR (300 MHz, DMSO-d₆) 8.22 (s, 1H, H-8), 7.69 (s, 2H), NH₂), 6.00 (d, J=2.70 Hz, 1H, H-1), 5.21 (m, 1H, H-2), 5.07 (bs, 1H, OH), 4.88 (m, 1H, H-3), 4.13 (m, 1H, H-4), 3.47 (m, 2H, H-5), 1.49 and 1.28 (s, 3H, C(CH₃)₂).

Preparation 6: (2S,1R,4R,5R)-4-(6-amino-2-iodopurin-9-yl)-7,7-dimethyl-3,6,8-trioxabicyclo[3.3.0]octane-2-carboxylic acid (6.7)

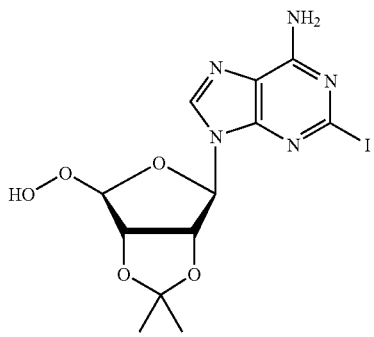

To a stirred solution of 1.6 g (3.7 mmol) of [(1R,2R,4R,5R)-4-(6-amino-2-iodopurin-9-yl)-7-7-dimethyl-3,6,8-trioxabicyclo[3.3.0]oct-2-yl]methan-1-ol (6.6) in 200 mL of H₂O was added 0.60 g of KOH and, dropwise, a solution of 1.70 g (10.8 mml) of KMnO₄ in 50 mL of H₂O. The mixture was placed in the dark at room temperature for 2-4 days. The reaction mixture was then cooled to 5-10° C. and decolorized by a solution of 4 mL of 30% H₂O₂ in 16 mL of water, while the temperature was maintained below 10° C. using an ice-salt bath. The mixture was filtered through Celite and the filtrate was concentrated under reduced pressure to about 10 mL and then acidified to pH 4 with 2N HCl. The resulting precipitate was filtered off and washed with ether to yield 6.7 (70%) after drying as a white solid, m.p. 187-190 C. ¹H NMR (300 MHz, DMSO-d₆) 8.11 (s, 1H, H-8), 7.62 (s, 2H, NH₂), 7.46 (s, 1H, COOH), 6.22 (s, 1H, H-1), 5.42 (d, J=5.71 Hz, 1H, H-2), 5.34 (d, J=6.16 Hz, 1H, H-3), 4.63 (s, 1H, H-4), 1.46 and 1.30 (s, 3H, C(CH₃)₂).

Preparation 7: (2S,3S,4R,5R)-5-(6-amino-2-iodopurin-9-yl)-3,4-dihydroxyoxolane-2-carboxylic acid (6.8)

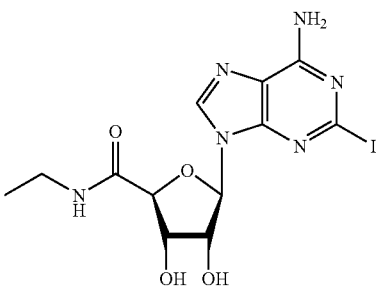

A solution of 1.72 g (3.85 mmol) of (2S,1R,4R,5R)-4-(6-amino-2-iodopurin-9-yl)-7,7-dimethyl-3,6,8-trioxabicyclo[3.3.0]octane-2-carboxylic acid (6.7) in 80 mL of 50% HCOOH was stirred at 80° C. for 1.5 hours. The reaction mixture was evaporated under reduced pressure, dissolved in H₂O, and the solvent was evaporated again. This process was repeated until there was no odor of formic acid in the residue. Recrystallization from water provided 1.33 g (85%) 6.8 as a white solid, m.p. 221-223° C., dec. ¹H NMR (300 MHz, DMSO-d₆) 8.31 (s, 1H, H-8), 7.68 (s, 2H, NH₂), 5.90 (d, J=6.55 Hz, 1H, H-1), 4.42 (m, 1H, H-2), 4.35 (d, J=2.31 Hz, 1H, H-4), 4.22 (m, 1H, H-3).

Preparation 8: [(2S,3S,4R,5R)-5-(6-amino-2-iodopurin-9-yl)-3,4-dihydroxyoxolan-2-yl]-N-ethylcarboxamide (6.9)

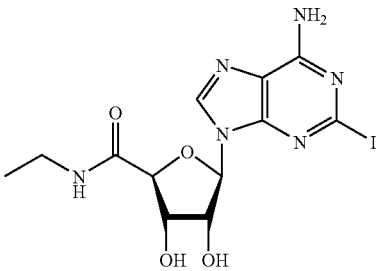

To a cooled (5° C.) and stirred solution of 1.29 g (3.17 mmol) of (2S,3S,4R,5R)-5-(6-amino-2-iodopurin-9-yl)-3,4-dihydroxyoxolane-2-carboxylic acid (6.8) in 150 mL of absolute ethanol was added dropwise 1.15 mL of ice-cooled $SOCl_2$. The mixture was stirred at room temperature overnight and then brought to pH 8 with saturated aqueous $NaHCO_3$. The mixture was filtered, and then the filtrate was concentrated under reduced pressure to yield a white solid which was dried and then redissolved in 20 mL of dry ethylamine at −20° C. for 3 hours and then at room temperature overnight. The reaction mixture was diluted with absolute ethanol, and the precipitated product was filtered off and washed with dry ether to provide 530 mg (72%) of 6.9 as a pure solid, m.p. 232-234° C. $^1H$ NMR (300 MHz, DMSO-$d_6$) 8.34 (s, 1H, H-8), 8.12 (t, 1H, NH), 7.73 (s, 2H, $NH_2$), 5.85, (d, J=6.93 Hz, 1H, H-1), 4.54 (m, 1H, H-2), 4.25 (d, J=1.92 Hz, 1H, H-4), 4.13 (m, 1H, H-3), 3.28 (m, 2H, $CH_2CH_3$), 1.00 (t, J=7.2 Hz, 3H, $CH_2CH_3$).

Preparation 9: [4-(tert-Butyl-dimethyl-silanyloxymethyl)-cyclohexyl]-methanol (83)

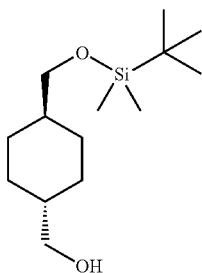

To a 100 mL-flask containing 79 (4.0 g, 27.8 mmol) in DMF (40 mL) was added TBDMSCl (3.56 g, 23.6 mmol) and imidazole (3.79 g, 55.6 mmol). The reaction was allowed to stir at 25° C. for 16 hours after which time saturated aqueous LiBr (50 mL) was added and the reaction extracted with ether (2×50 mL). The ether layers were pooled and extracted again with LiBr (2×35 mL). The ether layer became clear. The ether layer was then concentrated in vacuo and the product purified by flash chromatography, on a silica gel column, eluting with 1:2 ether/petroleum ether to yield 83 (3.80 g, 62%) as a homogenous oil. $^1H$ NMR ($CDCl_3$) δ 3.46 (d, J=6.2 Hz, 2H), 3.39 (d, J=6.2 Hz, 2H), 1.95-1.72 (m, 4H), 1.65 (m, 1H), 1.40 (m, 1H), 1.03-0.89 (m, 4H), 0.88 (s, 9H), 0.04 (s, 6H); $^{13}C$ NMR ($CDCl_3$) δ 69.2, 69.1, 41.2, 41.1, 29.5, 26.5, 18.9, −4.8; APCI m/z (rel intensity) 259 ($MH^+$, 100).

Preparation 10: Toluene-4-sulfonic acid 4-(tert-butyl-dimethyl-silanyloxymethyl)-cyclohexylmethyl ester (84)

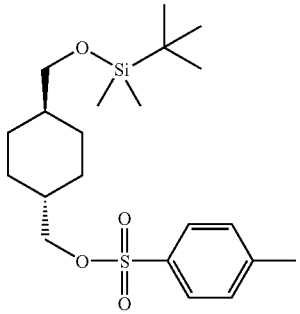

To a 100 mL-flask containing 83 (3.4 g, 13.2 mmol) in $CHCl_3$ (30 mL) was added tosyl chloride (3.26 g, 17.1 mmol) and pyidine (3.2 mL, 39.6 mmol). The reaction was allowed to stir at 25° C. for 14 hours after which time the reaction was concentrated in vacuo to yield a wet white solid. To this solid was added ether (50 mL) and the solid was filtered and subsequently washed with additional ether (2×50 mL) The ether layers were pooled, concentrated in vacuo to yield a clear oil which was purified by flash chromatography, on a silica gel column, eluting with 1:4 ether/petroleum ether to yield 84 (4.5 g, 83%) as a white solid. $^1H$ NMR ($CDCl_3$) δ 7.78 (d, J=7.7, 2H), 7.33 (d, J=7.7 Hz, 2H), 3.81 (d, J=6.2 Hz, 2H), 3.37 (d, J=6.2 Hz, 2H), 2.44 (s, 3H), 1.95-1.72 (m, 4H), 1.65 (m, 1H), 1.40 (m, 1H), 1.03-0.89 (m, 4H), 0.88 (s, 9H), 0.04 (s, 6H); $^{13}C$ NMR ($CDCl_3$) δ 145.1, 133.7, 130.3, 128.4, 75.8, 68.9, 40.7, 38.0, 29.1, 26.5, 22.1, 18.9, −4.9; APCI m/z (rel intensity) 413 ($MH^+$, 100).

Preparation 11:
(4-Prop-2-ynyl-cyclohexyl)-methanol (86)

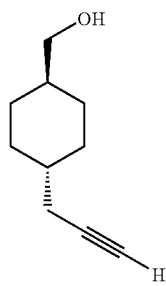

A 3-neck 250 mL-flask equipped with a gas inlet tube and dry-ice condenser was cooled to −78° C. and charged with liquid ammonia (40 mL). To the reaction mixture was added lithium wire (600 mg, 86.4 mmol) generating a deep blue solution. The mixture was allowed to stir for 1 hour. Acetylene, passed through a charcoal drying tube, was added to the ammonia until all the lithium had reacted and the solution turned colorless, at which time the flow of acetylene was stopped, the acetylene-inlet tube and condenser removed and the flask outfitted with a thermometer. DMSO (20 mL) was added and the ammonia evaporated with a warm water bath until the mixture reached a temperature of 30° C. The solution was stirred at this temperature for 2 hours until the solution stopped bubbling. The mixture was cooled to 5° C. and compound 84 (11.25 g, 27.3 mmol), in DMSO (10 mL), was added. The temperature was maintained at 5° C. The mixture was allowed to stir at 5° C. for 0.5 hours. Then the solution was gradually warmed to room temperature and stirred for an additional 18 hours. The brown/black reaction mixture was poured slowly over ice (300 g) and extracted with ether (4×100 mL), dried with anhydrous sodium sulfate, and concentrated in vacuo to yield a yellow oil. The oil was subsequently dissolved in THF (200 mL) and changed to a brownish color upon addition of TBAF hydrate (11.20 g, 35.5 mmol). The solution was allowed to stir for 24 hours under $N_2$ atmosphere. After stirring, the reaction was quenched with water (200 mL) and extracted with ether (3×100 mL). The ether extracts were combined and concentrated in vacuo. The crude product was purified by chromatography, on a silica gel column, eluting with 1:1 ether/petroleum ether to yield 86 (3.91 g, 93%) as a yellow oil. $^1$H NMR (CDCl$_3$) δ 3.45 (d, J=6.2, 2H), 2.10 (d, J=6.2, 2H), 1.9 (s, 1H), 1.94-1.69 (m, 4H), 1.52-1.34 (m, 2H), 1.16-0.83 (m, 4H); $^{13}$C NMR (CDCl$_3$) δ 83.8, 69.5, 69.0, 40.8, 37.7, 32.3, 29.7, 26.5.

Preparation 12: (4-prop-2-ynylcyclohexyl)methyl acetate (87)

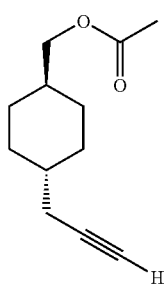

To a solution of 960 mg (6.31 mmol) of 86 in 6 mL DMF was added 0.62 mL (7.57 mmol) pyridine and 0.78 mL (8.27 mmol) acetic anhydride. The reaction was allowed to stir overnight at room temperature. After 16 hours, starting material still remained. The reaction mixture was heated at 75° C. for 3 hours. The solvent was removed under reduced pressure to yield a yellow oil which was purified by flash chromatography, on silica gel, eluting with 1:3 ether/petroleum ether to yield 1.12 g (91%) of 87 as an oil. $^1$H NMR (CDCl$_3$) δ 3.87 (d, J=6.2 Hz, 2H), 2.06 (d, J=4.3 Hz, 2H), 2.03 (s, 3H), 1.98-1.93 (m, 1H), 1.92-1.83 (m, 2H), 1.83-1.74 (m, 2H), 1.63-1.36 (m, 2H), 1.12-0.90 (m, 4H); $^{13}$C NMR (CDCl$_3$) δ 171.7, 83.7, 69.9, 69.6, 37.4, 37.3, 32.1, 29.7, 26.5, 21.4; APCI m/z (rel intensity) 195 (M$^+$, 30), 153 (M$^+$, 70), 135 (M$^+$, 100).

Preparation 13: 4-prop-2-ynyl-cyclohexanecarboxylic acid (88)

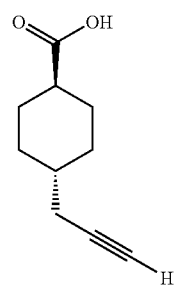

A solution of chromium trioxide (600 mg, 6.0 mmol) in 1.5 M H$_2$SO$_4$ (2.6 mL, 150 mmol) was cooled to 5° C. and added to a solution of 86 (280 mg, 1.84 mmol) in acetone (15 mL). The mixture was allowed to warm to room temperature and allowed to stir overnight. Isopropanol (4 mL) was added to the green/black solution, which turned light blue after 1 hr. After adding water (15 mL), the solution was extracted with CHCl$_3$ (6×25 mL). The organic layers were pooled and concentrated in vacuo to yield a white solid. The solid was dissolved in ether (50 mL) and extracted with 1 M NaOH (2×30 mL). The basic extracts were pooled, acidified w/10% HCl, and re-extracted with ether (3×30 mL). The ether layers were combined, dried with sodium sulfate and concentrated in vacuo to yield a white solid. The product was recrystallized from acetone/water to yield 88 (222 mg, 73%) as white needles: mp 84-85° C.; $^1$H NMR (CDCl$_3$) δ 2.30-2.23 (m, 1H), 2.17-2.11 (m, 2H), 2.07-2.03 (m, 2H), 1.97-1.91 (m, 3H), 1.51-1.39 (m, 3H), 1.13-1.01 (m, 2H); $^{13}$C NMR (CDCl$_3$) δ 182.5, 83.8, 69.6, 40.7, 37.7, 32.3, 29.6, 26.5; APCI m/z (rel intensity) 165 (M$^-$, 100).

Preparation 14: Methyl 4-prop-2-ynylcyclohexanecarboxylate (89)

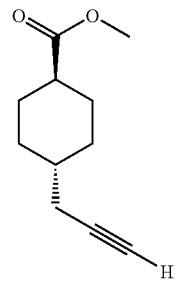

To a solution of 88 (240 mg, 1.45 mmol) in 7:3 CH$_2$Cl$_2$:MeOH (10 mL) was added TMS Diazomethane (2.0 M in hexanes) (0.9 mL, 1.8 mmol) in 0.2 ml aliquots until the color remained yellow. The reaction was allowed to stir for an additional 0.25 hours at room temperature. After stirring, glacial acetic acid was added dropwise until the solution became colorless. The reaction was concentrated in vacuo to an oil which was purified by flash chromatography on silica gel using ether:petroleum ether (1:9) to yield 89 (210 mg, 80%) as a clear oil. $^1$H NMR (CDCl$_3$) δ 3.60 (s, 3H), 2.25-2.13 (m, 1H), 2.08-1.94 (m, 3H), 1.95-1.90 (m, 2 H), 1.49-1.31 (m, 3H), 1.10-0.93 (m, 2H); $^{13}$C NMR (CDCl$_3$) δ 176.7, 83.3, 69.8, 51.9, 43.4, 36.7, 31.9, 29.2, 26.3; APCI m/z (rel intensity) 181 (MH$^+$, 100).

Preparation 15: Trans[4-(1-Propargyl)cyclohexylmethyl]methyl carbonate (90)

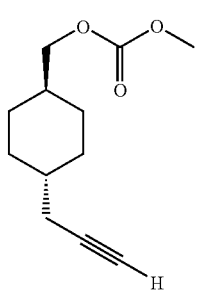

Yield: 345 mg, 81%. $^1$H NMR (CDCl$_3$) δ 0.98-1.07, 1.40-1.52, 1.57-1.70, 1.78-1.93 (4×m, 10H, cyclohexyl), 1.96 (t, 1H, acetylene), 2.10 (dd, 2H, —C$_6$H$_{10}$CH$_2$CCH), 3.78 (s, 3H, —OCH$_3$), 3.96 (d, —C$_6$H$_{10}$CH$_2$O—).

Preparation 16: Trans[4-(1-Propargyl)cyclohexylmethyl] iso-butyl carbonate (91)

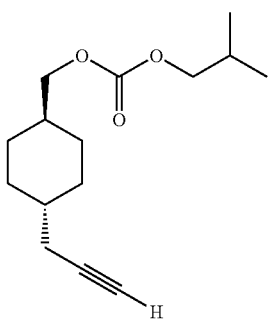

Yield: 433 mg, 83%. $^1$H NMR (CDCl$_3$) δ 0.95 (d, 4H, —OCH$_2$CH(CH$_3$)$_2$), 0.98-1.09, 1.40-1.51, 1.57-1.70, 1.78-1.93 (4×m, 10H, cyclohexyl), 1.94-2.04 (m, 1H, —OCH$_2$CH(CH$_3$)$_2$), 1.96 (t, 1H, acetylene), 2.10 (dd, 2H, —C$_6$H$_{10}$CH$_2$CCH), 3.91, 3.95 (2×d, 4H, —OCH$_2$CH(CH$_3$)$_2$, —C$_6$H$_{10}$CH$_2$O—).

Preparation 17: Trans[4-(1-Propargyl)cyclohexylmethyl]benzyl carbonate (92)

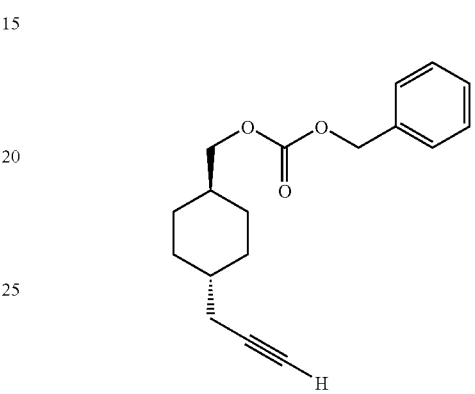

Yield: 340 mg, 69%. $^1$H NMR (CDCl$_3$) δ 0.97-1.08, 1.40-1.49, 1.55-1.69, 1.77-1.93 (4×m, 10H, cyclohexyl), 1.96 (t, 1H, acetylene), 2.10 (dd, 2H, —C$_6$H$_{10}$CH$_2$CCH), 3.98 (d, —C$_6$H$_{10}$CH$_2$O—), 5.15 (s, 2H, —OCH$_2$Ph), 7.33-7.40 (m, 5H, Ar).

Preparation 18: 4-(Toluene-4-sulfonyloxymethyl)-piperidine-1-carboxylic acid tert-butyl ester (JR3215)

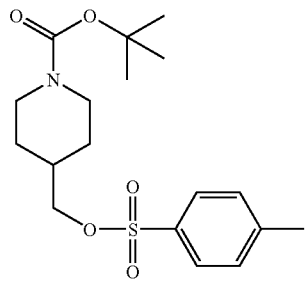

JR3215

A solution of N-Boc-4-piperidinemethanol, 5.0 g (23.2 mmol) in chloroform, 50 mL, was prepared. Toluene sulfonyl chloride, 5.75 g (30.2 mmol), in 5.6 mL of pyridine (69.6 mmol) was added. The solution was stirred under nitrogen allowed to stir for 24 hours. Standard workup and chromatographic purification provided the title compound. Yield 6.0 g

Preparation 19: (R)-1-Ethynyl-(R)-3-methyl-cyclohexanol (JR3217A), (S)-1-Ethynyl-(R)-3-methyl-cyclohexanol (JR3217B)

To a solution of 1.0 g (8.9 mmol) (R)-(+)-3-methyl-cyclohexanone in 50 mL of THF was added 54 mL (26.7 mmol) of 0.5 M ethynylmagnesium bromide in THF. The solution was allowed to stir at 20° C. for 20 hours. Analysis by TLC indicated that the starting material had been consumed. The reaction was quenched with 5 mL of water, filtered over a plug of sand and silica, washed with EtOAc, and evaporated to yield 1.15 g of a yellow oil containing two spots (r.f.'s 0.33 (minor, JR3217A) and 0.25 (major, JR3217B), 20% EtOAc/Hexanes) which were visualized with Vanillin. The compound was purified via flash chromatography using 10% EtOAc/Hexanes (225 mL silica) to provide JR3217A and JR3217B.

Preparation 20: 1-Prop-2-ynyl-piperidine-2-carboxylic acid methyl ester (JR3249)

The title compound was prepared starting with 4.0 g (22.3 mmol) of methylpipecolinate hydrochloride according to general method 2.

Preparation 21: 1-Prop-2-ynyl-piperidine-4-carboxylic acid methyl ester (JR3245)

To a solution of methyl isonipecotate 3.5 g (24.4 mmol, 3.30 mL) in 100 mL dichloromethane was added TEA (1.5 eq, 36.6 mmol, 5.1 mL), propargyl bromide (3.0 eq, 73.2 mmol, 6.5 ml), at room temperature for 36 hrs. The reaction was quenched with 35 mL water to yield to provide a clear solution. The solution was extracted with dichloromethane 2×25 mL, dried with Na2SO4, and the solvent evaporated to provide a yellow oil. r.f. (40% EtOAc/Hexanes) 0.26 stains faint white with Vanillin, starting material r.f. 0.05 stains yellow with Vanillin. The product appeared pure after extraction.

Preparation 22: 1-Prop-2-ynyl-piperidine-4-carboxylic acid ethyl ester (JR3271)

The title compound was prepared starting with 2.0 g (12.7 mmol) of ethyl isonipecotate according to general method 2.

Preparation 23:
4-Prop-2-ynyl-piperazine-1-carboxylic acid tert-butyl ester (JR3275)

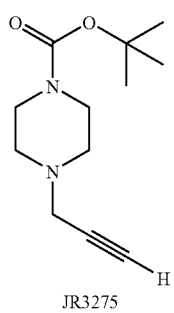

JR3275

To a solution of 10.0 g (54.8 mmol) of tert-butyl-1-piperazine carboxylate in 60 mL acetonitile was added 5.20 mL (60.4 mmol) propargyl bromide and 37.9 g (274 mmol) anhydrous potassium carbonate. Additional propargy bromide, 1.5 mL, was added after stirring for 36 hours at room temperature. The residue was evaporated to dryness. Dichloromethane, 50 mL, and water, 50 mL, were added. The reaction mixture was extracted with $CH_2Cl_2$, 4×40 mL, dried over magnesium sulfate, and evaporate to provide a brown oil. The oil was dissolved in dichloromethane and purify with a RT Scientific system using hexane/ethyl acetate gradient to yield 5.5 g (46%) of yellow oil, which ultimately crystallized upon standing.

Preparation 24:
4-Cyanomethyl-piperazine-1-carboxylic acid ethyl ester (JR3287)

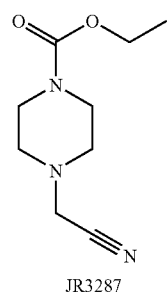

JR3287

To a solution of 3 g (19.0 mmol) of ethyl N-piperazinecarboxylate in 25 mL of $CH_3CN$ was added 1.57 g (1.32 mL 20.1 mmol) of 2-chloroacetonitrile and 15.6 g (95 mmol) $K_2CO_3.1½H_2O$. The suspension was stirred at room temperature for 16 hours. The reaction was analyzed using TLC (35% Ethyl acetate/Hexanes, product r.f. 0.38 vs. sm r.f. of 0.02). The analysis indicated the reaction was complete. The golden yellow solution was evaporated to dryness. The residue was extracted with $CH_2Cl_2/H_2O$, dried with $MgSO_4$, and concentrated.

Preparation 25: 5-Prop-2-ynyl-2,5-diaza-bicyclo[2.2.1]heptane-2-carboxylic acid tert-butyl ester (JR4013)

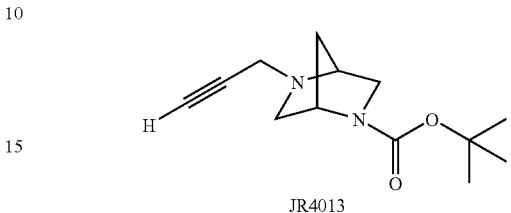

JR4013

The title compound was prepared starting with 500 mg (2.52 mmol) of 2,5-Diaza-bicyclo[2.2.1]heptane-2-carboxylic acid tert-butyl ester according to general method 2.

Preparation 26:
1-Cyclohexyl-4-prop-2-ynyl-piperazine (JR4019)

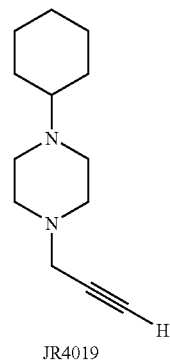

JR4019

The title compound was prepared starting with 3 g (17.9 mmol) of 1-cyclohexylpiperazine according to general method 2

Preparation 27: 1-Prop-2-ynyl-piperazine (JR4029)

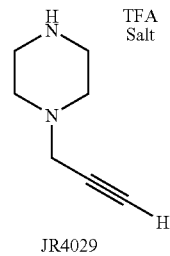

JR4029

To a flame-dried 25 mL round bottom flask under nitrogen was added 2.1 g of 4-Prop-2-ynyl-piperazine-1-carboxylic acid tert-butyl ester. To this solid was added 5 mL of 98% TFA in 1 mL portions. The solution turned wine red, bubbled and smoked. The additional portions of TFA were added when this activity subsided. After the third portion of TFA had been added only minimal bubbling occurred. The solution was allowed to stir under nitrogen at room temperature for an additional hour and evaporated under reduced pressure to yield the product as a thick red syrup. Assumed quantitative yield of 1.16 g. The residue was suspended in 20 mL dichloromethane and used immediately without further purification for the preparation of compounds JR4031, JR4033, and JR4035.

Preparation 28:
4-Prop-2-ynyl-piperazine-1-carboxylic acid methyl ester (JR4031)

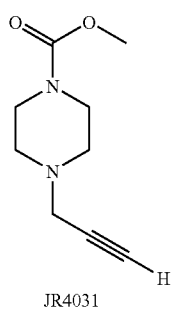

The title compound was prepared starting with 385 mg (3.1 mmol) of JR4029 and using methylchloroformate according to general method 3.

Preparation 29:
4-Prop-2-ynyl-piperazine-1-carboxylic acid isobutyl ester (JR4035)

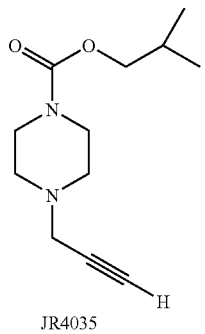

The title compound was prepared starting with 385 mg (3.1 mmol) of JR4029 and using isobutylchloroformate according to general method 3.

Preparation 30: 3,3-Dimethyl-1-(4-prop-2-ynyl-piperidin-1-yl)-butan-1-one (JR4041)

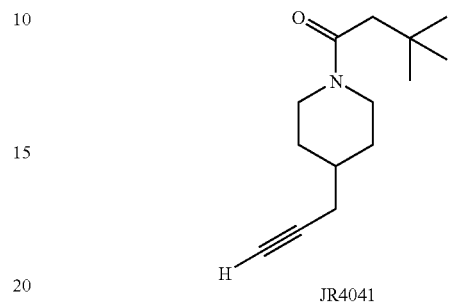

The title compound was prepared starting with tert-butyl ester (JR3257) and using tert-butylacetylchloride according to general method 3.

Preparation 31: 1-(4-Prop-2-ynyl-piperazin-1-yl)-ethanone (JR4043)

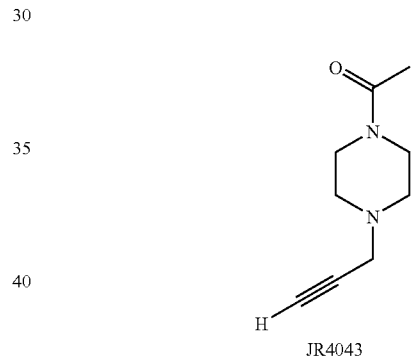

The title compound was prepared starting with 385 mg (3.1 mmol) of JR4029 and using acetyl chloride according to general method 3.

Preparation 32: Piperidine-1,4-dicarboxylic acid mono-tert-butyl ester

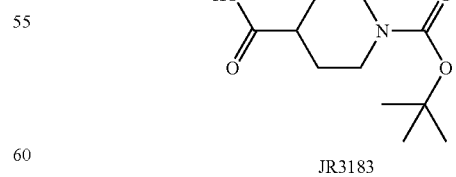

To a solution of piperidine-4-carboxylic acid (10 g, 77.5 mmol) and potassium carbonate (21.4 g, 155 mmol) in 150 mL of water was prepared. A solution of di-tert-butyl dicarbonate (16.9 g, 77.5 mmol) in 40 mL of THF was added dropwise via addition funnel at 0° C. The reaction was allowed to warm to room temperature gradually over 30 minutes and stirred for an additional 4 hours. The THF was removed under reduced pressure and the aqueous phase extracted with 50 mL of ether. The aqueous phase was then adjusted to pH 2 with 10% HCl and extracted with EtOAc, 4×50 mL. The combined organic layers were dried over anhydrous sodium sulfate, filtered, and concentrated in vacuo to yield 17.2 g (97%) of JR3183 as a white solid. Rf=0.2 (35% EtOAc/Hexanes stained w/vanillin). $^1$H NMR (CDCl$_3$) δ 11.83 (s, 1H), 3.98 (d, J=11.8 Hz, 2H), 2.83 (t, J=11.8, 2H), 2.46 (m, 1H), 1.88 (d, J=12.9 hz, 2H), 1.2 (m, 2H), 1.42 (s, 9H). $^{13}$C NMR (CDCl$_3$) δ 180.0, 154.8, 79.8, 42.9, 40.8, 28.3, 27.7. APCI m/z (rel intensity) M$^-$ 228.2 (100).

Preparation 33

The following intermediate compounds are prepared using the general method 1 described herein and the appropriate starting materials.

(R)-1-Ethynyl-3-tent-butyl-cyclohexanol (JR3255A), (S)-1-Ethynyl-3-tert-butyl-cyclohexanol (JR3255B)

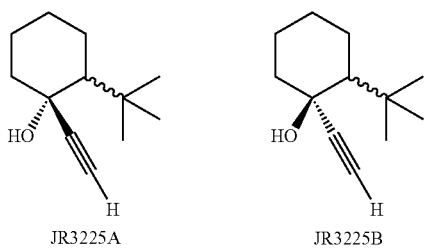

JR3225A  JR3225B

Toluene-4-sulfonic acid 4-prop-2-ynyl-cyclohexylmethyl ester (JR3077)

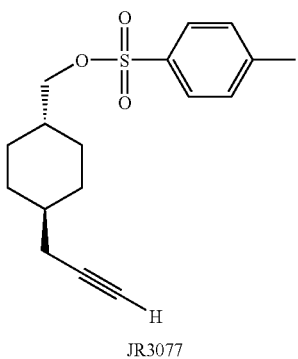

JR3077

1-Ethyl-4-prop-2-ynyl-cyclohexane (JR3083)

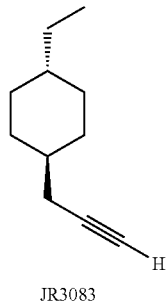

JR3083

1-(4-Prop-2-ynyl-cyclohexyl)-ethanone (JR3115)

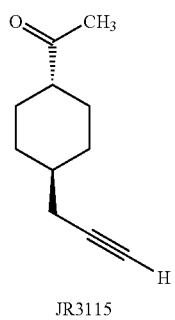

JR3115

1,1-Dicyclohexyl-prop-2-yn-1-ol (JR3127)

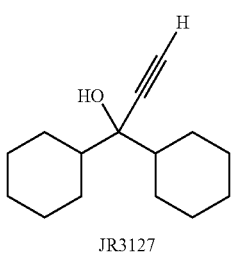

JR3127

| 51 | 52 |
|---|---|
| 1-Cyclohexyl-prop-2-yn-1-ol (JR3129) | 1-Ethynyl-3,3,5,5-tetramethyl-cyclohexanol (JR3151) |
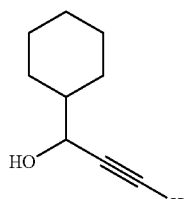
JR3129
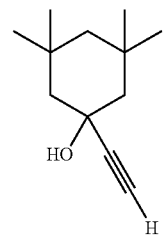
JR3151
4-Ethyl-1-ethynyl-cyclohexanol (JR3143)                              1-Ethynyl-4-phenyl-cyclohexanol (JR3153)
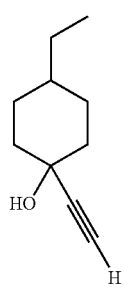
JR3143
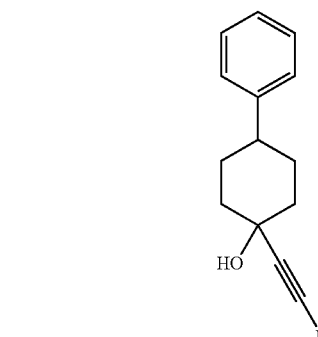
JR3153
1-Ethynyl-3-methyl-cyclohexanol                                  1-Ethynyl-2-methyl-cyclohexanol (JR3167B)
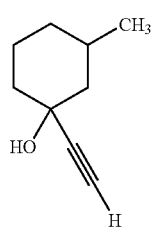
JR3147B
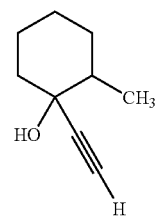
JR3167B

53
4-tert-Butyl-1-ethynyl-cyclohexanol (JR3191)
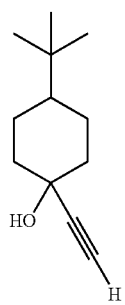
JR3191
1-Ethynyl-3,3-dimethyl-cyclohexanol (JR3193)
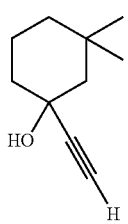
JR3193
Piperidine-1,4-dicarboxylic acid 1-tert-butyl ester 4-methyl ester (JR3195)
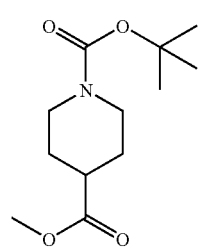
JR3195
54
4-Hydroxymethyl-piperidine-1-carboxylic acid tert-butyl ester (JR3199)
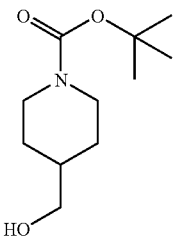
JR3199
4-Prop-2-ynyl-piperazine-1-carboxylic acid ethyl ester (JR3211)
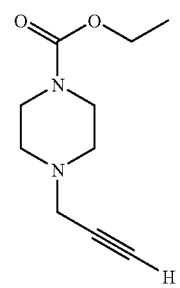
JR3211
4-Prop-2-ynyl-piperidine-1-carboxylic acid tert-butyl ester (JR3257)
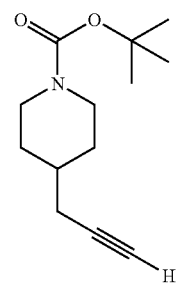
JR3257

4-Prop-2-ynyl-piperidine-1-carboxylic acid ethyl ester (JR3267B)

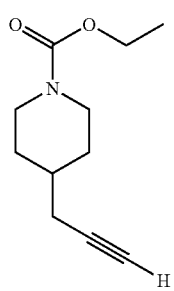

JR3267B 2-(4-Prop-2-ynyl-piperazin-1-yl)-pyrimidine (JR3277)

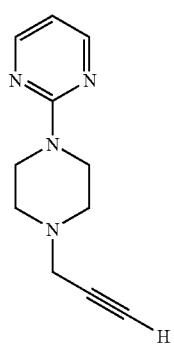

JR3277

1-(4-Prop-2-ynyl-piperidin-1-yl)-ethanone (JR4037)

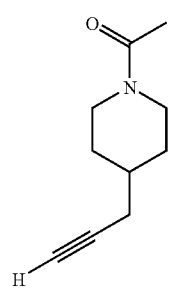

JR4037

2,2-Dimethyl-1-(4-prop-2-ynyl-piperidin-1-yl)-propan-1-one (JR4039)

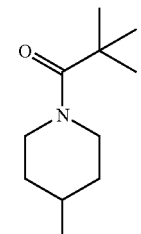

JR4039

Example 1

4-{3-[6-Amino-9-(5-ethylcarbamoyl-3,4-dihydroxytetrahydrofuran-2-yl)-9H-purin-2-yl]-prop-2-ynyl}-cyclohexanecarboxylic acid (109)

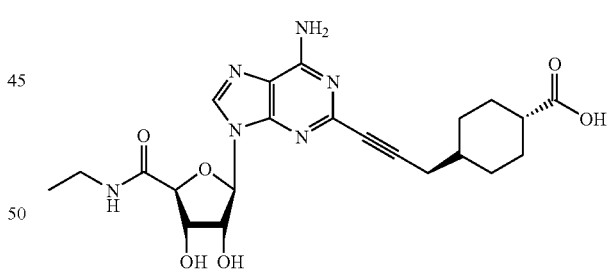

The reaction of 110 with five equivalents of LiOH in THF/water for 6 hours gave 109 (7 mg, 72%) as a white solid which was crystallized from MeOH/H$_2$O (0.1% TFA) after purification by reverse phase HPLC. $^1$H NMR (DMSO-d6) δ 8.70 (s, 1H), 8.41 (s, 1H), 7.62 (s, 2H), 5.89 (d, J=7.25 Hz, 1H), 4.53 (m, 1H), 4.27 (s, 1H), 4.08 (d, J=3.6 Hz, 1H), 2.29 (d, J=6.4 Hz, 2H), 2.15-1.99 (m, 1H), 1.92-1.76 (m, 4H), 1.52-1.38 (m, 1H), 1.38-1.19 (m, 2H), 1.02 (t, J=6.3 Hz 3H); $^{13}$C NMR (DMSO-d6) 176.7, 169.2, 155.6, 148.9, 145.2, 141.6, 119.0, 87.7, 85.0, 84.6, 81.6, 73.1, 71.9, 43.2, 35.9, 33.3, 31.2, 28.3, 25.6, 15.0. HRMS (FAB) m/z 474.2196 [(M+H)+ cacld for $C_{22}H_{29}N_6O_6$ 474.2182].

Example 2

4-{3-[6-Amino-9-(5-ethylcarbamoyl-3,4-dihydroxytetrahydrofuran-2-yl)-9H-purin-2-yl]-prop-2-ynyl}-cyclohexanecarboxylic acid methyl ester (110)

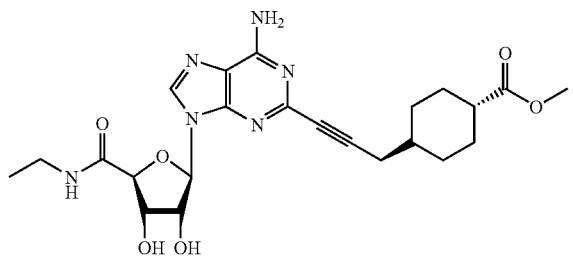

The reaction of 89 with 2-IodoNECA under the general conditions described above provided 110 (74 mg, 60%) as a white solid. $^1$H NMR (CD$_3$OD) δ 8.23 (s, 1H), 5.92 (d, J=7.7 Hz, 1H), 4.69-4.65 (dd, J=7.7 Hz, 4.6 Hz, 1H), 4.40 (s, 1H), 4.24 (d, J=4.6 Hz, 1H), 3.59 (s, 3H), 3.49-3.31 (m, 2H), 2.31 (d, J=6.6 Hz, 2H), 2.10-2.09 (m, 1H), 2.01-1.89 (m, 4H), 1.61-1.32 (m, 5H), 1.13 (t, J=7.3 Hz, 3H); $^{13}$C NMR (CD$_3$OD) δ 177.1, 171.1, 156.3, 149.3, 146.7, 142.4, 119.7 89.6, 86.0, 85.5, 81.6, 74.0, 72.2, 51.2, 43.2, 36.8, 34.2, 31.8, 28.9, 26.2, 14.4; HRMS (FAB) m/z 487.2325 [(M+H)+ cacld for $C_{23}H_{31}N_6O_6$ 487.2305].

Example 3

Acetic acid 4-{3-[6-amino-9-(5-ethylcarbamoyl-3,4-dihydroxy-tetrahydrofuran-2-yl)-9H-purin-2-yl]-prop-2-ynyl}-cyclohexylmethyl ester (111)

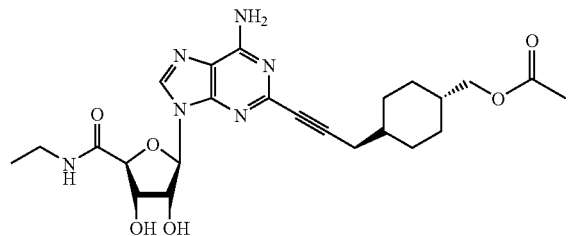

The reaction of 87 with 2-IodoNECA under the general conditions described above gave 111 (78 mg, 62%) as a white solid. $^1$H NMR (CD$_3$OD) δ 8.22 (s, 1H), 5.92 (d, J=8.1 Hz, 1H), 4.70-4.66 (dd, J=8.1 Hz, 4.6 Hz, 1H), 4.40 (d, J=1.2 Hz, 1H), 4.25-4.23 (dd, J=4.6 Hz, 1.2 Hz, 1H), 3.83 (d, J=6.5, 2H), 3.53-3.31 (m, 2H), 2.29 (d, J=6.5 Hz, 2H), 1.97 (s, 3H), 1.93-1.89 (m, 2H), 1.79-1.75 (m, 2H), 1.64-1.42 (m, 2H), 1.12 (t, J=7.3 Hz, 3H), 1.09-0.91 (m, 4H); $^{13}$C NMR (CD$_3$OD) δ 172.0, 171.2, 156.2, 149.3, 146.7, 142.5, 119.7, 89.6, 86.3, 85.5, 81.5, 74.0, 72.2, 69.6, 37.4, 37.2, 34.2, 32.1, 29.4, 26.4, 19.9, 14.5; HRMS (FAB) m/z 501.2469 [(M+H)+ cacld for $C_{24}H_{33}N_6O_6$ 501.2462].

Example 4

5-{6-Amino-2-[3-(4-hydroxymethyl-cyclohexyl)-prop-1-ynyl]-purin-9-yl}-3,4-dihydroxytetrahydrofuran-2-carboxylic acid ethylamide (112)

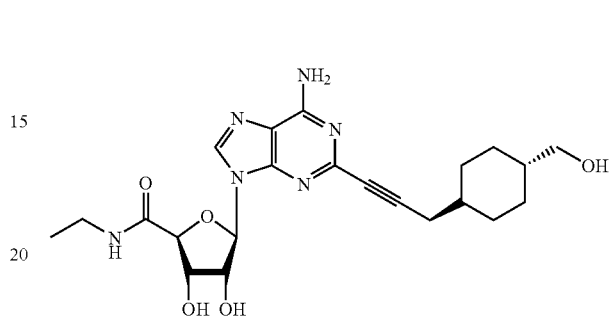

The reaction of 86 (30 mg, 0.2 mmol) with 2-IodoNECA (28 mg, 0.07 mmol) under the general conditions described above gave 112 (7 mg, 24%) as a white solid. $^1$H NMR (CD$_3$OD) δ 8.22 (s, 1H), 5.92 (d, J=7.7 Hz, 1H), 4.70-4.66 (dd, J=7.7 Hz, 4.8 Hz, 1H), 4.40 (d, J=1.2 Hz, 1H), 4.25-4.23 (dd, J=4.8 Hz, 1.2 Hz, 1H), 3.51-3.37 (m, 2H), 3.31 (d, J=6 Hz, 2H), 2.30 (d, J=6.8 Hz, 2H), 1.94-1.89 (m, 2H), 1.83-1.78 (m, 2H), 1.64-1.42 (m, 2H), 1.12 (t, J=7.3 Hz, 3H), 1.09-0.91 (m, 4H); $^{13}$C NMR (CD$_3$OD) δ 170.3, 155.4, 148.5, 146.0, 141.6, 118.8, 88.7, 85.5, 84.6, 80.6, 73.1, 71.3, 66.8, 39.6, 36.9, 33.3, 31.5, 28.6, 25.6, 13.5; HRMS (FAB) m/z 459.2373 [(M+H)+ cacld for $C_{22}H_{31}N_6O_5$ 459.2356].

Example 5

5-{6-Amino-2-[3-(4-ethylcarbamoyl-cyclohexyl)-prop-1-ynyl]-purin-9-yl}-3,4-dihydroxytetrahydrofuran-2-carboxylic acid ethylamide (JR3037)

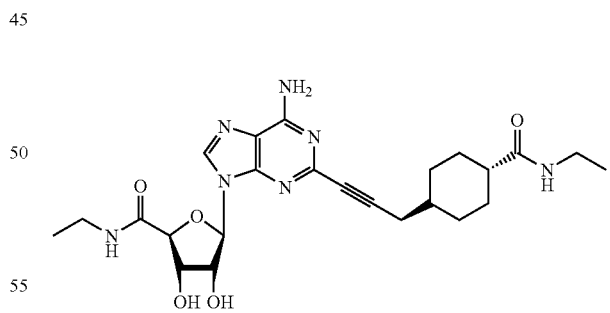

JR3037

To a sealed tube containing 5 mL of freshly distilled ethylamine was added 10 mg (0.02 mmol) of ATL146e. The flask was sealed and allowed to stir at 60° C. for 80 hours. After this time the reaction was only about 50% complete by HPLC. The vessel was cooled to 0° C., opened, and the ethylamine was removed in vacuo to yield 4.5 mg (73%) of JR3037 as a white solid and the recovery of 4.0 mg of starting material after the residue was purified by RP-HPLC. $^1$H NMR (CD$_3$OD-d$_4$) δ. $^{13}$C NMR (CD$_3$OD-d$_4$) δ. APCI m/z (rel intensity) 500.8 (MH$^+$, 100), 327.4 (3).

Example 6

5-{6-Amino-2-[3-(4-carbamoyl-cyclohexyl)-prop-1-ynyl]-purin-9-yl}-3,4-dihydroxytetrahydrofuran-2-carboxylic acid ethylamide (JR3055)

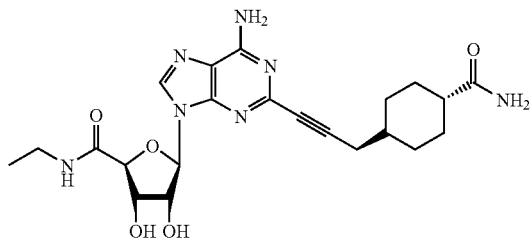

JR3055

To a sealed tube containing 10 mL of saturated MeOH/NH$_3$ solution was added 5 mg (0.01 mmol) of ATL146e. The flask was sealed and allowed to stir at 25° C. for 48 hours. The vessel was cooled to 0° C., opened, and the ammonia removed by bubbling N$_2$ for 1 hour. The remaining solvent was then removed in vacuo to yield 4.0 mg (83%) of JR3055 as a white solid after the residue was purified by RP-HPLC. $^1$H NMR (CD$_3$OD-d$_4$) δ 8.41 (s, 1H), 5.98 (d, J=7.2 Hz, 1H), 4.65 (dd, J=7.3 Hz, 4.8 Hz, 1H), 4.41 (d, J=2.0 Hz, 1H), 4.28 (dd, J=4.6 Hz, 2.0 Hz, 1H), 3.35 (m, 2H), 2.37 (d, J=6.4 Hz, 2H) 2.10 (m, 1H), 1.90 (m, _H), 1.53 (m, _H_), 1.23 (m, _H), 1.12 (t, J=7.3 Hz, 3H). $^{13}$C NMR (CD$_3$OD-d$_4$) δ. APCI m/z (rel intensity) 472.3 (MH$^+$, 100), 299.4 (10).

Example 7

5-{6-Amino-2-[3-(4-methylcarbamoyl-cyclohexyl)-prop-1-ynyl]-purin-9-yl}-3,4-dihydroxytetrahydrofuran-2-carboxylic acid ethylamide (JR3065)

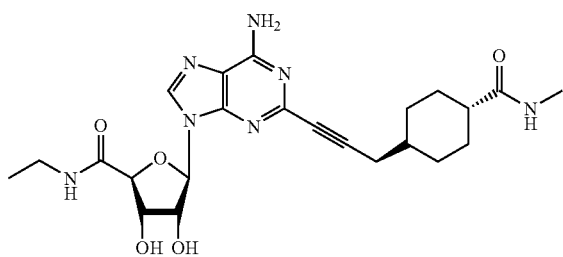

JR3065

To a sealed tube containing 10 mL 2.0 M methylamine in methanol was added 16.5 mg (0.03 mmol) of ATL146e. The flask was sealed and allowed to stir at 70° C. for 120 hours. The vessel was cooled to 0° C., opened, and the solvent was removed in vacuo to yield 8.0 mg (48%) of JR3065 as a white solid after the residue was purified by RP-HPLC. $^1$H NMR (CD$_3$OD-d$_4$) δ. $^{13}$C NMR (CD$_3$OD-d$_4$) δ. APCI m/z (rel intensity) 486.3 (MH$^+$, 100), 313.4 (35).

Example 8

5-[6-Amino-2-(1-hydroxy-cyclopentylethynyl)-purin-9-yl]-3,4-dihydroxytetrahydrofuran-2-carboxylic acid ethylamide (JR3135)

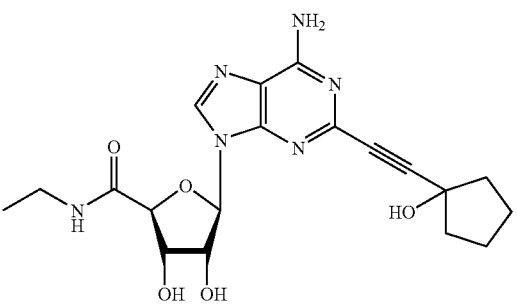

JR3135

The title compound was prepared using the appropriate starting materials and procedures described herein. The results are as follows:

$^1$H NMR (CD$_3$OD-d$_4$) δ 8.48 (s, 1H), 6.04 (d, J=6.9 Hz, 1H), 4.72 (dd, J=6.9 Hz, J=4.4 Hz, 1H), 4.46 (d, J=2.3 Hz, 1H), 4.33 (dd, J=4.6 Hz, J=1.9 Hz, 1H), 3.42 (m, 2H), 2.04 (m, 4H), 1.83, (m, 4H), 1.16 (t, J=7.3 Hz, 3H). $^{13}$C NMR (CD$_3$OD-d$_4$) δ 171.9, 155.3, 150.0, 144.3, 120.6, 95.4, 90.6, 89.5, 86.2, 79.9, 74.9, 74.0, 70.5, 42.9, 35.3, 24.4, 15.3. APCI m/z (rel intensity) 417.2 (MH$^+$, 100), 399.4 (85), 244.3 (15), 26.5 (25). HRMS M$^+$ actual 417.18864, observed 417.18880.

Example 9

5-[6-Amino-2-(3,3-dicyclohexyl-3-hydroxy-prop-1-ynyl)-purin-9-yl]-3,4-dihydroxytetrahydrofuran-2-carboxylic acid ethylamide (JR3139)

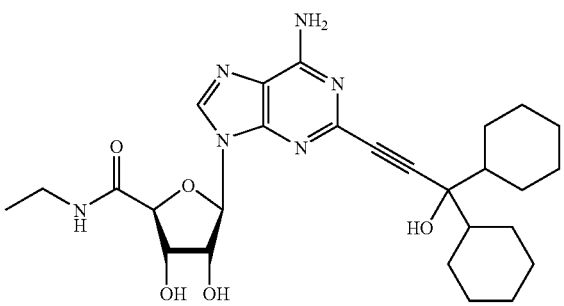

JR3139

The title compound was prepared using the appropriate starting materials and procedures described herein. The results are as follows:

$^1$H NMR (CD$_3$OD-d$_4$) δ 8.57 (s, 1H), 6.09 (d, J=6.6 Hz, 1H), 4.77 (dd, J=6.7, Hz, J=4.8 Hz, 1H), 4.46 (d, J=2.3 Hz, 1H), 4.37 (dd, J=4.6 Hz, J=2.3 Hz, 1H), 3.42 (m, 2H) 1.80 (m,

13H), 1.28 (m, 9H), 1.13 (t, J=7.3 Hz, 3H). $^{13}$C NMR (CD$_3$OD-d$_4$) δ. APCI m/z (rel intensity) 527.3 (MH$^+$, 60), 509.5 (100), 354.4 (5), 336.5 (5), 279.5 (8). HRMS M$^+$ actual 527.29819, observed 527.29830

Example 10

5-[6-Amino-2-(4-ethyl-1-hydroxy-cyclohexylethynyl)-purin-9-yl]-3,4-dihydroxytetrahydrofuran-2-carboxylic acid ethylamide (JR3149)

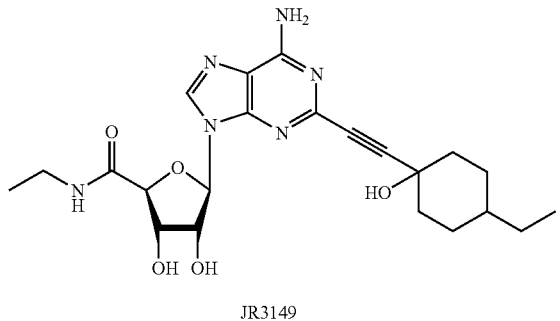

JR3149

The title compound was prepared using the appropriate starting materials and procedures described herein. The results are as follows:

$^1$H NMR (CD$_3$OD-d$_4$) δ 8.51 (s, 1H), 6.06 (d, J=7.0 Hz, 1H), 4.75 (dd, J=6.4 Hz, J=4.9 Hz, 1H), 4.46 (d, J=1.9 Hz, 1H), 4.34 (dd, J=4.9 Hz, J=2.1 Hz, 1H), 3.42 (m, 2H), 2.12 (d, J=11.9 Hz, 2H), 1.80 (d, J=11.9 Hz, 2H), 1.58 (t, J=12.1 Hz, 2H), 1.28 (m, 4H), 1.15 (t, J=7.1 Hz, 3H), 0.91 (t, J=7.1 Hz, 3H). $^{13}$C NMR (CD$_3$OD-d$_4$) δ 171.9, 155.4, 150.0, 144.2, 143.8, 120.6, 94.5, 90.5, 86.1, 81.8, 74.9, 74.1, 70.3, 40.5, 39.8, 35.3, 31.0, 30.2, 15.2, 12.0. APCI m/z (rel intensity) 459.4 (MH$^+$, 100), 441.4 (60), 268.4 (10). HRMS M$^+$ actual 459.23559, observed 459.23550.

Example 11

5-[6-Amino-2-(1-hydroxy-4-phenyl-cyclohexylethynyl)-purin-9-yl]-3,4-dihydroxytetrahydrofuran-2-carboxylic acid ethylamide (JR3161)

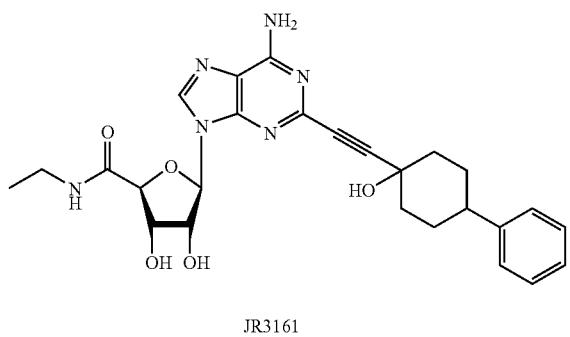

JR3161

The title compound was prepared using the appropriate starting materials and procedures described herein. The results are as follows:

$^1$H NMR (CD$_3$OD-d$_4$) δ 8.45 (s, 1H), 7.26 (m, 4H), 7.14 (m, 1H), 6.05 (d, J=7.3 Hz, 1H), 4.80 (dd, J=7.3 Hz, J=4.8 Hz, 1H), 4.46 (d, J=1.6 Hz, 1H), 4.34 (dd, J=4.7 Hz, J=1.8 Hz, 1H), 3.44 (m, 2H), 2.58 (m, 1H), 2.23 (d, J=11.7H, 2H), 1.92 (m, 4H), 1.78, (m, 2H), 1.15 (t, J=7.2 Hz, 3H). $^{13}$C NMR (CD$_3$OD-d$_4$) δ. APCI m/z (rel intensity) 507.3 (MH$^+$, 100) 489.4 (70), 334.3 (5), 316.5 (8). HRMS M$^+$ actual 507.23559, observed 507.23580.

Example 12

5-[6-Amino-2-(1-hydroxy-3,3,5,5-tetramethyl-cyclohexylethynyl)-purin-9-yl]-3,4-dihydroxytetrahydrofuran-2-carboxylic acid ethylamide (JR3163)

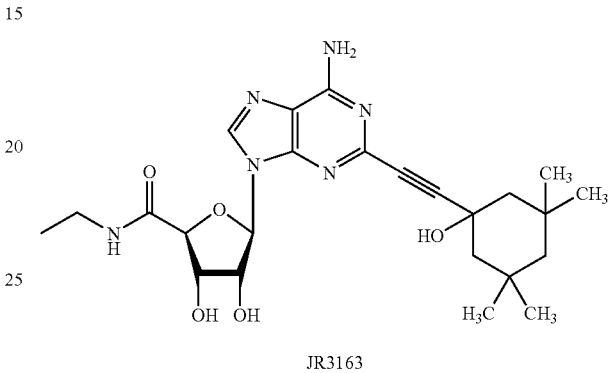

JR3163

The title compound was prepared using the appropriate starting materials and procedures described herein. The results are as follows:

$^1$H NMR (CD$_3$OD-d$_4$) δ 8.54 (s, 1H), 6.04 (d, J=6.9 Hz, 1H), 4.74 (dd, J=6.9 Hz, J=5.0 Hz, 1H), 4.46 (d, J=1.9 Hz, 1H), 4.34 (dd, J=4.7 Hz, J=1.9 Hz, 1H), 3.44 (m, 2H), 1.74 (s, 4H), 1.13 (m, 17H). APCI m/z (rel intensity) 487.3 (MH$^+$, 75), 469.4 (100), 296.4 (10).

Example 13

5-[6-Amino-2-(1-hydroxy-2-methyl-cyclohexylethynyl)-purin-9-yl]-3,4-dihydroxytetrahydrofuran-2-carboxylic acid ethylamide (JR3177A, JR3177B)

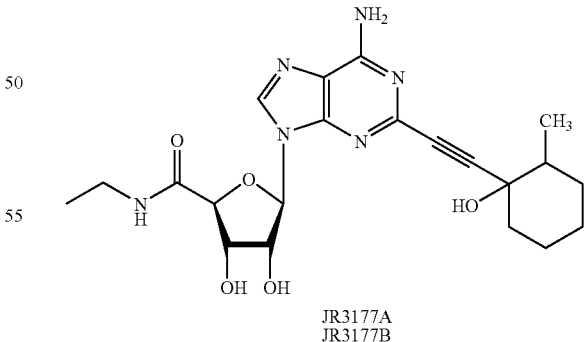

JR3177A
JR3177B

The reaction of 1-Ethynyl-2-methyl-cyclohexanol (JR3169B) (100 mg, 0.72 mmol) with 2-iodo-NECA (25 mg, 0.06 mmol) under the general coupling conditions gave JR3177A (8.0 mg) and JR3177B (8.2 mg) (overall yield 65%) as white solids after purification by a silica plug and RP-HPLC. JR3177A: $^1$H NMR (CD$_3$OD-d$_4$) δ 8.47 (s, 1H), 6.05

(d, J=6.9 Hz, 1H), 4.77 (dd, J=6.9 Hz, J=4.9 Hz, 1H), 4.45 (d, J=1.9 Hz, 1H), 4.34 (dd, J=4.6 Hz, J=2.1 Hz, 1H), 3.41 (m, 2H), 2.13 (d, J=12.7 Hz, 2H), 1.65 (m, 5H), 1.32 (m, 2H), 1.14 (t, J=7.0 Hz, 3H), 1.13 (d, J=6.6 Hz, 3H). $^{13}$C NMR (CD$_3$OD-d$_4$) δ. APCI m/z (rel intensity) 445.3 (MH$^+$, 100), 427.4 (80), 254.4 (14). $^1$H NMR (CD$_3$OD-d$_4$) δ 8.49 (s, 1H), 6.05 (d, J=6.9 Hz, 1H), 4.78 (dd, J=6.4 Hz, J=4.9 Hz, 1H), 4.45 (d, J=1.9 Hz, 1H), 4.34 (dd, J=4.6 Hz, J=1.6 Hz, 1H), 3.42 (m, 2H), 2.12 (d, J=12.3 Hz, 2H), 1.65 (m, 4H), 1.35 (m, 4H), 1.14 (t, J=7.3 Hz, 3H), 1.12 (d, J=6.6 Hz, 3H). $^{13}$C NMR (CD$_3$OD-d$_4$) δ. APCI m/z (rel intensity) 445.7 (MH$^+$, 100), 427.3 (35), 254.4 (3.5).

Example 14

5-[6-Amino-2-(1-hydroxy-3-methyl-cyclohexylethynyl)-purin-9-yl]-3,4-dihydroxytetrahydrofuran-2-carboxylic acid ethylamide (JR3179)

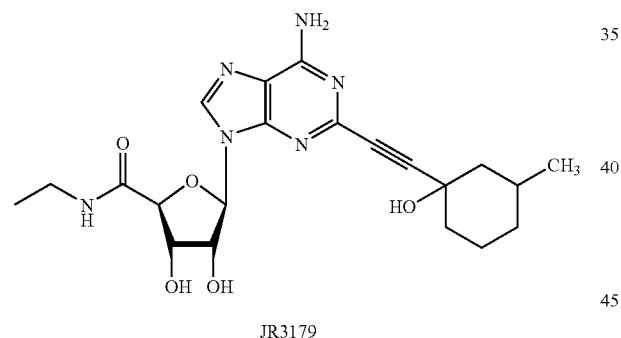

JR3179

The reaction of 1-Ethynyl-3-methyl-cyclohexanol (JR3149B) (100 mg, 0.72 mmol) with 2-iodo-NECA (25 mg, 0.06 mmol) under the general coupling conditions gave JR3179 (15.0 mg, 59%) as a white solid after purification by a silica plug and RP-HPLC. $^1$H NMR (CD$_3$OD-d$_4$) δ 8.49 (s, 1H), 6.06 (d, J=6.9 Hz, 1H), 4.75 (dd, J=6.4 Hz, J=4.9 Hz, 1H), 4.46 (d, J=1.9 Hz, 1H), 4.34 (dd, J=4.9 Hz, J=2.1 Hz, 1H), 3.42 (m, 2H), 2.09 (d, J=12.3 Hz, 2H), 1.73 (m, 4H), 1.46 (m, 1H), 1.23 (m, 1H), 1.16 9 (t, J=7.1 Hz, 3H), 0.95 (d, J=6.2 Hz, 3H), 0.89 (m, 1H). $^{13}$C NMR (CD$_3$OD-d$_4$) δ. APCI m/z (rel intensity) 445.3 (MH$^+$, 100), 427.4 (40), 254.4 (4).

Example 15

4-{3-[6-Amino-9-(5-ethylcarbamoyl-3,4-dihydroxytetrahydrofuran-2-yl)-9H-purin-2-yl]-prop-2-ynyl}-piperazine-1-carboxylic acid ethyl ester (JR3213)

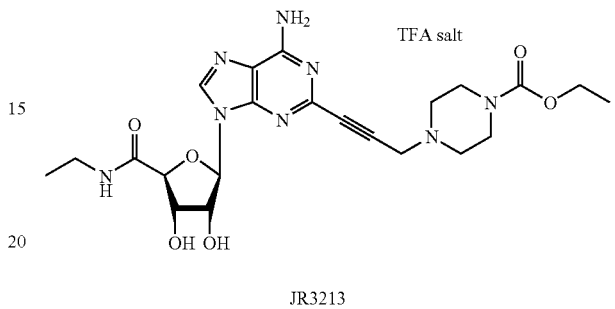

JR3213

The title compound was prepared using the appropriate starting materials and procedures described herein. The results are as follows:

$^1$H NMR (CD$_3$OD-d$_4$) δ 8.48 (s, 1H), 6.00 (d, J=6.9 Hz, 1H), 4.67 (dd, J=6.5 Hz, J=5.0 Hz, 1H), 4.42 (d, J=1.9 Hz, 1H)), 4.39 (s, 2H), 4.35 (dd, J=4.7 Hz, J=1.9 Hz, 1H), 4.13 (q,) 3.42 (m, 2H). $^{13}$C NMR (CD$_3$OD-d$_4$) δ. APCI m/z (rel intensity) 503.4 (MH$^+$, 100), 330.3 (6).

Example 16

5-[6-Amino-2-(3-hydroxy-2-oxo-azepan-3-ylethynyl)purin-9-yl]-3,4-dihydroxytetrahydrofuran-2-carboxylic acid ethylamide (JR3243A, JR3243B)

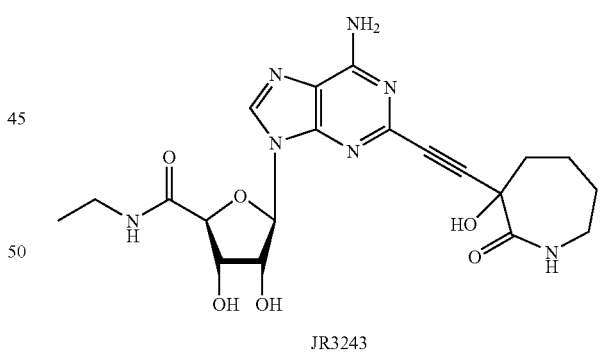

JR3243

35 mg (0.081 mmol) IodoNECA (62 mg alkyne, 0.41 mmol), 2 ml DMF, 4 ml Acetonitrile, 0.2 ml TEA, d(PPH3)4, Cut Stirred overnight at room temperature (Nov. 29, 2001). Rxn is tan w/brown precipitate. TLC (20% MeOH/CH$_2$Cl$_2$) indicates rxn complete (r.f. INECA=0.67, r.f. product=0.45). Filtered mixture through celite, washed with 3×2 mL DMF, and evaporated under vacuum to brown oil. (solid precipitates out upon the addition of MeOH, thus used DMF to load on prep plate).

The following compounds can be prepared by following the general method 4 described herein and the appropriate intermediate compounds described herein.

Example 17

N-Ethyl 2-{3-[trans-4-(methoxycarbonyloxamethyl)-cyclohexyl]-1-propyn-1-yl}adenosine-5'-uronamide (ATL214)

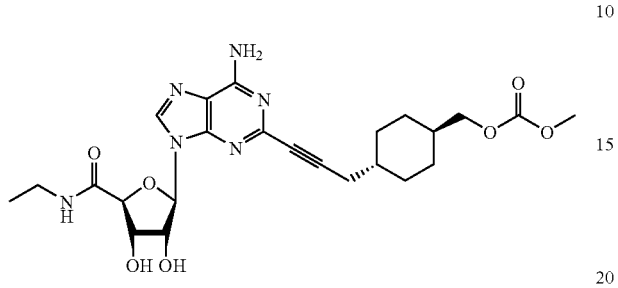

Yield 3.4 mg, 10%. $^1$H NMR (CD$_3$OD) δ 1.18 (t, 3H, —NHCH$_2$CH$_3$), 1.03-1.20, 1.51-1.70, 1.79-1.85, 1.94-2.01 (4×m, 10H, cyclohexyl), 2.35 (d, 2H, —C$_6$H$_{10}$CH$_2$CC—), 3.46 (m, 2H, —NHCH$_2$CH$_3$), 3.73 (s, 3H, —OCH$_3$), 3.94 (d, 2H, —C$_6$H$_{10}$CH$_2$O—), 4.29 (dd, 1H, 3'-H), 4.45 (d, 1H, 4'-H), 4.72 (dd, 1H, 2'-H), 5.97 (d, 1H, 1'-H), 8.27 (s, 1H, 8-H). APCI m/z 517.4 (M+H$^+$).

Example 18

N-Ethyl 2-{3-[trans-4-(isobutoxyoxycarbonyloxamethyl)-cyclohexyl]-1-propyn-1-yl}adenosine-5'-uronamide (ATL215)

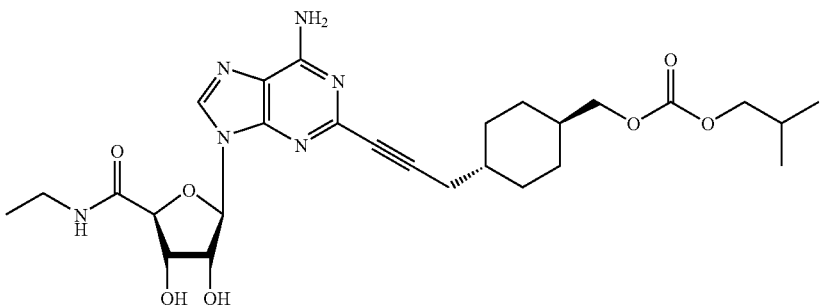

Yield 8.5 mg, 30%. $^1$H NMR (CD$_3$OD) δ 0.94 (d, 4H, —OCH$_2$CH(CH$_3$)$_2$), 1.18 (t, 3H, —NHCH$_2$CH$_3$), 1.04-1.24, 1.54-1.72, 1.79-2.03 (3×m, 11H, cyclohexyl, —OCH$_2$CH(CH$_3$)$_2$), 2.38 (d, 2H, —C$_6$H$_{10}$CH$_2$CC—), 3.43 (m, 2H, —NHCH$_2$CH$_3$), 3.89, 3.94 (2×d, 4H, —C$_6$H$_{10}$CH$_2$O—, —OCH$_2$CH(CH$_3$)$_2$), 4.30 (dd, 1H, 3'-H), 4.46 (d, 1H, 4'-H), 4.71 (dd, 1H, 2'-H), 6.00 (d, 1H, 1'-H), 8.37 (br s, 1H, 8-H). APCI m/z 559.5 (M+H$^+$).

Example 19

N-Ethyl 2-{3-[trans-4-(benzoxycarbonyloxamethyl)-cyclohexyl]-1-propyn-1-yl}adenosine-5'-uronamide (ATL216)

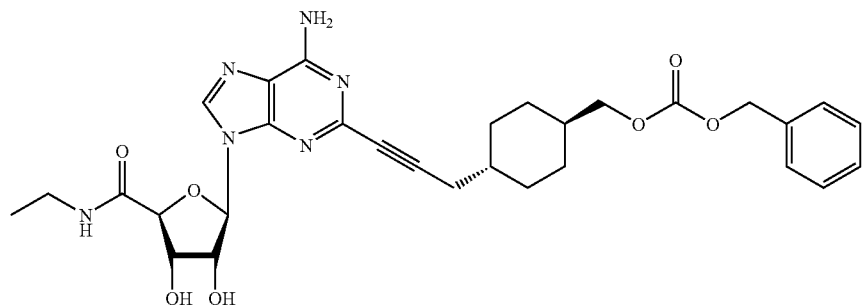

Yield 1.0 mg, 3%. $^1$H NMR (CD$_3$OD) δ 1.17 (t, 3H, —NHCH$_2$CH$_3$), 1.03-1.23, 1.52-1.71, 1.78-1.86, 1.93-2.02 (4×m, 10H, cyclohexyl), 2.35 (d, 2H, —C$_6$H$_{10}$CH$_2$CC—), 3.45 (m, 2H, —NHCH$_2$CH$_3$), 3.97 (d, 2H, —C$_6$H$_{10}$CH$_2$O—), 4.29 (dd, 1H, 3'-H), 4.45 (d, 1H, 4'-H), 4.72 (dd, 1H, 2'-H), 5.13 (s, 2H, —OCH$_2$Ph), 5.97 (d, 1H, 1'-H), 7.33-7.37 (m, 5H, Ar), 8.30 (br s, 1H, 8-H). APCI m/z 593.3 (M+H$^+$).

Example 20

4-{3-[6-Amino-9-(5-ethylcarbamoyl-3,4-dihydroxy-tetrahydro-furan-2-yl)-9H-purin-2-yl]-prop-2-ynyl}-cyclohexanecarboxylic acid 2-tert-butoxycarbony-lamino-ethyl ester

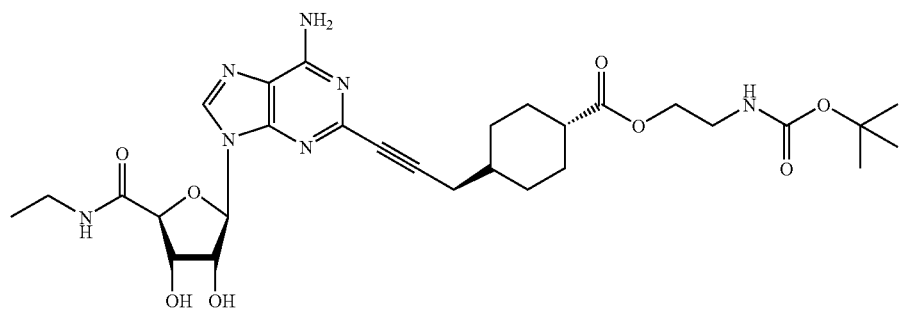

Example 21

5-{6-Amino-2-[3-(4-dimethylaminomethyl-cyclohexyl)-prop-1-ynyl]-purin-9-yl}-3,4-dihydroxytetrahydrofuran-2-carboxylic acid ethylamide (JR2023)

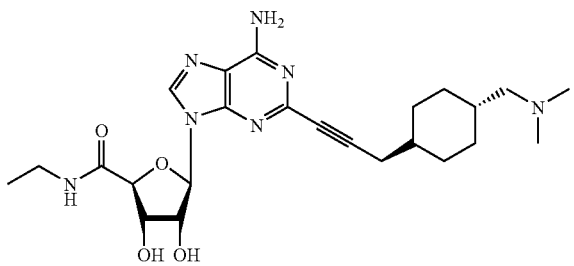

Example 22

4-{3-[6-Amino-9-(5-ethylcarbamoyl-3,4-dihydroxytetrahydro-furan-2-yl)-9H-purin-2-yl]-prop-2-ynyl}-cyclohexanecarboxylic acid 2-amino-ethyl ester (JR3033)

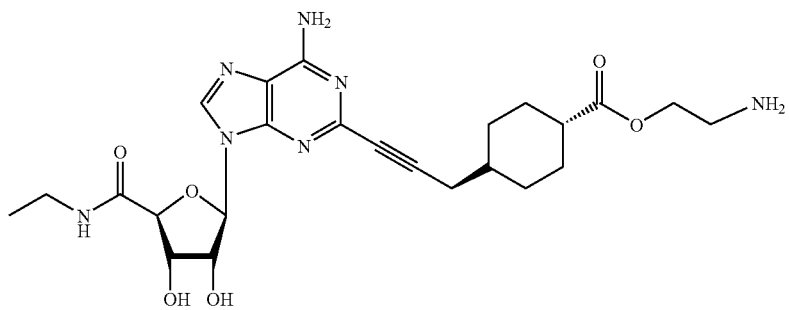

JR3033

Example 23

4-{3-[6-Amino-9-(5-ethylcarbamoyl-3,4-dihydroxytetrahydro-furan-2-yl)-9H-purin-2-yl]-prop-2-ynyl}-1-methyl-cyclohexanecarboxylic acid methyl ester (JR3067A)

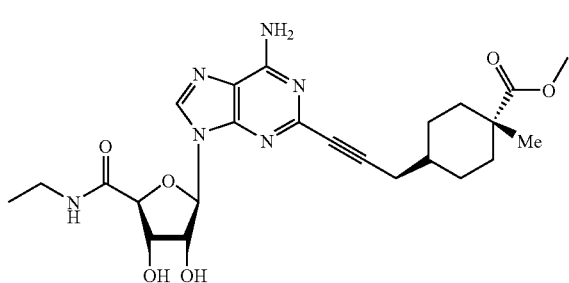

JR3067A

Example 24

4-{3-[6-Amino-9-(5-ethylcarbamoyl-3,4-dihydroxytetrahydro-furan-2-yl)-9H-purin-2-yl]-prop-2-ynyl}-1-methyl-cyclohexanecarboxylic acid methyl ester (JR3067B)

JR3067B

Example 25

5-{6-Amino-2-[3-(4-ethyl-cyclohexyl)-prop-1-ynyl]-purin-9-yl}-3,4-dihydroxytetrahydrofuran-2-carboxylic acid ethylamide (JR3087)

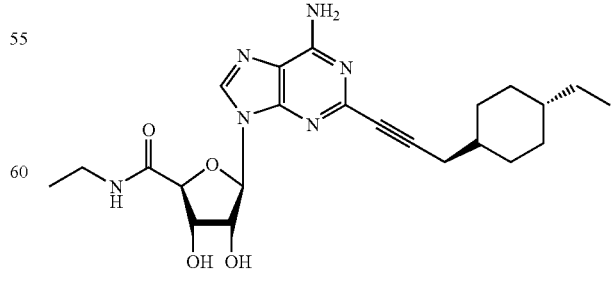

JR3087

Example 26

5-{2-[3-(4-Acetyl-cyclohexyl)-prop-1-ynyl]-6-aminopurin-9-yl}-3,4-dihydroxytetrahydrofuran-2-carboxylic acid ethylamide (JR3119)

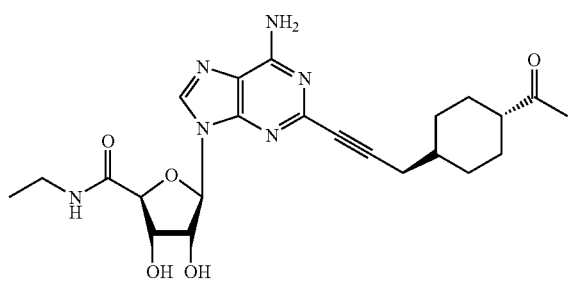

JR3119

Example 27

5-(6-Amino-2-{3-[4-(1-hydroxy-ethyl)-cyclohexyl]-prop-1-ynyl}-purin-9-yl)-3,4-dihydroxytetrahydrofuran-2-carboxylic acid ethylamide

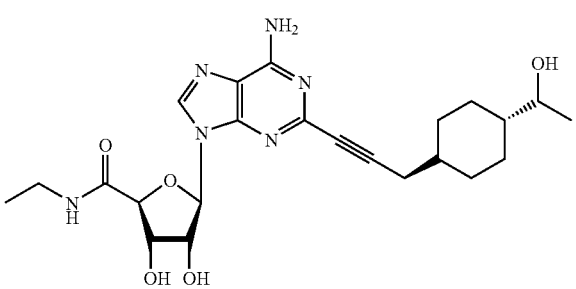

JR3121

Example 28

5-[6-Amino-2-(1-hydroxy-2-methyl-cyclohexylethynyl)-purin-9-yl]-3,4-dihydroxytetrahydrofuran-2-carboxylic acid ethylamide (JR3181A, JR3181B)

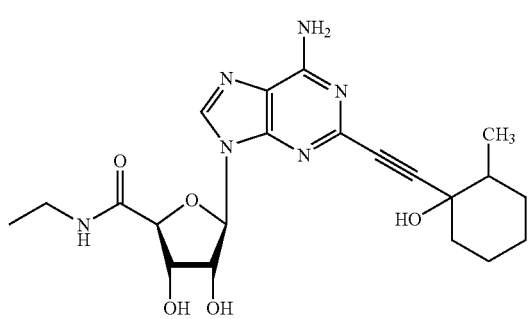

JR3181A
JR3181B

Example 29

5-[6-Amino-2-(1-hydroxy-3,3-dimethylcyclohexylethynyl)-purin-9-yl]-3,4-dihydroxytetrahydrofuran-2-carboxylic acid ethylamide (JR3201B)

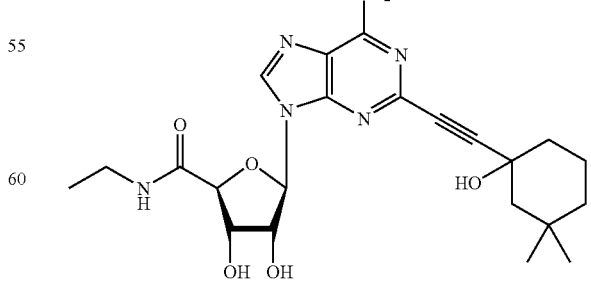

JR3201B

Example 30

5-[6-Amino-2-(4-tert-butyl-1-hydroxycyclohexyl-ethynyl)purin-9-yl]-3,4-dihydroxytetrahydrofuran-2-carboxylic acid ethylamide (JR3203)

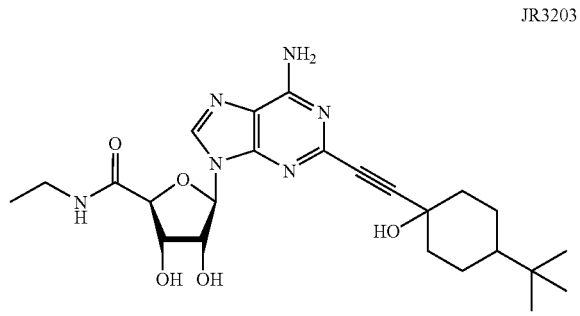

Example 31

5-[6-Amino-2-(1-hydroxy-3-methylcyclohexylethynyl)purin-9-yl]-3,4-dihydroxytetrahydrofuran-2-carboxylic acid ethylamide (JR3221)

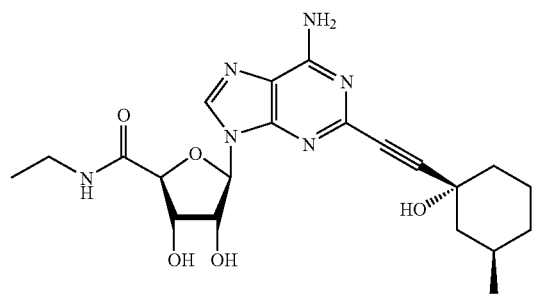

Example 32

5-[6-Amino-2-(1-hydroxy-3-methylcyclohexylethynyl)purin-9-yl]-3,4-dihydroxytetrahydrofuran-2-carboxylic acid ethylamide (JR3223)

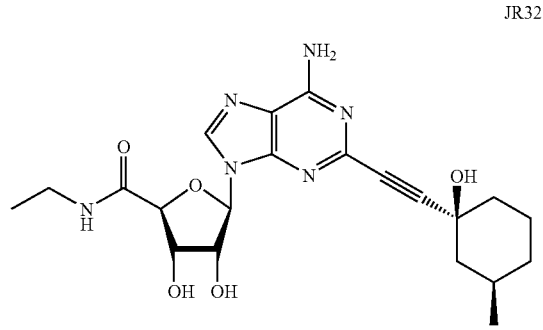

Example 33

5-[6-Amino-2-(2-tert-butyl-1-hydroxycyclohexyl-ethynyl)purin-9-yl]-3,4-dihydroxytetrahydrofuran-2-carboxylic acid ethylamide (JR3227)

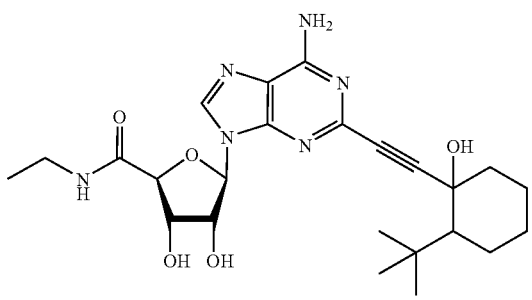

Example 34

1-{3-[6-Amino-9-(5-ethylcarbamoyl-3,4-dihydroxytetrahydro-furan-2-yl)-9H-purin-2-yl]-prop-2-ynyl}-piperidine-4-carboxylic acid methyl ester (JR3251)

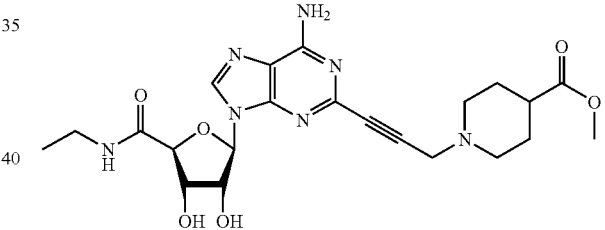

Example 35

1-{3-[6-Amino-9-(5-ethylcarbamoyl-3,4-dihydroxytetrahydro-furan-2-yl)-9H-purin-2-yl]-prop-2-ynyl}-piperidine-2-carboxylic acid methyl ester (JR3253)

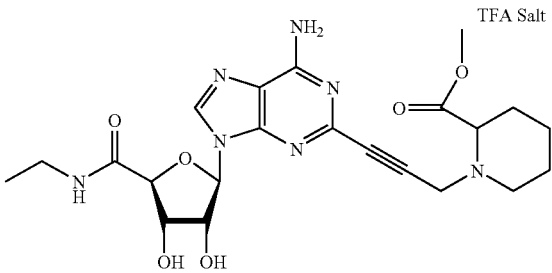

Example 36

4-{3-[6-Amino-9-(5-ethylcarbamoyl-3,4-dihydroxytetrahydro-furan-2-yl)-9H-purin-2-yl]-prop-2-ynyl}-piperidine-1-carboxylic acid tert-butyl ester (JR3259)

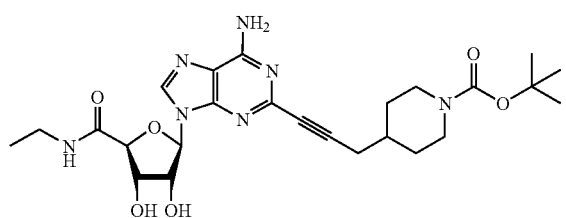

Example 37

4-{3-[6-Amino-9-(5-ethylcarbamoyl-3,4-dihydroxytetrahydro-furan-2-yl)-9H-purin-2-yl]-prop-2-ynyl}-piperidine-1-carboxylic acid ethyl ester (JR3269)

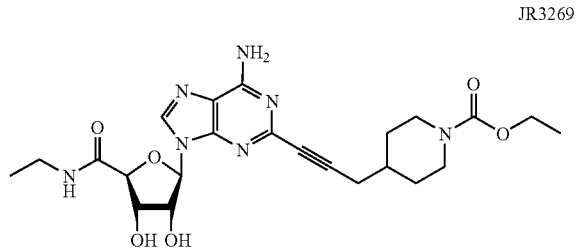

Example 38

1-{3-[6-Amino-9-(5-ethylcarbamoyl-3,4-dihydroxytetrahydro-furan-2-yl)-9H-purin-2-yl]-prop-2-ynyl}-piperidine-4-carboxylic acid ethyl ester (JR3279)

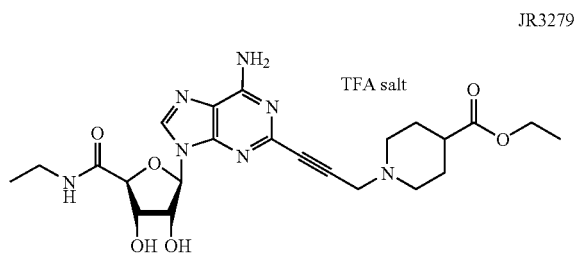

Example 39

4-{3-[6-Amino-9-(5-ethylcarbamoyl-3,4-dihydroxytetrahydro-furan-2-yl)-9H-purin-2-yl]-prop-2-ynyl}-piperazine-1-carboxylic acid tert-butyl ester (JR3281)

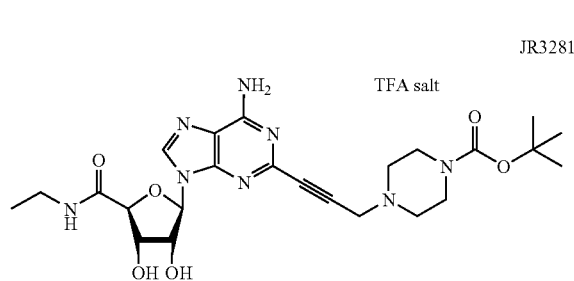

Example 40

5-{6-Amino-2-[3-(4-pyrimidin-2-yl-piperazin-1-yl)-prop-1-ynyl]-purin-9-yl}-3,4-dihydroxytetrahydrofuran-2-carboxylic acid ethylamide (JR3283)

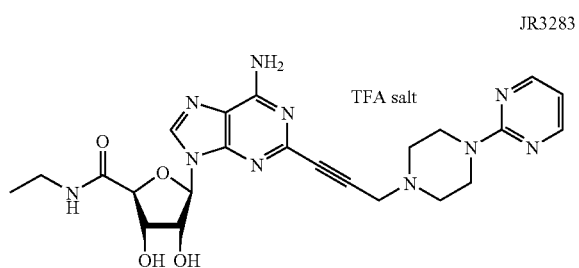

Example 41

5-[6-Amino-2-(3-piperazin-1-yl-prop-1-ynyl)purin-9-yl]-3,4-dihydroxytetrahydrofuran-2-carboxylic acid ethylamide (JR3289)

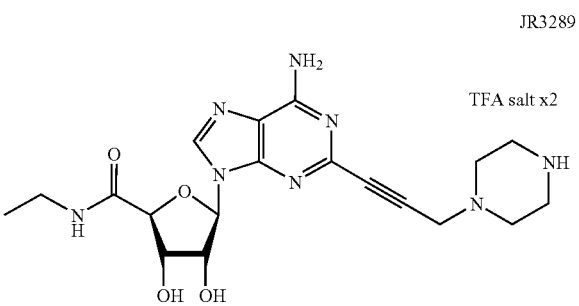

Example 42

1-{3-[6-Amino-9-(5-ethylcarbamoyl-3,4-dihydroxytetrahydro-furan-2-yl)-9H-purin-2-yl]-prop-2-ynyl}-piperidine-4-carboxylic acid (JR3291)

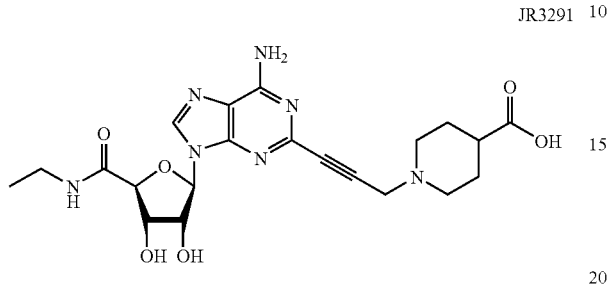

Example 43

4-{3-[6-Amino-9-(5-ethylcarbamoyl-3,4-dihydroxytetrahydro-furan-2-yl)-9H-purin-2-yl]-prop-2-ynyl}-piperidine-1-carboxylic acid methyl ester (JR4007)

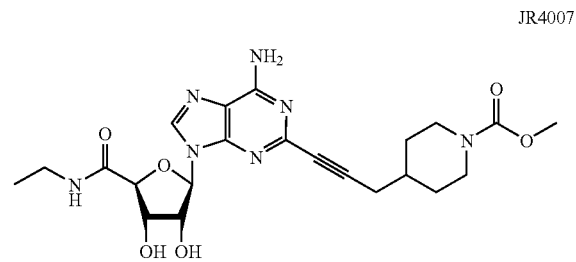

Example 44

4-{3-[6-Amino-9-(5-ethylcarbamoyl-3,4-dihydroxytetrahydro-furan-2-yl)-9H-purin-2-yl]-prop-2-ynyl}-piperidine-1-carboxylic acid isopropyl ester (JR4009)

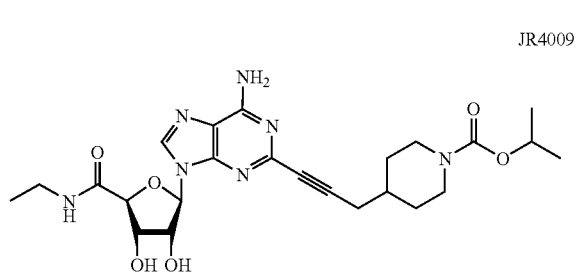

Example 45

4-{3-[6-Amino-9-(5-ethylcarbamoyl-3,4-dihydroxytetrahydro-furan-2-yl)-9H-purin-2-yl]-prop-2-ynyl}-piperidine-1-carboxylic acid isobutyl ester (JR4011)

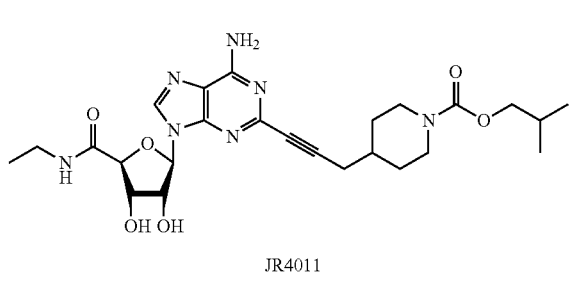

Example 46

5-{3-[6-Amino-9-(5-ethylcarbamoyl-3,4-dihydroxytetrahydro-furan-2-yl)-9H-purin-2-yl]prop-2-ynyl}-2,5-diazabicyclo[2.2.1]heptane-2-carboxylic acid tert-butyl ester (JR4015)

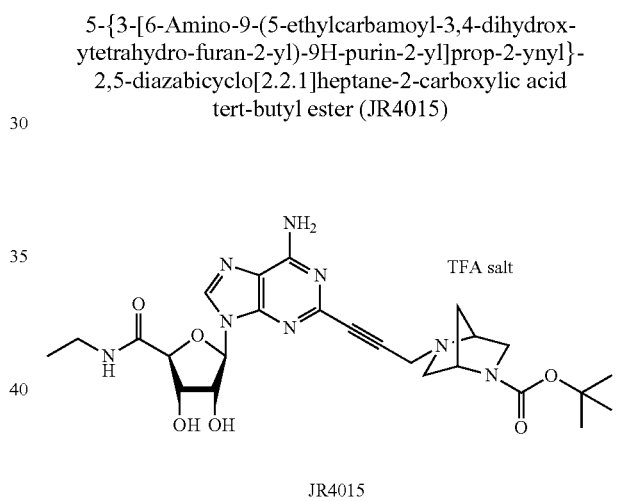

Example 47

5-(6-Amino-2-{3-[1-(3,3-dimethyl-butyryl)-piperidin-4-yl]-prop-1-ynyl}purin-9-yl)-3,4-dihydroxytetrahydrofuran-2-carboxylic acid ethylamide (JR4047)

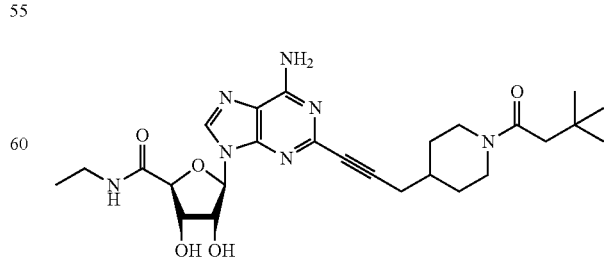

Example 48

5-(6-Amino-2-{3-[1-(2,2-dimethyl-propionyl)-piperidin-4-yl]prop-1-ynyl}-purin-9-yl)-3,4-dihydroxytetrahydrofuran-2-carboxylic acid ethylamide (JR4051)

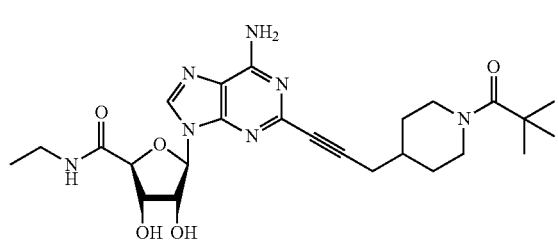

JR4051

Example 49

4-{3-[6-Amino-9-(5-ethylcarbamoyl-3,4-dihydroxytetrahydro-furan-2-yl)-9H-purin-2-yl]-prop-2-ynyl}-piperazine-1-carboxylic acid isobutyl ester (JR4049)

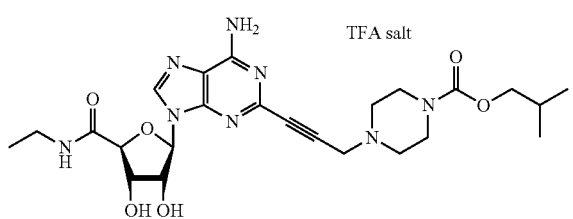

JR4049

Example 50

5-{2-[3-(4-Acetyl-piperazin-1-yl)-prop-1-ynyl]-6-aminopurin-9-yl}-3,4-dihydroxytetrahydrofuran-2-carboxylic acid ethylamide (JR4053)

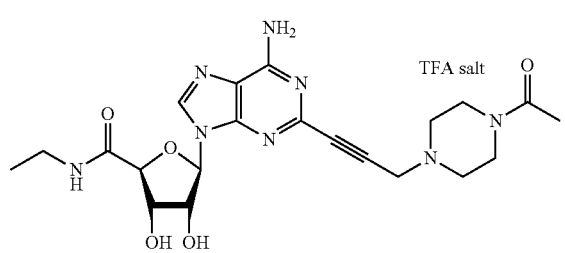

JR4053

Example 51

The following compounds can be prepared by following the general methods described herein and the appropriate intermediate compounds:

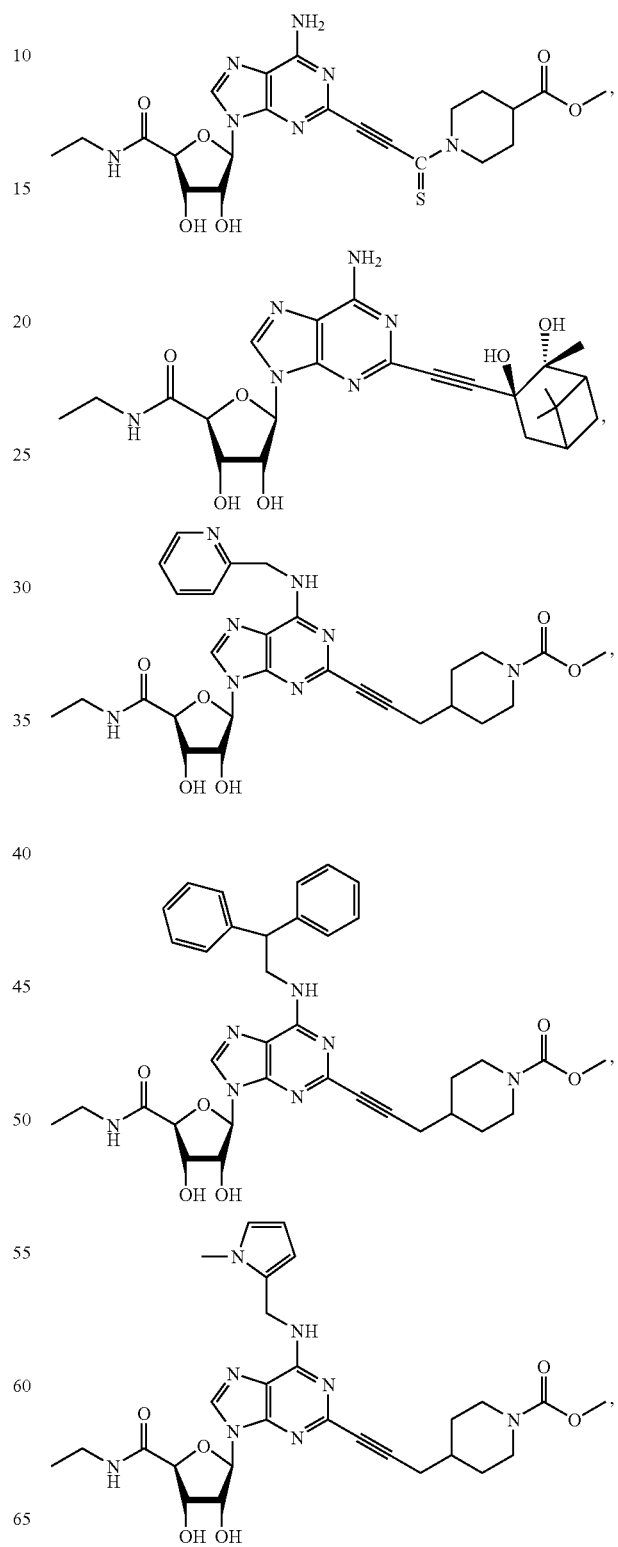

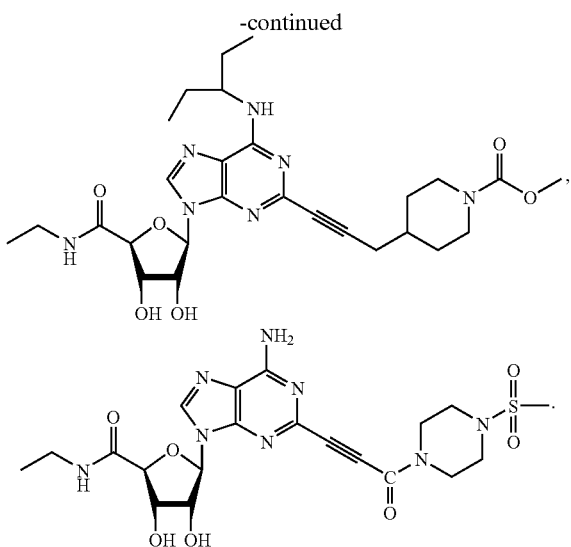

Example 52

Cell Culture and Membrane Preparation

Sf9 cells were cultured in Grace's medium supplemented with 10% fetal bovine serum, 2.5 µg/ml amphotericin B and 50 µg/ml gentamycin in an atmosphere of 50% $N_2$/50% $O_2$. Viral infection was performed at a density of $2.5 \times 10^6$ cells/mL with a multiplicity of infection of two for each virus used. Infected cells were harvested 3 days post-infection and washed twice in insect PBS (PBS pH 6.3). Cells were then resuspended in lysis buffer (20 mM HEPES pH 7.5, 150 mM NaCl, 3 mM $MgCl_2$, 1 mM β-mercaptoethanol (BME), 5 µg/mL leupeptin, 5 µg/mL pepstatin A, 1 µg/mL aprotinin, and 0.1 mM PMSF) and snap frozen for storage at −80° C. Cells were thawed on ice, brought to 30 mL total volume in lysis buffer, and burst by $N_2$ cavitation (600 psi for 20 minutes). A low-speed centrifugation was performed to remove any unlysed cells (1000×g for 10 minutes), followed by a high-speed centrifugation (17,000×g for 30 minutes). The pellet from the final centrifugation was homogenized in buffer containing 20 mM HEPES pH 8, 100 mM NaCl, 1% glycerol, 2 µg/mL leupeptin, 2 µg/mL pepstatin A, 2 µg/mL Aprotinin, 0.1 mM PMSF, and 10 µM GDP using a small glass homogenizer followed by passage through a 26 gauge needle. Membranes were aliquoted, snap frozen in liquid $N_2$, and stored at −80° C. Membranes from cells stably expressing the human $A_1$ AR (CHO K1 cells) or $A_3$ AR (HEK 293 cells) were prepared as described (Robeva et al., 1996).

Example 53

Radioligand Binding Assays

Radioligand binding to recombinant human $A_{2A}$ receptors in Sf9 cell membranes was performed using either the radiolabeled agonist, $^{125}$I-APE (Luthin et al., 1995) or the radiolabeled antagonist, $^{125}$I-ZM241385 ($^{125}$I-ZM). To detect the high affinity, GTPγS-sensitive state of $A_1$ and $A_3$ AR, we used the agonist, $^{125}$I-ABA (Linden et al., 1985; Linden et al., 1993). Binding experiments were performed in triplicate with 5 µg ($A_{2A}$) or 25 µg ($A_1$ and $A_3$) membrane protein in a total volume of 0.1 mL HE buffer (20 mM HEPES and 1 mM EDTA) with 1 U/mL adenosine deaminase and 5 mM $MgCl_2$ with or without 50 µM GTPγS. Membranes were incubated with radioligands at room temperature for three hours (for agonists) or two hours (for antagonists) in Millipore Multiscreen® 96-well GF/C filter plates and assays were terminated by rapid filtration on a cell harvester (Brandel, Gaithersburg, Md.) followed by 4×150 µl washes over 30 seconds with ice cold 10 mM Tris-HCl, pH 7.4, 10 mM $MgCl_2$. Non-specific binding was measured in the presence of 50 µM NECA. Competition binding assays were performed as described (Robeva et al., 1996) using 0.5-1 nM $^{125}$I-APE, $^{125}$I-ZM241385, or $^{125}$I-ABA. We found that it was sometimes important to change pipette tips following each serial dilution to prevent transfer on tips of potent hydrophobic compounds. The $K_i$ values for competing compound binding to a single site were derived from $IC_{50}$ values with correction for radioligand and competing compound depletion as described previously (Linden, 1982).

Linden J (1982) Calculating the Dissociation Constant of an Unlabeled Compound From the Concentration Required to Displace Radiolabel Binding by 50%. *J Cycl Nucl Res* 8: 163-172.

Linden J, Patel A and Sadek S (1985) [$^{125}$I]Aminobenzyladenosine, a New Radioligand With Improved Specific Binding to Adenosine Receptors in Heart. *Circ Res* 56: 279-284.

Linden J, Taylor H E, Robeva A S, Tucker A L, Stehle J H, Rivkees S A, Fink J S and Reppert S M (1993) Molecular Cloning and Functional Expression of a Sheep $A_3$ Adenosine Receptor With Widespread Tissue Distribution. *Mol Pharmacol* 44: 524-532.

Luthin D R, Olsson R A, Thompson R D, Sawmiller D R and Linden J (1995) Characterization of Two Affinity States of Adenosine $A_{2A}$ Receptors With a New Radioligand, 2-[2-(4-Amino-3-[$^{125}$I]Iodophenyl)Ethylamino]Adenosine. *Mol Pharmacol* 47: 307-313.

Robeva A S, Woodard R, Luthin D R, Taylor H E and Linden J (1996) Double Tagging Recombinant $A_1$- and $A_{2A}$-Adenosine Receptors With Hexahistidine and the FLAG Epitope. Development of an Efficient Generic Protein Purification Procedure. *Biochem Pharmacol* 51: 545-555.

Chemiluminescence Methods: Luminol enhanced chemiluminescence, a measure of neutrophil oxidative activity, is dependent upon both superoxide production and mobilization of the granule enzyme myeloperoxidase. The light is emitted from unstable high-energy oxygen species such as hypochlorous acid and singlet oxygen generated by activated neutrophils.

Purified human neutrophils (2×106/ml) suspended in Hanks balanced salt solution containing 0.1% human serum albumin (HA), adenosine deaminase (1 U/mL) and rolipram (100 nM) were incubated (37 C.) in a water bath for 15 min with or without rhTNF (10 U/ml). Following incubation 100 L aliquots of the PMN were transferred to wells (White walled clear bottom 96 well tissue culture plates Costar #3670; 2 wells/condition) containing 501 HA and luminol (final concentration 100M) with or without adenosine agonist (final agonist concentrations 0.01-1000 nM). The plate was incubated 5 min (37 C.) and then fMLP (50 1 in HA; final concentration 1M) was added to all wells.

Peak chemiluminescence was determined with a Victor 1420 Multilabel Counter in the chemiluminescence mode using the Wallac Workstation software. Data are presented as peak chemiluminescence as percent of activity in the absence of an adenosine agonist. The EC50 was determined using PRISM software. All compounds were tested with PMNs from three separate donors. The results are summarized in Table 8.

TABLE 8

Binding Affinity And Selectivity For $A_{2A}$ Agonists

| Agonist | A2A ± SEM | A1 ± SEM | A3 ± SEM | A1/A2A | A3/A2A | PMN oxid (−log EC50) | PMN oxid + roli (−log EC50) |
|---|---|---|---|---|---|---|---|
| ATL-146a | 29.6 ± 1.2 | 189 ± 19 | 29 ± 10 | 6.4 | 1.0 | 6.04 | 7.72 |
| ATL-146e | 0.5 ± 0.04 | 77.0 ± 12 | 45.0 ± 15 | 154.0 | 90.0 | 8.45 | 9.33 |
| ATL-193 | 1.1 ± 0.2 | 71.0 ± 14 | 231.0 ± 91 | 64.5 | 210.0 | 8.51 | 9.46 |
| ATL-2037 | 1.5 ± 0.01 | 19.0 ± 1 | 76.0 ± 6 | 12.6 | 50.3 | 7.49 | 8.7 |
| NECA | 2.0 ± 0.4 | 2.0 ± 1.4 | 32.0 ± 9 | 1.0 | 16.0 | 7.82 | 8.95 |
| CCPA | 11.0 ± 1.9 | 0.3 ± 0.1 | 65.0 ± 6 | 0.0 | 5.9 | 5.37 | 7.26 |
| CGS-21680 | 4.9 ± 0.3 | 316.0 ± 59 | 82.0 ± 18 | 64.5 | 16.7 | 7.52 | 8.55 |
| CI-IBMECA | 18.3 ± 3.2 | 33.0 ± 9 | 2.4 ± 0.3 | 1.8 | 0.1 | 4.34 | 7.49 |
| CPA | 19.8 ± 3.2 | 0.4 ± 0.1 | 93.0 ± 7 | 0.02 | 4.7 | 4.03 | 7.06 |
| IBMECA | 6.3 ± 1.3 | 9.0 ± 0.8 | 1.5 ± 0.3 | 1.4 | 0.2 | 6.49 | 8.01 |
| JR-2145 | 0.7 ± 0.16 | 28.3 ± 7.3 | 101.0 ± 22 | 42.2 | 150.7 | 7.19 | 8.57 |
| JR-2147 | 0.9 ± 0.38 | 17.5 ± 5.2 | 89.0 ± 21 | 19.0 | 96.7 | 7.13 | 8.57 |
| JR-2171 | 1.2 ± 0.09 | 132.0 ± 13 | 62.0 ± 12 | 110.0 | 51.7 | 8.1 | 9.27 |
| JR-3021 | 1.6 ± 0.5 | 107.0 ± 10 | 41.0 ± 1 | 66.9 | 25.6 | 7.58 | 8.58 |
| JR-3023 | 3.8 ± 2 | 14.0 ± 0.8 | 61.0 ± 6 | 3.7 | 16.3 | 7.37 | 8.66 |
| JR-3027 | 0.8 ± 0.1 | 23.4 ± 3.7 | 26.0 ± 9 | 28.2 | 31.3 | 8.46 | 9.46 |
| JR-3031 | 13.8 ± 2.8 | 734.0 ± 126 | 126.0 ± 20 | 53.2 | 9.1 | 6.26 | 7.75 |
| JR-3033 | 1.6 ± 0.02 | 15.1 ± 3.9 | 26.0 ± 14 | 9.7 | 16.7 | 7.31 | 8.67 |
| JR-3037 | 4.1 ± 0.9 | 113.0 ± 11 | 93.0 ± 21 | 27.6 | 22.7 | 7.34 | 8.68 |
| JR-3041 | 12.0 ± 4.8 | 7.1 ± 2.2 | 82.0 ± 8 | 0.6 | 6.8 | 4.19 | 6.95 |
| JR-3055 | 1.8 ± 0.2 | 36.0 ± 2 | 28.0 ± 3 | 20.0 | 15.6 | 7.5 | 8.64 |
| JR-3063 | 0.3 ± 0.02 | 0.2 ± 0.03 | 1.3 ± 0.4 | 0.9 | 5.2 | 9.63 | 10.33 |
| JR-3065 | 3.6 ± 0.5 | 55.0 ± 13 | 28.0 ± 13 | 15.3 | 7.8 | 6.99 | 8.29 |
| JR-3067A | 1.3 ± 0.8 | 99.0 ± 27 | 39.0 ± 3 | 76.2 | 30.0 | 7.65 | 8.7 |
| JR-3067B | 4.0 ± 0.2 | 121.0 ± 44 | 212.0 ± 95 | 30.3 | 53.0 | 6.83 | 8.2 |
| JR-3079 | 1.1 ± 0.33 | 0.5 ± 0.04 | 15.6 ± 3 | 0.4 | 14.1 | 7.85 | 9.11 |
| JR-3081 | 0.9 ± 0.18 | 0.5 ± 0.09 | 14.7 ± 7.5 | 0.6 | 15.6 | 8.34 | 9.57 |
| JR-3085 | 0.5 ± 0.18 | 1.0 ± 0.26 | 2.0 ± 1.3 | 2.0 | 4.1 | 8.41 | 9.6 |
| JR-3087 | 2.2 ± 0.2 | 20.3 ± 4.5 | 17.8 ± 5.5 | 9.2 | 8.1 | 7.33 | 8.51 |
| JR-3089 | 0.7 ± 0.05 | 7.1 ± 1.1 | 4.4 ± 11 | 10.8 | 6.7 | 9.14 | 9.9 |
| JR-3101 | 0.9 ± 0.16 | 2.7 ± 0.23 | 6.2 ± 0.6 | 3.1 | 7.0 | 8.41 | 9.5 |
| JR-3103 | 1.7 ± 0.21 | 2.0 ± 0.61 | 5.0 ± 2.3 | 1.2 | 3.0 | 7.95 | 9.03 |
| JR-3119 | 2.4 ± 0.2 | 28.7 ± 3.3 | 18.6 ± 4.4 | 11.9 | 7.7 | 7.54 | 8.7 |
| JR-3121 | 5.7 ± 0.6 | 52.3 ± 7.6 | 71.0 ± 16 | 9.3 | 12.6 | 6.98 | 8.31 |
| JR-3135 | 0.8 ± 0.3 | 5.0 ± 1.3 | 3.5 ± 1.2 | 6.3 | 4.4 | 8.9 | 9.6 |
| JR-3137 | 1.2 ± 0.35 | 13.5 ± 3.2 | 7.4 | 11.3 | 6.2 | 7.59 | 8.72 |
| JR-3139 | 166.0 ± 42 | 801.0 ± 99 | 83.7 ± 30 | 4.8 | 0.5 | 5.39 | 6.75 |
| JR-3141 | 0.8 ± 0.28 | 9.7 ± 2.3 | 70.0 | 11.5 | 83.3 | 8.19 | 9.4 |
| JR-3149 | 0.5 ± 0.05 | 3.8 ± 0.4 | 7.3 ± 1.9 | 7.0 | 13.5 | 8.66 | 9.63 |
| JR-3159A | 0.6 ± 0.06 | 0.9 ± 0.05 | 3.9 ± 1.5 | 1.4 | 6.6 | 8.43 | 9.34 |
| JR-3159B | 0.4 ± 0.07 | 2.0 ± 0.21 | 2.6 ± 0.3 | 5.7 | 7.4 | 9.44 | 10.36 |
| JR-3161 | 0.9 ± 0.04 | 10.9 ± 0.5 | 113.0 ± 6 | 12.2 | 127.0 | 8.35 | 9.29 |
| JR-3163 | 11.1 ± 2.8 | 784.0 ± 94 | 152.0 ± 62 | 70.6 | 13.7 | 6.27 | 7.67 |
| JR-3177A | 1.2 ± 0.35 | 8.7 ± 0.07 | 6.7 ± 0.3 | 7.1 | 5.5 | 7.53 | 9.03 |
| JR-3177B | 0.7 ± 0.07 | 15.5 ± 0.7 | 7.5 ± 4.5 | 23.1 | 11.2 | 8.5 | 9.45 |
| JR-3179 | 0.4 ± 0.05 | 8.5 ± 0.3 | 12.6 ± 3.6 | 19.3 | 28.6 | 9.18 | 10.07 |
| JR-3181A | 1.2 ± 0.15 | 44.9 ± 17.2 | 69.7 ± 43 | 38.1 | 59.1 | 7.73 | 8.77 |
| JR-3181B | 0.7 ± 0.07 | 24.2 ± 6.2 | 38.9 ± 4.8 | 36.1 | 58.1 | 8.57 | 9.67 |
| JR-3201B | 1.6 ± 0.28 | 157.0 ± 14 | 23.6 ± 0.35 | 98.1 | 14.8 | 8.06 | 9.2 |
| JR-3203 | 1.5 ± 0.22 | 14.7 ± 2.2 | 43.3 ± 18 | 9.5 | 28.1 | 7.85 | 9.11 |
| JR-3205 | 3.4 ± 0.3 | 14.2 ± 1.08 | 31.6 ± 26.5 | 4.2 | 9.3 | 7.22 | 8.08 |
| JR-3213 | 1.9 ± 0.4 | 15.8 ± 0.48 | 42.3 ± 18.3 | 8.3 | 22.3 | 8.46 | 9.11 |
| JR-3221 | 5.08 ± 0.81 | 19.5 ± 0.12 | 9.0 ± 5.5 | 3.8 | 1.8 | 7.3 | 8.21 |
| JR-3223 | 0.92 ± 0.2 | 4.8 ± 0.3 | 0.7 ± 0.02 | 5.2 | 0.8 | 9.47 | 10.15 |
| JR-3229 | 20.8 ± 2.5 | 234 | 15.3 ± 5.42 | 11.3 | 0.7 | 6.65 | 7.58 |
| JR-3227 | 25.1 ± 1.3 | 536 | 50 | 21.4 | 2.0 | 5.13 | 7.14 |
| JR-3243A | 11.9 ± 1.3 | 29.6 ± 4.8 | 31.1 ± 7.2 | 2.5 | 2.6 | 6.42 | 7.65 |
| JR-3243B | 2.25 ± 0.35 | 12 ± 5 | 3.34 ± 0.48 | 5.3 | 1.5 | 7.81 | 8.91 |
| JR-3251 | 6.02 ± 0.57 | 47.3 ± 24.2 | 58.5 ± 8 | 7.9 | 9.7 | 7.52 | 8.5 |
| JR-3253 | 3.29 ± 0.49 | 13.8 ± 0.5 | 31.3 ± 9.3 | 4.2 | 9.5 | 7.36 | 8.42 |
| JR-3259 | 0.9 ± 0.10 | 205 ± 2.6 | 45.6 ± 10 | 227.8 | 50.7 | 8.46 | 9.26 |
| JR-3261 | 5.7 ± 1.8 | 47.3 ± 11.6 | 86.7 ± 3.75 | 8.3 | 15.2 | 6.4 | 7.6 |
| JR-3269 | 1.26 ± 0.21 | 134 ± 12.5 | 68.6 | 106.0 | 54.4 | 8.65 | |
| JR-3279 | 3.82 ± 0.95 | 14.4 | | 3.8 | 0.0 | 7.86 | |
| JR-3281 | 2.36 ± 0.50 | 9.15 ± 1.35 | 38 | 3.9 | 16.1 | 8.19 | |
| JR-3283 | 2.00 ± 0.25 | 15.3 ± 0.4 | 66.2 | 4.6 | 19.0 | 8.24 | |
| JR-4007 | 0.97 ± 0.33 | 34.6 ± 1.4 | 65.2 | 35.7 | 67.2 | 8.77 | |
| JR-4009 | 1.43 ± 0.23 | 167 ± 13.5 | 86 | 116.4 | 60.1 | 8.45 | |
| JR-4011 | 0.61 ± 0.06 | | 71.7 | 0.0 | 117.5 | 8.46 | |
| JR-4015 | 4.25 ± 1.0 | | | 0.0 | 0.0 | | |
| ATL214 | 0.8 | 100 | 100 | 125 | 125 | 2 | .6 |
| ATL215 | 4.8 | | | | | 20 | 2.8 |

TABLE 8-continued

Binding Affinity And Selectivity For $A_{2A}$ Agonists

| Agonist | A2A ± SEM | A1 ± SEM | A3 ± SEM | A1/A2A | A3/A2A | PMN oxid (−log EC50) | PMN oxid + roli (−log EC50) |
|---|---|---|---|---|---|---|---|
| ATL216 | 2.7 | | | | | 13 | 1.8 |
| AB-1 | 0.71 ± 0.09 | 76.7 ± 8.9 | 4.9 ± 0.23 | 108.0 | 6.9 | 8.94 | 9.54 |
| AB-3 | 2.55 ± 0.20 | 75.7 ± 9.2 | 7.8 ± 2.8 | 29.7 | 3.0 | 8.39 | 9.4 |
| AB-5 | 5.48 ± 1.1 | 55.4 ± 4.8 | 12.5 ± 5.7 | 10.1 | 2.3 | 7.8 | 8.83 |
| AB-6 | 5.8 ± 1.6 | 25.9 ± 3.5 | 11.1 ± 1.72 | 4.5 | 1.9 | 7.53 | 8.51 |
| AB-8 | 1.20 ± 0.05 | 36.9 ± 6.1 | 11.9 ± 1.86 | 30.8 | 9.9 | 7.76 | 8.72 |

PMN oxid (−log EC50) = human neutrophil experiment as described in Example 54 w/o Rolipram
PMN oxid + roli (−log EC50) = human neutrophil experiment as described in Example 54 w/ Rolipram

Example 54

Effect of $A_{2A}$ Agonists on Neutrophil Oxidative Activity

A. Materials.

f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Santa Fe, N. Mex.) and Accurate Chemicals and Scientific (Westerbury, N.Y.). endotoxin (lipopolysaccharide; *E. coli* K235) was from List Biologicals (Campbell, Calif.). Hanks balanced salt solution (HBSS), and *limulus amebocyte* lysate assay kit were from BioWittaker (Walkersville, Md.). Human serum albumin (HSA) was from Cutter Biological (Elkhart, Ind.). Recombinant human tumor necrosis factor-alpha was supplied by Dianippon Pharmaceutical Co. Ltd. (Osaka, Japan). ZM241385 (4-(2-[7-amino-2-(2-furyl)[1,2,4]triazolo[2,3-a][1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

B. Human Neutrophil Preparation

Purified neutrophils (~98% neutrophils and >95% viable by trypan blue exclusion) containing <1 platelet per 5 neutrophils and <50 pg/ml endotoxin (*limulus amebocyte* lysate assay) were obtained from normal heparinized (10 U/ml) venous blood by a one step Ficoll-hypaque separation procedure (A. Ferrante et al., *J. Immunol. Meth.*, 36, 109 (1980)).

C. Release of Inflammatory Reactive Oxygen Species from Primed and Stimulated Human Neutrophils Chemiluminescence Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils ($5-10\times10^5$/ml) were incubated in Hanks balanced salt solution containing 0.1% human serum albumin (1 ml) with the tested $A_{2A}$ agonist with or without rolipram and with or without tumor necrosis factor-alpha (1 U/ml) for 30 minutes at 37° C. in a shaking water bath. Then luminol ($1\times10^{-4}$ M) enhanced f-met-leu-phe (1 mcM) stimulated chemiluminescence was read with a Chronolog® Photometer (Crono-log Corp., Havertown, Pa.) at 37° C. for 2-4 minutes. Chemiluminescence is reported as relative peak light emitted (=height of the curve) compared to samples with tumor necrosis factor-alpha and without agonist or rolipram.

Example 55

In Vivo Rat Blood Pressure Experiments

Sprague-Dawley rats (mean weights, 250-300 grams) were anthesthetized and jugular and carotid catheters are implanted ipsilaterally and the animals are allowed to recover 24-48 hours. Prior to each experiment a baseline blood pressure reading is established for 30 minutes with each drug injection being preceeded by a vehicle control. Drugs are injected bolus I.V. through a jugular catheter in a 200 microliter volume of saline and the catheter is flushed with an additional 300 microliters of saline. To measure blood pressure, a central line from the carotid catheter is attached to the pressure transducer of a Digi-Med Blood Pressure Analyzer. Systolic pressure, diastolic pressure, mean pressure, and heart rate are all recorded in real time at 30-60 second intervals. Data is recorded until mean blood pressure has returned to baseline and remained constant for 20 minutes. The data is presented as a fraction of the mean blood pressure averaged over the 10 minutes immediately prior to drug injection. The blood pressures are recorded and plotted over time as a means of determining potency of the compounds as well as biological half-life.

The results are illustrated in FIGS. 1-6.

Example 56

In Vivo Coronary Dog Flow Experiments

Fasted, adult mongrel dogs (mean weight, 24.8±0.6 kg; range, 20.9 to 28.2 kg) were anaesthetized with sodium pentobarbital (30 mg·kg$^{-1}$), tracheally intubated, and mechanically ventilated with room air on a respirator (model 613, Harvard Apparatus) with positive end-expiratory pressure of 5 cm $H_2O$. The surgical preparation and instrumentation of the animals has been thoroughly described previously (Glover D. K. et al., *Circulation* 1996, 94, pages 1726-1732). Throughout each experiment, heart rate, mean arterial and left atrial pressures, ultrasonically measured LCx flow, and dP/dt were continuously monitored and recorded on a 16-channel thermal array chart recorder (K2-G, Astro-med, Inc) and digitised and stored on an IBM-compatible personal computer. All experiments were performed with the approval of the University of Virginia Animal Care and Use Committee and were in compliance with the position of the American Heart Association on the use of research animals. The compounds tested were intravenously administered by bolus injection and the parameters above were measured and recorded.

The results are illustrated in FIGS. 7-16.

Example 57

Liver I/R Injury Protocol

Mice were anesthetized by intraperitoneal injection of ketamine 100 mg/kg and xylazine 10 mg/kg. Glycopyrrolate (Robinul-V®) 0.05 mg/kg was delivered subcutaneously before the operation. The ambient temperature was controlled in the range of 24° C. to 26° C. Mice were placed on a 37° C. heat pad with their core temperature monitored by a TH-8 Thermalert® Monitoring Thermometer (Physitemp®)) and maintained at 36-37° C. by a TCAT-1A Temperature Control and Alarm Unit (Physitemp®) during the entire procedure. After midline laparotomy, a microaneurysm clip was applied to the hepatic triad above the bifurcation to clamp the flow of the hepatic artery, portal vein, and bile duct. The peritoneum was closed after superfusion of 200 μl of warm saline. After 60 minutes of ischemia, the peritoneum was reopened and the microaneurysm clip was removed. Immediately after reperfusion was initiated, each mouse received a loading dose of ATL-146e (1 ug/kg) or vehicle in 200 uL warm saline, and a primed Alzet® osmotic minipump was placed intraperitoneally. The surgical wound was closed with metal staples. Mice were maintained on the heat pad to monitor and maintain body temperature until the anesthetic wore off.

Drug Administration.

Alzet® osmotic minipumps (model 1003D; Alza Corp., Palo Alto, Calif., USA) were primed according to the manufacture's instruction in order to release compounds shortly after implantation. A solution containing ATL146e was prepared in normal saline and placed in osmotic minipumps to deliver 10 ng/kg/min. Minipumps containing vehicle or ATL146e were implanted during operation.

Example 58

Serum Enzyme Determination

Serum GPT (ALT) levels were measured using a Transaminase® kit (505, Sigma). Briefly, 20 μL serum sample was mixed with 100 (L pre-heated Alanine-α-KG substrate and incubated in a 37° C. water bath for 30 minutes. Then we added 100 (L Sigma Color Reagent to the reaction and left it at room temperature for 20 minutes. We stopped the reaction with 1.0 ml 0.4N sodium hydroxide solution. Absorbance of each sample at 505 nm was measured and converted into SF unit/ml.

Example 59

Tissue Myeloperoxidase Measurement

Mouse livers were removed after 24 hours reperfusion. The tissue was immediately submerged in 10 volumes of ice-cold 50 mM KPO4 buffer, pH 7.4 and homogenized with a Tekmar® tissue grinder. The homogenate was centrifuged at 15,000×g for 15 minutes at 4° C., and the supernatant was discarded. The pellet was washed twice, resuspended in 10 volumes of ice-cold 50 mM KPO4 buffer pH 7.4 with 0.5% hexadecyltrimethylammonium bromide and then sonicated. The suspension was subjected to three freeze/thaw cycles. Samples were sonicated for 10 seconds, and centrifuged at 15,000×g for 15 minutes at 4° C. The supernatant was added to an equal volume of a solution consisting of o-dianisidine (10 mg/ml), 0.3% H2O2, and 50 mM KPO4, pH 6.0. Absorbance was measured at 460 nm over a period of five minutes.

Figure 17:
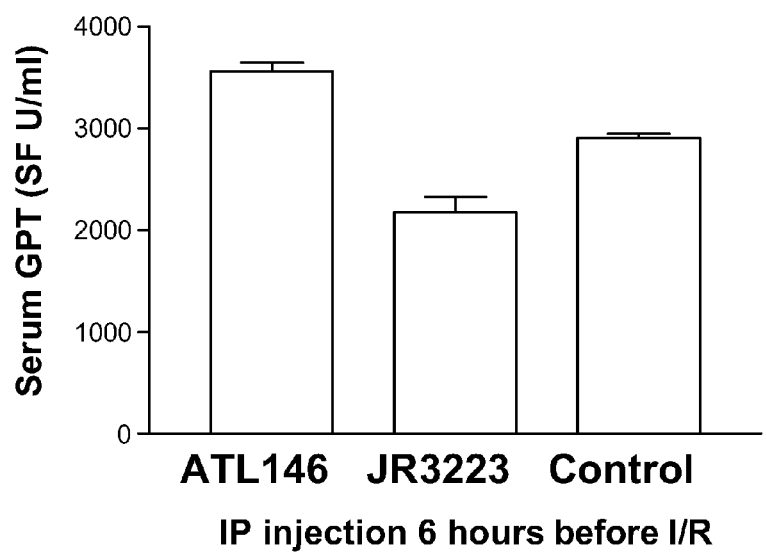
FIG. 17 illustrates the results of the liver ischemia/reperfusion injury test

FIG. 17 illustrates the longer duration of action of JR3223 vs. a control compound and ATL146e for liver tissue protection after an ischemia/reperfusion injury. The test compounds were administered 6 hours prior to I/R injury. Tissue protection is measured by amount of Serum GPT present in the in a serum sample 24 hours later, with smaller GPT concentrations indicating better liver function.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound having formula (I):

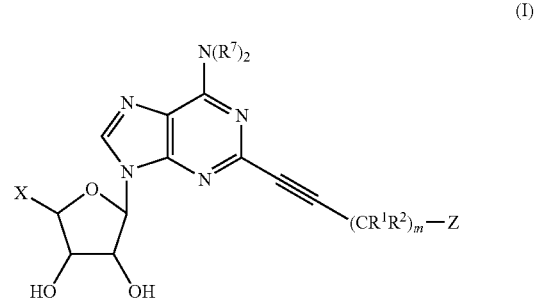

(I)

wherein
Z is $CR^3R^4R^5$;
each $R^1$ is independently hydrogen, halo, $OR^a$, $SR^a$, $(C_1-C_8)$alkyl, cyano, nitro, trifluoromethyl, trifluoromethoxy, $(C_3-C_8)$cycloalkyl, heterocyclyl, heterocyclyl$(C_1-C_8)$alkylene, aryl, aryl$(C_1-C_8)$alkylene, heteroaryl, heteroaryl$(C_1-C_8)$alkylene, $CO_2R^a$, $R^aC(=O)O$, $R^aC(=O)$, $OCO_2R^a$, $R^aR^bNC(=O)O$, $R^bOC(=O)N(R^a)$, $R^aR^bN$, $R^aR^bNC(=O)$, $R^aC(=O)N(R^b)$, $R^aR^bNC(=O)N(R^b)$, $R^aR^bNC(=S)N(R^b)$, $R^aOC(=S)$, $R^aC(=S)$, $SSR^a$, $R^aS(=O)$, $R^aS(=O)_2$, or $N=NR^a$;
each $R^2$ is independently hydrogen, halo, $(C_1-C_8)$alkyl, $(C_3-C_8)$cycloalkyl, heterocyclyl, heterocyclyl$(C_1-C_8)$alkylene, aryl, aryl$(C_1-C_8)$alkylene, heteroaryl, or heteroaryl$(C_1-C_8)$alkylene; or
$R^1$ and $R^2$ and the atom to which they are attached is $C=O$, $C=S$ or $C=NR^c$;
$R^4$ and $R^5$ together with the atoms to which they are attached form a ring selected from

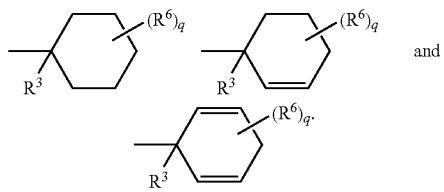

and wherein any ring comprising $R^4$ and $R^5$ is substituted with from 1 to 4 $R^6$ groups, such that q is 1 to 4;

wherein each $R^6$ is independently halo, $OR^a$, $SR^a$, $(C_1-C_8)$alkyl, cyano, nitro, trifluoromethyl, trifluoromethoxy, $(C_1-C_8)$cycloalkyl, $(C_6-C_{12})$bicycloalkyl, heterocyclyl or heterocyclyl $(C_1-C_8)$alkylene, aryl, aryl $(C_1-C_8)$alkylene, heteroaryl, heteroaryl$(C_1-C_8)$alkylene, $CO_2R^a$, $R^aC(=O)O$, $R^aC(=O)$, $OCO_2R^a$, $R^aR^bNC(=O)O$, $R^bOC(=O)N(R^a)$, $R^aR^bN$, $R^aR^bNC(=O)$, $R^aC(=O)N(R^b)$, $R^aR^bNC(=O)N(R^b)$, $R^aR^bNC(=S)N(R^b)$, $R^aOC(=S)$, $R^aC(=S)$, $SSR^a$, $R^aS(=O)$, or $NNR^a$;

or two $R^6$ groups and the atom to which they are attached is C=O, C=S or two $R^6$ groups together with the atom or atoms to which they are attached form a carbocyclic or heterocyclic ring;

$R^3$ is halo, $OR^a$, $SR^a$, cyano, nitro, trifluoromethyl, trifluoromethoxy, $(C_3-C_8)$cycloalkyl, heterocyclyl, heterocyclyl$(C_1-C_8)$alkylene, aryl, aryl$(C_1-C_8)$alkylene, heteroaryl, heteroaryl$(C_1-C_8)$alkylene, $CO_2R^a$, $R^aC(=O)O$, $R^aC(=O)$, $OCO_2R^a$, $R^aR^bNC(=O)O$, $R^bOC(=O)N(R^a)$, $R^aR^bN$, $R^aR^bNC(=O)$, $R^aC(=O)N(R^b)$, $R^aR^bNC(=O)N(R^b)$, $R^aR^bNC(=S)N(R^b)$, $R^aOC(=S)$, $R^aC(=S)$, $SSR^a$, $R^aS(=O)$, $R^aS(=O)_2$, or $NNR^a$;

each $R^7$ is independently hydrogen, $(C_1-C_8)$alkyl, $(C_3-C_8)$cycloalkyl, aryl or aryl$(C_1-C_8)$alkylene, heteroaryl, heteroaryl$(C_1-C_8)$alkylene-;

X is $CH_2OR^a$, $CO_2R^a$, $OC(O)R^a$, $CH_2OC(O)R^a$, $C(O)NR^aR^b$, $CH_2SR^a$, $C(S)OR^a$, $OC(S)R^a$, $CH_2OC(S)R^a$, $C(S)NR^aR^b$ or $CH_2N(R^a)(R^b)$;

wherein any of the alkyl, cycloalkyl, heterocyclyl, aryl, or heteroaryl, groups of $R^1$, $R^2$, $R^3$, $R^6$ and $R^7$ is optionally substituted on carbon with one or more (e.g. 1, 2, 3, or 4) substituents selected from the group consisting of halo, $OR^a$, $SR^a$, $(C_1-C_8)$alkyl, cyano, nitro, trifluoromethyl, trifluoromethoxy, $(C_3-C_8)$cycloalkyl, $(C_6-C_{12})$bicycloalkyl, heterocyclyl or heterocyclyl$(C_1-C_8)$alkylene, aryl, aryloxy, aryl $(C_1-C_8)$alkylene, heteroaryl, heteroaryl$(C_1-C_8)$alkylene, $CO_2R^a$, $R^aC(=O)O$, $R^aC(=O)$, $OCO_2R^a$, $R^aR^bNC(=O)O$, $R^bOC(=O)N(R^a)$, $R^aR^bN$, $R^aR^bNC(=O)$, $R^aC(=O)N(R^b)$, $R^aR^bNC(=O)N(R^b)$, $R^aR^bNC(=S)N(R^b)$, $R^aOC(=S)$, $R^aC(=S)$, $SSR^a$, $R^aS(=O)_p$, $R^aR^bNS(O)_p$, and $N=NR^a$;

wherein any $(C_1-C_8)$alkyl, $(C_3-C_8)$cycloalkyl, $(C_6-C_{12})$bicycloalkyl, $(C_1-C_8)$alkoxy, $(C_1-C_8)$alkanoyl, $(C_1-C_8)$alkylene, or heterocyclyl, is optionally partially unsaturated;

$R^a$ and $R^b$ are each independently hydrogen, $(C_1-C_8)$ alkyl, or $(C_1-C_8)$alkyl substituted with 1-3 $(C_1-C_8)$ alkoxy, $(C_3-C_8)$cycloalkyl, $(C_1-C_8)$alkylthio, aryl, aryl$(C_1-C_8)$alkylene, heteroaryl, or heteroaryl$(C_1-C_8)$alkylene; or $R^a$ and $R^b$, together with the nitrogen to which they are attached, form a pyrrolidino, piperidino, morpholino, or thiomorpholino ring; and $R^c$ is hydrogen or $(C_1-C_6)$alkyl;

m is 0 to 8 and p is 0 to 2;

or a pharmaceutically acceptable salt thereof.

2. The compound of claim 1, wherein $R^1$ is hydrogen, OH, $CH_2OH$, $OCH_3$, $OC(O)CH_3$, $NH_2$, $NHCH_3$, $N(CH_3)_2$ or $NHC(O)CH_3$.

3. The compound of claim 1, wherein $R^1$ is hydrogen, OH, $OCH_3$, $OC(O)CH_3$, $NH_2$, $NHCH_3$, $N(CH_3)_2$ or $NHC(O)CH_3$.

4. The compound of claim 1, wherein $R^1$ is hydrogen, OH, OMe, or $NH_2$.

5. The compound of claim 1, wherein $R^1$ is hydrogen, OH, or $NH_2$.

6. The compound of claim 1, wherein $R^1$ is hydrogen or OH.

7. The compound of claim 1, wherein $R^2$ is hydrogen, $(C_1-C_8)$alkyl, cyclopropyl, cyclohexyl or benzyl.

8. The compound of claim 1, wherein $R^2$ is hydrogen, methyl, ethyl or propyl.

9. The compound of claim 1, wherein $R^2$ is hydrogen or methyl.

10. The compound of claim 1, wherein $R^2$ is hydrogen.

11. The compound of claim 1, wherein $R^1$, $R^2$ and the carbon atom to which they are attached is carbonyl (C=O).

12. The compound of claim 1, wherein $R^3$ is OH, $OCH_3$, $OC(O)CH_3$, $NH_2$, $NHCH_3$, $N(CH_3)_2$ or $NHC(O)CH_3$.

13. The compound of claim 1, wherein $R^3$ is OH, $OCH_3$, or $NH_2$.

14. The compound of claim 1, wherein $R^3$ is OH, or $NH_2$.

15. The compound of claim 1, wherein $R^3$ is OH.

16. The compound of claim 1, wherein $R^6$ is $(C_1-C_8)$alkyl, or substituted $(C_1-C_8)$alkyl, $OR^a$, $CO_2R^a$, $R^aC(=O)$, $R^aC(=O)O$, $R^aR^bN$, $R^aR^bNC(=O)$, or aryl.

17. The compound of claim 1, wherein $R^6$ is $(C_1-C_8)$alkyl, $OR^a$, $CO_2R^a$, $R^aC(=O)$, $R^aC(=O)O$, $R^aR^bN$, $R^aR^bNC(=O)$, or aryl.

18. The compound of claim 1, wherein $R^6$ is methyl, ethyl, butyl, OH, $OR^a$, $CO_2R^a$, $R^aC(=O)$, $OC(=O)CH_2CH_3$, $CONR^aR^b$, $NR^aR^b$ or phenyl.

19. The compound of claim 1, wherein $R^6$ is OH, $OCH_3$, methyl, ethyl, t-butyl, $CO_2R^a$, $CONR^aR^b$, $OC(O)CH_3$, $NH_2$, $NHCH_3$, $N(CH_3)_2$, $NHCH_2CH_3$, or $N(CH_2CH_3)_2$.

20. The compound of claim 1, wherein $R^6$ is methyl, ethyl, t-butyl, phenyl, $CO_2R^a$, $CONR^aR^b$, or $C(=O)R^a$.

21. The compound of claim 1, wherein $R^6$ is methyl, ethyl, $CO_2R^aCONR^aR^b$, or $OC(O)CH_3$.

22. The compound of claim 1, wherein $R^6$ is $(CH_2)_{1-2}OR^a$, $(CH_2)_{1-2}C(=O)OR^a$, $(CH_2)_{1-2}OC(=O)R^a$, $(CH_2)_{1-2}C(=O)R^a$, $(CH_2)_{1-2}OCO_2R^a$, $(CH_2)_{1-2}NHR^a$, $(CH_2)_{1-2}NR^aR^b$, $(CH_2)_{1-2}OC(=O)NHR^a$, or $(CH_2)_{1-2}OC(=O)NR^aR^b$.

23. The compound of claim 1, wherein $R^6$ is $CH_2OH$, $CH_2OC(O)CH_3$, $CH_2OCH_3$, $CH_2C(=O)OCH_3$, $CH_2C(=O)CH_3$, $CH_2C(=O)CH_3$, $CH_2OCO_2CH_3$, $CH_2NH(CH_3)$, Or $(CH_2)_{1-2}N(CH_3)_2$.

24. The compound of claim 1, wherein $R^6$ is $CH_2OH$, $CH_2OC(O)CH_3$, $C(=O)OCH_3$, $C(=O)CH_3$, $OCO_2CH_3$, $OCO_2CH_3$, $CH_2NH(CH_3)$, or $(CH_2)_{1-2}N(CH_3)_2$.

25. The compound of claim 1, wherein $R^a$ and $R^b$ are independently hydrogen, $(C_1-C_4)$alkyl, aryl or aryl$(C_1-C_8)$ alkylene.

26. The compound of claim 1, wherein $R^a$ and $R^b$ are independently hydrogen, methyl or ethyl, phenyl or benzyl.

27. The compound of claim 1, wherein $R^a$ is $(C_1-C_8)$alkyl.

28. The compound of claim 1, wherein $R^a$ is methyl, ethyl, propyl or butyl.

29. The compound of claim 1, wherein $R^a$ is, methyl, ethyl, i-propyl, i-butyl or tert-butyl.

30. The compound of claim 1, wherein $R^a$ and $R^b$ form a ring.

31. The compound of claim 1, wherein $R^7$ is hydrogen, alkyl, aryl or aryl$(C_1-C_8)$alkylene.

32. The compound of claim 1, wherein $R^7$ is hydrogen, methyl or ethyl, phenyl or benzyl.

33. The compound of claim 1, wherein $R^7$ is H or methyl.

34. The compound of claim 1, wherein $N(R^7)_2$ is amino, methylamino, dimethylamino, ethylamino, pentylamino, diphenylethylamino, diethylamino, or benzylamino.

35. The compound of claim 1, wherein —N(R$^7$)$_2$ is amino, methylamino, dimethylamino, ethylamino, diethylamino, or benzylamino.

36. The compound of claim 1, wherein N(R$^7$)$_2$ is amino or methylamino.

37. The compound of claim 1, wherein X is CH$_2$OR$^a$, CO$_2$R$^a$, OC(O)R$^a$, CH$_2$OC(O)R$^a$, or C(O)NR$^a$R$^b$.

38. The compound of claim 1, wherein X is CH$_2$OR$^2$, or C(O)NR$^a$R$^b$.

39. The compound of claim 1, wherein X is CH$_2$OH or C(O)NHCH$_2$CH$_3$.

40. The compound of claim 1, wherein m is 0, 1, or 2.

41. The compound of claim 1, wherein m is 0, or 1.

42. The compound of claim 1, wherein R$^4$, R$^5$ and the atom to which they are connected are

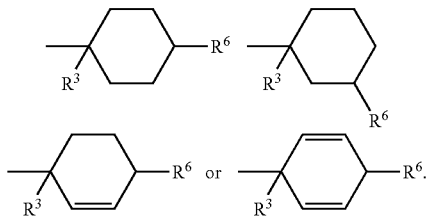

43. A compound of claim 1, having the formula:

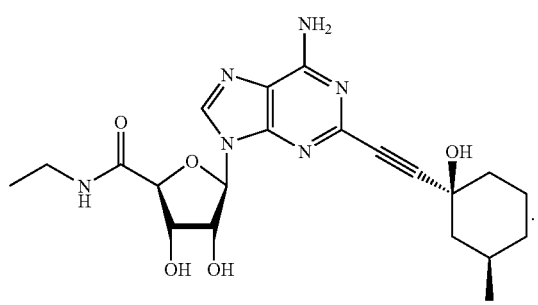

44. A compound of claim 1, having the formula:

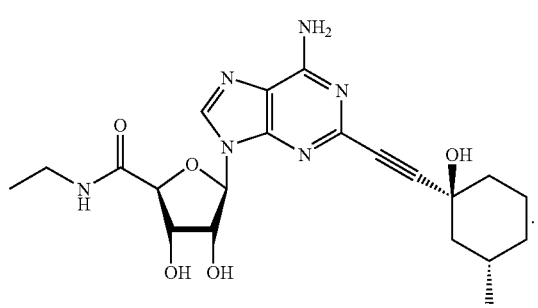

45. A compound of claim 1, having the formula:

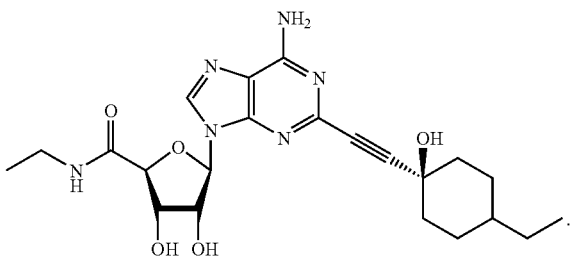

46. A compound of claim 1, having the formula:

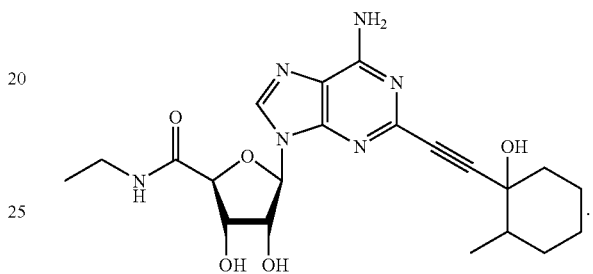

47. A compound of claim 1, having the formula:

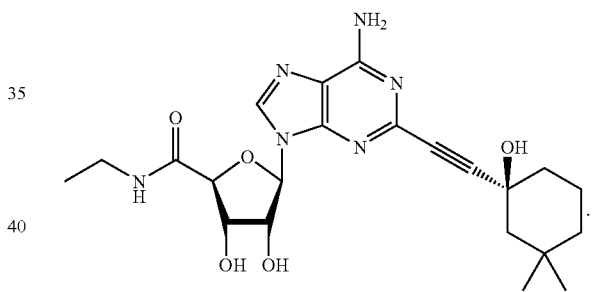

48. A therapeutic composition comprising a compound of claim 1, in combination with a pharmaceutically acceptable carrier.

49. The composition of claim 48 further comprising a Type IV phosphodiesterase inhibitor.

50. The composition of claim 49 wherein the inhibitor is rolipram.

51. The composition of claim 48, wherein the carrier is a liquid carrier.

52. The composition of claim 48, which is adapted for parenteral, aerosol or transdermal administration.

* * * * *